(12) United States Patent
Cravatt et al.

(10) Patent No.: US 9,981,972 B2
(45) Date of Patent: May 29, 2018

(54) N-HYDROXY BICYCLIC HYDANTOIN CARBAMATES AS TOOLS FOR IDENTIFICATION OF SERINE HYDROLASE TARGETS

(71) Applicants: ABIDE THERAPEUTICS, INC., San Diego, CA (US); THE SCRIPPS RESEARCH INSTITUTE, La Jolla, CA (US)

(72) Inventors: Benjamin F. Cravatt, La Jolla, CA (US); Armand B. Cognetta, San Diego, CA (US); Jonathan J. Hulce, San Diego, CA (US); Micah J. Niphakis, San Diego, CA (US); Todd K. Jones, Solana Beach, CA (US); Cheryl A. Grice, Encinitas, CA (US)

(73) Assignees: ABIDE THERAPEUTICS, INC., San Diego, CA (US); THE SCRIPPS RESEARCH INSTITUTE, La Jolla, CA (US)

( * ) Notice: Subject to any disclaimer, the term of this patent is extended or adjusted under 35 U.S.C. 154(b) by 0 days. days.

(21) Appl. No.: 15/313,012

(22) PCT Filed: May 20, 2015

(86) PCT No.: PCT/US2015/031838
§ 371 (c)(1),
(2) Date: Nov. 21, 2016

(87) PCT Pub. No.: WO2015/179563
PCT Pub. Date: Nov. 26, 2015

(65) Prior Publication Data
US 2017/0183353 A1    Jun. 29, 2017

Related U.S. Application Data

(60) Provisional application No. 62/001,869, filed on May 22, 2014.

(51) Int. Cl.
| | | |
|---|---|---|
| C07D 401/12 | (2006.01) |
| C07D 401/14 | (2006.01) |
| C07D 413/14 | (2006.01) |
| C07D 487/04 | (2006.01) |
| C07D 471/04 | (2006.01) |
| C12Q 1/34 | (2006.01) |

(52) U.S. Cl.
CPC ............ *C07D 487/04* (2013.01); *C12Q 1/34* (2013.01)

(58) Field of Classification Search
CPC .. C07D 401/12; C07D 401/14; C07D 413/14; C07D 487/04; C07D 471/04
See application file for complete search history.

(56) References Cited

U.S. PATENT DOCUMENTS

| | | |
|---|---|---|
| 4,003,912 A | 1/1977 | Franz |
| 5,439,790 A | 8/1995 | Muthyala et al. |
| 2014/0018318 A1 | 1/2014 | Cravatt et al. |
| 2015/0080364 A1 | 3/2015 | Cisar et al. |

FOREIGN PATENT DOCUMENTS

| | | |
|---|---|---|
| DE | 2740248 A1 | 3/1979 |
| JP | 2004177416 A | 6/2004 |
| WO | WO-2009071638 A2 | 6/2009 |
| WO | WO-2009100155 A1 | 8/2009 |
| WO | WO-2009117444 A1 | 9/2009 |
| WO | WO-2010045401 A1 | 4/2010 |
| WO | WO-2010056309 A2 | 5/2010 |
| WO | WO-2013142307 A1 | 9/2013 |
| WO | WO-2015179563 A2 | 11/2015 |

OTHER PUBLICATIONS

Batz et al. Pharmakologisch active Polymere. Die Makromolekulare Chemie. 172:27-47 (1973) (w/English Abstract).
Blizzard et al. Side chain SAR of bicyclic 2-lactamase inhibitors (BLIs). 1. Discovery of a class C BLI for combination with imipinem. Bioorg Med Chem Lett 20(3):918-921 (2010).
Chang et al. Proteome-wide reactivity profiling identifies diverse carbamate chemotypes tuned for serine hydrolase inhibition. ACS Chem Biol 8:1590-1599 (2013).
Chen et al. Monoacylglycerol lipase is a therapeutic target for Alzheimer's disease. Cell Rep. 2(5):1329-1339 (2012).
Hora. Stabilization of Bacillus subtilis α-amylase by amino group acylation. Biochimica et Biophysica Acta (BBA)—Protein Structure 310(1):264-267 (1973).
Iriepa et al. Synthesis, Structural and conformational study of some ureas derived from 3-methyl-2,4-diphenyl-3-azabicyclo[3.3.1]nonan-9beta-amine. Journal of Molecular Structure 482-483:431-436 (1999).
Jaouadi et al. Novel Preparation of N-Protected Amino Acid Active Esters Using 1.2.2.2-Tetrachloroethyl Carbonates. J Org Chem 52(12):2364-2367 (1987).
Nimura et al. Activated Carbamate Reagent as Derivatizing Agent for Amino Compounds in High-Performance Liquid Chromatography. Anal Chem 58(12): 2372-2375 (1986).
Nomura et al. Activation of the endocannabinoid system by organophosphorus nerve agents. Nat Chem Biol. 4(6):373-378 (2008).
Nomura et al. Endocannabinoid hydrolysis generates brain prostaglandins that promote neuroinflammation. Science 334(6057):809-813 (2011).
Nomura et al. Monoacylglycerol lipase regulates 2-arachidonoylglycerol action and arachidonic acid levels. Bioorg Med Chem Lett. 18(22):5875-5878 (2008).
PCT/US2013/031907 International Preliminary Report on Patentability dated Sep. 23, 2014.

(Continued)

Primary Examiner — Bruck Kifle
(74) Attorney, Agent, or Firm — Wilson, Sonsini, Goodrich & Rosati

(57) ABSTRACT

Provided herein are N-hydroxy bicyclic hydantoin carbamates and pharmaceutical compositions comprising said compounds. The subject compounds and compositions are useful as modulators of serine hydrolases. Furthermore, the subject compounds and compositions are useful for the treatment of one or more of cancer, pain, diabetes, obesity/metabolic syndrome, epilepsy, traumatic brain injury, and inflammation.

20 Claims, 29 Drawing Sheets

(56) References Cited

OTHER PUBLICATIONS

PCT/US2013/031907 International Search Report dated Jun. 25, 2013.
Piro et al. A dysregulated endocannabinoid-eicosanoid network supports pathogenesis in a mouse model of Alzheimer's disease. Cell Rep. 1(6):617-623 (2012).
Qiao et al. 5'-O-[( N-Acyl)sulfamoyl]adenosines as Antitubercular Agents that Inhibit MbtA: An Adenylation Enzyme Required for Siderophore Biosynthesis of the Mycobactins. J Med Chem 50(24):6080-6094 (2007).
Schmidt et al. Chroman and tetrahydroquinoline ureas as potent TRPV1 antagonists. Bioorg Med Chem Lett 21(5):1338-1341 (2011).
U.S. Appl. No. 14/383,076 Office Action dated Apr. 4, 2016.
U.S. Appl. No. 14/383,076 Office Action dated Jul. 15, 2016.
U.S. Appl. No. 14/383,076 Office Action dated Nov. 19, 2015.
Vasilevich et al. Conversion of O-succinimidyl carbamates to N-(O-carbamoyl)-succinmonoamides and ureas: effects of N-substituents and reaction conditions on the reaction pathway. Tetrahedron Letters 43(37):6649-6652 (2002).
Vasilevich et al. Selective conversion of O-succinimidyl carbamates to N-(O-carbamoyl)-succinmonoamides and Ureas. Tetrahedron Letters 43(18):3443-3445 (2002).
Adibekian et al. Characterization of a Selective, Reversible Inhibitor of Lysophospholipase 1 (LYPLA1), in Probe Reports from the NIH Molecular Libraries Program. in press: Bethesda (MD) (14 pgs) (2010).
Adibekian et al. Characterization of a Selective, Reversible Inhibitor of Lysophospholipase 2 (LYPLA2), in Probe Reports from the NIH Molecular Libraries Program. in press: Bethesda (MD) (52 pgs) (2010).
Adibekian et al. Click-generated triazole ureas as ultrapotent in vivo-active serine hydrolase inhibitors. Nat Chem Biol 7(7):469-478 (2011).
Adibekian et al. Confirming target engagement for reversible inhibitors in vivo by kinetically tuned activity-based probes. J Am Chem Soc 134(25):10345-10348 (2012).
Adibekian et al. Optimization and characterization of a triazole urea dual inhibitor for lysophospholipase 1 (LYPLA1) and lysophospholipase 2 (LYPLA2), in Probe Reports from the NIH Molecular Libraries Program. Bethesda (MD) (2010) (36 pgs).
Adibekian et al. Optimization and characterization of a triazole urea inhibitor for alpha/beta hydrolase domain-containing protein 11 (ABHD11): anti-probe for LYPLA1/LYPLA2 dual inhibitor ML211, in Probe Reports from the NIH Molecular Libraries Program. Bethesda (MD) (31 pgs) (2010).
Alexander et al. Mechanism of carbamate inactivation of FAAH: implications for the design of covalent inhibitors and in vivo functional probes for enzymes. Chem Biol 12(11):1179-1187 (2005).
Bachovchin et al. Identification of selective inhibitors of uncharacterized enzymes by high-throughput screening with fluorescent activity-based probes. Nat Biotechnol 27(4):387-394 (2009).
Bachovchin et al. The pharmacological landscape and therapeutic potential of serine hydrolases. Nat Rev Drug Discov 11(1):52-68 (2012).
Bachovichin et al. Superfamily-wide portrait of serine hydrolase inhibition achieved by library-versus-library screening. PNAS USA 107(49):20941-20946 (2010).
Berge et al. Pharmaceutical Salts. Journal of Pharmaceutical Sciences 66(1):1-19 (Jan. 1977).
Berger et al. Activity-based protein profiling: applications to biomarker discovery, in vivo imaging and drug discovery. Am J Pharmacogenomics 4(6):371-381 (2004).
Biel et al. Synthesis and evaluation of acyl protein thioesterase 1 (APT1) inhibitors. Chemistry 12(15):412141-43 (2006).
Blankman et al. A comprehensive profile of brain enzymes that hydrolyze the endocannabinoid 2-arachidonoylglycerol. Chem. Biol. 14:1347-1356 (2007).
Chang et al. A potent and selective inhibitor of KIAA1363/AADACL1 that impairs prostate cancer pathogenesis. Chem Biol 18(4):476-484 (2011).
Chang et al. Proteome-Wide Reactivity Profiling Identifies Diverse Carbamate Chemotypes Tuned for Serine Hydrolase Inhibition. ACS Chem Biol 8(7):1590-1599 (2013).
Chiang et al. An enzyme that regulates ether lipid signaling pathways in cancer annotated by multidimensional profiling. Chem Biol 13(10):1041-1050 (2006).
Cognetta et al. Selective N-Hydroxyhydantoin Carbamate Inhibitors of Mammalian Serine Hydrolases. Chem Biol 22(7):928-937 (2015).
Cravatt et al. Activity-based protein profiling: from enzyme chemistry to proteomic chemistry. Annu Rev 77:383-414 (2008).
Deck et al. Development and biological evaluation of acyl protein thioesterase 1 (APT1) inhibitors. Angew Chem Int Ed Engl 44(31):4975-4980 (2005).
Dekker et al. Small-molecule inhibition of APT1 affects Ras localization and signaling. Nat Chem Biol 6:449-456 (2010).
Duncan et al. A cytoplasmic acyl-protein thioesterase that removes palmitate from G protein alpha subunits and p21(RAS). J Biol Chem 273(25):15830-15837 (1998).
Harkewicz et al. Applications of mass spectrometry to lipids and membranes. Annu Rev Biochem 80:301-325 (2011).
Heal et al. Activity-based probes: discovering new biology and new drug targets. Chem Soc Rev 40(1):246-257 (2011).
Hirano et al. Thioesterase activity and subcellular localization of acylprotein thioesterase 1/lysophospholipase 1. Biochim Biophys Acta 1791(8):797-805 (2009).
Hoover et al. Selectivity of inhibitors of endocannabinoid biosynthesis evaluated by activity-based protein profiling. Bioorg Med Chem Lett 18(22):5838-5841 (2008).
Hsu et al. Discovery and optimization of piperidyl-1,2,3-triazole ureas as potent, selective, and in vivo-active inhibitors of α/β-hydrolase domain containing 6 (ABHD6). J Med Chem 56:8270-8279 (2012).
Hsu et al. Optimization and characterization of a triazole urea inhibitor for diacylglycerol lipase beta (DAGL-beta), in Probe Reports from the NIH Molecular Libraries Program. Bethesda (MD) (18 pgs) (2010).
Hsu et al. Optimization and characterization of triazole urea inhibitors for abhydrolase domain containing protein 6 (ABHD6), in Probe Reports from the NIH Molecular Libraries Program. Bethesda (MD) (20 pgs) (2010).
Jessani et al. Enzyme activity profiles of the secreted and membrane proteome that depict cancer cell invasiveness. PNAS USA 99(16):10335-10340 (2002).
Johnson et al. Strategies for discovering and derisking covalent, irreversible enzyme inhibitors. Future Med Chem 2(6):949-964 (2010).
Kathuria et al. Modulation of anxiety through blockade of anandamide hydrolysis. Nat Med 9(1):76-81 (2003).
Kodadek et al. Rethinking screening. Nat Chem Biol 6(3):162-165 (2010).
Lenz et al. Probing small molecule-protein interactions: A new perspective for functional proteomics. J Proteomics 75(1):100-115 (2011).
Leung et al. Discovering potent and selective reversible inhibitors of enzymes in complex proteomes. Nat Biotechnol 21(6):687-691 (2003).
Li et al. Activity-based protein profiling: an enabling technology in chemical biology research. Curr Opin Chem Biol 16(1-2):227-233 (2012).
Liu et al. Activity-based protein profiling: the serine hydrolases. PNAS USA 96(26):14694-14699 (1999).
Long et al. Dual blockade of FAAH and MAGL identifies behavioral processes regulated by endocannabinoid crosstalk in vivo. PNAS USA 106(48):20270-20275 (2009).

(56) References Cited

OTHER PUBLICATIONS

Long et al. Selective blockade of 2-arachidonoylglycerol hydrolysis produces cannabinoid behavioral effects. Nat Chem Biol. 5(1):37-44 (2009).

Magee et al. Release of fatty acids from virus glycoproteins by hydroxylamine. Biochim Biophys Acta 798(2):156-166 (1984).

Martin et al. Global profiling of dynamic protein palmitoylation. Nat Methods 9(1):84-89 (2012).

Martin et al. Large-scale profiling of protein palmitoylation in mammalian cells. Nat Methods 6(2):135-138 (2009).

Nagano et al. Optimization and characterization of a carbamate inhibitor for plasma platelet-activating factor acetylhydrolase (pPAFAH), in Probe Reports from the NIH Molecular Libraries Program. Bethesda (MD) (37 pgs) (2010).

Nagano et al. Selective inhibitors and tailored activity probes for lipoprotein-associated phospholipase A(2). Bioorg Med Chem Lett 23(3):839-843 (2013).

Nomura et al. Activity-based protein profiling for biochemical pathway discovery in cancer. Nat Rev Cancer 10(9):630-638 (2010).

Ong et al. Stable isotope labeling by amino acids in cell culture, SILAC, as a simple and accurate approach to expression proteomics. Mol Cell Proteomics 1(5):376-386 (2002).

PCT/US2015/031838 International Preliminary Report on Patentability dated Dec. 1, 2016.

PCT/US2015/031838 International Search Report and Written Opinion dated Apr. 18, 2016.

Potashman et al. Covalent modifiers: an orthogonal approach to drug design. J Med Chem 52(5):1231-46 (2009).

Robertson. Mechanistic basis of enzyme-targeted drugs. Biochemistry 44(15):5561-71 (2005).

Rose et al. The presence of cysteine in the cytoplasmic domain of the vesicular stomatitis virus glycoprotein is required for palmitate addition. PNAS USA 81(7):2050-2054 (1984).

Rostovtsev et al. A stepwise huisgen cycloaddition process: copper (i)-catalyzed regioselective "ligation" of azides and terminal alkynes. Angew. Chem. Int. Ed. Engl. 41(14):2596-2599 (2002).

Simon et al. Determining target engagement in living systems. Nat Chem Biol 9(4):200-205 (2013).

Singh et al. The resurgence of covalent drugs. Nat Rev Drug Discov 10(4):307-317 (2011).

Smotrys et al. Palmitoylation of intracellular signaling proteins: regulation and function. Annu Rev Biochem 73:559-587 (2004).

Speers et al. Profiling enzyme activities in vivo using click chemistry methods. Chem Biol 11(4):535-546 (2004).

Sugimoto et al. cDNA cloning, and regulation of lysophospholipase from rat liver. J Biol Chem 271(13):7705-7711 (1996).

Toyoda et al. Sequence, expression in *Escherichia coli*, and characterization of lysophospholipase II. Biochim Biophys Acta 1437(2):182-193 (1999).

Van Diggelen et al. A rapid fluorogenic palmitoyl-protein thioesterase assay: pre- and postnatal diagnosis of INCL. Mol Genet Metab 66:240-244 (1999).

Vincent et al. Anticancer efficacy of the irreversible EGFr tyrosine kinase inhibitor PD 0169414 against human tumor xenografts. Cancer Chemother Pharmacol 45(3):231-238 (2000).

Weerapana et al. Quantitative reactivity profiling predicts functional cysteines in proteomes. Nature 468:790-795 (2010).

Willumsen et al. Novel determinants of H-Ras plasma membrane localization and transformation. Oncogene 13(9):1901-1909 (1996).

Legend: for each set of 2 bars:
Top bar: ABC44
Bottom bar: ABC51

N-HYDROXY BICYCLIC HYDANTOIN CARBAMATES AS TOOLS FOR IDENTIFICATION OF SERINE HYDROLASE TARGETS

CROSS-REFERENCE

This application is a U.S. National State Entry of PCT/US2015/031838, filed on May 20, 2015; which claims the benefit of priority from U.S. Provisional Application No. 62/001,869, filed May 22, 2014, all of which are incorporated herein by reference in its entirety.

STATEMENT OF GOVERNMENT SUPPORT

This invention was made with government support under DA033760 and MH084512 awarded by the National Institutes of Health. The government has certain rights in the invention.

BACKGROUND

Serine hydrolase inhibitors, which facilitate enzyme function assignment and are used to treat a range of human disorders, often act by an irreversible mechanism that involves covalent modification of the serine hydrolase catalytic nucleophile.

BRIEF SUMMARY OF THE INVENTION

This disclosure is directed, in various embodiments, to a compound having modulatory bioactivity with respect to a serine hydrolase.

One embodiment provides a compound of Formula (I):

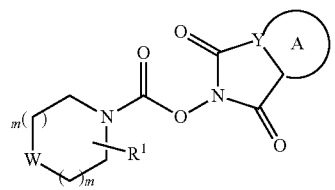

wherein
W is

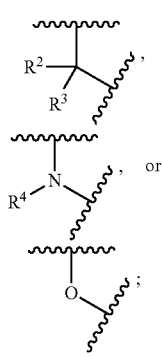

each m is independently 0, 1, or 2;
Y is N or CH;
$R^1$ is H, halo, —OH, cyano, amino, substituted or unsubstituted ($C_1$-$C_8$)alkyl, substituted or unsubstituted ($C_1$-$C_8$)alkoxy, substituted or unsubstituted ($C_6$-$C_{10}$)aryl, or substituted or unsubstituted ($C_6$-$C_{10}$)aryl($C_1$-$C_8$)alkyl;
$R^2$ is H, —COOR$^5$, or —CONR$^5$R$^6$;
$R^3$ is H, substituted or unsubstituted ($C_6$-$C_{10}$)aryl, substituted or unsubstituted 5-9 membered heteroaryl, substituted or unsubstituted ($C_6$-$C_{10}$)aryl($C_1$-$C_8$)alkyl, or substituted or unsubstituted 5-9 membered heteroaryl ($C_1$-$C_8$)alkyl;
$R^4$ is substituted or unsubstituted ($C_6$-$C_{10}$)aryl, substituted or unsubstituted 5-9 membered heteroaryl, substituted or unsubstituted ($C_6$-$C_{10}$)aryl($C_1$-$C_8$)alkyl, substituted or unsubstituted 5-9 membered heteroaryl ($C_1$-$C_8$)alkyl, substituted or unsubstituted di($C_6$-$C_{10}$) aryl($C_1$-$C_8$)alkyl;
$R^5$ is H or substituted or unsubstituted ($C_1$-$C_8$)alkyl;
$R^6$ is substituted or unsubstituted ($C_6$-$C_{10}$)aryl, substituted or unsubstituted 5-9 membered heteroaryl, substituted or unsubstituted ($C_6$-$C_{10}$)aryl($C_1$-$C_8$)alkyl, or substituted or unsubstituted 5-9 membered heteroaryl ($C_1$-$C_8$)alkyl;
Ring A is a 5-7 membered heterocyclyl containing 0-2 NR', wherein:
each R' is independently H, substituted or unsubstituted ($C_1$-$C_8$)alkyl, substituted or unsubstituted ($C_1$-$C_8$) alkoxy, substituted or unsubstituted ($C_1$-$C_8$)alkylcarbonyl, substituted or unsubstituted ($C_1$-$C_8$)alkoxycarbonyl, substituted or unsubstituted ($C_3$-$C_9$)cycloalkyl, substituted or unsubstituted ($C_3$-$C_9$)cycloalkyl($C_1$-$C_8$) alkyl, substituted or unsubstituted ($C_3$-$C_9$)cycloalkylcarbonyl, substituted or unsubstituted ($C_3$-$C_9$)cycloalkoxycarbonyl, substituted or unsubstituted ($C_6$-$C_{10}$)aryl, substituted or unsubstituted ($C_6$-$C_{10}$) arylcarbonyl, substituted or unsubstituted ($C_6$-$C_{10}$) aryloxycarbonyl, substituted or unsubstituted ($C_6$-$C_{10}$) aryl($C_1$-$C_8$)alkyl, substituted or unsubstituted ($C_6$-$C_{10}$) aryl($C_1$-$C_8$)alkylcarbonyl, substituted or unsubstituted ($C_6$-$C_{10}$)aryl($C_1$-$C_8$)alkoxycarbonyl, substituted or unsubstituted 5-9 membered heterocyclyl, substituted or unsubstituted 5-9 membered heterocyclyl($C_1$-$C_8$) alkyl, substituted or unsubstituted 5-9-membered heterocyclylcarbonyl, substituted or unsubstituted 5-9 membered heteroaryl, substituted or unsubstituted 5-9 membered heteroaryl($C_1$-$C_8$)alkyl, or substituted or unsubstituted 5-9 membered heteroarylcarbonyl.

Another embodiment provides a pharmaceutical composition comprising an N-hydroxy bicyclic hydantoin carbamate described herein and at least one pharmaceutically acceptable excipient.

Another embodiment provides a method of modulation of a serine hydrolase, comprising contacting the serine hydrolase with an effective amount or concentration of an N-hydroxy bicyclic hydantoin carbamate described herein.

Another embodiment provides a method of treatment of a medical condition in a patient, wherein modulation of a serine hydrolase is medically indicated, comprising administering an effective dose of an N-hydroxy bicyclic hydantoin carbamate described herein.

In some embodiments, the medical condition is selected from cancer, pain, diabetes, obesity/metabolic syndrome, epilepsy, traumatic brain injury, and inflammation.

BRIEF DESCRIPTION OF THE DRAWINGS

FIG. 7A-1 shows Compounds 1, 2, 5, 7, 13, 21, 23, 31, and 38 in vitro inhibition profiles in a mouse brain membrane proteome.

FIG. 7A-2 shows ABPP-SILAC analysis to identify SH targets of Compound 5.

DETAILED DESCRIPTION OF THE INVENTION

Figure 1:
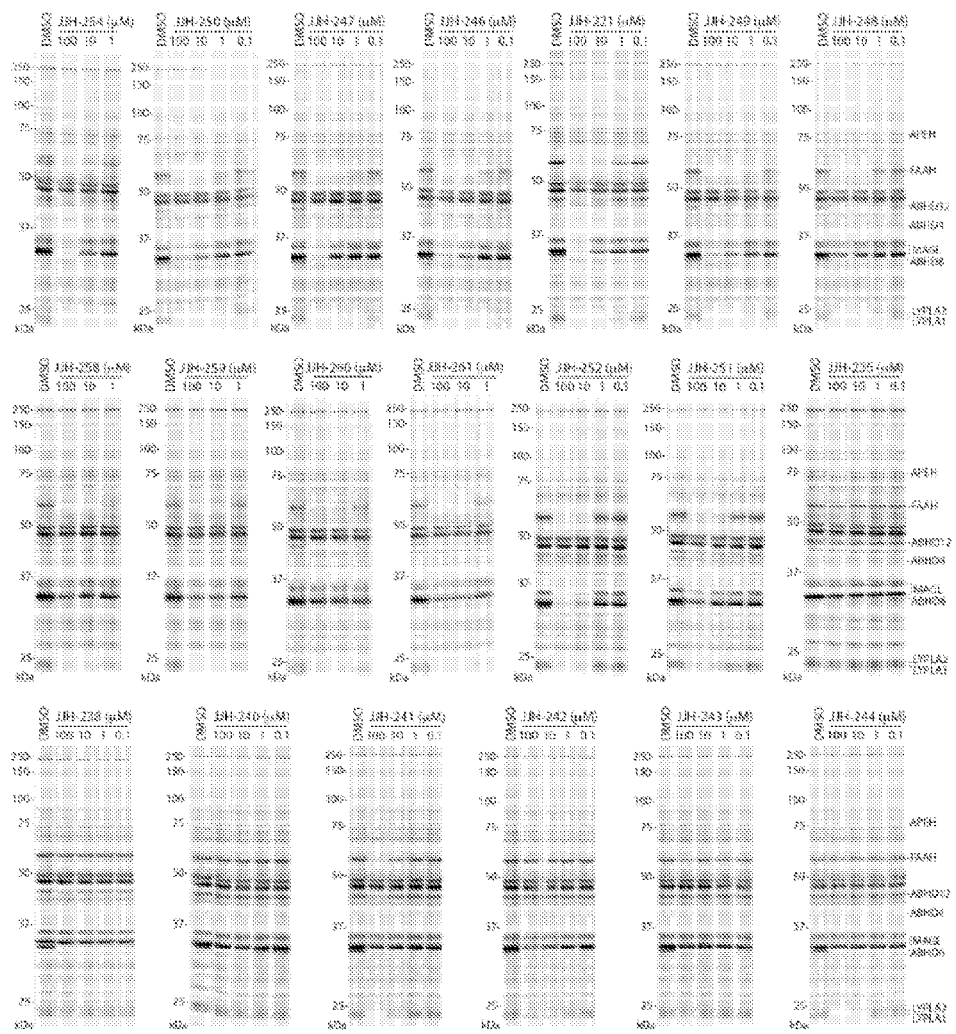
FIG. 1 shows potency and selectivity of N-hydroxy bicyclic hydantoin carbamates (1-20) as assessed by gel-based competitive ABPP with the SH-specific ABPP probe FP-Rh in the mouse brain membrane proteome.

This disclosure is directed, in various embodiments, to a compound having modulatory bioactivity with respect to a serine hydrolase.

Serine hydrolases (SHs) represent one of the largest and most diverse enzyme classes in Nature and perform myriad biochemical functions in physiology and disease. SHs use a conserved mechanism involving a base-activated serine nucleophile to hydrolyze amide, ester, and thioester bonds in biomolecules; however, these enzymes also display markedly different structures and folds, distribute across virtually all subcellular compartments in the cell, and accept an expansive array of small- and macro-molecule substrates. In accordance with their diverse biological activities, SHs are targeted by drugs that are used to treat a wide range of diseases, including cognitive dementia, obesity, diabetes, and bacterial and viral infections.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —$NH_2$ radical.
"Carbonyl" refers to the >C=O radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N–H radical.
"Oximo" refers to the =N—OH radical.

"Alkyl" refers to a straight or branched hydrocarbon chain radical consisting solely of carbon and hydrogen atoms, containing no unsaturation, having from one to fifteen carbon atoms (e.g., ($C_1$-$C_{15}$)alkyl). In certain embodiments, an alkyl comprises one to thirteen carbon atoms (e.g., ($C_1$-$C_{13}$)alkyl). In certain embodiments, an alkyl comprises one to eight carbon atoms (e.g., ($C_1$-$C_8$)alkyl). In other embodiments, an alkyl comprises one to five carbon atoms (e.g., ($C_1$-$C_5$)alkyl). In other embodiments, an alkyl comprises one to four carbon atoms (e.g., ($C_1$-$C_4$)alkyl). In other embodiments, an alkyl comprises one to three carbon atoms (e.g., ($C_1$-$C_3$)alkyl). In other embodiments, an alkyl comprises one to two carbon atoms (e.g., ($C_1$-$C_2$)alkyl). In other embodiments, an alkyl comprises one carbon atom (e.g., ($C_1$)alkyl). In other embodiments, an alkyl comprises five to fifteen carbon atoms (e.g., ($C_5$-$C_{15}$)alkyl). In other embodiments, an alkyl comprises five to eight carbon atoms (e.g., ($C_5$-$C_8$)alkyl). In other embodiments, an alkyl comprises two to five carbon atoms (e.g., ($C_2$-$C_5$)alkyl). In other embodiments, an alkyl comprises three to five carbon atoms (e.g., ($C_3$-$C_5$)alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^f$, —OC(O)—N$R^aR^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In certain embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In certain embodiments, an alkynyl comprises two to six carbon atoms. In other embodiments, an alkynyl has two to four carbon atoms. The alkynyl is attached to the rest of the molecule by a single bond, for example, ethynyl, propynyl, butyryl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., (C$_1$-C$_8$)alkylene). In other embodiments, an alkylene comprises one to five carbon atoms (e.g., (C$_1$-C$_5$)alkylene). In other embodiments, an alkylene comprises one to four carbon atoms (e.g., (C$_1$-C$_4$)alkylene). In other embodiments, an alkylene comprises one to three carbon atoms (e.g., (C$_1$-C$_3$)alkylene). In other embodiments, an alkylene comprises one to two carbon atoms (e.g., (C$_1$-C$_2$)alkylene). In other embodiments, an alkylene comprises one carbon atom (e.g., (C$_1$)alkylene). In other embodiments, an alkylene comprises five to eight carbon atoms (e.g., (C$_5$-C$_8$)alkylene). In other embodiments, an alkylene comprises two to five carbon atoms (e.g., (C$_2$-C$_5$)alkylene). In other embodiments, an alkylene comprises three to five carbon atoms (e.g., (C$_3$-C$_5$)alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms (e.g., (C$_5$-C$_{18}$)aryl), where at least one of the rings in the ring system is fully unsaturated, i.e., it contains a cyclic, delocalized (4n+2) π-electron system in accordance with the Hückel theory. In certain embodiments, an aryl comprises six to ten carbon atoms (e.g., (C$_6$-C$_{10}$)aryl). In certain embodiments, an aryl comprises six carbon atoms (e.g., (C$_6$)aryl). The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" or "arylalkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group. In some embodiments, the aralkyl is described as (C$_6$-C$_{10}$)aryl(C$_1$-C$_8$)alkyl where the (C$_6$-C$_{10}$) aryl and (C$_1$-C$_8$)alkyl are as defined above.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated, (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., ($C_3$-$C_8$)cycloalkyl). In other embodiments, a cycloalkyl comprises three to seven carbon atoms (e.g., ($C_3$-$C_7$)cycloalkyl). In other embodiments, a cycloalkyl comprises three to six carbon atoms (e.g., ($C_3$-$C_6$)cycloalkyl). In other embodiments, a cycloalkyl comprises three to five carbon atoms (e.g., ($C_3$-$C_5$)cycloalkyl). In other embodiments, a cycloalkyl comprises three to four carbon atoms (e.g., ($C_3$-$C_4$)cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above. In some embodiments, the carbocyclylalkyl is described as ($C_3$-$C_8$)carbocyclyl($C_1$-$C_8$)alkyl where the ($C_3$-$C_8$)carbocyclyl and ($C_1$-$C_8$)alkyl are as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which includes fused or bridged ring systems. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkyl" refers to a radical of the formula —$R^c$-heterocyclyl where $R^c$ is an alkylene chain as defined above. The alkylene chain and the carbocyclyl radical is optionally substituted as defined above. In some embodiments, the heterocyclylalkyl is described as ($C_2$-$C_8$)heterocyclyl($C_1$-$C_8$)alkyl where the ($C_2$-$C_8$)heterocyclyl and ($C_1$-$C_8$)alkyl are as defined above.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms (e.g., ($C_2$-$C_{18}$)heteroaryl) and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$_t R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group. In some embodiments, the heteroarylalkyl is described as ($C_2$-$C_{10}$)heteroaryl($C_1$-$C_8$)alkyl where the ($C_2$-$C_{10}$)heteroaryl and ($C_1$-$C_8$)alkyl are as defined above.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

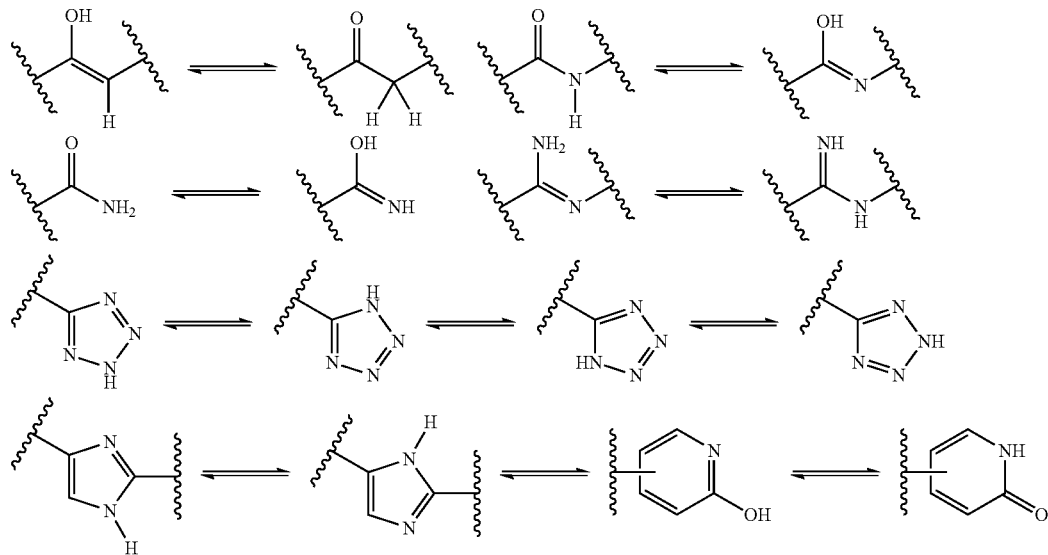

"Optional" or "optionally" means that a subsequently described event or circumstance may or may not occur and that the description includes instances when the event or circumstance occurs and instances in which it does not. For example, "optionally substituted aryl" means that the aryl radical is or is not substituted and that the description includes both substituted aryl radicals and aryl radicals having no substitution. "Optionally substituted" and "substituted or unsubstituted" are interchangeable.

"Pharmaceutically acceptable salt" includes both acid and base addition salts. A pharmaceutically acceptable salt of any one of the N-hydroxy bicyclic hydantoin carbamates described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

N-hydroxy bicyclic hydantoin carbamates are described herein which are inhibitors of serine hydrolase. These compounds, and compositions comprising these compounds, are useful for the treatment of cancer, pain, diabetes, obesity/metabolic syndrome, epilepsy, traumatic brain injury, and/or inflammation.

One embodiment provides a compound of Formula (I):

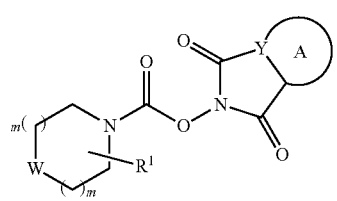

(I)

wherein
W is

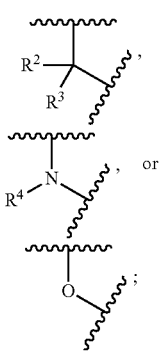

each m is independently 0, 1, or 2;
Y is N or CH;
$R^1$ is H, halo, —OH, cyano, amino, substituted or unsubstituted $(C_1-C_8)$alkyl, substituted or unsubstituted $(C_1-C_8)$alkoxy, substituted or unsubstituted $(C_6-C_{10})$aryl, or substituted or unsubstituted $(C_6-C_{10})$aryl$(C_1-C_8)$alkyl;
$R^2$ is H, —COOR$^5$, or —CONR$^5$R$^6$;
$R^3$ is H, substituted or unsubstituted $(C_6-C_{10})$aryl, substituted or unsubstituted 5-9-membered heteroaryl, substituted or unsubstituted $(C_6-C_{10})$aryl$(C_1-C_8)$alkyl, or substituted or unsubstituted 5-9-membered heteroaryl$(C_1-C_8)$alkyl;

$R^4$ is substituted or unsubstituted $(C_6-C_{10})$aryl, substituted or unsubstituted 5-9-membered heteroaryl, substituted or unsubstituted $(C_6-C_{10})$aryl$(C_1-C_8)$alkyl, substituted or unsubstituted 5-9-membered heteroaryl$(C_1-C_8)$alkyl, or substituted or unsubstituted di$(C_6-C_{10})$aryl$(C_1-C_8)$alkyl;
$R^5$ is H or substituted or unsubstituted $(C_1-C_8)$alkyl;
$R^6$ is substituted or unsubstituted $(C_6-C_{10})$aryl, substituted or unsubstituted 5-9-membered heteroaryl, substituted or unsubstituted $(C_6-C_{10})$aryl$(C_1-C_8)$alkyl, or substituted or unsubstituted 5-9-membered heteroaryl$(C_1-C_8)$alkyl;
Ring A is a 5-7-membered heterocyclyl containing 0-2 NR', wherein:
each R' is independently H, substituted or unsubstituted $(C_1-C_8)$alkyl, substituted or unsubstituted $(C_1-C_8)$alkoxy, substituted or unsubstituted $(C_1-C_8)$alkylcarbonyl, substituted or unsubstituted $(C_1-C_8)$alkoxycarbonyl, substituted or unsubstituted $(C_3-C_9)$cycloalkyl, substituted or unsubstituted $(C_3-C_9)$cycloalkyl$(C_1-C_8)$alkyl, substituted or unsubstituted $(C_3-C_9)$cycloalkylcarbonyl, substituted or unsubstituted $(C_3-C_9)$cycloalkoxycarbonyl, substituted or unsubstituted $(C_6-C_{10})$aryl, substituted or unsubstituted $(C_6-C_{10})$arylcarbonyl, substituted or unsubstituted $(C_6-C_{10})$aryloxycarbonyl, substituted or unsubstituted $(C_6-C_{10})$aryl$(C_1-C_8)$alkyl, substituted or unsubstituted $(C_6-C_{10})$aryl$(C_1-C_8)$alkylcarbonyl, substituted or unsubstituted $(C_6-C_{10})$aryl$(C_1-C_8)$alkoxycarbonyl, substituted or unsubstituted 5-9-membered heterocyclyl, substituted or unsubstituted 5-9-membered heterocyclyl$(C_1-C_8)$alkyl, substituted or unsubstituted 5-9-membered heterocyclylcarbonyl, substituted or unsubstituted 5-9-membered heteroaryl, substituted or unsubstituted 5-9-membered heteroaryl$(C_1-C_8)$alkyl, or substituted or unsubstituted 5-9-membered heteroarylcarbonyl.

In some embodiments of a compound of Formula (I), each m is 0. In some embodiments of a compound of Formula (I), one m is 0 and the other m is 1. In some embodiments of a compound of Formula (I), each m is 1. In some embodiments of a compound of Formula (I), $R^1$ is H, halo, —OH, cyano, amino, $(C_1-C_8)$alkyl, $(C_1-C_8)$alkoxy, $(C_6-C_{10})$aryl, or $(C_6-C_{10})$aryl$(C_1-C_8)$alkyl. In some embodiments of a compound of Formula (I), $R^1$ is H. In some embodiments of a compound of Formula (I), $R^1$ is F or Cl. In some embodiments of a compound of Formula (I), $R^1$ is methyl or methoxy. In some embodiments of a compound of Formula (I), $R^1$ is phenyl. In some embodiments of a compound of Formula (I), $R^1$ is benzyl.

In some embodiments of a compound of Formula (I), W is

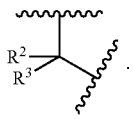

In some embodiments of a compound of Formula (I), W is

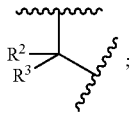

$R^2$ is H; and $R^3$ is substituted or unsubstituted $(C_6-C_{10})$aryl, or substituted or unsubstituted 5-9-membered heteroaryl. In some embodiments of a compound of Formula (I), W is

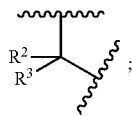

$R^2$ is H; and $R^3$ is substituted or unsubstituted $(C_6-C_{10})$aryl, or substituted or unsubstituted $(C_6-C_{10})$aryl$(C_1-C_8)$alkyl. In some embodiments of a compound of Formula (I), W is

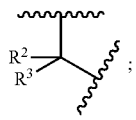

$R^2$ is H; and $R^3$ is substituted or unsubstituted $(C_6-C_{10})$aryl $(C_1-C_8)$alkyl, or substituted or unsubstituted 5-9-membered heteroaryl$(C_1-C_8)$alkyl.

In some embodiments of a compound of Formula (I), W is

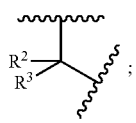

$R^2$ is H; and $R^3$ is substituted or unsubstituted $(C_6-C_{10})$aryl. In some embodiments of a compound of Formula (I), W is

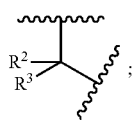

$R^2$ is H; and $R^3$ is substituted or unsubstituted phenyl. In some embodiments of a compound of Formula (I), W is

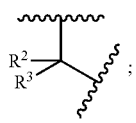

$R^2$ is H; and $R^3$ is unsubstituted phenyl. In some embodiments of a compound of Formula (I), W is

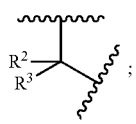

$R^2$ is H; and $R^3$ is phenyl substituted with one or more substituents selected from halo, $(C_1-C_8)$alkyl, $(C_1-C_8)$alkoxy, $(C_2-C_6)$alkenyl, $(C_2-C_6)$alkynyl, $(C_2-C_6)$alkenyloxy, and $(C_2-C_6)$alkynyloxy. In some embodiments of a compound of Formula (I), W is

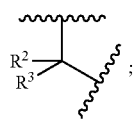

$R^2$ is H; and $R^3$ is phenyl substituted with one or more substituents selected from fluoro, chloro, bromo, methoxy, ethynyl, and propargyloxy. In some embodiments of Formula (I), W is

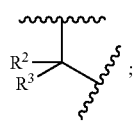

$R^2$ is H; and $R^3$ is mono-substituted phenyl. In some embodiments of Formula (I), W is

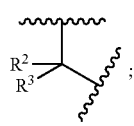

$R^2$ is H; and $R^3$ is di-substituted phenyl. In some embodiments of a compound of Formula (I), W is

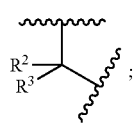

$R^2$ is H; and $R^3$ is methoxy substituted phenyl. In some embodiments of a compound of Formula (I), W is

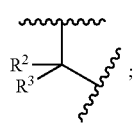

$R^2$ is H; and $R^3$ is propargyloxy substituted phenyl. In some embodiments of a compound of Formula (I), W is

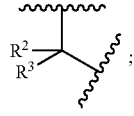

$R^2$ is H; and $R^3$ is fluoro substituted phenyl. In some embodiments of a compound of Formula (I), W is

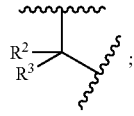

$R^2$ is H; and $R^3$ is chloro substituted phenyl. In some embodiments of a compound of Formula (I), W is

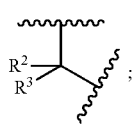

$R^2$ is H; and $R^3$ is ethynyl substituted phenyl.

In some embodiments of a compound of Formula (I), W is

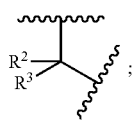

$R^2$ is H; and $R^3$ is

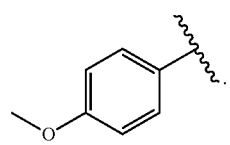 [SMILES: *c1ccc(OC)cc1]

In some embodiments of a compound of Formula (I), W is

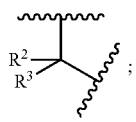

$R^2$ is H; and $R^3$ is

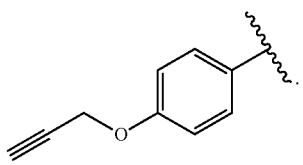 [SMILES: *c1ccc(OCC#C)cc1]

In some embodiments of a compound of Formula (I), W is

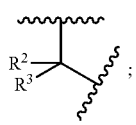

$R^2$ is H; and $R^3$ is substituted or unsubstituted 5-9-membered heteroaryl. In some embodiments of a compound of Formula (I), W is

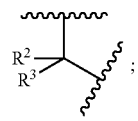

$R^2$ is H; and $R^3$ is substituted 5-9-membered heteroaryl. In some embodiments of a compound of Formula (I), W is

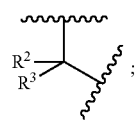

$R^2$ is H; and $R^3$ is unsubstituted 5-9-membered heteroaryl.

In some embodiments of a compound of Formula (I), W is

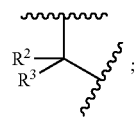

$R^2$ is H; and $R^3$ is substituted or unsubstituted $(C_6$-$C_{10})$aryl $(C_1$-$C_8)$alkyl. In some embodiments of a compound of Formula (I), W is

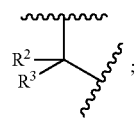

$R^2$ is H; and $R^3$ is substituted or unsubstituted benzyl. In some embodiments of a compound of Formula (I), W is

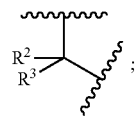

$R^2$ is H; and $R^3$ is unsubstituted benzyl. In some embodiments of a compound of Formula (I), W is

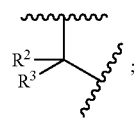

$R^2$ is H; and $R^3$ is benzyl substituted with one or more substituents selected from halo, $(C_1$-$C_8)$alkyl, $(C_1$-$C_8)$alkoxy, $(C_2$-$C_6)$alkenyl, $(C_2$-$C_6)$alkynyl, $(C_2$-$C_6)$alkenyloxy, and $(C_2-C_6)$alkynyloxy. In some embodiments of a compound of Formula (I), W is

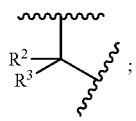

$R^2$ is H; and $R^3$ is benzyl substituted with one or more substituents selected from fluoro, chloro, bromo, methoxy, ethynyl, and propargyloxy. In some embodiments of Formula (I), W is

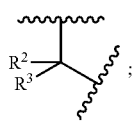

$R^2$ is H; and $R^3$ is mono-substituted benzyl. In some embodiments of Formula (I), W is

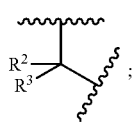

$R^2$ is H; and $R^3$ is di-substituted benzyl. In some embodiments of a compound of Formula (I), W is

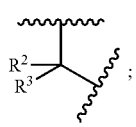

$R^2$ is H; and $R^3$ is methoxy substituted benzyl. In some embodiments of a compound of Formula (I), W is

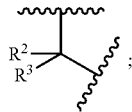

$R^2$ is H; and $R^3$ is propargyloxy substituted benzyl. In some embodiments of a compound of Formula (I), W is

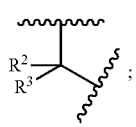

$R^2$ is H; and $R^3$ is fluoro substituted benzyl. In some embodiments of a compound of Formula (I), W is

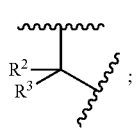

$R^2$ is H; and $R^3$ is chloro substituted benzyl. In some embodiments of a compound of Formula (I), W is

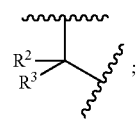

$R^2$ is H; and $R^3$ is ethynyl substituted benzyl.

In some embodiments of a compound of Formula (I), W is

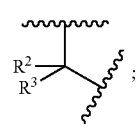

$R^2$ is H; and $R^3$ is substituted or unsubstituted $(C_6-C_{10})$aryl $(C_1-C_8)$alkyl. In some embodiments of a compound of Formula (I), W is

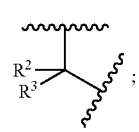

$R^2$ is H; and $R^3$ is substituted or unsubstituted phenethyl. In some embodiments of a compound of Formula (I), W is

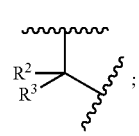

$R^2$ is H; and $R^3$ is unsubstituted phenethyl. In some embodiments of a compound of Formula (I), W is

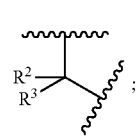

$R^2$ is H; and $R^3$ is phenethyl substituted with one or more substituents selected from halo, $(C_1-C_8)$alkyl, $(C_1-C_8)$alkoxy, $(C_2-C_6)$alkenyl, $(C_2-C_6)$alkynyl, $(C_2-C_6)$alkenyloxy, and $(C_2-C_6)$alkynyloxy. In some embodiments of a compound of Formula (I), W is

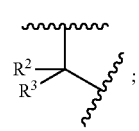

$R^2$ is H; and $R^3$ is phenethyl substituted with one or more substituents selected from fluoro, chloro, bromo, methoxy, ethynyl, and propargyloxy. In some embodiments of Formula (I), W is

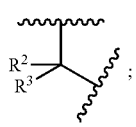

$R^2$ is H; and $R^3$ is mono-substituted phenethyl. In some embodiments of Formula (I), W is

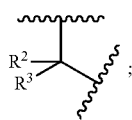

$R^2$ is H; and $R^3$ is di-substituted phenethyl. In some embodiments of a compound of Formula (I), W is

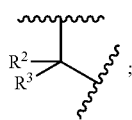

$R^2$ is H; and $R^3$ is methoxy substituted phenethyl. In some embodiments of a compound of Formula (I), W is

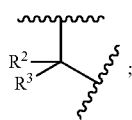

$R^2$ is H; and $R^3$ is propargyloxy substituted phenethyl. In some embodiments of a compound of Formula (I), W is

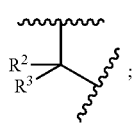

$R^2$ is H; and $R^3$ is fluoro substituted phenethyl. In some embodiments of a compound of Formula (I), W is

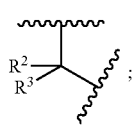

$R^2$ is H; and $R^3$ is chloro substituted phenethyl. In some embodiments of a compound of Formula (I), W is

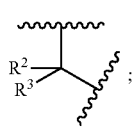

$R^2$ is H; and $R^3$ is ethynyl substituted phenethyl.

In some embodiments of a compound of Formula (I), W is

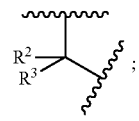

$R^2$ is H; and $R^3$ is

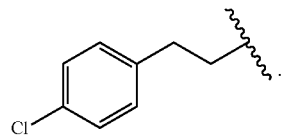 [SMILES: *CCc1ccc(Cl)cc1]

In some embodiments of a compound of Formula (I), W is

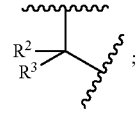

$R^2$ is H; and $R^3$ is

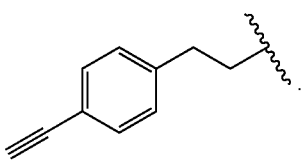 [SMILES: *CCc1ccc(C#C)cc1]

In some embodiments of a compound of Formula (I), W is

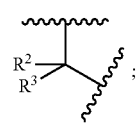

$R^2$ is H; and $R^3$ is substituted or unsubstituted phenyl, substituted or unsubstituted benzyl, or substituted or unsubstituted phenethyl. In some embodiments of a compound of Formula (I), W is

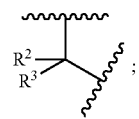

$R^2$ is H; and $R^3$ is phenyl, benzyl, or phenethyl, and $R^3$ is substituted with one or more substituents selected from the group consisting of halo, $(C_1-C_8)$alkyl, $(C_1-C_8)$alkoxy, $(C_2-C_6)$alkenyl, $(C_2-C_6)$alkynyl, $(C_2-C_6)$alkenyloxy, and $(C_2-C_6)$alkynyloxy. In some embodiments of a compound of Formula (I), W is

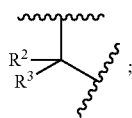

$R^2$ is H; and $R^3$ is phenyl or phenethyl, and $R^3$ is substituted with one substituent selected from the group consisting of fluoro, chloro, bromo, methoxy, ethynyl, and propargyloxy.

In some embodiments of a compound of Formula (I), W is

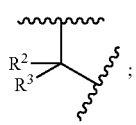

$R^2$ is H; and $R^3$ is substituted or unsubstituted 5-9-membered heteroaryl($C_1$-$C_8$)alkyl. In some embodiments of a compound of Formula (I), W is

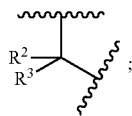

$R^2$ is H; and $R^3$ is substituted 5-9-membered heteroaryl($C_1$-$C_8$)alkyl. In some embodiments of a compound of Formula (I), W is

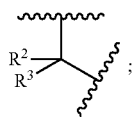

$R^2$ is H; and $R^3$ is unsubstituted 5-9-membered heteroaryl ($C_1$-$C_8$)alkyl.

In some embodiments of a compound of Formula (I), W is

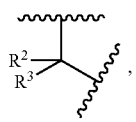

$R^2$ is —$COOR^5$ or —$CONR^5R^6$; and $R^3$ is H. In some embodiments of a compound of Formula (I), W is

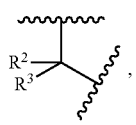

$R^2$ is —$COOR^5$; and $R^3$ is H. In some embodiments of a compound of Formula (I), W is

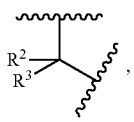

$R^2$ is —$CONR^5R^6$; and $R^3$ is H.

In some embodiments of a compound of Formula (I), W is

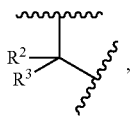

$R^2$ is —$COOR^5$; and $R^5$ is H or methyl. In some embodiments of a compound of Formula (I), W is

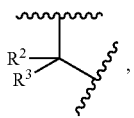

$R^2$ is —$COOR^5$; $R^5$ is methyl; and $R^3$ is H.

In some embodiments of a compound of Formula (I), W is

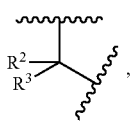

$R^2$ is —$CONR^5R^6$; $R^5$ is H, methyl or ethyl; and $R^6$ is phenyl.

In some embodiments of a compound of Formula (I), W is

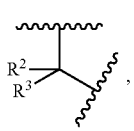

$R^2$ is H; and $R^3$ is H.

In some embodiments of a compound of Formula (I), W is

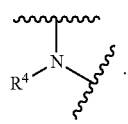

In some embodiments of a compound of Formula (I), W is

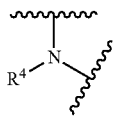

and R⁴ is substituted or unsubstituted $(C_6-C_{10})$aryl or substituted or unsubstituted 5-9-membered heteroaryl. In some embodiments of a compound of Formula (I), W is

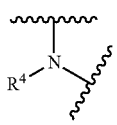

and R⁴ is substituted or unsubstituted $(C_6-C_{10})$aryl, or substituted or unsubstituted $(C_6-C_{10})$aryl$(C_1-C_8)$alkyl. In some embodiments of a compound of Formula (I), W is

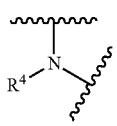

and R⁴ is substituted or unsubstituted $(C_6-C_{10})$aryl$(C_1-C_8)$alkyl, or substituted or unsubstituted di$(C_6-C_{10})$aryl$(C_1-C_8)$alkyl. In some embodiments of Formula (I), W is

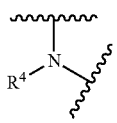

and R⁴ is mono-substituted $(C_6-C_{10})$aryl, mono-substituted 5-9-membered heteroaryl, mono-substituted $(C_6-C_{10})$aryl$(C_1-C_8)$alkyl, or mono-substituted 5-9-membered heteroaryl$(C_1-C_8)$alkyl. In some embodiments of Formula (I), W is

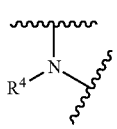

and R⁴ is di-substituted $(C_6-C_{10})$aryl, di-substituted 5-9-membered heteroaryl, di-substituted $(C_6-C_{10})$aryl$(C_1-C_8)$alkyl, or di-substituted 5-9-membered heteroaryl$(C_1-C_8)$alkyl.

In some embodiments of a compound of Formula (I), W is

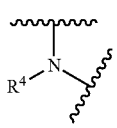

and R⁴ is substituted or unsubstituted $(C_6-C_{10})$aryl. In some embodiments of a compound of Formula (I), W is

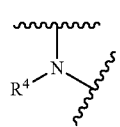

and R⁴ is substituted or unsubstituted phenyl. In some embodiments of a compound of Formula (I), W is

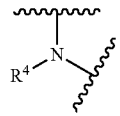

and R⁴ is unsubstituted phenyl. In some embodiments of a compound of Formula (I), W is

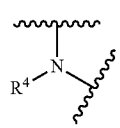

and R⁴ is substituted phenyl. In some embodiments of a compound of Formula (I), W is

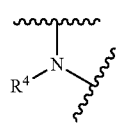

and R⁴ is phenyl substituted with one or more substituents selected from halo, $(C_1-C_8)$alkyl, $(C_1-C_8)$alkoxy, $(C_2-C_6)$alkenyl, $(C_2-C_6)$alkynyl, $(C_2-C_6)$alkenyloxy, and $(C_2-C_6)$alkynyloxy. In some embodiments of a compound of Formula (I), W is

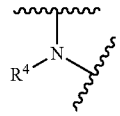

and R⁴ is phenyl substituted with one or more substituents selected from fluoro, chloro, bromo, methoxy, ethynyl, and propargyloxy. In some embodiments of Formula (I), R⁴ is mono-substituted phenyl. In some embodiments of Formula (I), R⁴ is di-substituted phenyl. In some embodiments of a compound of Formula (I), W is

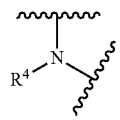

and R⁴ is methoxy substituted phenyl. In some embodiments of a compound of Formula (I), W is

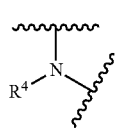

and R⁴ is propargyloxy substituted phenyl. In some embodiments of a compound of Formula (I), W is

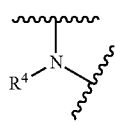

and R⁴ is fluoro substituted phenyl. In some embodiments of a compound of Formula (I), W is

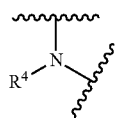

and R⁴ is chloro substituted phenyl. In some embodiments of a compound of Formula (I), W is

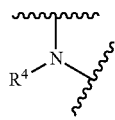

and R⁴ is ethynyl substituted phenyl.

In some embodiments of a compound of Formula (I), W is

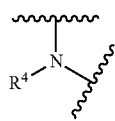

and R⁴ is

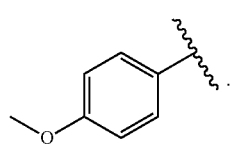 [SMILES: *c1ccc(OC)cc1]

In some embodiments of a compound of Formula (I), W is

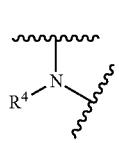

and R⁴ is

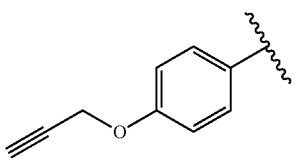

In some embodiments of a compound of Formula (I), W is

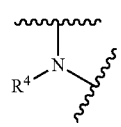

and R⁴ is substituted or unsubstituted 5-9-membered heteroaryl. In some embodiments of a compound of Formula (I), W is

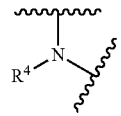

and R⁴ is substituted 5-9-membered heteroaryl. In some embodiments of a compound of Formula (I), W is

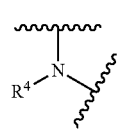

and R⁴ is unsubstituted 5-9-membered heteroaryl.

In some embodiments of a compound of Formula (I), W is

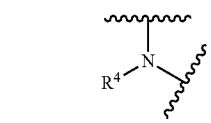

and R⁴ is substituted or unsubstituted $(C_6-C_{10})aryl(C_1-C_8)$ alkyl. In some embodiments of a compound of Formula (I), W is

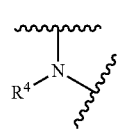

and R⁴ is substituted or unsubstituted benzyl. In some embodiments of a compound of Formula (I), W is

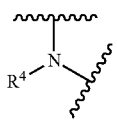

and R⁴ is unsubstituted benzyl. In some embodiments of a compound of Formula (I), W is

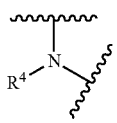

and R⁴ is substituted benzyl. In some embodiments of a compound of Formula (I), W is

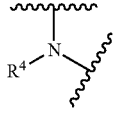

and R⁴ is benzyl substituted with one or more substituents selected from halo, $(C_1-C_8)$alkyl, $(C_1-C_8)$alkoxy, $(C_2-C_6)$alkenyl, $(C_2-C_6)$alkynyl, $(C_2-C_6)$alkenyloxy, and $(C_2-C_6)$alkynyloxy. In some embodiments of a compound of Formula (I), W is

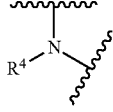

and R⁴ is benzyl substituted with one or more substituents selected from fluoro, chloro, bromo, methoxy, ethynyl, and propargyloxy. In some embodiments of Formula (I), W is

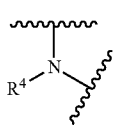

and R⁴ is mono-substituted benzyl. In some embodiments of Formula (I), W is

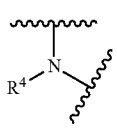

and R⁴ is di-substituted benzyl. In some embodiments of a compound of Formula (I), W is

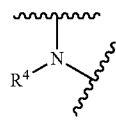

and R⁴ is methoxy substituted benzyl. In some embodiments of a compound of Formula (I), W is

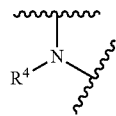

and R⁴ is propargyloxy substituted benzyl. In some embodiments of a compound of Formula (I), W is

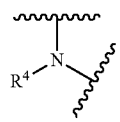

and R⁴ is fluoro substituted benzyl. In some embodiments of a compound of Formula (I), W is

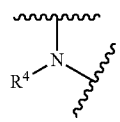

and R⁴ is chloro substituted benzyl. In some embodiments of a compound of Formula (I), W is

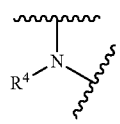

and R⁴ is ethynyl substituted benzyl.

In some embodiments of a compound of Formula (I), W is

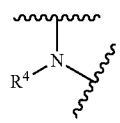

and R⁴ is substituted or unsubstituted $(C_6-C_{10})$aryl$(C_1-C_8)$alkyl. In some embodiments of a compound of Formula (I), W is

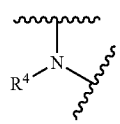

and $R^4$ is substituted or unsubstituted phenethyl. In some embodiments of a compound of Formula (I), W is

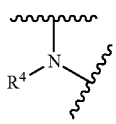

and $R^4$ is unsubstituted phenethyl. In some embodiments of a compound of Formula (I), W is

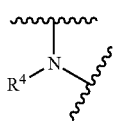

and $R^4$ is substituted phenethyl. In some embodiments of a compound of Formula (I), W is

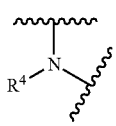

and $R^4$ is phenethyl substituted with one or more substituents selected from halo, $(C_1-C_8)$alkyl, $(C_1-C_8)$alkoxy, $(C_2-C_6)$alkenyl, $(C_2-C_6)$alkynyl, $(C_2-C_6)$alkenyloxy, and $(C_2-C_6)$alkynyloxy. In some embodiments of a compound of Formula (I), W is

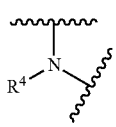

and $R^4$ is phenethyl substituted with one or more substituents selected from fluoro, chloro, bromo, methoxy, ethynyl, and propargyloxy. In some embodiments of Formula (I), W is

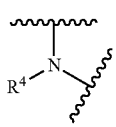

and $R^4$ is mono-substituted phenethyl. In some embodiments of Formula (I), W is

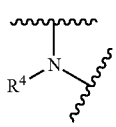

and $R^4$ is di-substituted phenethyl. In some embodiments of a compound of Formula (I), W is

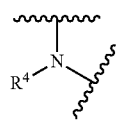

and $R^4$ is methoxy substituted phenethyl. In some embodiments of a compound of Formula (I), W is

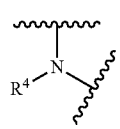

and $R^4$ is propargyloxy substituted phenethyl. In some embodiments of a compound of Formula (I), W is

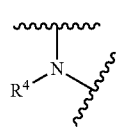

and $R^4$ is fluoro substituted phenethyl. In some embodiments of a compound of Formula (I), W is

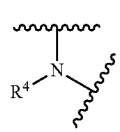

and $R^4$ is chloro substituted phenethyl. In some embodiments of a compound of Formula (I), W is

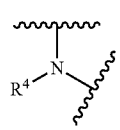

and $R^4$ is ethynyl substituted phenethyl.

In some embodiments of a compound of Formula (I), $R^4$ is

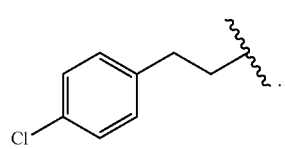

In some embodiments of a compound of Formula (I), $R^4$ is

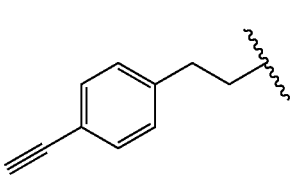

In some embodiments of a compound of Formula (I), W is

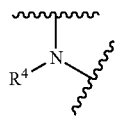

and $R^4$ is substituted or unsubstituted phenyl, substituted or unsubstituted benzyl, or substituted or unsubstituted phenethyl. In some embodiments of a compound of Formula (I), W is

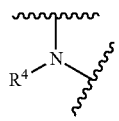

and $R^4$ is phenyl, benzyl, or phenethyl and $R^4$ is substituted with one or more substituents selected from the group consisting of halo, $(C_1-C_8)$alkyl, $(C_1-C_8)$alkoxy, $(C_2-C_6)$alkenyl, $(C_2-C_6)$alkynyl, $(C_2-C_6)$alkenyloxy, and $(C_2-C_6)$alkynyloxy. In some embodiments of a compound of Formula (I), W is

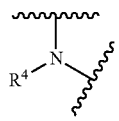

and $R^4$ is phenyl, benzyl, or phenethyl, and $R^4$ is substituted with one substituent selected from the group consisting of fluoro, chloro, bromo, methoxy, ethynyl, and propargyloxy.

In some embodiments of a compound of Formula (I), W is

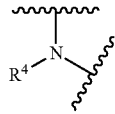

and $R^4$ is substituted or unsubstituted 5-9-membered heteroaryl$(C_1-C_8)$alkyl. In some embodiments of a compound of Formula (I), W is

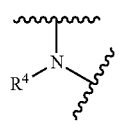

and $R^4$ is substituted 5-9-membered heteroaryl$(C_1-C_8)$alkyl.

In some embodiments of a compound of Formula (I), W is

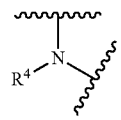

and $R^4$ is unsubstituted 5-9-membered heteroaryl$(C_1-C_8)$alkyl.

In some embodiments of a compound of Formula (I), W is

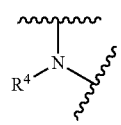

and $R^4$ is substituted or unsubstituted di$(C_6-C_{10})$aryl$(C_1-C_8)$alkyl. In some embodiments of a compound of Formula (I), W is

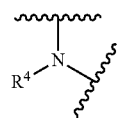

and $R^4$ is substituted or unsubstituted diphenylmethyl. In some embodiments of a compound of Formula (I), W is

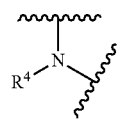

and $R^4$ is unsubstituted diphenylmethyl. In some embodiments of a compound of Formula (I), W is

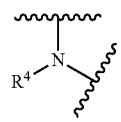

and $R^4$ is substituted diphenylmethyl. In some embodiments of a compound of Formula (I), W is

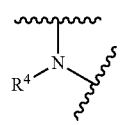

and $R^4$ is diphenylmethyl substituted with one or more substituents selected from halo, $(C_1-C_8)$alkyl, $(C_1-C_8)$alkoxy, $(C_2-C_6)$alkenyl, $(C_2-C_6)$alkynyl, $(C_2-C_6)$alkenyloxy, and $(C_2-C_6)$alkynyloxy. In some embodiments of a compound of Formula (I), W is

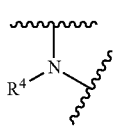

and $R^4$ is diphenylmethyl substituted with one or more substituents selected from fluoro, chloro, bromo, methoxy, ethynyl, and propargyloxy. In some embodiments of Formula (I), W is

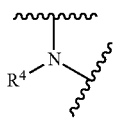

and $R^4$ is mono-substituted diphenylmethyl. In some embodiments of Formula (I), W is

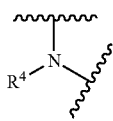

and $R^4$ is di-substituted diphenylmethyl. In some embodiments of a compound of Formula (I), W is

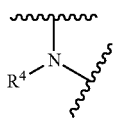

and $R^4$ is methoxy substituted diphenylmethyl. In some embodiments of a compound of Formula (I), W is

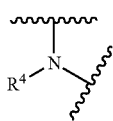

and $R^4$ is propargyloxy substituted phenyl. In some embodiments of a compound of Formula (I), W is

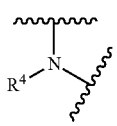

and $R^4$ is fluoro substituted diphenylmethyl. In some embodiments of a compound of Formula (I), W is

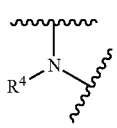

and $R^4$ is chloro substituted diphenylmethyl. In some embodiments of a compound of Formula (I), W is

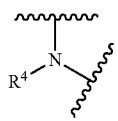

and $R^4$ is ethynyl substituted diphenylmethyl.

In some embodiments of a compound of Formula (I), W is

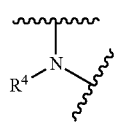

and $R^4$ is

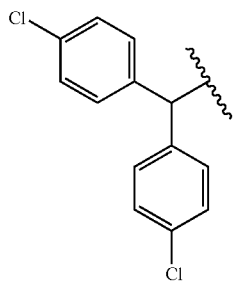

In some embodiments of a compound of Formula (I), W is

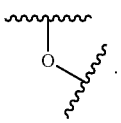

In some embodiments of a compound of Formula (I), Y is CH. In some embodiments of a compound of Formula (I), Y is N.

In some embodiments of a compound of Formula (I), Ring A is a 5-7-membered heterocyclyl containing 0-2 NR'. In some embodiments of a compound of Formula (I), Ring A is a 5-7-membered heterocyclyl containing 0 NR'. In some embodiments of a compound of Formula (I), Ring A is a 5-7-membered heterocyclyl containing 1 NR'. In some embodiments of a compound of Formula (I), Ring A is a 5-7-membered heterocyclyl containing 2 NR'. In some embodiments of a compound of Formula (I), Ring A is a 5-membered heterocyclyl containing 0 NR'. In some embodiments of a compound of Formula (I), Ring A is a 5-membered heterocyclyl containing 1 NR'. In some embodiments of a compound of Formula (I), Ring A is a 5-membered heterocyclyl containing 2 NR'. In some embodiments of a compound of Formula (I), Ring A is a 6-membered heterocyclyl containing 0 NR'. In some embodiments of a compound of Formula (I), Ring A is a 6-membered heterocyclyl containing 1 NR'. In some embodiments of a compound of Formula (I), Ring A is a 6-membered heterocyclyl containing 2 NR'. In some embodiments of a compound of Formula (I), Ring A is a 7-membered heterocyclyl containing 0 NR'. In some embodiments of a compound of Formula (I), Ring A is a 7-membered heterocyclyl containing 1 NR'. In some embodiments of a compound of Formula (I), Ring A is a 7-membered heterocyclyl containing 2 NR'.

In some embodiments of a compound of Formula (I), Ring A is a 6-membered heterocyclyl containing 1 NR'; and R' is substituted or unsubstituted $(C_1-C_8)$alkylcarbonyl, substituted or unsubstituted $(C_1-C_8)$alkoxycarbonyl, substituted or unsubstituted $(C_3-C_9)$cycloalkylcarbonyl, substituted or unsubstituted $(C_3-C_9)$cycloalkoxycarbonyl, substituted or unsubstituted $(C_6-C_{10})$arylcarbonyl, substituted or unsubstituted $(C_6-C_{10})$aryloxycarbonyl, substituted or unsubstituted $(C_6-C_{10})$aryl$(C_1-C_8)$alkylcarbonyl, substituted or unsubstituted $(C_6-C_{10})$aryl$(C_1-C_8)$alkoxycarbonyl, substituted or unsubstituted 5-9-membered heterocyclylcarbonyl, or substituted or unsubstituted 5-9-membered heteroarylcarbonyl.

In some embodiments of a compound of Formula (I), Ring A is a 6-membered heterocyclyl containing 1 NR'; and R' is substituted or unsubstituted $(C_1-C_8)$alkylcarbonyl, substituted or unsubstituted $(C_3-C_9)$cycloalkylcarbonyl, substituted or unsubstituted $(C_6-C_{10})$arylcarbonyl, substituted or unsubstituted $(C_6-C_{10})$aryl$(C_1-C_8)$alkylcarbonyl, substituted or unsubstituted 5-9-membered heterocyclylcarbonyl, or substituted or unsubstituted 5-9-membered heteroarylcarbonyl.

In some embodiments of a compound of Formula (I), Ring A is a 6-membered heterocyclyl containing 1 NR'; and R' is substituted or unsubstituted $(C_1-C_8)$alkoxycarbonyl, substituted or unsubstituted $(C_3-C_9)$cycloalkoxycarbonyl, substituted or unsubstituted $(C_6-C_{10})$aryloxycarbonyl, or substituted or unsubstituted $(C_6-C_{10})$aryl$(C_1-C_8)$alkoxycarbonyl.

In some embodiments of a compound of Formula (I), Ring A is a 6-membered heterocyclyl containing 1 NR'; and R' is substituted or unsubstituted $(C_1-C_8)$alkyl, substituted or unsubstituted $(C_1-C_8)$alkoxy, substituted or unsubstituted $(C_3-C_9)$cycloalkyl, substituted or unsubstituted $(C_3-C_9)$cycloalkyl$(C_1-C_8)$alkyl, substituted or unsubstituted 5-9-membered heterocyclyl, or substituted or unsubstituted 5-9-membered heterocyclyl$(C_1-C_8)$alkyl.

In some embodiments of a compound of Formula (I), Ring A is a 6-membered heterocyclyl containing 1 NR'; and R' is substituted or unsubstituted $(C_1-C_8)$alkyl, or substituted or unsubstituted $(C_1-C_8)$alkoxy.

In some embodiments of a compound of Formula (I), Ring A is a 6-membered heterocyclyl containing 1 NR'; and R' is substituted or unsubstituted $(C_3-C_9)$cycloalkyl, substituted or unsubstituted $(C_3-C_9)$cycloalkyl$(C_1-C_8)$alkyl, substituted or unsubstituted 5-9-membered heterocyclyl, or substituted or unsubstituted 5-9-membered heterocyclyl$(C_1-C_8)$alkyl. In some embodiments of a compound of Formula (I), Ring A is a 6-membered heterocyclyl containing 1 NR'; and R' is substituted or unsubstituted $(C_3-C_9)$cycloalkyl, or substituted or unsubstituted $(C_3-C_9)$cycloalkyl$(C_1-C_8)$alkyl. In some embodiments of a compound of Formula (I), Ring A is a 6-membered heterocyclyl containing 1 NR'; and R' is substituted or unsubstituted 5-9-membered heterocyclyl, or substituted or unsubstituted 5-9-membered heterocyclyl$(C_1-C_8)$alkyl.

In some embodiments of a compound of Formula (I), Ring A is a 6-membered heterocyclyl containing 1 NR'; and R' is substituted or unsubstituted $(C_6-C_{10})$aryl, substituted or unsubstituted $(C_6-C_{10})$aryl$(C_1-C_8)$alkyl, substituted or unsubstituted 5-9-membered heteroaryl, or substituted or unsubstituted 5-9-membered heteroaryl$(C_1-C_8)$alkyl. In some embodiments of a compound of Formula (I), Ring A is a 6-membered heterocyclyl containing 1 NR'; and R' is substituted or unsubstituted $(C_6-C_{10})$aryl, or substituted or unsubstituted $(C_6-C_{10})$aryl$(C_1-C_8)$alkyl. In some embodiments of a compound of Formula (I), Ring A is a 6-membered heterocyclyl containing 1 NR'; and R' is substituted or unsubstituted 5-9-membered heteroaryl, or substituted or unsubstituted 5-9-membered heteroaryl$(C_1-C_8)$alkyl.

In some embodiments of a compound of Formula (I), R' is H. In some embodiments of a compound of Formula (I), Ring A is a 6-membered heterocyclyl containing 1 NR'; and R' is H.

In some embodiments of a compound of Formula (I), R' is H, substituted or unsubstituted $(C_1-C_8)$alkyl, substituted or unsubstituted $(C_1-C_8)$alkylcarbonyl, substituted or unsubstituted $(C_1-C_8)$alkoxycarbonyl, substituted or unsubstituted $(C_6-C_{10})$arylcarbonyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl.

In some embodiments of a compound of Formula (I), R' is substituted or unsubstituted $(C_1-C_8)$alkyl. In some embodiments of a compound of Formula (I), R' is unsubstituted $(C_1-C_8)$alkyl. In some embodiments of a compound of Formula (I), R' is substituted $(C_1-C_8)$alkyl. In some embodiments of a compound of Formula (I), Ring A is a 6-membered heterocyclyl containing 1 NR'; and R' is substituted or unsubstituted $(C_1-C_8)$alkyl.

In some embodiments of a compound of Formula (I), R' is substituted or unsubstituted $(C_1-C_8)$alkylcarbonyl. In some embodiments of a compound of Formula (I), R' is unsubstituted $(C_1-C_8)$alkylcarbonyl. In some embodiments of a compound of Formula (I), R' is substituted $(C_1-C_8)$alkylcarbonyl. In some embodiments of a compound of Formula (I), R' is

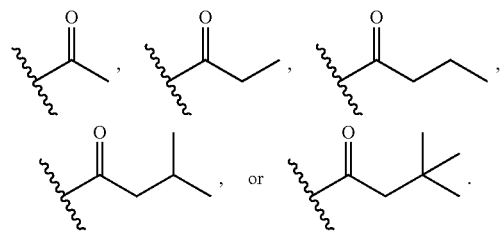

In some embodiments of a compound of Formula (I), Ring A is a 6-membered heterocyclyl containing 1 NR'; and R' is substituted or unsubstituted $(C_1-C_8)$alkylcarbonyl.

In some embodiments of a compound of Formula (I), R' is substituted or unsubstituted $(C_6-C_{10})$aryl$(C_1-C_8)$alkylcarbonyl. In some embodiments of a compound of Formula (I), R' is unsubstituted $(C_6-C_{10})$aryl$(C_1-C_8)$alkylcarbonyl. In some embodiments of a compound of Formula (I), R' is substituted $(C_6-C_{10})$aryl$(C_1-C_8)$alkylcarbonyl. In some embodiments of a compound of Formula (I), R' is

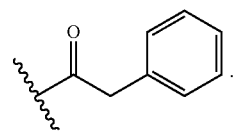 [SMILES: *C(=O)Cc1ccccc1]

In some embodiments of a compound of Formula (I), Ring A is a 6-membered heterocyclyl containing 1 NR'; and R' is substituted or unsubstituted $(C_6$-$C_{10})$aryl$(C_1$-$C_8)$alkylcarbonyl.

In some embodiments of a compound of Formula (I), R' is substituted or unsubstituted $(C_1$-$C_8)$alkoxycarbonyl. In some embodiments of a compound of Formula (I), R' is unsubstituted $(C_1$-$C_8)$alkoxycarbonyl. In some embodiments of a compound of Formula (I), R' is substituted $(C_1$-$C_8)$alkoxycarbonyl. In some embodiments of a compound of Formula (I), R' is tert-butoxycarbonyl. In some embodiments of a compound of Formula (I), the compound is

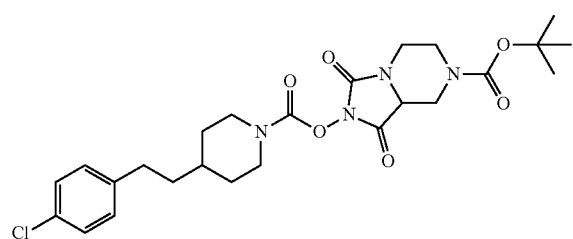

In some embodiments of a compound of Formula (I), Ring A is a 6-membered heterocyclyl containing 1 NR'; and R' is substituted or unsubstituted $(C_1$-$C_8)$alkoxycarbonyl.

In some embodiments of a compound of Formula (I), R' is substituted or unsubstituted $(C_6$-$C_{10})$arylcarbonyl. In some embodiments of a compound of Formula (I), R' is unsubstituted $(C_6$-$C_{10})$arylcarbonyl. In some embodiments of a compound of Formula (I), R' is substituted $(C_6$-$C_{10})$arylcarbonyl. In some embodiments of a compound of Formula (I), Ring A is a 6-membered heterocyclyl containing 1 NR'; and R' is substituted or unsubstituted $(C_6$-$C_{10})$arylcarbonyl. In some embodiments of a compound of Formula (I), Ring A is a 6-membered heterocyclyl containing 1 NR'; and R' is substituted or unsubstituted phenylcarbonyl.

In some embodiments of a compound of Formula (I), R' is phenylcarbonyl substituted with one or more substituents selected from the group consisting of halo, nitro, —N$(R^5)_2$, $(C_1$-$C_8)$alkyl, $(C_1$-$C_8)$alkoxy, $(C_6$-$C_{10})$aryloxy, and 5-9-membered heteroaryloxy.

In some embodiments of a compound of Formula (I), R' is phenylcarbonyl substituted with one or more substituents selected from the group consisting of fluoro, chloro, bromo, nitro, dimethylamino, methyl, and methoxy.

In some embodiments of a compound of Formula (I), R' is

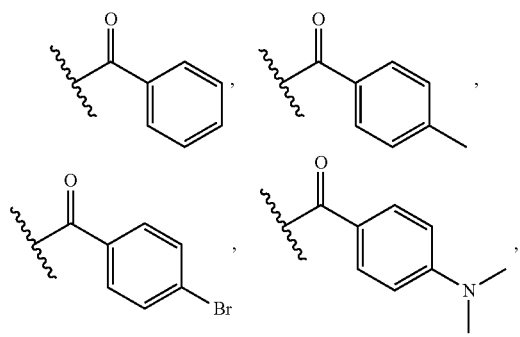

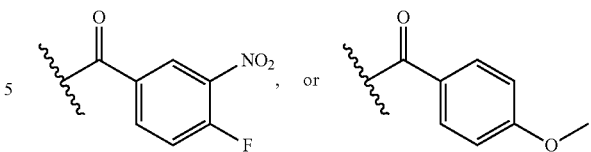

In some embodiments of a compound of Formula (I), R' is substituted or unsubstituted $(C_6$-$C_{10})$aryl$(C_1$-$C_8)$alkyl. In some embodiments of a compound of Formula (I), R' is unsubstituted $(C_6$-$C_{10})$aryl$(C_1$-$C_8)$alkyl. In some embodiments of a compound of Formula (I), R' is substituted $(C_6$-$C_{10})$aryl$(C_1$-$C_8)$alkyl. In some embodiments of a compound of Formula (I), Ring A is a 6-membered heterocyclyl containing 1 NR'; and R' is substituted or unsubstituted $(C_6$-$C_{10})$aryl$(C_1$-$C_8)$alkyl. In some embodiments of a compound of Formula (I), Ring A is a 6-membered heterocyclyl containing 1 NR'; and R' is substituted or unsubstituted benzyl.

In some embodiments of a compound of Formula (I), R' is benzyl substituted with one or more substituents selected from the group consisting of halo, nitro, —N$(R^5)_2$, $(C_1$-$C_8)$alkyl, $(C_1$-$C_8)$alkoxy, $(C_6$-$C_{10})$aryloxy, and 5-9-membered heteroaryloxy.

In some embodiments of a compound of Formula (I), R' is benzyl substituted with one or more substituents selected from the group consisting of fluoro, chloro, bromo, nitro, dimethylamino, methyl, methoxy, and phenoxy.

In some embodiments of a compound of Formula (I), R' is

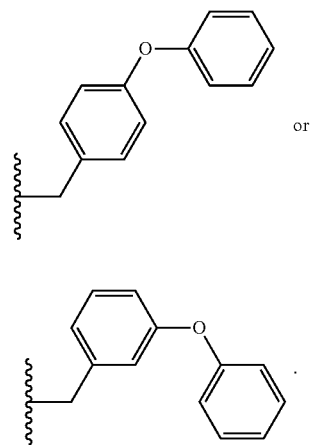

In some embodiments of a compound of Formula (I), R' is

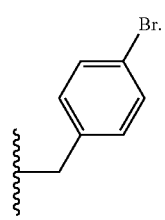 [SMILES: *Cc1ccc(Br)cc1]

In some embodiments of a compound of Formula (I), R' is
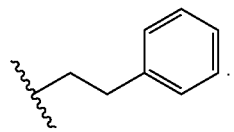 [SMILES: *CCc1ccccc1]
In some embodiments of a compound of Formula (I), the compound is
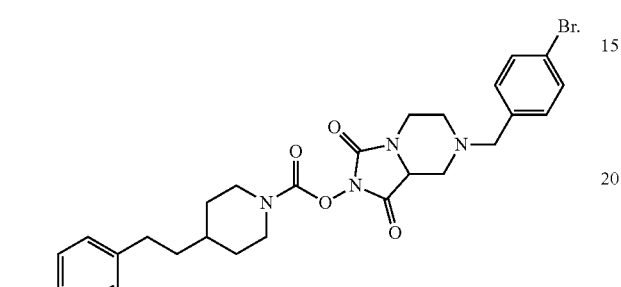
In some embodiments of a compound of Formula (I), the compound is
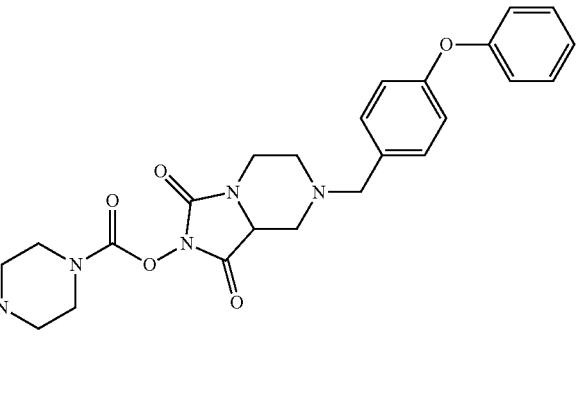
In some embodiments of a compound of Formula (I), the compound is
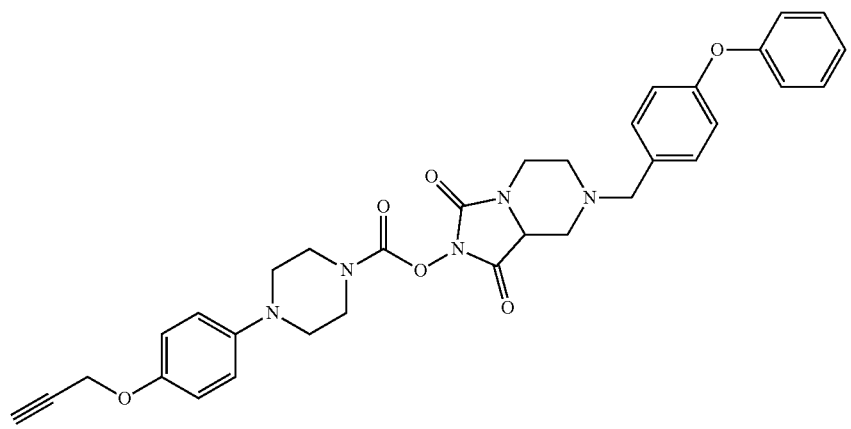
In some embodiments of a compound of Formula (I), the compound is In some embodiments of a compound of Formula (I), the compound is

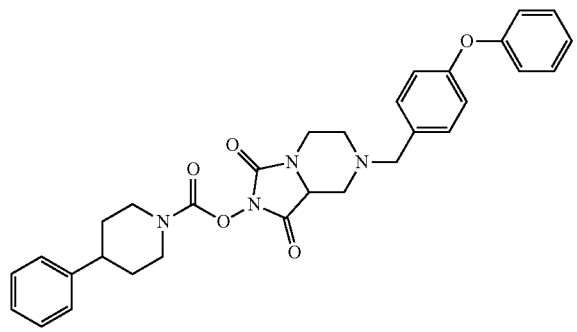

In some embodiments of a compound of Formula (I), the compound is

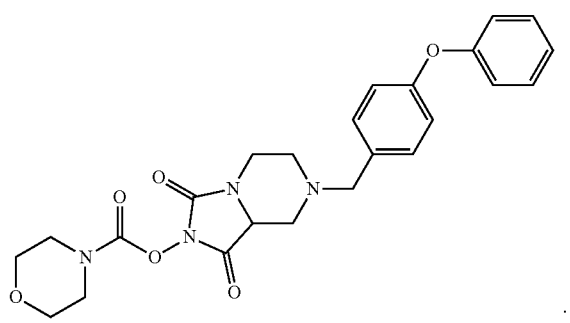 [SMILES: O=C(ON1C(=O)C2CN(Cc3ccc(Oc4ccccc4)cc3)CCN2C1=O)N1CCOCC1]

In some embodiments of a compound of Formula (I), R' is substituted or unsubstituted 5-9-membered heterocyclyl($C_1$-$C_8$)alkyl. In some embodiments of a compound of Formula (I), R' is substituted or unsubstituted 5-membered heterocyclyl($C_1$-$C_8$)alkyl. In some embodiments of a compound of Formula (I), R' is unsubstituted 5-membered heterocyclyl($C_1$-$C_8$)alkyl. In some embodiments of a compound of Formula (I), R' is substituted 5-membered heterocyclyl($C_1$-$C_8$)alkyl. In some embodiments of a compound of Formula (I), R' is

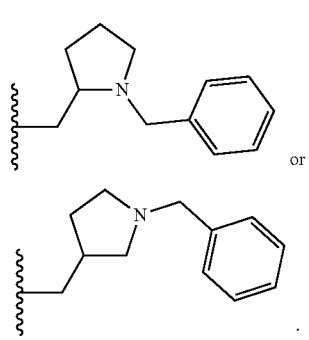

In some embodiments of a compound of Formula (I), R' is substituted or unsubstituted 6-membered heterocyclyl($C_1$-$C_8$)alkyl. In some embodiments of a compound of Formula (I), R' is unsubstituted 6-membered heterocyclyl($C_1$-$C_8$)alkyl. In some embodiments of a compound of Formula (I), R' is substituted 6-membered heterocyclyl($C_1$-$C_8$)alkyl.

In some embodiments of a compound of Formula (I), R' is 4-piperidylmethyl substituted with ($C_6$-$C_{10}$)aryl($C_1$-$C_8$)alkyl.

In some embodiments of a compound of Formula (I), R' is

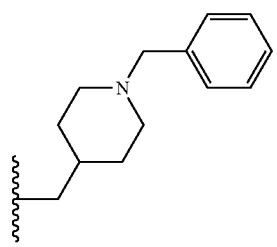

In some embodiments of a compound of Formula (I), R' is

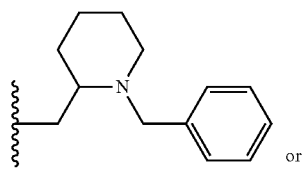

or

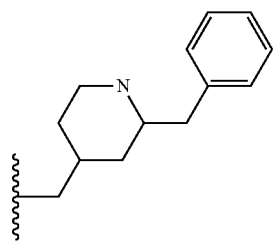

In some embodiments of a compound of Formula (I), the compound is

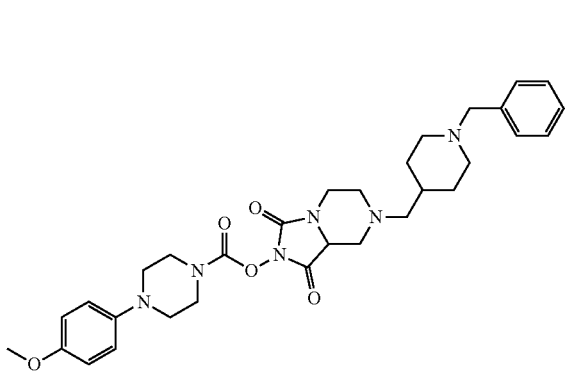

In some embodiments of a compound of Formula (I), the compound is

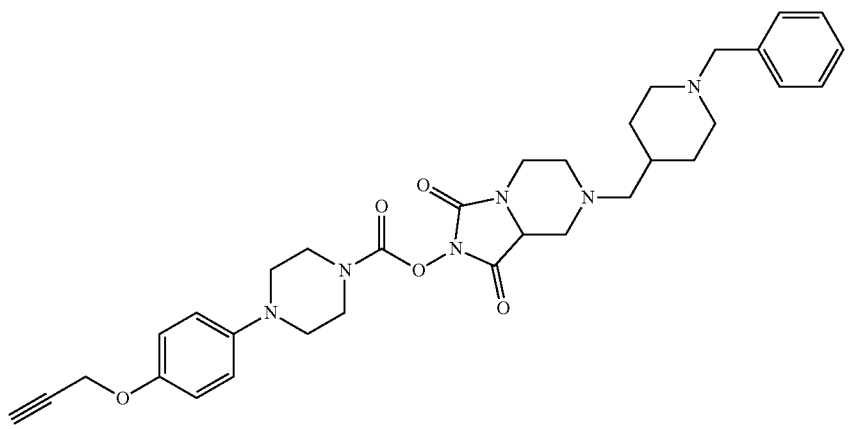

In some embodiments of a compound of Formula (I), R' is substituted or unsubstituted 7-membered heterocyclyl($C_1$-$C_8$)alkyl. In some embodiments of a compound of Formula (I), R' is unsubstituted 7-membered heterocyclyl($C_1$-$C_8$)alkyl. In some embodiments of a compound of Formula (I), R' is substituted 7-membered heterocyclyl($C_1$-$C_8$)alkyl.

In some embodiments of a compound of Formula (I), R' is substituted or unsubstituted 8-membered heterocyclyl($C_1$-$C_8$)alkyl. In some embodiments of a compound of Formula (I), R' is unsubstituted 8-membered heterocyclyl($C_1$-$C_8$)alkyl. In some embodiments of a compound of Formula (I), R' is substituted 8-membered heterocyclyl($C_1$-$C_8$)alkyl.

In some embodiments of a compound of Formula (I), R' is substituted or unsubstituted 9-membered heterocyclyl($C_1$-$C_8$)alkyl. In some embodiments of a compound of Formula (I), R' is unsubstituted 9-membered heterocyclyl($C_1$-$C_8$)alkyl. In some embodiments of a compound of Formula (I), R' is substituted 9-membered heterocyclyl($C_1$-$C_8$)alkyl.

In some embodiments of a compound of Formula (I), Ring A is a 6-membered heterocyclyl containing 1 NR'; and R' is substituted or unsubstituted 5-9-membered heterocyclyl($C_1$-$C_8$)alkyl. In some embodiments of a compound of Formula (I), Ring A is a 6-membered heterocyclyl containing 1 NR'; and R' is substituted or unsubstituted 5-membered heterocyclyl($C_1$-$C_8$)alkyl. In some embodiments of a compound of Formula (I), Ring A is a 6-membered heterocyclyl containing 1 NR'; and R' is substituted or unsubstituted 6-membered heterocyclyl($C_1$-$C_8$)alkyl. In some embodiments of a compound of Formula (I), Ring A is a 6-membered heterocyclyl containing 1 NR'; and R' is substituted or unsubstituted 7-membered heterocyclyl($C_1$-$C_8$)alkyl. In some embodiments of a compound of Formula (I), Ring A is a 6-membered heterocyclyl containing 1 NR'; and R' is substituted or unsubstituted 8-membered heterocyclyl($C_1$-$C_8$)alkyl. In some embodiments of a compound of Formula (I), Ring A is a 6-membered heterocyclyl containing 1 NR'; and R' is substituted or unsubstituted 9-membered heterocyclyl($C_1$-$C_8$)alkyl.

In some embodiments of a compound of Formula (I), R' is substituted or unsubstituted 5-9-membered heterocyclylcarbonyl. In some embodiments of a compound of Formula (I), R' is

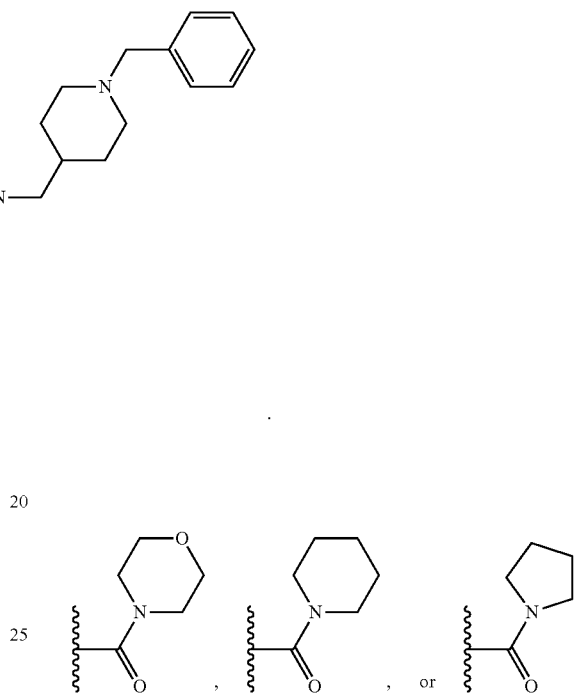

In some embodiments of a compound of Formula (I), R' is substituted or unsubstituted 5-membered heterocyclylcarbonyl. In some embodiments of a compound of Formula (I), R' is unsubstituted 5-membered heterocyclylcarbonyl. In some embodiments of a compound of Formula (I), R' is substituted 5-membered heterocyclylcarbonyl.

In some embodiments of a compound of Formula (I), R' is

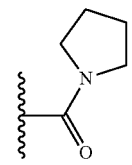

In some embodiments of a compound of Formula (I), R' is substituted or unsubstituted 6-membered heterocyclylcarbonyl. In some embodiments of a compound of Formula (I), R' is unsubstituted 6-membered heterocyclylcarbonyl. In some embodiments of a compound of Formula (I), R' is substituted 6-membered heterocyclylcarbonyl. In some embodiments of a compound of Formula (I), R' is

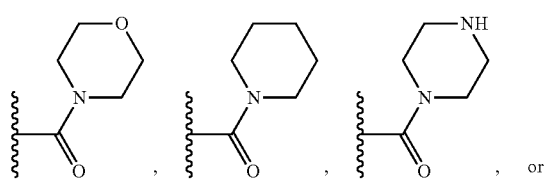

In some embodiments of a compound of Formula (I), R' is

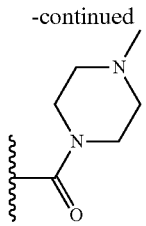

In some embodiments of a compound of Formula (I), R' is

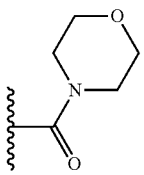

In some embodiments of a compound of Formula (I), the compound is

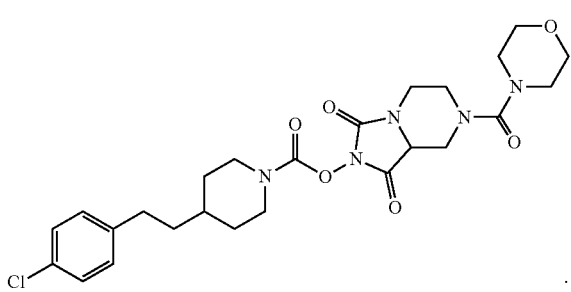 [SMILES: O=C(ON1C(=O)C2CN(C(=O)N3CCOCC3)CCN2C1=O)N1CCC(CCc2ccc(Cl)cc2)CC1]

In some embodiments of a compound of Formula (I), R' is substituted or unsubstituted 7-membered heterocyclylcarbonyl. In some embodiments of a compound of Formula (I), R' is unsubstituted 7-membered heterocyclylcarbonyl. In some embodiments of a compound of Formula (I), R' is substituted 7-membered heterocyclylcarbonyl.

In some embodiments of a compound of Formula (I), R' is substituted or unsubstituted 8-membered heterocyclylcarbonyl. In some embodiments of a compound of Formula (I), R' is unsubstituted 8-membered heterocyclylcarbonyl. In some embodiments of a compound of Formula (I), R' is substituted 8-membered heterocyclylcarbonyl.

In some embodiments of a compound of Formula (I), R' is substituted or unsubstituted 9-membered heterocyclylcarbonyl. In some embodiments of a compound of Formula (I), R' is unsubstituted 9-membered heterocyclylcarbonyl. In some embodiments of a compound of Formula (I), R' is substituted 9-membered heterocyclylcarbonyl.

In some embodiments of a compound of Formula (I), Ring A is a 6-membered heterocyclyl containing 1 NR'; and R' is substituted or unsubstituted 6-membered heterocyclylcarbonyl. In some embodiments of a compound of Formula (I), Ring A is a 6-membered heterocyclyl containing 1 NR'; and R' is substituted or unsubstituted 7-membered heterocyclylcarbonyl. In some embodiments of a compound of Formula (I), Ring A is a 6-membered heterocyclyl containing 1 NR'; and R' is substituted or unsubstituted 8-membered heterocyclylcarbonyl. In some embodiments of a compound of Formula (I), Ring A is a 6-membered heterocyclyl containing 1 NR'; and R' is substituted or unsubstituted 9-membered heterocyclylcarbonyl.

In some embodiments of a compound of Formula (I), each m is 1; W is

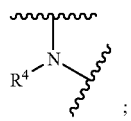

and Ring A is a 6-membered heterocyclyl containing 1 NR'. In some embodiments of a compound of Formula (I), each m is 1; W is

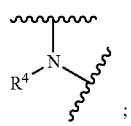

and Ring A is a 6-membered heterocyclyl containing 1 NR'; and R' is substituted or unsubstituted $(C_1\text{-}C_8)$alkyl, substituted or unsubstituted $(C_1\text{-}C_8)$alkoxy, substituted or unsubstituted $(C_1\text{-}C_8)$alkylcarbonyl, substituted or unsubstituted $(C_1\text{-}C_8)$alkoxycarbonyl, substituted or unsubstituted $(C_3\text{-}C_9)$cycloalkyl, substituted or unsubstituted $(C_3\text{-}C_9)$cycloalkyl$(C_1\text{-}C_8)$alkyl, substituted or unsubstituted $(C_3\text{-}C_9)$cycloalkylcarbonyl, substituted or unsubstituted $(C_3\text{-}C_9)$cycloalkoxycarbonyl, substituted or unsubstituted $(C_6\text{-}C_{10})$aryl, substituted or unsubstituted $(C_6\text{-}C_{10})$arylcarbonyl, substituted or unsubstituted $(C_6\text{-}C_{10})$aryloxycarbonyl, substituted or unsubstituted $(C_6\text{-}C_{10})$aryl$(C_1\text{-}C_8)$alkyl, substituted or unsubstituted $(C_6\text{-}C_{10})$aryl$(C_1\text{-}C_8)$alkylcarbonyl, substituted or unsubstituted $(C_6\text{-}C_{10})$aryl$(C_1\text{-}C_8)$alkoxycarbonyl, substituted or unsubstituted 5-9-membered heterocyclyl, substituted or unsubstituted 5-9-membered heterocyclyl$(C_1\text{-}C_8)$alkyl, substituted or unsubstituted 5-9-membered heterocyclylcarbonyl, substituted or unsubstituted 5-9-membered heteroaryl, substituted or unsubstituted 5-9-membered heteroaryl$(C_1\text{-}C_8)$alkyl, or substituted or unsubstituted 5-9-membered heteroarylcarbonyl.

In some embodiments of a compound of Formula (I), each m is 1; W is

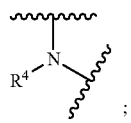

and Ring A is a 6-membered heterocyclyl containing 1 NR'; and R' is H, substituted or unsubstituted $(C_1\text{-}C_8)$alkyl, substituted or unsubstituted $(C_6\text{-}C_{10})$aryl$(C_1\text{-}C_8)$alkyl, substituted or unsubstituted 5-9-membered heterocyclyl$(C_1\text{-}C_8)$alkyl, or substituted or unsubstituted 5-9-membered heterocyclylcarbonyl. In some embodiments of a compound of Formula (I), each m is 1; W is

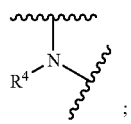

and Ring A is a 6-membered heterocyclyl containing 1 NR';
R' is H, substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl; and $R^4$ is substituted or unsubstituted $(C_6-C_{10})$aryl, or substituted or unsubstituted $(C_6-C_{10})$aryl$(C_1-C_8)$alkyl.

In some embodiments of a compound of Formula (I), each m is 1; W is

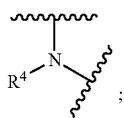

and Ring A is a 6-membered heterocyclyl containing 1 NR'; and R' is substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl. In some embodiments of a compound of Formula (I), each m is 1; W is

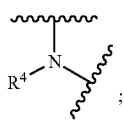

and Ring A is a 6-membered heterocyclyl containing 1 NR'; R' is substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl; and $R^4$ is substituted or unsubstituted $(C_6-C_{10})$aryl, or substituted or unsubstituted $(C_6-C_{10})$aryl$(C_1-C_8)$alkyl.

In some embodiments of a compound of Formula (I), each m is 1; W is

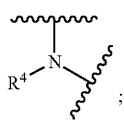

and Ring A is a 6-membered heterocyclyl containing 1 NR'; and R' is substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl. In some embodiments of a compound of Formula (I), each m is 1; W is

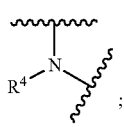

and Ring A is a 6-membered heterocyclyl containing 1 NR'; R' is substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl; and $R^4$ is substituted or unsubstituted $(C_6-C_{10})$aryl, or substituted or unsubstituted $(C_6-C_{10})$aryl$(C_1-C_8)$alkyl.

In some embodiments of a compound of Formula (I), each m is 1; Y is N; W is

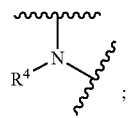

and Ring A is a 6-membered heterocyclyl containing 1 NR'. In some embodiments of a compound of Formula (I), each m is 1; Y is N; W is

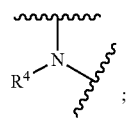

and Ring A is a 6-membered heterocyclyl containing 1 NR'; and R' is substituted or unsubstituted $(C_1-C_8)$alkyl, substituted or unsubstituted $(C_1-C_8)$alkoxy, substituted or unsubstituted $(C_1-C_8)$alkylcarbonyl, substituted or unsubstituted $(C_1-C_8)$alkoxycarbonyl, substituted or unsubstituted $(C_3-C_9)$cycloalkyl, substituted or unsubstituted $(C_3-C_9)$cycloalkyl$(C_1-C_8)$alkyl, substituted or unsubstituted $(C_3-C_9)$cycloalkylcarbonyl, substituted or unsubstituted $(C_3-C_9)$cycloalkoxycarbonyl, substituted or unsubstituted $(C_6-C_{10})$aryl, substituted or unsubstituted $(C_6-C_{10})$arylcarbonyl, substituted or unsubstituted $(C_6-C_{10})$aryloxycarbonyl, substituted or unsubstituted $(C_6-C_{10})$aryl$(C_1-C_8)$alkyl, substituted or unsubstituted $(C_6-C_{10})$aryl$(C_1-C_8)$alkylcarbonyl, substituted or unsubstituted $(C_6-C_{10})$aryl$(C_1-C_8)$alkoxycarbonyl, substituted or unsubstituted 5-9-membered heterocyclyl, substituted or unsubstituted 5-9-membered heterocyclyl$(C_1-C_8)$alkyl, substituted or unsubstituted 5-9-membered heterocyclylcarbonyl, substituted or unsubstituted 5-9-membered heteroaryl, substituted or unsubstituted 5-9-membered heteroaryl$(C_1-C_8)$alkyl, or substituted or unsubstituted 5-9-membered heteroarylcarbonyl.

In some embodiments of a compound of Formula (I), each m is 1; Y is N; W is

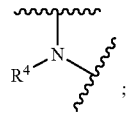

and Ring A is a 6-membered heterocyclyl containing 1 NR'; and R' is H, substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl. In some embodiments of a compound of Formula (I), each m is 1; Y is N; W is

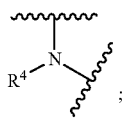

and Ring A is a 6-membered heterocyclyl containing 1 NR';
R' is H, substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl; and $R^4$ is substituted or unsubstituted $(C_6-C_{10})$aryl, or substituted or unsubstituted $(C_6-C_{10})$aryl$(C_1-C_8)$alkyl.

In some embodiments of a compound of Formula (I), each m is 1; Y is N; W is

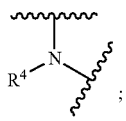

and Ring A is a 6-membered heterocyclyl containing 1 NR'; and R' is substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl. In some embodiments of a compound of Formula (I), each m is 1; Y is N; W is

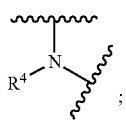

and Ring A is a 6-membered heterocyclyl containing 1 NR'; R' is substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl; and $R^4$ is substituted or unsubstituted $(C_6-C_{10})$aryl, or substituted or unsubstituted $(C_6-C_{10})$aryl$(C_1-C_8)$alkyl.

In some embodiments of a compound of Formula (I), each m is 1; Y is N; W is

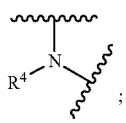

and Ring A is a 6-membered heterocyclyl containing 1 NR'; and R' is substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl. In some embodiments of a compound of Formula (I), each m is 1; Y is N; W is

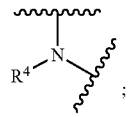

and Ring A is a 6-membered heterocyclyl containing 1 NR'; R' is substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl; and $R^4$ is substituted or unsubstituted $(C_6-C_{10})$aryl, or substituted or unsubstituted $(C_6-C_{10})$aryl$(C_1-C_8)$alkyl.

In some embodiments of a compound of Formula (I), each m is 1; Y is CH; W is

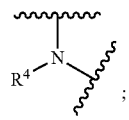

and Ring A is a 6-membered heterocyclyl containing 1 NR'.
In some embodiments of a compound of Formula (I), each m is 1; Y is CH; W is

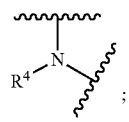

and Ring A is a 6-membered heterocyclyl containing 1 NR'; and R' is substituted or unsubstituted $(C_1-C_8)$alkyl, substituted or unsubstituted $(C_1-C_8)$alkoxy, substituted or unsubstituted $(C_1-C_8)$alkylcarbonyl, substituted or unsubstituted $(C_1-C_8)$alkoxycarbonyl, substituted or unsubstituted $(C_3-C_9)$cycloalkyl, substituted or unsubstituted $(C_3-C_9)$cycloalkyl$(C_1-C_8)$alkyl, substituted or unsubstituted $(C_3-C_9)$cycloalkylcarbonyl, substituted or unsubstituted $(C_3-C_9)$cycloalkoxycarbonyl, substituted or unsubstituted $(C_6-C_{10})$aryl, substituted or unsubstituted $(C_6-C_{10})$arylcarbonyl, substituted or unsubstituted $(C_6-C_{10})$aryloxycarbonyl, substituted or unsubstituted $(C_6-C_{10})$aryl$(C_1-C_8)$alkyl, substituted or unsubstituted $(C_6-C_{10})$aryl$(C_1-C_8)$alkylcarbonyl, substituted or unsubstituted $(C_6-C_{10})$aryl$(C_1-C_8)$alkoxycarbonyl, substituted or unsubstituted 5-9-membered heterocyclyl, substituted or unsubstituted 5-9-membered heterocyclyl$(C_1-C_8)$alkyl, substituted or unsubstituted 5-9-membered heterocyclylcarbonyl, substituted or unsubstituted 5-9-membered heteroaryl, substituted or unsubstituted 5-9-membered heteroaryl$(C_1-C_8)$alkyl, or substituted or unsubstituted 5-9-membered heteroarylcarbonyl.

In some embodiments of a compound of Formula (I), each m is 1; Y is CH; W is

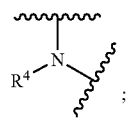

and Ring A is a 6-membered heterocyclyl containing 1 NR'; and R' is H, substituted or unsubstituted $(C_1-C_8)$alkyl, substituted or unsubstituted $(C_6\text{-}C_{10})$aryl$(C_1\text{-}C_8)$alkyl, substituted or unsubstituted 5-9-membered heterocyclyl$(C_1\text{-}C_8)$alkyl, or substituted or unsubstituted 5-9-membered heterocyclylcarbonyl. In some embodiments of a compound of Formula (I), each m is 1; Y is CH; W is

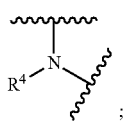

and Ring A is a 6-membered heterocyclyl containing 1 NR'; R' is H, substituted or unsubstituted $(C_1\text{-}C_8)$alkyl, substituted or unsubstituted $(C_6\text{-}C_{10})$aryl$(C_1\text{-}C_8)$alkyl, substituted or unsubstituted 5-9-membered heterocyclyl$(C_1\text{-}C_8)$alkyl, or substituted or unsubstituted 5-9-membered heterocyclylcarbonyl; and $R^4$ is substituted or unsubstituted $(C_6\text{-}C_{10})$aryl, or substituted or unsubstituted $(C_6\text{-}C_{10})$aryl$(C_1\text{-}C_8)$alkyl.

In some embodiments of a compound of Formula (I), each m is 1; Y is CH; W is

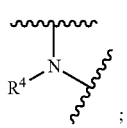

and Ring A is a 6-membered heterocyclyl containing 1 NR'; and R' is substituted or unsubstituted $(C_1\text{-}C_8)$alkyl, substituted or unsubstituted $(C_6\text{-}C_{10})$aryl$(C_1\text{-}C_8)$alkyl, substituted or unsubstituted 5-9-membered heterocyclyl$(C_1\text{-}C_8)$alkyl, or substituted or unsubstituted 5-9-membered heterocyclylcarbonyl. In some embodiments of a compound of Formula (I), each m is 1; Y is CH; W is

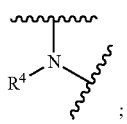

and Ring A is a 6-membered heterocyclyl containing 1 NR'; R' is substituted or unsubstituted $(C_1\text{-}C_8)$alkyl, substituted or unsubstituted $(C_6\text{-}C_{10})$aryl$(C_1\text{-}C_8)$alkyl, substituted or unsubstituted 5-9-membered heterocyclyl$(C_1\text{-}C_8)$alkyl, or substituted or unsubstituted 5-9-membered heterocyclylcarbonyl; and $R^4$ is substituted or unsubstituted $(C_6\text{-}C_{10})$aryl, or substituted or unsubstituted $(C_6\text{-}C_{10})$aryl$(C_1\text{-}C_8)$alkyl.

In some embodiments of a compound of Formula (I), each m is 1; Y is CH; W is

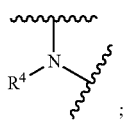

and Ring A is a 6-membered heterocyclyl containing 1 NR'; and R' is substituted or unsubstituted $(C_6\text{-}C_{10})$aryl$(C_1\text{-}C_8)$alkyl, substituted or unsubstituted 5-9-membered heterocyclyl$(C_1\text{-}C_8)$alkyl, or substituted or unsubstituted 5-9-membered heterocyclylcarbonyl. In some embodiments of a compound of Formula (I), each m is 1; Y is CH; W is

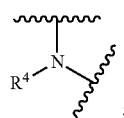

and Ring A is a 6-membered heterocyclyl containing 1 NR'; R' is substituted or unsubstituted $(C_6\text{-}C_{10})$aryl$(C_1\text{-}C_8)$alkyl, substituted or unsubstituted 5-9-membered heterocyclyl$(C_1\text{-}C_8)$alkyl, or substituted or unsubstituted 5-9-membered heterocyclylcarbonyl; and $R^4$ is substituted or unsubstituted $(C_6\text{-}C_{10})$aryl, or substituted or unsubstituted $(C_6\text{-}C_{10})$aryl$(C_1\text{-}C_8)$alkyl.

In some embodiments of a compound of Formula (I), each m is 1; Y is N; $R^1$ is H; W is

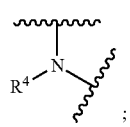

and Ring A is a 6-membered heterocyclyl containing 1 NR'. In some embodiments of a compound of Formula (I), each m is 1; Y is N; $R^1$ is H; W is

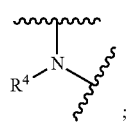

and Ring A is a 6-membered heterocyclyl containing 1 NR'; and R' is substituted or unsubstituted $(C_1\text{-}C_8)$alkyl, substituted or unsubstituted $(C_1\text{-}C_8)$alkoxy, substituted or unsubstituted $(C_1\text{-}C_8)$alkylcarbonyl, substituted or unsubstituted $(C_1\text{-}C_8)$alkoxycarbonyl, substituted or unsubstituted $(C_3\text{-}C_9)$cycloalkyl, substituted or unsubstituted $(C_3\text{-}C_9)$cycloalkyl$(C_1\text{-}C_8)$alkyl, substituted or unsubstituted $(C_3\text{-}C_9)$cycloalkylcarbonyl, substituted or unsubstituted $(C_3\text{-}C_9)$cycloalkoxycarbonyl, substituted or unsubstituted $(C_6\text{-}C_{10})$aryl, substituted or unsubstituted $(C_6\text{-}C_{10})$arylcarbonyl, substituted or unsubstituted $(C_6\text{-}C_{10})$aryloxycarbonyl, substituted or unsubstituted $(C_6\text{-}C_{10})$aryl$(C_1\text{-}C_8)$alkyl, substituted or unsubstituted $(C_6\text{-}C_{10})$aryl$(C_1\text{-}C_8)$alkylcarbonyl, substituted or unsubstituted $(C_6\text{-}C_{10})$aryl$(C_1\text{-}C_8)$alkoxycarbonyl, substituted or unsubstituted 5-9-membered heterocyclyl, substituted or unsubstituted 5-9-membered heterocyclyl$(C_1\text{-}C_8)$alkyl, substituted or unsubstituted 5-9-membered heterocyclylcarbonyl, substituted or unsubstituted 5-9-membered heteroaryl, substituted or unsubstituted 5-9-membered heteroaryl$(C_1\text{-}C_8)$alkyl, or substituted or unsubstituted 5-9-membered heteroarylcarbonyl.

In some embodiments of a compound of Formula (I), each m is 1; Y is N; $R^1$ is H; W is

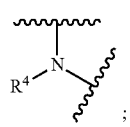

and Ring A is a 6-membered heterocyclyl containing 1 NR'; and R' is H, substituted or unsubstituted $(C_1\text{-}C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl. In some embodiments of a compound of Formula (I), each m is 1; Y is N; $R^1$ is H; W is

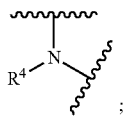

and Ring A is a 6-membered heterocyclyl containing 1 NR'; R' is H, substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl; and $R^4$ is substituted or unsubstituted $(C_6-C_{10})$aryl, or substituted or unsubstituted $(C_6-C_{10})$aryl$(C_1-C_8)$alkyl.

In some embodiments of a compound of Formula (I), each m is 1; Y is N; $R^1$ is H; W is

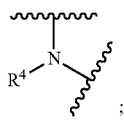

and Ring A is a 6-membered heterocyclyl containing 1 NR'; and R' is substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl. In some embodiments of a compound of Formula (I), each m is 1; Y is N; $R^1$ is H; W is

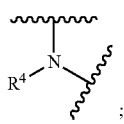

and Ring A is a 6-membered heterocyclyl containing 1 NR'; R' is substituted or unsubstituted $(C_1-C_8)$alkyl, substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl; and $R^4$ is substituted or unsubstituted $(C_6-C_{10})$aryl, or substituted or unsubstituted $(C_6-C_{10})$aryl$(C_1-C_8)$alkyl.

In some embodiments of a compound of Formula (I), each m is 1; Y is N; $R^1$ is H; W is

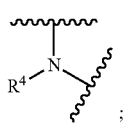

and Ring A is a 6-membered heterocyclyl containing 1 NR'; and R' is substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl. In some embodiments of a compound of Formula (I), each m is 1; Y is N; $R^1$ is H; W is

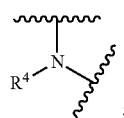

and Ring A is a 6-membered heterocyclyl containing 1 NR'; R' is substituted or unsubstituted $(C_6-C_{10})$aryl$(C_1-C_8)$alkyl, substituted or unsubstituted 5-9-membered heterocyclyl$(C_1-C_8)$alkyl, or substituted or unsubstituted 5-9-membered heterocyclylcarbonyl; and $R^4$ is substituted or unsubstituted $(C_6-C_{10})$aryl, or substituted or unsubstituted $(C_6-C_{10})$aryl$(C_1-C_8)$alkyl.

In some embodiments of a compound of Formula (I), each m is 1; Y is CH; $R^1$ is H; W is

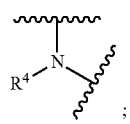

and Ring A is a 6-membered heterocyclyl containing 1 NR'.
In some embodiments of a compound of Formula (I), each m is 1; Y is CH; $R^1$ is H; W is

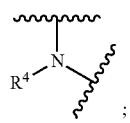

and Ring A is a 6-membered heterocyclyl containing 1 NR'; and R' is substituted or unsubstituted $(C_1-C_8)$alkyl, substituted or unsubstituted $(C_1-C_8)$alkoxy, substituted or unsubstituted $(C_1-C_8)$alkylcarbonyl, substituted or unsubstituted $(C_1-C_8)$alkoxycarbonyl, substituted or unsubstituted $(C_3-C_9)$cycloalkyl, substituted or unsubstituted $(C_3-C_9)$cycloalkyl$(C_1-C_8)$alkyl, substituted or unsubstituted $(C_3-C_9)$cycloalkylcarbonyl, substituted or unsubstituted $(C_3-C_9)$cycloalkoxycarbonyl, substituted or unsubstituted $(C_6-C_{10})$aryl, substituted or unsubstituted $(C_6-C_{10})$arylcarbonyl, substituted or unsubstituted $(C_6-C_{10})$aryloxycarbonyl, substituted or unsubstituted $(C_6-C_{10})$aryl$(C_1-C_8)$alkyl, substituted or unsubstituted $(C_6-C_{10})$aryl$(C_1-C_8)$alkylcarbonyl, substituted or unsubstituted $(C_6-C_{10})$aryl$(C_1-C_8)$alkoxycarbonyl, substituted or unsubstituted 5-9-membered heterocyclyl, substituted or unsubstituted 5-9-membered heterocyclyl$(C_1-C_8)$alkyl, substituted or unsubstituted 5-9-membered heterocyclylcarbonyl, substituted or unsubstituted 5-9-membered heteroaryl, substituted or unsubstituted 5-9-membered heteroaryl$(C_1-C_8)$alkyl, or substituted or unsubstituted 5-9-membered heteroarylcarbonyl.

In some embodiments of a compound of Formula (I), each m is 1; Y is CH; $R^1$ is H; W is

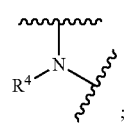

and Ring A is a 6-membered heterocyclyl containing 1 NR'; and R' is H, substituted or unsubstituted $(C_1-C_8)$alkyl, substituted or unsubstituted (C$_6$-C$_{10}$)aryl(C$_1$-C$_8$)alkyl, substituted or unsubstituted 5-9-membered heterocyclyl(C$_1$-C$_8$)alkyl, or substituted or unsubstituted 5-9-membered heterocyclylcarbonyl. In some embodiments of a compound of Formula (I), each m is 1; Y is CH; R$^1$ is H; W is

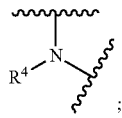

and Ring A is a 6-membered heterocyclyl containing 1 NR'; R' is H, substituted or unsubstituted (C$_1$-C$_8$)alkyl, substituted or unsubstituted (C$_6$-C$_{10}$)aryl(C$_1$-C$_8$)alkyl, substituted or unsubstituted 5-9-membered heterocyclyl(C$_1$-C$_8$)alkyl, or substituted or unsubstituted 5-9-membered heterocyclylcarbonyl; and R$^4$ is substituted or unsubstituted (C$_6$-C$_{10}$)aryl, or substituted or unsubstituted (C$_6$-C$_{10}$)aryl(C$_1$-C$_8$)alkyl.

In some embodiments of a compound of Formula (I), each m is 1; Y is CH; R$^1$ is H; W is

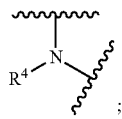

and Ring A is a 6-membered heterocyclyl containing 1 NR'; and R' is substituted or unsubstituted (C$_1$-C$_8$)alkyl, substituted or unsubstituted (C$_6$-C$_{10}$)aryl(C$_1$-C$_8$)alkyl, substituted or unsubstituted 5-9-membered heterocyclyl(C$_1$-C$_8$)alkyl, or substituted or unsubstituted 5-9-membered heterocyclylcarbonyl. In some embodiments of a compound of Formula (I), each m is 1; Y is CH; R$^1$ is H; W is

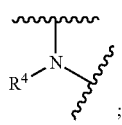

and Ring A is a 6-membered heterocyclyl containing 1 NR'; R' is substituted or unsubstituted (C$_1$-C$_8$)alkyl, substituted or unsubstituted (C$_6$-C$_{10}$)aryl(C$_1$-C$_8$)alkyl, substituted or unsubstituted 5-9-membered heterocyclyl(C$_1$-C$_8$)alkyl, or substituted or unsubstituted 5-9-membered heterocyclylcarbonyl; and R$^4$ is substituted or unsubstituted (C$_6$-C$_{10}$)aryl, or substituted or unsubstituted (C$_6$-C$_{10}$)aryl(C$_1$-C$_8$)alkyl.

In some embodiments of a compound of Formula (I), each m is 1; Y is CH; R$^1$ is H; W is

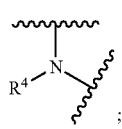

and Ring A is a 6-membered heterocyclyl containing 1 NR'; and R' is substituted or unsubstituted (C$_6$-C$_{10}$)aryl(C$_1$-C$_8$)alkyl, substituted or unsubstituted 5-9-membered heterocyclyl(C$_1$-C$_8$)alkyl, or substituted or unsubstituted 5-9-membered heterocyclylcarbonyl. In some embodiments of a compound of Formula (I), each m is 1; Y is CH; R$^1$ is H; W is

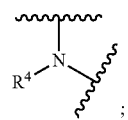

and Ring A is a 6-membered heterocyclyl containing 1 NR'; R' is substituted or unsubstituted (C$_6$-C$_{10}$)aryl(C$_1$-C$_8$)alkyl, substituted or unsubstituted 5-9-membered heterocyclyl(C$_1$-C$_8$)alkyl, or substituted or unsubstituted 5-9-membered heterocyclylcarbonyl; and R$^4$ is substituted or unsubstituted (C$_6$-C$_{10}$)aryl, or substituted or unsubstituted (C$_6$-C$_{10}$)aryl (C$_1$-C$_8$)alkyl.

One embodiment provides a compound of Formula (Ia):

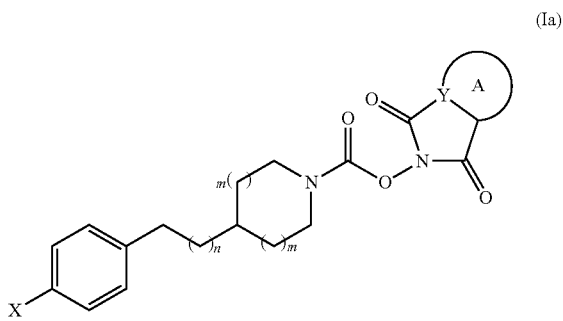

(Ia)

wherein

X is halo;

n is 0, 1, or 2;

each m is independently 0, 1, or 2;

Y is N or CH;

ring A is a 5-7 membered heterocyclyl containing 0-2 additional nitrogen atoms NR', wherein R' is independently at each occurrence H, (C$_1$-C$_8$)alkyl, (C$_1$-C$_8$) alkylcarbonyl, (C$_1$-C$_8$)alkoxycarbonyl, (C$_3$-C$_9$)cycloalkyl, (C$_3$-C$_9$)cycloalkylcarbonyl, (C$_3$-C$_9$) cycloalkoxycarbonyl, (C$_6$-C$_{10}$)aryl, (C$_6$-C$_{10}$) arylcarbonyl, (C$_6$-C$_{10}$)aryloxycarbonyl, (C$_6$-C$_{10}$)aryl (C$_1$-C$_8$)alkyl, (C$_6$-C$_{10}$)aryl(C$_1$-C$_8$)alkylcarbonyl, (C$_6$-C$_{10}$)aryl(C$_1$-C$_8$)alkoxycarbonyl, 5-9-membered heterocyclyl, 5-9-membered heterocyclylcarbonyl, 5-9-membered heteroaryl, or 5-9-membered heteroarylcarbonyl, wherein any alkyl, cycloalkyl, aryl, heterocyclyl, or heteroaryl can be substituted or unsubstituted.

In some embodiments of a compound of Formula (Ia), X is chloro. In some embodiments of a compound of Formula (Ia), n=1. In some embodiments of a compound of Formula (Ia), m=1. In some embodiments of a compound of Formula (Ia), Y is N.

In some embodiments of a compound of Formula (Ia), the compound has a structure of Formula (Ia-1)

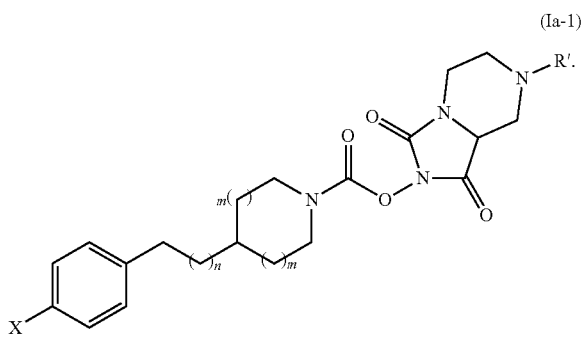

(Ia-1)

In some embodiments of a compound of Formula (Ia-1), R' is a tert-butoxycarbonyl (Boc) group.

In some embodiments of a compound of Formula (Ia-1), the compound is:

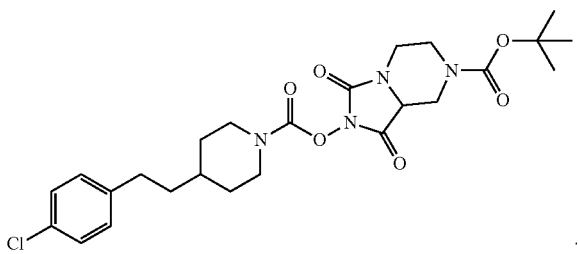 [SMILES: CC(C)(C)OC(=O)N1CCN2C(=O)N(OC(=O)N3CCC(CCc4ccc(Cl)cc4)CC3)C(=O)C2C1]

In some embodiments of a compound of Formula (Ia-1), the compound is

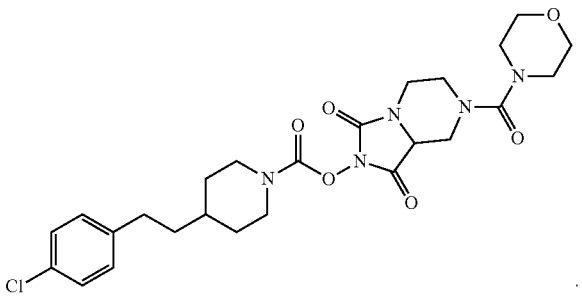 [SMILES: O=C(ON1C(=O)C2CN(C(=O)N3CCOCC3)CCN2C1=O)N1CCC(CCc2ccc(Cl)cc2)CC1]

One embodiment provides a compound of Formula (Ib)

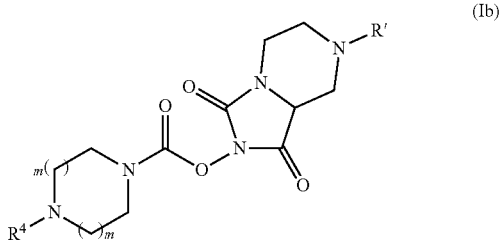

(Ib)

wherein
each m is independently 0, 1, or 2;
$R^4$ is substituted or unsubstituted $(C_6-C_{10})$aryl, substituted or unsubstituted 5-9-membered heteroaryl, substituted or unsubstituted $(C_6-C_{10})$aryl$(C_1-C_8)$alkyl, substituted or unsubstituted 5-9-membered heteroaryl$(C_1-C_8)$alkyl, substituted or unsubstituted di$(C_6-C_{10})$aryl$(C_1-C_8)$alkyl;

R' is independently H, substituted or unsubstituted $(C_1-C_8)$alkyl, substituted or unsubstituted $(C_1-C_8)$alkoxy, substituted or unsubstituted $(C_1-C_8)$alkylcarbonyl, substituted or unsubstituted $(C_1-C_8)$alkoxycarbonyl, substituted or unsubstituted $(C_3-C_9)$cycloalkyl, substituted or unsubstituted $(C_3-C_9)$cycloalkyl$(C_1-C_8)$alkyl, substituted or unsubstituted $(C_3-C_9)$cycloalkylcarbonyl, substituted or unsubstituted $(C_3-C_9)$cycloalkoxycarbonyl, substituted or unsubstituted $(C_6-C_{10})$aryl, substituted or unsubstituted $(C_6-C_{10})$arylcarbonyl, substituted or unsubstituted $(C_6-C_{10})$aryloxycarbonyl, substituted or unsubstituted $(C_6-C_{10})$aryl$(C_1-C_8)$alkyl, substituted or unsubstituted $(C_6-C_{10})$aryl$(C_1-C_8)$alkylcarbonyl, substituted or unsubstituted $(C_6-C_{10})$aryl$(C_1-C_8)$alkoxycarbonyl, substituted or unsubstituted 5-9-membered heterocyclyl, substituted or unsubstituted 5-9-membered heterocyclyl$(C_1-C_8)$alkyl, substituted or unsubstituted 5-9-membered heterocyclylcarbonyl, substituted or unsubstituted 5-9-membered heteroaryl, substituted or unsubstituted 5-9-membered heteroaryl$(C_1-C_8)$alkyl, or substituted or unsubstituted 5-9-membered heteroarylcarbonyl.

In some embodiments of a compound of Formula (Ib), each m=1.

In some embodiments of a compound of Formula (Ib), R' is substituted or unsubstituted $(C_1-C_8)$alkyl, substituted or unsubstituted $(C_1-C_8)$alkoxy, substituted or unsubstituted $(C_3-C_9)$cycloalkyl, substituted or unsubstituted $(C_3-C_9)$cycloalkyl$(C_1-C_8)$alkyl, substituted or unsubstituted $(C_6-C_{10})$aryl$(C_1-C_8)$alkyl, substituted or unsubstituted 5-9-membered heterocyclyl, substituted or unsubstituted 5-9-membered heterocyclyl$(C_1-C_8)$alkyl, substituted or unsubstituted 5-9-membered heteroaryl, or substituted or unsubstituted 5-9-membered heteroaryl$(C_1-C_8)$alkyl. In some embodiments of a compound of Formula (Ib), R' is substituted or unsubstituted $(C_1-C_8)$alkyl, or substituted or unsubstituted $(C_1-C_8)$alkoxy. In some embodiments of a compound of Formula (Ib), R' is substituted or unsubstituted $(C_3-C_9)$cycloalkyl, or substituted or unsubstituted $(C_3-C_9)$cycloalkyl$(C_1-C_8)$alkyl. In some embodiments of a compound of Formula (Ib), R' is substituted or unsubstituted 5-9-membered heterocyclyl, or substituted or unsubstituted 5-9-membered heterocyclyl$(C_1-C_8)$alkyl. In some embodiments of a compound of Formula (Ib), R' is substituted or unsubstituted $(C_6-C_{10})$aryl, or substituted or unsubstituted $(C_6-C_{10})$aryl$(C_1-C_8)$alkyl. In some embodiments of a compound of Formula (Ib), R' is substituted or unsubstituted 5-9-membered heteroaryl, or substituted or unsubstituted 5-9-membered heteroaryl$(C_1-C_8)$alkyl.

In some embodiments of a compound of Formula (Ib), R' is substituted or unsubstituted $(C_1-C_8)$alkylcarbonyl, substituted or unsubstituted $(C_1-C_8)$alkoxycarbonyl, substituted or unsubstituted $(C_3-C_9)$cycloalkylcarbonyl, substituted or unsubstituted $(C_3-C_9)$cycloalkoxycarbonyl, substituted or unsubstituted $(C_6-C_{10})$arylcarbonyl, substituted or unsubstituted $(C_6-C_{10})$aryloxycarbonyl, substituted or unsubstituted $(C_6-C_{10})$aryl$(C_1-C_8)$alkylcarbonyl, substituted or unsubstituted $(C_6-C_{10})$aryl$(C_1-C_8)$alkoxycarbonyl, substituted or unsubstituted 5-9-membered heterocyclylcarbonyl, or substituted or unsubstituted 5-9-membered heteroarylcarbonyl. In some embodiments of a compound of Formula (Ib), R' is substituted or unsubstituted $(C_1-C_8)$alkylcarbonyl, substituted or unsubstituted $(C_3-C_9)$cycloalkylcarbonyl, substituted or unsubstituted $(C_6-C_{10})$arylcarbonyl, substituted or unsubstituted $(C_6-C_{10})$aryl$(C_1-C_8)$alkylcarbonyl, substituted or unsubstituted 5-9-membered heterocyclylcarbonyl, or substituted or unsubstituted 5-9-membered heteroarylcarbonyl. In some embodiments of a compound of Formula (Ib), R' is substituted or unsubstituted $(C_1-C_8)$alkoxycarbonyl, substituted or unsubstituted $(C_3-C_9)$cycloalkoxycarbonyl, substituted or unsubstituted $(C_6-C_{10})$aryloxycarbonyl, or substituted or unsubstituted $(C_6-C_{10})$aryl$(C_1-C_8)$alkoxycarbonyl.

In some embodiments of a compound of Formula (Ib), R' is H.

In some embodiments of a compound of Formula (Ib), R' is substituted or unsubstituted $(C_1-C_8)$alkyl. In some embodiments of a compound of Formula (Ib), R' is unsubstituted $(C_1-C_8)$alkyl. In some embodiments of a compound of Formula (Ib), R' is substituted $(C_1-C_8)$alkyl.

In some embodiments of a compound of Formula (Ib), R' is substituted or unsubstituted $(C_1-C_8)$alkoxy. In some embodiments of a compound of Formula (Ib), R' is substituted $(C_1-C_8)$alkoxy. In some embodiments of a compound of Formula (Ib), R' is unsubstituted $(C_1-C_8)$alkoxy.

In some embodiments of a compound of Formula (Ib), R' is substituted or unsubstituted $(C_1-C_8)$alkylcarbonyl. In some embodiments of a compound of Formula (Ib), R' is unsubstituted $(C_1-C_8)$alkylcarbonyl. In some embodiments of a compound of Formula (Ib), R' is substituted $(C_1-C_8)$alkylcarbonyl. In some embodiments of a compound of Formula (I), R' is

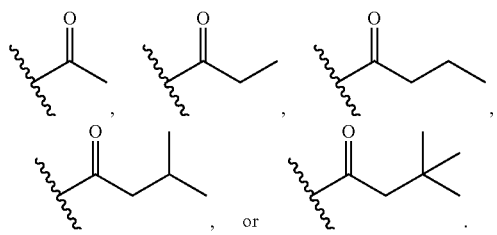

In some embodiments of a compound of Formula (I), R' is substituted or unsubstituted $(C_1-C_8)$alkoxycarbonyl. In some embodiments of a compound of Formula (Ib), R' is unsubstituted $(C_1-C_8)$alkoxycarbonyl. In some embodiments of a compound of Formula (I), R' is substituted $(C_1-C_8)$alkoxycarbonyl. In some embodiments of a compound of Formula (Ib), R' is tert-butoxycarbonyl.

In some embodiments of a compound of Formula (Ib), R' is substituted or unsubstituted $(C_3-C_9)$cycloalkyl. In some embodiments of a compound of Formula (Ib), R' is substituted $(C_3-C_9)$cycloalkyl. In some embodiments of a compound of Formula (Ib), R' is unsubstituted $(C_3-C_9)$cycloalkyl.

In some embodiments of a compound of Formula (Ib), R' is substituted or unsubstituted $(C_3-C_9)$cycloalkyl$(C_1-C_8)$alkyl. In some embodiments of a compound of Formula (Ib), R' is substituted $(C_3-C_9)$cycloalkyl$(C_1-C_8)$alkyl. In some embodiments of a compound of Formula (Ib), R' is unsubstituted $(C_3-C_9)$cycloalkyl$(C_1-C_8)$alkyl.

In some embodiments of a compound of Formula (Ib), R' is substituted or unsubstituted $(C_3-C_9)$cycloalkylcarbonyl. In some embodiments of a compound of Formula (Ib), R' is substituted $(C_3-C_9)$cycloalkylcarbonyl. In some embodiments of a compound of Formula (Ib), R' is unsubstituted $(C_3-C_9)$cycloalkylcarbonyl.

In some embodiments of a compound of Formula (Ib), R' is substituted or unsubstituted $(C_3-C_9)$cycloalkoxycarbonyl.

In some embodiments of a compound of Formula (Ib), R' is substituted $(C_3-C_9)$cycloalkoxycarbonyl. In some embodiments of a compound of Formula (Ib), R' is unsubstituted $(C_3-C_9)$cycloalkoxycarbonyl.

In some embodiments of a compound of Formula (Ib), R' is substituted or unsubstituted $(C_6-C_{10})$aryl. In some embodiments of a compound of Formula (Ib), R' is substituted $(C_6-C_{10})$aryl. In some embodiments of a compound of Formula (Ib), R' is unsubstituted $(C_6-C_{10})$aryl.

In some embodiments of a compound of Formula (Ib), R' is substituted or unsubstituted $(C_6-C_{10})$arylcarbonyl. In some embodiments of a compound of Formula (I), R' is unsubstituted $(C_6-C_{10})$arylcarbonyl. In some embodiments of a compound of Formula (I), R' is substituted $(C_6-C_{10})$arylcarbonyl.

In some embodiments of a compound of Formula (Ib), R' is phenylcarbonyl substituted with one or more substituents selected from the group consisting of halo, nitro, —N(R$^5$)$_2$, $(C_1-C_8)$alkyl, $(C_1-C_8)$alkoxy, $(C_6-C_{10})$aryloxy, and 5-9-membered heteroaryloxy.

In some embodiments of a compound of Formula (Ib), R' is phenylcarbonyl substituted with one or more substituents selected from the group consisting of fluoro, chloro, bromo, nitro, dimethylamino, methyl, and methoxy.

In some embodiments of a compound of Formula (Ib), R' is

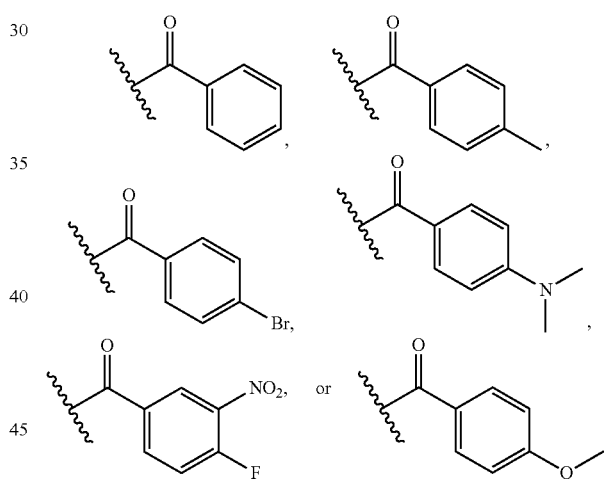

In some embodiments of a compound of Formula (Ib), R' is substituted or unsubstituted $(C_6-C_{10})$aryloxycarbonyl. In some embodiments of a compound of Formula (Ib), R' is substituted $(C_6-C_{10})$aryloxycarbonyl. In some embodiments of a compound of Formula (Ib), R' is unsubstituted $(C_6-C_{10})$aryloxycarbonyl.

In some embodiments of a compound of Formula (I), R' is substituted or unsubstituted $(C_6-C_{10})$aryl$(C_1-C_8)$alkyl. In some embodiments of a compound of Formula (Ib), R' is unsubstituted $(C_6-C_{10})$aryl$(C_1-C_8)$alkyl. In some embodiments of a compound of Formula (I), R' is substituted $(C_6-C_{10})$aryl$(C_1-C_8)$alkyl.

In some embodiments of a compound of Formula (Ib), R' is benzyl substituted with one or more substituents selected from the group consisting of halo, nitro, —N(R$^5$)$_2$, $(C_1-C_8)$alkyl, $(C_1-C_8)$alkoxy, $(C_6-C_{10})$aryloxy, and 5-9-membered heteroaryloxy.

In some embodiments of a compound of Formula (Ib), R' is benzyl substituted with one or more substituents selected from the group consisting of fluoro, chloro, bromo, nitro, dimethylamino, methyl, methoxy, and phenoxy.

In some embodiments of a compound of Formula (Ib), R' is

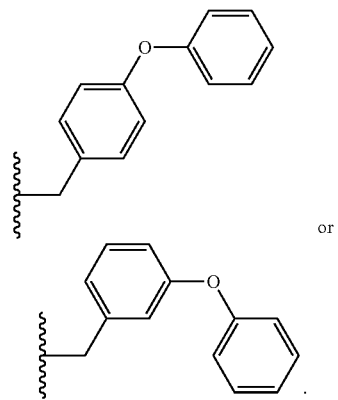

or

In some embodiments of a compound of Formula (Ib), R' is

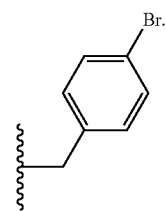 [SMILES: *Cc1ccc(Br)cc1]

In some embodiments of a compound of Formula (Ib), R' is substituted or unsubstituted phenethyl. In some embodiments of a compound of Formula (Ib), R' is

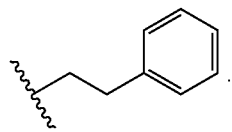 [SMILES: *CCc1ccccc1]

In some embodiments of a compound of Formula (Ib), R' is substituted or unsubstituted $(C_6-C_{10})$aryl$(C_1-C_8)$alkylcarbonyl. In some embodiments of a compound of Formula (I), R' is unsubstituted $(C_6-C_{10})$aryl$(C_1-C_8)$alkylcarbonyl. In some embodiments of a compound of Formula (Ib), R' is substituted $(C_6-C_{10})$aryl$(C_1-C_8)$alkylcarbonyl. In some embodiments of a compound of Formula (Ib), R' is

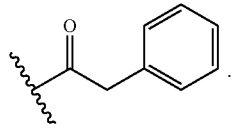 [SMILES: *C(=O)Cc1ccccc1]

In some embodiments of a compound of Formula (Ib), R' is substituted or unsubstituted $(C_6-C_{10})$aryl$(C_1-C_8)$alkoxycarbonyl. In some embodiments of a compound of Formula (Ib), R' is substituted $(C_6-C_{10})$aryl$(C_1-C_8)$alkoxycarbonyl. In some embodiments of a compound of Formula (Ib), R' is unsubstituted $(C_6-C_{10})$aryl$(C_1-C_8)$alkoxycarbonyl.

In some embodiments of a compound of Formula (Ib), the compound is:

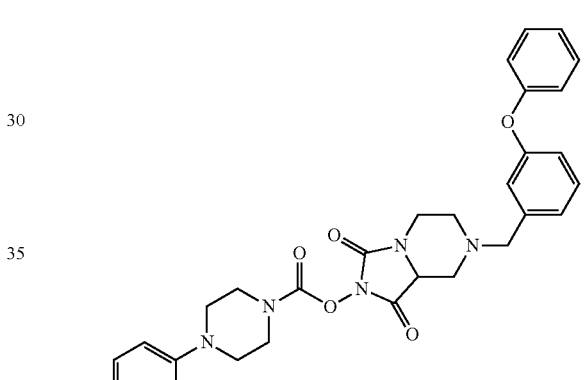

In some embodiments of a compound of Formula (Ib), the compound is:

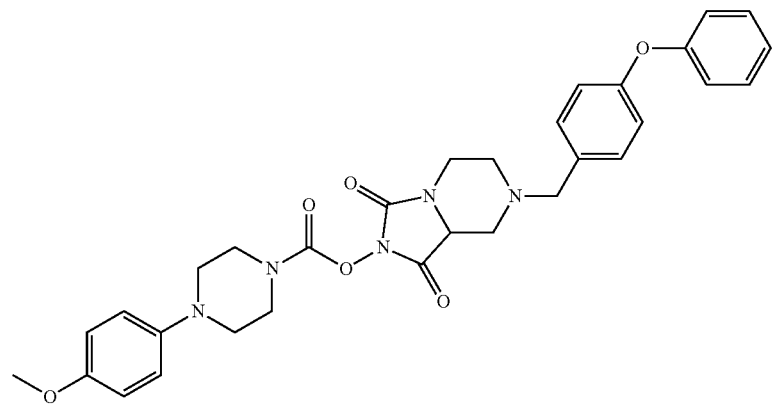

In some embodiments of a compound of Formula (Ib), the compound is:

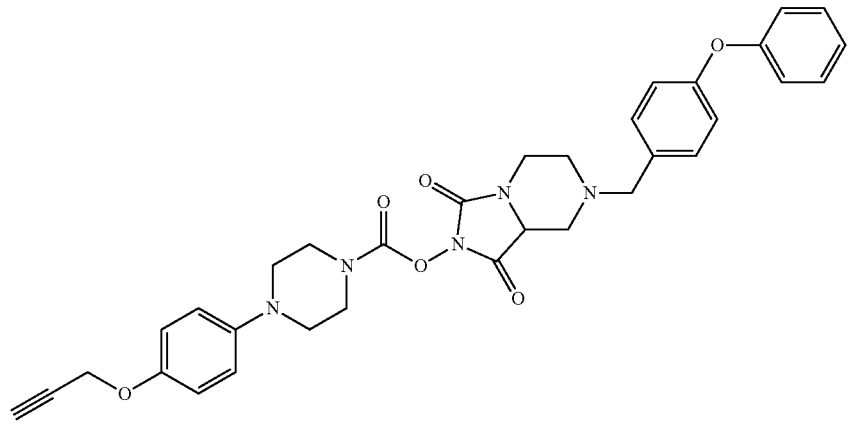

In some embodiments of a compound of Formula (Ib), R' is substituted or unsubstituted 5-9-membered heterocyclyl($C_1$-$C_8$)alkyl. In some embodiments of a compound of Formula (Ib), R' is substituted or unsubstituted 5-membered heterocyclyl($C_1$-$C_8$)alkyl. In some embodiments of a compound of Formula (Ib), R' is unsubstituted 5-membered heterocyclyl($C_1$-$C_8$)alkyl. In some embodiments of a compound of Formula (Ib), R' is substituted 5-membered heterocyclyl($C_1$-$C_8$)alkyl. In some embodiments of a compound of Formula (I), R' is

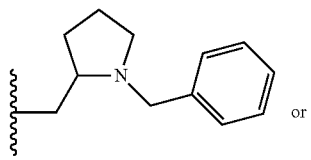

or

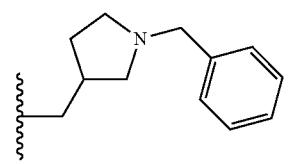

In some embodiments of a compound of Formula (Ib), R' is substituted or unsubstituted 6-membered heterocyclyl($C_1$-$C_8$)alkyl. In some embodiments of a compound of Formula (Ib), R' is unsubstituted 6-membered heterocyclyl($C_1$-$C_8$)alkyl. In some embodiments of a compound of Formula (Ib), R' is substituted 6-membered heterocyclyl($C_1$-$C_8$)alkyl.

In some embodiments of a compound of Formula (Ib), R' is 4-piperidylmethyl substituted with ($C_6$-$C_{10}$)aryl($C_1$-$C_8$)alkyl. In some embodiments of a compound of Formula (Ib), R' is

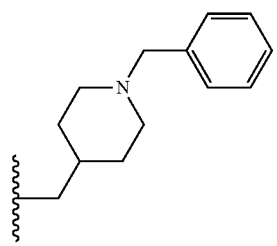

In some embodiments of a compound of Formula (Ib), R' is

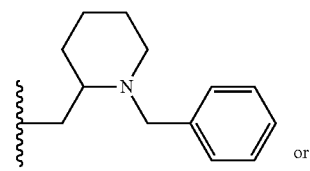

or

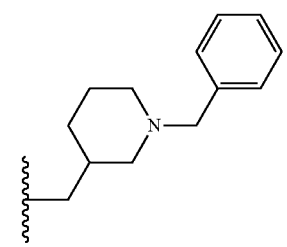

In some embodiments of a compound of Formula (Ib), the compound is:

In some embodiments of a compound of Formula (Ib), the compound is:

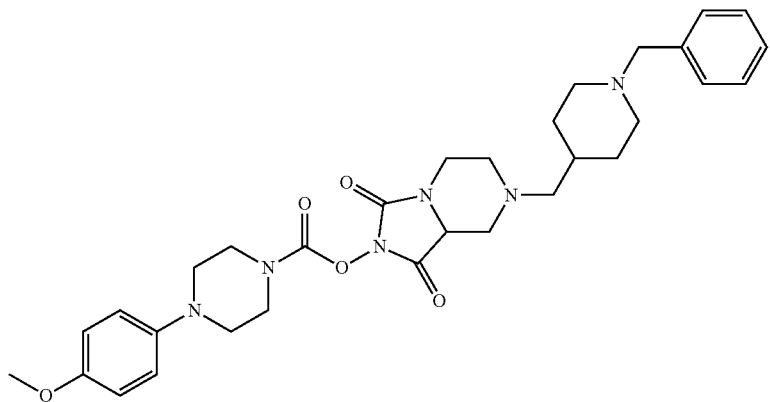

In some embodiments of a compound of Formula (Ib), R' is substituted or unsubstituted 7-membered heterocyclyl(C$_1$-C$_8$)alkyl. In some embodiments of a compound of Formula (Ib), R' is unsubstituted 7-membered heterocyclyl(C$_1$-C$_8$) alkyl. In some embodiments of a compound of Formula (Ib), R' is substituted 7-membered heterocyclyl(C$_1$-C$_8$)alkyl.

In some embodiments of a compound of Formula (Ib), R' is substituted or unsubstituted 8-membered heterocyclyl(C$_1$-C$_8$)alkyl. In some embodiments of a compound of Formula (Ib), R' is unsubstituted 8-membered heterocyclyl(C$_1$-C$_8$) alkyl. In some embodiments of a compound of Formula (Ib), R' is substituted 8-membered heterocyclyl(C$_1$-C$_8$)alkyl.

In some embodiments of a compound of Formula (Ib), R' is substituted or unsubstituted 9-membered heterocyclyl(C$_1$-C$_8$)alkyl. In some embodiments of a compound of Formula (Ib), R' is unsubstituted 9-membered heterocyclyl(C$_1$-C$_8$) alkyl. In some embodiments of a compound of Formula (Ib), R' is substituted 9-membered heterocyclyl(C$_1$-C$_8$)alkyl.

In some embodiments of a compound of Formula (Ib), R' is substituted or unsubstituted 5-9-membered heterocyclylcarbonyl.

In some embodiments of a compound of Formula (Ib), R' is substituted or unsubstituted 5-membered heterocyclylcarbonyl. In some embodiments of a compound of Formula (Ib), R' is unsubstituted 5-membered heterocyclylcarbonyl. In some embodiments of a compound of Formula (Ib), R' is substituted 5-membered heterocyclylcarbonyl. In some embodiments of a compound of Formula (Ib), R' is

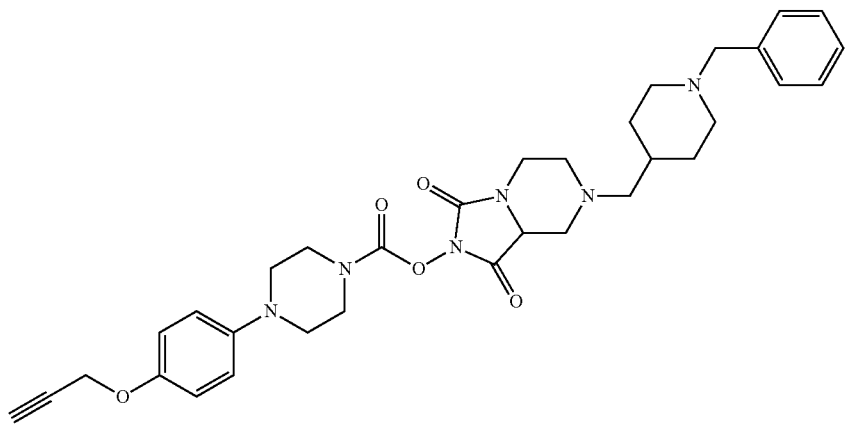

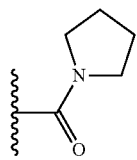

In some embodiments of a compound of Formula (Ib), R' is substituted or unsubstituted 6-membered heterocyclylcarbonyl. In some embodiments of a compound of Formula (Ib), R' is unsubstituted 6-membered heterocyclylcarbonyl. In some embodiments of a compound of Formula (Ib), R' is substituted 6-membered heterocyclylcarbonyl. In some embodiments of a compound of Formula (I), R' is

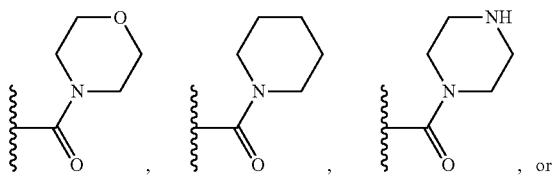

, or

In some embodiments of a compound of Formula (Ib), R' is

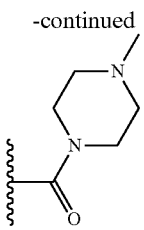

In some embodiments of a compound of Formula (Ib), R' is

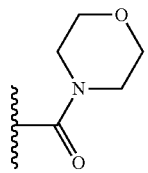

In some embodiments of a compound of Formula (Ib), R' is substituted or unsubstituted 7-membered heterocyclylcarbonyl. In some embodiments of a compound of Formula (Ib), R' is unsubstituted 7-membered heterocyclylcarbonyl. In some embodiments of a compound of Formula (Ib), R' is substituted 7-membered heterocyclylcarbonyl.

In some embodiments of a compound of Formula (Ib), R' is substituted or unsubstituted 8-membered heterocyclylcarbonyl. In some embodiments of a compound of Formula (Ib), R' is unsubstituted 8-membered heterocyclylcarbonyl. In some embodiments of a compound of Formula (Ib), R' is substituted 8-membered heterocyclylcarbonyl.

In some embodiments of a compound of Formula (Ib), R' is substituted or unsubstituted 9-membered heterocyclylcarbonyl. In some embodiments of a compound of Formula (Ib), R' is unsubstituted 9-membered heterocyclylcarbonyl. In some embodiments of a compound of Formula (Ib), R' is substituted 9-membered heterocyclylcarbonyl.

In some embodiments of a compound of Formula (Ib), R' is substituted or unsubstituted 5-9-membered heteroaryl. In some embodiments of a compound of Formula (Ib), R' is substituted 5-9-membered heteroaryl. In some embodiments of a compound of Formula (Ib), R' is unsubstituted 5-9-membered heteroaryl.

In some embodiments of a compound of Formula (Ib), R' is substituted or unsubstituted 5-9-membered heteroaryl($C_1$-$C_8$)alkyl. In some embodiments of a compound of Formula (Ib), R' is substituted 5-9-membered heteroaryl($C_1$-$C_8$)alkyl. In some embodiments of a compound of Formula (Ib), R' is unsubstituted 5-9-membered heteroaryl($C_1$-$C_8$)alkyl.

In some embodiments of a compound of Formula (Ib), R' is substituted or unsubstituted 5-9-membered heteroarylcarbonyl. In some embodiments of a compound of Formula (Ib), R' is substituted 5-9-membered heteroarylcarbonyl. In some embodiments of a compound of Formula (Ib), R' is unsubstituted 5-9-membered heteroarylcarbonyl.

In some embodiments of a compound of Formula (Ib), $R^4$ is substituted or unsubstituted ($C_6$-$C_{10}$)aryl, substituted or unsubstituted ($C_6$-$C_{10}$)aryl($C_1$-$C_8$)alkyl, or substituted or unsubstituted di($C_6$-$C_{10}$)aryl($C_1$-$C_8$)alkyl. In some embodiments of a compound of Formula (Ib), $R^4$ is substituted or unsubstituted 5-9-membered heteroaryl, or substituted or unsubstituted 5-9-membered heteroaryl($C_1$-$C_8$)alkyl.

In some embodiments of a compound of Formula (Ib), $R^4$ is substituted or unsubstituted ($C_6$-$C_{10}$)aryl. In some embodiments of a compound of Formula (Ib), $R^4$ is substituted or unsubstituted phenyl. In some embodiments of a compound of Formula (Ib), $R^4$ is unsubstituted phenyl. In some embodiments of a compound of Formula (Ib), $R^4$ is substituted phenyl. In some embodiments of a compound of Formula (Ib), $R^4$ is phenyl substituted with one or more substituents selected from halo, ($C_1$-$C_8$)alkyl, ($C_1$-$C_8$)alkoxy, ($C_2$-$C_6$)alkenyl, ($C_2$-$C_6$)alkynyl, ($C_2$-$C_6$)alkenyloxy, and ($C_2$-$C_6$)alkynyloxy. In some embodiments of a compound of Formula (Ib), $R^4$ is phenyl substituted with one or more substituents selected from fluoro, chloro, bromo, methoxy, ethynyl, and propargyloxy. In some embodiments of Formula (Ib), $R^4$ is mono-substituted phenyl. In some embodiments of Formula (Ib), $R^4$ is di-substituted phenyl. In some embodiments of a compound of Formula (Ib), $R^4$ is methoxy substituted phenyl. In some embodiments of a compound of Formula (Ib), $R^4$ is propargyloxy substituted phenyl. In some embodiments of a compound of Formula (Ib), $R^4$ is fluoro substituted phenyl. In some embodiments of a compound of Formula (Ib), $R^4$ is chloro substituted phenyl. In some embodiments of a compound of Formula (Ib), $R^4$ is ethynyl substituted phenyl.

In some embodiments of a compound of Formula (Ib), $R^4$ is

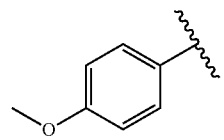

In some embodiments of a compound of Formula (Ib), $R^4$ is

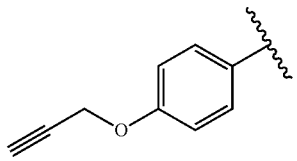

In some embodiments of a compound of Formula (Ib), $R^4$ is substituted or unsubstituted 5-9-membered heteroaryl. In some embodiments of a compound of Formula (Ib), $R^4$ is substituted 5-9-membered heteroaryl. In some embodiments of a compound of Formula (Ib), $R^4$ is unsubstituted 5-9-membered heteroaryl.

In some embodiments of a compound of Formula (Ib), $R^4$ is substituted or unsubstituted ($C_6$-$C_{10}$)aryl($C_1$-$C_8$)alkyl. In some embodiments of a compound of Formula (Ib), $R^4$ is substituted or unsubstituted benzyl. In some embodiments of a compound of Formula (Ib), $R^4$ is unsubstituted benzyl. In some embodiments of a compound of Formula (Ib), $R^4$ is substituted benzyl. In some embodiments of a compound of Formula (Ib), $R^4$ is benzyl substituted with one or more substituents selected from halo, ($C_1$-$C_8$)alkyl, ($C_1$-$C_8$)alkoxy, ($C_2$-$C_6$)alkenyl, ($C_2$-$C_6$)alkynyl, ($C_2$-$C_6$)alkenyloxy, and ($C_2$-$C_6$)alkynyloxy. In some embodiments of a compound of Formula (Ib), $R^4$ is benzyl substituted with one or more substituents selected from fluoro, chloro, bromo, methoxy, ethynyl, and propargyloxy. In some embodiments of Formula (Ib), $R^4$ is mono-substituted benzyl. In some embodiments of Formula (Ib), $R^4$ is di-substituted benzyl. In some embodiments of a compound of Formula (Ib), $R^4$ is methoxy substituted benzyl. In some embodiments of a compound of Formula (Ib), R⁴ is propargyloxy substituted benzyl. In some embodiments of a compound of Formula (Ib), R⁴ is fluoro substituted benzyl. In some embodiments of a compound of Formula (Ib), R⁴ is chloro substituted benzyl. In some embodiments of a compound of Formula (Ib), R⁴ is ethynyl substituted benzyl.

In some embodiments of a compound of Formula (Ib), R⁴ is substituted or unsubstituted phenethyl. In some embodiments of a compound of Formula (Ib), R⁴ is unsubstituted phenethyl. In some embodiments of a compound of Formula (Ib), R⁴ is substituted phenethyl. In some embodiments of a compound of Formula (Ib), R⁴ phenethyl substituted with one or more substituents selected from is halo, $(C_1\text{-}C_8)$alkyl, $(C_1\text{-}C_8)$alkoxy, $(C_2\text{-}C_6)$alkenyl, $(C_2\text{-}C_6)$alkynyl, $(C_2\text{-}C_6)$alkenyloxy, and $(C_2\text{-}C_6)$alkynyloxy. In some embodiments of a compound of Formula (Ib), R⁴ is phenethyl substituted with one or more substituents selected from fluoro, chloro, bromo, methoxy, ethynyl, or propargyloxy. In some embodiments of Formula (Ib), R⁴ is mono-substituted phenethyl. In some embodiments of Formula (Ib), R⁴ is di-substituted phenethyl. In some embodiments of a compound of Formula (Ib), R⁴ is methoxy substituted phenethyl. In some embodiments of a compound of Formula (Ib), R⁴ is propargyloxy substituted phenethyl. In some embodiments of a compound of Formula (Ib), R⁴ is fluoro substituted phenethyl. In some embodiments of a compound of Formula (Ib), R⁴ is chloro substituted phenethyl. In some embodiments of a compound of Formula (Ib), R⁴ is ethynyl substituted phenethyl.

In some embodiments of a compound of Formula (Ib), R⁴ is

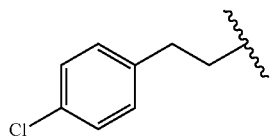

In some embodiments of a compound of Formula (Ib), R⁴ is

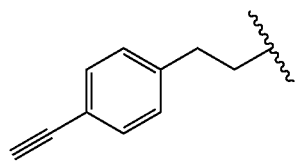

In some embodiments of a compound of Formula (Ib), R⁴ is substituted or unsubstituted 5-9-membered heteroaryl($C_1$-$C_8$)alkyl. In some embodiments of a compound of Formula (Ib), R⁴ is substituted 5-9-membered heteroaryl($C_1$-$C_8$)alkyl. In some embodiments of a compound of Formula (Ib), R⁴ is unsubstituted 5-9-membered heteroaryl($C_1$-$C_8$)alkyl.

In some embodiments of a compound of Formula (Ib), R⁴ is substituted or unsubstituted di($C_6$-$C_{10}$)aryl($C_1$-$C_8$)alkyl. In some embodiments of a compound of Formula (Ib), R⁴ is substituted or unsubstituted diphenylmethyl. In some embodiments of a compound of Formula (Ib), R⁴ is unsubstituted diphenylmethyl. In some embodiments of a compound of Formula (Ib), R⁴ is substituted diphenylmethyl. In some embodiments of a compound of Formula (Ib), R⁴ is diphenylmethyl substituted with one or more substituents selected from halo, $(C_1\text{-}C_8)$alkyl, $(C_1\text{-}C_8)$alkoxy, $(C_2\text{-}C_6)$alkenyl, $(C_2\text{-}C_6)$alkynyl, $(C_2\text{-}C_6)$alkenyloxy, and $(C_2\text{-}C_6)$alkynyloxy. In some embodiments of a compound of Formula (Ib), R⁴ is diphenylmethyl substituted with one or more substituents selected from fluoro, chloro, bromo, methoxy, ethynyl, and propargyloxy. In some embodiments of Formula (I), R⁴ is mono-substituted diphenylmethyl. In some embodiments of Formula (Ib), R⁴ is di-substituted diphenylmethyl. In some embodiments of a compound of Formula (Ib), R⁴ is methoxy substituted diphenylmethyl. In some embodiments of a compound of Formula (Ib), R⁴ is propargyloxy substituted phenyl. In some embodiments of a compound of Formula (Ib), R⁴ is fluoro substituted diphenylmethyl. In some embodiments of a compound of Formula (Ib), R⁴ is chloro substituted diphenylmethyl. In some embodiments of a compound of Formula (Ib), R⁴ is ethynyl substituted diphenylmethyl.

In some embodiments of a compound of Formula (Ib), R⁴ is

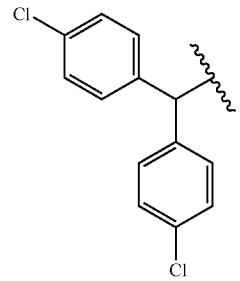

In some embodiments of a compound of Formula (Ib), R' is substituted or unsubstituted $(C_6\text{-}C_{10})$aryl$(C_1\text{-}C_8)$alkyl and R⁴ is substituted or unsubstituted $(C_6\text{-}C_{10})$aryl. In some embodiments of a compound of Formula (Ib), R' is benzyl substituted with one or more substituents selected from the group consisting of halo, $(C_1\text{-}C_8)$alkyl, $(C_1\text{-}C_8)$alkoxy, $(C_6\text{-}C_{10})$aryloxy, and 5-9-membered heteroaryloxy; and R⁴ is phenyl substituted with one substituent selected from the group consisting of fluoro, chloro, bromo, methoxy, ethynyl, and propargyloxy.

In some embodiments of a compound of Formula (Ib), R' is benzyl substituted with phenoxy; and R⁴ is phenyl substituted with one substituent selected from the group consisting of methoxy and propargyloxy. In some embodiments of a compound of Formula (Ib), R' is substituted or unsubstituted $(C_6\text{-}C_{10})$aryl$(C_1\text{-}C_8)$alkyl; and R⁴ is

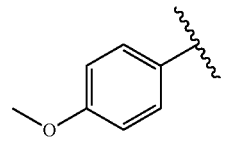

In some embodiments of a compound of Formula (Ib), R' is substituted or unsubstituted $(C_6\text{-}C_{10})$aryl$(C_1\text{-}C_8)$alkyl; and R⁴ is

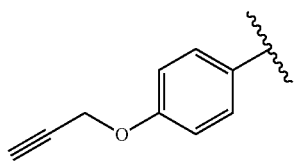

In some embodiments of a compound of Formula (Ib), R' is substituted or unsubstituted $(C_6-C_{10})$aryl$(C_1-C_8)$alkyl; and R' is

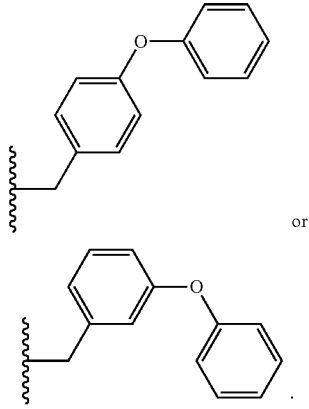

or

In some embodiments of a compound of Formula (Ib), R' is substituted or unsubstituted 5-9-membered heterocyclyl$(C_1-C_8)$alkyl; and $R^4$ is substituted or unsubstituted $(C_6-C_{10})$aryl.

In some embodiments of a compound of Formula (Ib), R' is 4-piperidylmethyl substituted with $(C_6-C_{10})$aryl$(C_1-C_8)$alkyl; and $R^4$ is phenyl substituted with one substituent selected from the group consisting of fluoro, chloro, bromo, methoxy, ethynyl, and propargyloxy.

In some embodiments of a compound of Formula (Ib), R' is

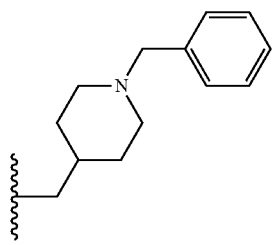

and $R^4$ is phenyl substituted with one substituent selected from the group consisting of methoxy and propargyloxy. In some embodiments of a compound of Formula (Ib), R' is substituted or unsubstituted 5-9-membered heterocyclyl$(C_1-C_8)$alkyl; and $R^4$ is

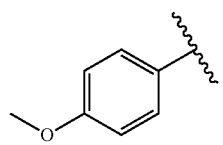

In some embodiments of a compound of Formula (Ib), R' is substituted or unsubstituted 5-9-membered heterocyclyl$(C_1-C_8)$alkyl; and $R^4$ is

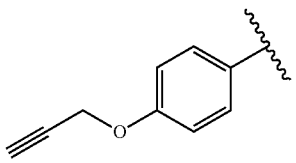

In some embodiments of a compound of Formula (Ib), each m is 1; R' is substituted or unsubstituted $(C_6-C_{10})$aryl$(C_1-C_8)$alkyl; and $R^4$ is substituted or unsubstituted $(C_6-C_{10})$aryl. In some embodiments of a compound of Formula (Ib), each m is 1; R' is benzyl substituted with one or more substituents selected from the group consisting of halo, $(C_1-C_8)$alkyl, $(C_1-C_8)$alkoxy, $(C_6-C_{10})$aryloxy, and 5-9-membered heteroaryloxy; and $R^4$ is phenyl substituted with one substituent selected from the group consisting of fluoro, chloro, bromo, methoxy, ethynyl, and propargyloxy.

In some embodiments of a compound of Formula (Ib), each m is 1; R' is benzyl substituted with phenoxy; and $R^4$ is phenyl substituted with one substituent selected from the group consisting of methoxy and propargyloxy. In some embodiments of a compound of Formula (Ib), each m is 1; R' is substituted or unsubstituted $(C_6-C_{10})$aryl$(C_1-C_8)$alkyl; and $R^4$ is

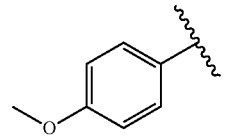

In some embodiments of a compound of Formula (Ib), each m is 1; R' is substituted or unsubstituted $(C_6-C_{10})$aryl$(C_1-C_8)$alkyl; and $R^4$ is

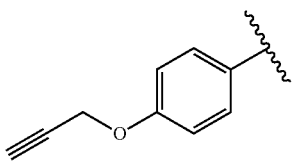

In some embodiments of a compound of Formula (Ib), each m is 1; R' is substituted or unsubstituted $(C_6-C_{10})$aryl$(C_1-C_8)$alkyl; and R' is

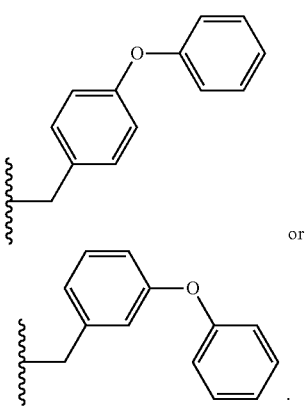

or

.

In some embodiments of a compound of Formula (Ib), each m is 1; R' is substituted or unsubstituted 5-9-membered heterocyclyl(C₁-C₈)alkyl; and R⁴ is substituted or unsubstituted (C₆-C₁₀)aryl.

In some embodiments of a compound of Formula (Ib), each m is 1; R' is 4-piperidylmethyl substituted with (C₆-C₁₀)aryl(C₁-C₈)alkyl; and R⁴ is phenyl substituted with one substituent selected from the group consisting of fluoro, chloro, bromo, methoxy, ethynyl, and propargyloxy.

In some embodiments of a compound of Formula (Ib), each m is 1; R' is

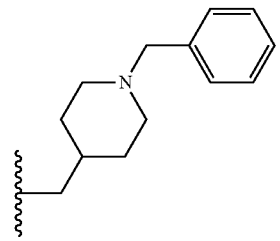

and R⁴ is phenyl substituted with one substituent selected from the group consisting of methoxy and propargyloxy. In some embodiments of a compound of Formula (Ib), each m is 1; R' is substituted or unsubstituted 5-9-membered heterocyclyl(C₁-C₈)alkyl; and R⁴ is

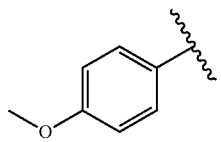

In some embodiments of a compound of Formula (Ib), each m is 1; R' is substituted or unsubstituted 5-9-membered heterocyclyl(C₁-C₈)alkyl; and R⁴ is

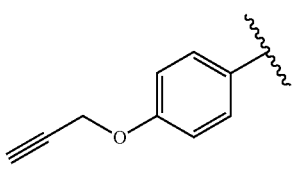

Further embodiments provided herein include combinations of one or more of the particular embodiments set forth above.

In some embodiments, the compound disclosed herein has the structure provided in Table 1.

TABLE 1

| Cpd. | Structure | Name |
|---|---|---|
| 1 | 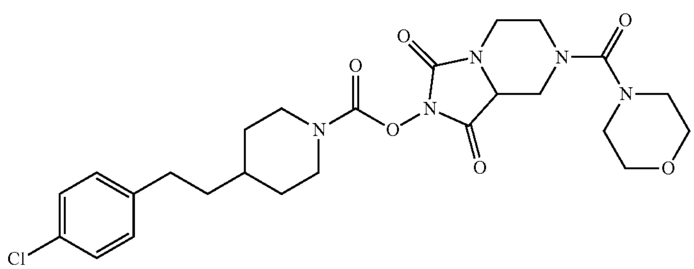 [SMILES: O=C(ON1C(=O)C2CN(C(=O)N3CCOCC3)CCN2C1=O)N1CCC(CCc2ccc(Cl)cc2)CC1] | 7-(morpholine-4-carbonyl)-1,3-dioxohexahydroimidazo[1,5-a]pyrazin-2(3H)-yl 4-(4-chlorophenethyl)piperidine-1-carboxylate |
| 2 | 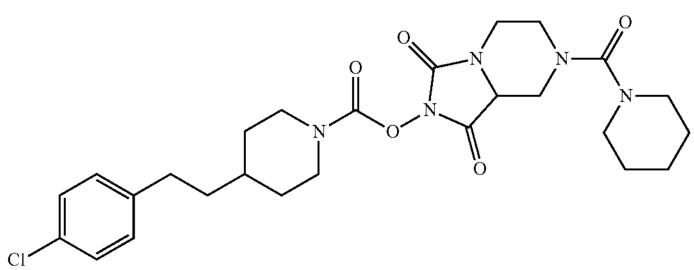 | 1,3-dioxo-7-(piperidine-1-carbonyl)hexahydroimidazo[1,5-a]pyrazin-2(3H)-yl 4-(4-chlorophenethyl)piperidine-1-carboxylate |
| 3 | 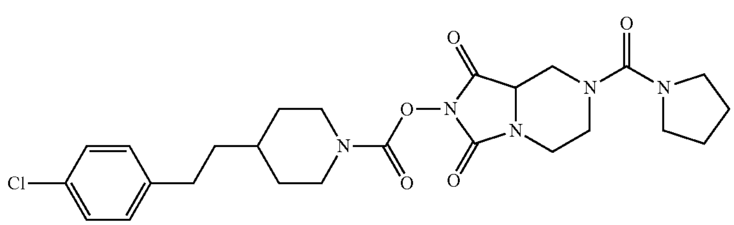 [SMILES: O=C(ON1C(=O)C2CN(C(=O)N3CCCC3)CCN2C1=O)N1CCC(CCc2ccc(Cl)cc2)CC1] | 1,3-dioxo-7-(pyrrolidine-1-carbonyl)hexahydroimidazo[1,5-a]pyrazin-2(3H)-yl 4-(4-chlorophenethyl)piperidine-1-carboxylate |

TABLE 1-continued

| Cpd. | Structure | Name |
|---|---|---|
| 4 | 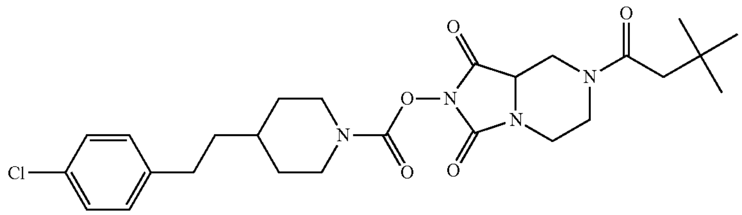 [SMILES: CC(C)(C)CC(=O)N1CCN2C(=O)N(OC(=O)N3CCC(CCc4ccc(Cl)cc4)CC3)C(=O)C2C1] | 7-(3,3-dimethylbutanoyl)-1,3-dioxohexahydroimidazo[1,5-a]pyrazin-2(3H)-yl 4-(4-chlorophenethyl)piperidine-1-carboxylate |
| 5 | 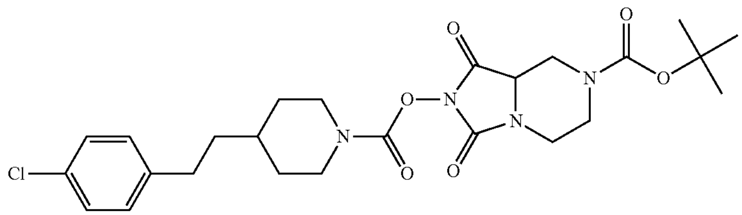 [SMILES: CC(C)(C)OC(=O)N1CCN2C(=O)N(OC(=O)N3CCC(CCc4ccc(Cl)cc4)CC3)C(=O)C2C1] | tert-butyl 2-(4-(4-chlorophenethyl)piperidine-1-carbonyloxy)-1,3-dioxohexahydroimidazo[1,5-a]pyrazine-7(1H)-carboxylate |
| 6 | 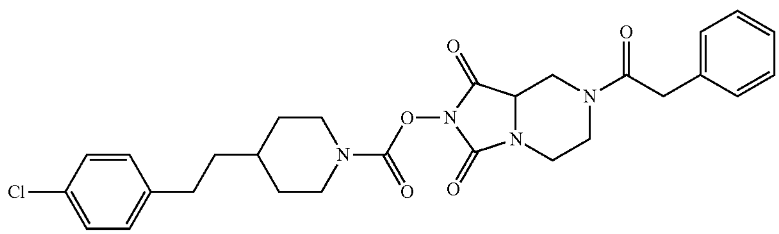 [SMILES: O=C(Cc1ccccc1)N1CCN2C(=O)N(OC(=O)N3CCC(CCc4ccc(Cl)cc4)CC3)C(=O)C2C1] | 1,3-dioxo-7-(2-phenylacetyl)hexahydroimidazo[1,5-a]pyrazin-2(3H)-yl 4-(4-chlorophenethyl)piperidine-1-carboxylate |
| 7 | 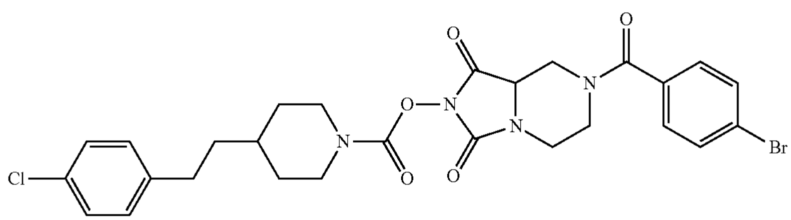 [SMILES: O=C(ON1C(=O)C2CN(C(=O)c3ccc(Br)cc3)CCN2C1=O)N1CCC(CCc2ccc(Cl)cc2)CC1] | 7-(4-bromobenzoyl)-1,3-dioxohexahydroimidazo[1,5-a]pyrazin-2(3H)-yl 4-(4-chlorophenethyl)piperidine-1-carboxylate |
| 8 | 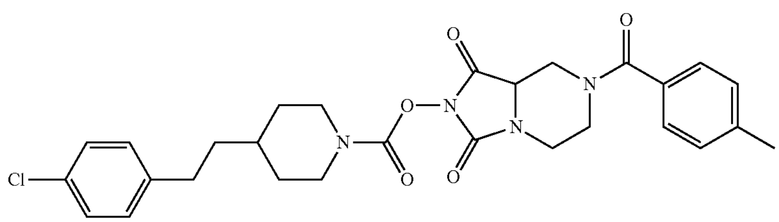 [SMILES: Cc1ccc(C(=O)N2CCN3C(=O)N(OC(=O)N4CCC(CCc5ccc(Cl)cc5)CC4)C(=O)C3C2)cc1] | 7-(4-methylbenzoyl)-1,3-dioxohexahydroimidazo[1,5-a]pyrazin-2(3H)-yl 4-(4-chlorophenethyl)piperidine-1-carboxylate |
| 9 | 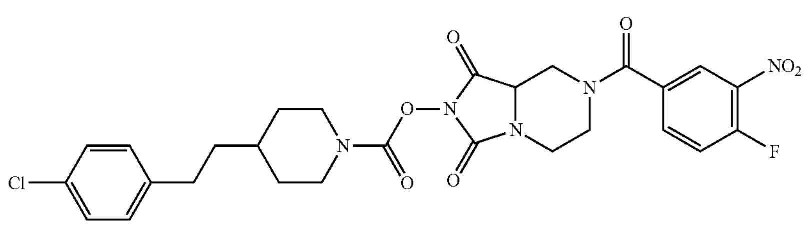 [SMILES: O=C(ON1C(=O)C2CN(C(=O)c3ccc(F)c([N+](=O)[O-])c3)CCN2C1=O)N1CCC(CCc2ccc(Cl)cc2)CC1] | 7-(4-fluoro-3-nitrobenzoyl)-1,3-dioxohexahydroimidazo[1,5-a]pyrazin-2(3H)-yl 4-(4-chlorophenethyl)piperidine-1-carboxylate |
| 10 | 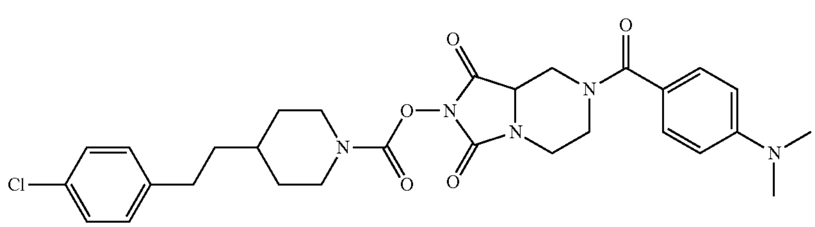 [SMILES: COc1ccc(C(=O)N2CCN3C(=O)N(OC(=O)N4CCC(CCc5ccc(Cl)cc5)CC4)C(=O)C3C2)cc1] | 7-(4-(dimethylamino)benzoyl)-1,3-dioxohexahydroimidazo[1,5-a]pyrazin-2(3H)-yl 4-(4-chlorophenethyl)piperidine-1-carboxylate |

TABLE 1-continued

| Cpd. | Structure | Name |
|---|---|---|
| 11 | 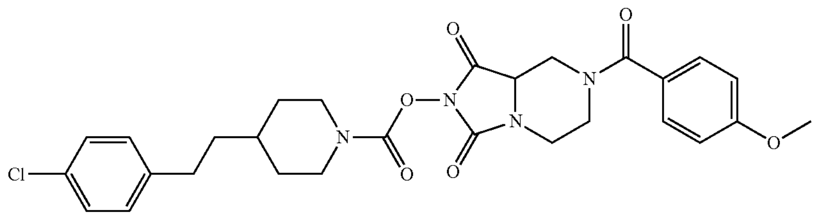 | 7-(4-methoxybenzoyl)-1,3-dioxohexahydroimidazo[1,5-a]pyrazin-2(3H)-yl 4-(4-chlorophenethyl)piperidine-1-carboxylate |
| 12 | 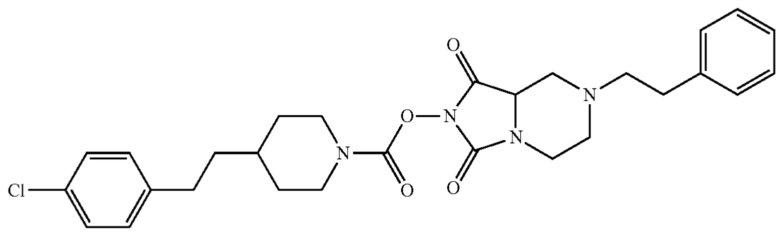 [SMILES: O=C(ON1C(=O)C2CN(CCc3ccccc3)CCN2C1=O)N1CCC(CCc2ccc(Cl)cc2)CC1] | 1,3-dioxo-7-phenethylhexahydroimidazo[1,5-a]pyrazin-2(3H)-yl 4-(4-chlorophenethyl)piperidine-1-carboxylate |
| 13 | 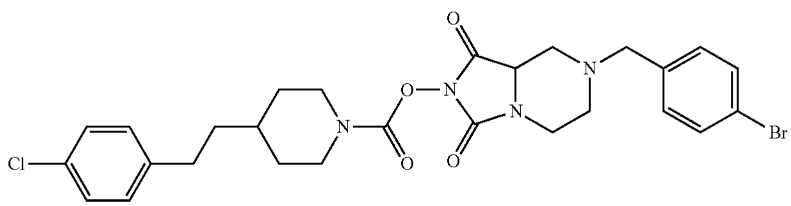 [SMILES: O=C(ON1C(=O)C2CN(Cc3ccc(Br)cc3)CCN2C1=O)N1CCC(CCc2ccc(Cl)cc2)CC1] | 7-(4-bromobenzyl)-1,3-dioxohexahydroimidazo[1,5-a]pyrazin-2(3H)-yl 4-(4-chlorophenethyl)piperidine-1-carboxylate |
| 14 | 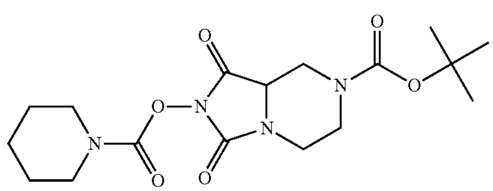 [SMILES: CC(C)(C)OC(=O)N1CCN2C(=O)N(OC(=O)N3CCCCC3)C(=O)C2C1] | tert-butyl 1,3-dioxo-2-(piperidine-1-carbonyloxy)hexahydroimidazo[1,5-a]pyrazine-7(1H)-carboxylate |
| 15 | 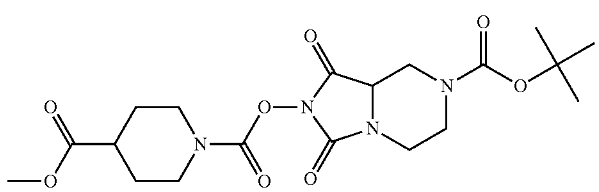 [SMILES: COC(=O)C1CCN(C(=O)ON2C(=O)C3CN(C(=O)OC(C)(C)C)CCN3C2=O)CC1] | 1-(7-(tert-butoxycarbonyl)-1,3-dioxohexahydroimidazo[1,5-a]pyrazin-2(3H)-yl) 4-methyl piperidine-1,4-dicarboxylate |
| 16 | 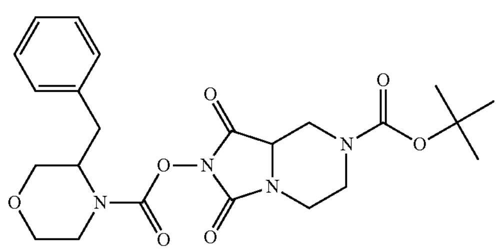 [SMILES: CC(C)(C)OC(=O)N1CCN2C(=O)N(OC(=O)N3CCOCC3Cc3ccccc3)C(=O)C2C1] | 7-(tert-butoxycarbonyl)-1,3-dioxohexahydroimidazo[1,5-a]pyrazin-2(3H)-yl 3-benzylmorpholine-4-carboxylate |
| 17 | 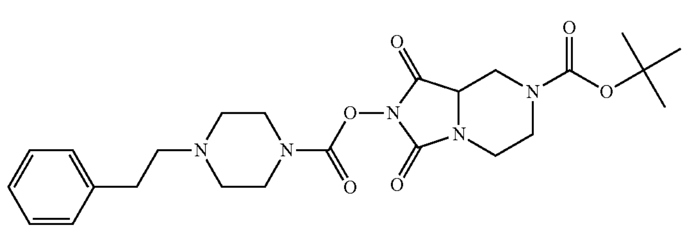 [SMILES: CC(C)(C)OC(=O)N1CCN2C(=O)N(OC(=O)N3CCN(CCc4ccccc4)CC3)C(=O)C2C1] | tert-butyl 1,3-dioxo-2-(4-phenethylpiperazine-1-carbonyloxy)hexahydroimidazo[1,5-a]pyrazine-7(1H)-carboxylate |

TABLE 1-continued

| Cpd. | Structure | Name |
|---|---|---|
| 18 | 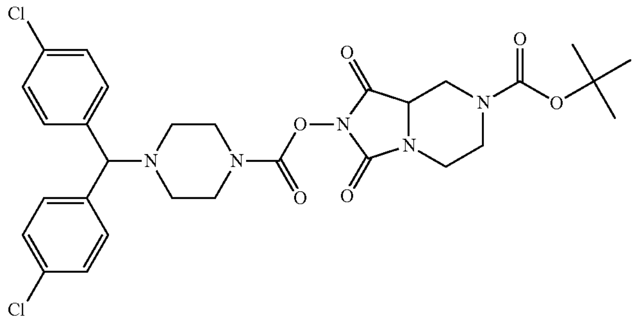 [SMILES: CC(C)(C)OC(=O)N1CCN2C(=O)N(OC(=O)N3CCN(C(c4ccc(Cl)cc4)c4ccc(Cl)cc4)CC3)C(=O)C2C1] | tert-butyl 2-(4-(bis(4-chlorophenyl)methyl)piperazine-1-carbonyloxy)-1,3-dioxohexahydroimidazo[1,5-a]pyrazine-7(1H)-carboxylate |
| 19 | 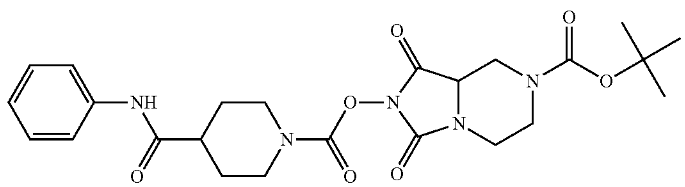 [SMILES: CC(C)(C)OC(=O)N1CCN2C(=O)N(OC(=O)N3CCC(C(=O)Nc4ccccc4)CC3)C(=O)C2C1] | tert-butyl 1,3-dioxo-2-(4-(phenylcarbamoyl)piperidine-1-carbonyloxy)hexahydroimidazo[1,5-a]pyrazine-7(1H)-carboxylate |
| 20 | 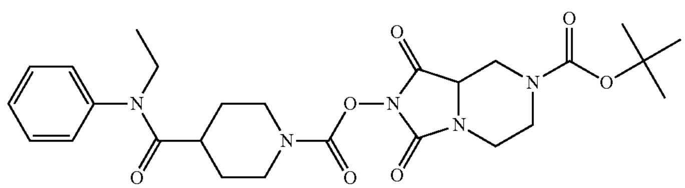 [SMILES: CCN(C(=O)C1CCN(C(=O)ON2C(=O)C3CN(C(=O)OC(C)(C)C)CCN3C2=O)CC1)c1ccccc1] | tert-butyl 2-(4-(ethyl(phenyl)carbamoyl)piperidine-1-carbonyloxy)-1,3-dioxohexahydroimidazo[1,5-a]pyrazine-7(1H)-carboxylate |
| 21 | 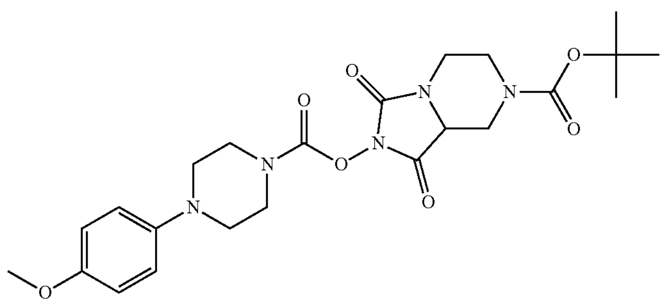 [SMILES: COc1ccc(N2CCN(C(=O)ON3C(=O)C4CN(C(=O)OC(C)(C)C)CCN4C3=O)CC2)cc1] | tert-butyl 2-((4-(4-methoxyphenyl)piperazine-1-carbonyl)oxy)-1,3-dioxohexahydroimidazo[1,5-a]pyrazine-7(1H)-carboxylate |
| 22 | 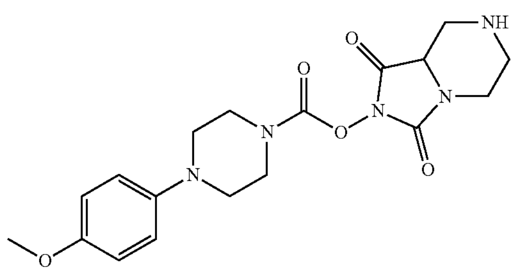 [SMILES: COc1ccc(N2CCN(C(=O)ON3C(=O)C4CNCCN4C3=O)CC2)cc1] | 1,3-dioxohexahydroimidazo[1,5-a]pyrazin-2(3H)-yl 4-(4-methoxyphenyl)piperazine-1-carboxylate |
| 23 | 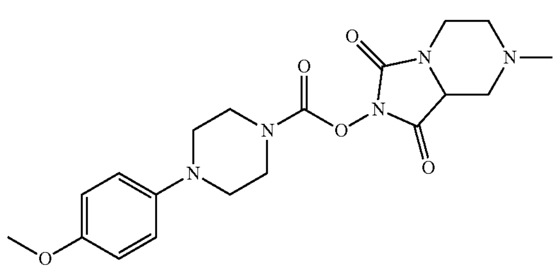 | 7-methyl-1,3-dioxohexahydroimidazo[1,5-a]pyrazin-2(3H)-yl 4-(4-methoxyphenyl)piperazine-1-carboxylate |

TABLE 1-continued

| Cpd. | Structure | Name |
|---|---|---|
| 24 | 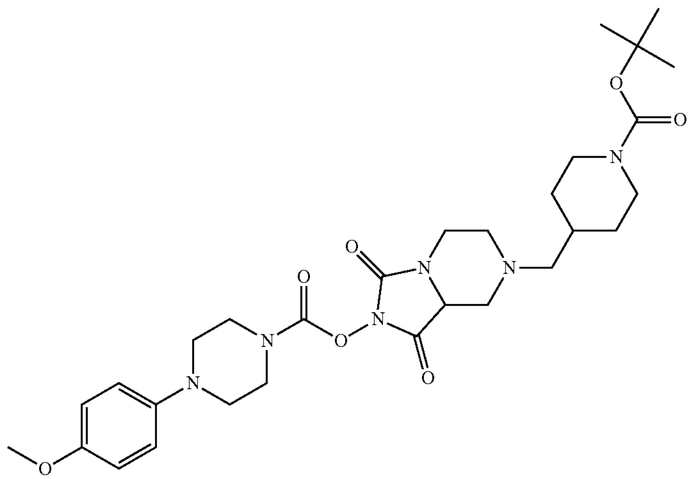 [SMILES: COc1ccc(N2CCN(C(=O)ON3C(=O)C4CN(CC5CCN(C(=O)OC(C)(C)C)CC5)CCN4C3=O)CC2)cc1] | 7-((1-(tert-butoxycarbonyl)piperidin-4-yl)methyl)-1,3-dioxohexahydroimidazo[1,5-a]pyrazin-2(3H)-yl 4-(4-methoxyphenyl)piperazine-1-carboxylate |
| 25 | 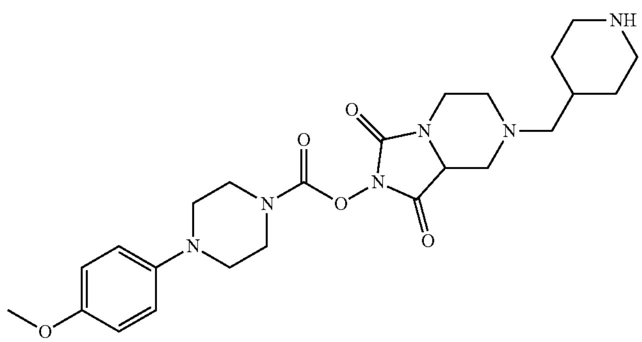 [SMILES: COc1ccc(N2CCN(C(=O)ON3C(=O)C4CN(CC5CCNCC5)CCN4C3=O)CC2)cc1] | 1,3-dioxo-7-(piperidin-4-ylmethyl)hexahydroimidazo[1,5-a]pyrazin-2(3H)-yl 4-(4-methoxyphenyl)piperidine-1-carboxylate |
| 26 | 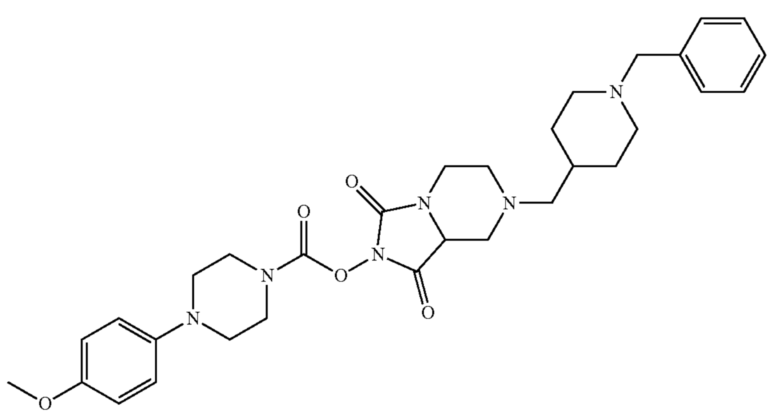 [SMILES: COc1ccc(N2CCN(C(=O)ON3C(=O)C4CN(CC5CCN(Cc6ccccc6)CC5)CCN4C3=O)CC2)cc1] | 7-((1-benzylpiperidin-4-yl)methyl)-1,3-dioxohexahydroimidazo[1,5-a]pyrazin-2(3H)-yl 4-(4-methoxyphenyl)piperazine-1-carboxylate |
| 27 | 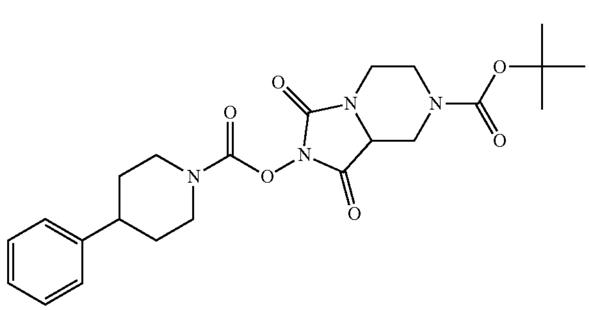 [SMILES: CC(C)(C)OC(=O)N1CCN2C(=O)N(OC(=O)N3CCC(c4ccccc4)CC3)C(=O)C2C1] | tert-butyl 1,3-dioxo-2-((4-phenylpiperidine-1-carbonyl)oxy)hexahydroimidazo[1,5-a]pyrazine-7(1H)-carboxylate |

TABLE 1-continued

| Cpd. | Structure | Name |
|---|---|---|
| 28 | 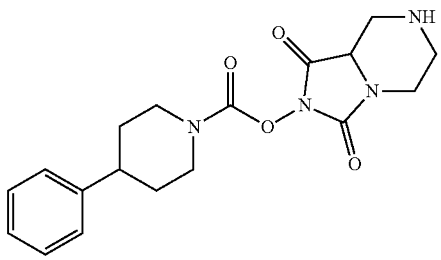 [SMILES: O=C(ON1C(=O)C2CNCCN2C1=O)N1CCC(c2ccccc2)CC1] | 1,3-dioxohexahydroimidazo[1,5-a]pyrazin-2(3H)-yl 4-phenylpiperidine-1-carboxylate |
| 29 | 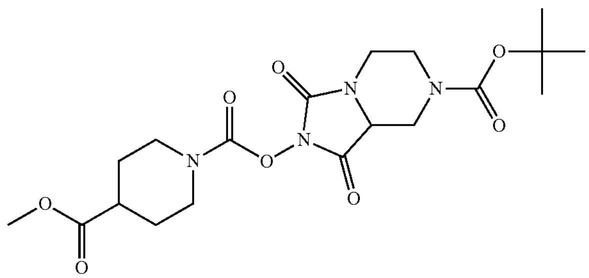 [SMILES: COC(=O)C1CCN(C(=O)ON2C(=O)C3CN(C(=O)OC(C)(C)C)CCN3C2=O)CC1] | 1-(7-(tert-Butoxycarbonyl)-1,3-dioxohexahydroimidazo[1,5-a]pyrazin-2(3H)-yl) 4-methyl piperidine-1,4-dicarboxylate |
| 30 | 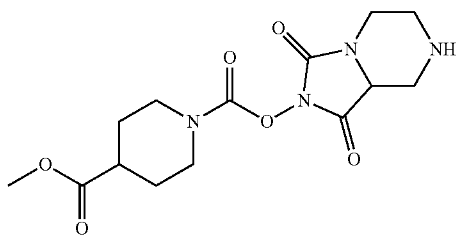 [SMILES: COC(=O)C1CCN(C(=O)ON2C(=O)C3CNCCN3C2=O)CC1] | 1-(1,3-Dioxohexahydroimidazo[1,5-a]pyrazin-2(3H)-yl) 4-methyl piperidine-1,4-dicarboxylate |
| 31 | 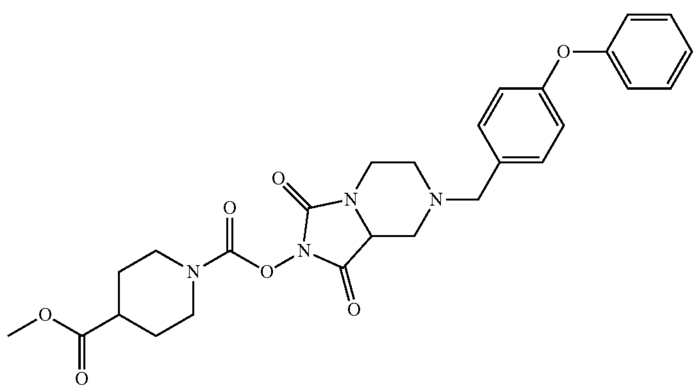 [SMILES: COC(=O)C1CCN(C(=O)ON2C(=O)C3CN(Cc4ccc(Oc5ccccc5)cc4)CCN3C2=O)CC1] | 1-(1,3-dioxo-7-(4-phenoxybenzyl)hexahydroimidazo[1,5-a]pyrazin-2(3H)-yl) 4-methyl piperidine-1,4-dicarboxylate |
| 32 | 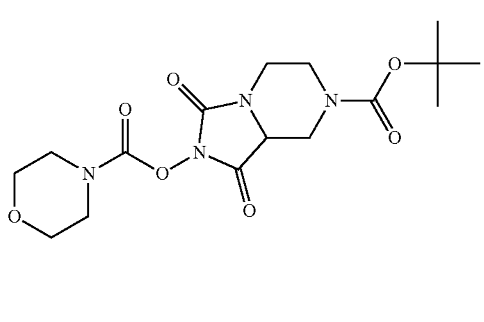 [SMILES: CC(C)(C)OC(=O)N1CCN2C(=O)N(OC(=O)N3CCOCC3)C(=O)C2C1] | 7-(tert-butoxycarbonyl)-1,3-dioxohexahydroimidazo[1,5-a]pyrazin-2(3H)-yl morpholine-4-carboxylate |

TABLE 1-continued

| Cpd. | Structure | Name |
|---|---|---|
| 33 | 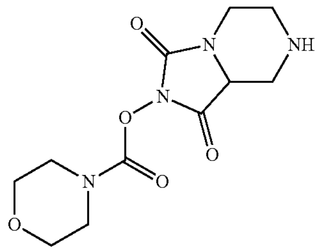 [SMILES: O=C(ON1C(=O)C2CNCCN2C1=O)N1CCOCC1] | 1,3-dioxohexahydroimidazo[1,5-a]pyrazin-2(3H)-yl morpholine-4-carboxylate |
| 34 | 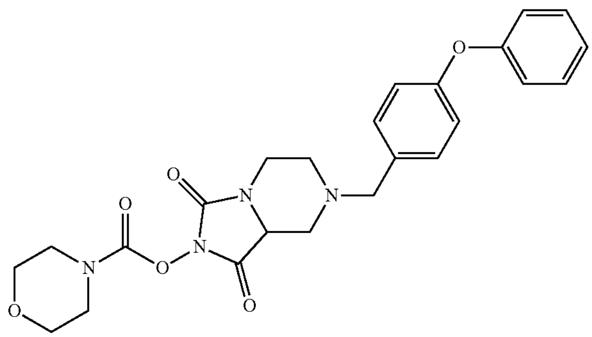 [SMILES: O=C(ON1C(=O)C2CN(Cc3ccc(Oc4ccccc4)cc3)CCN2C1=O)N1CCOCC1] | 1,3-dioxo-7-(4-phenoxybenzyl)hexahydroimidazo[1,5-a]pyrazin-2(3H)-yl morpholine-4-carboxylate |
| 35 | 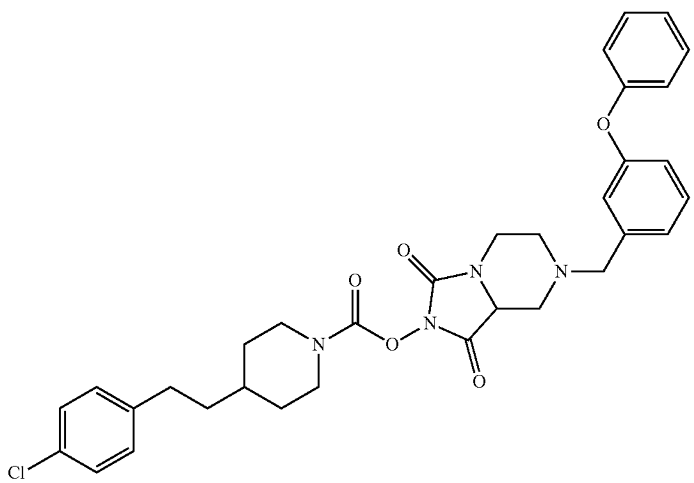 [SMILES: O=C(ON1C(=O)C2CN(Cc3cccc(Oc4ccccc4)c3)CCN2C1=O)N1CCC(CCc2ccc(Cl)cc2)CC1] | 1,3-dioxo-7-(3-phenoxybenzyl)hexahydroimidazo[1,5-a]pyrazin-2(3H)-yl 4-(4-chlorophenethyl)piperidine-1-carboxylate |
| 36 | 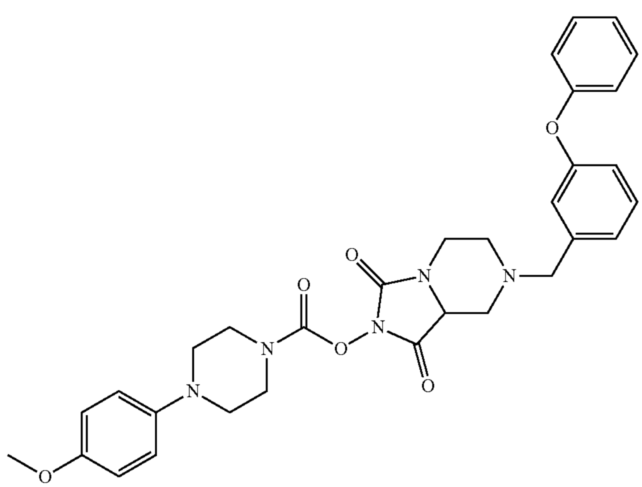 [SMILES: COc1ccc(N2CCN(C(=O)ON3C(=O)C4CN(Cc5cccc(Oc6ccccc6)c5)CCN4C3=O)CC2)cc1] | 1,3-dioxo-7-(3-phenoxybenzyl)hexahydroimidazo[1,5-a]pyrazin-2(3H)-yl 4-(4-methoxyphenyl)piperazine-1-carboxylate |

TABLE 1-continued

| Cpd. | Structure | Name |
|---|---|---|
| 37 | 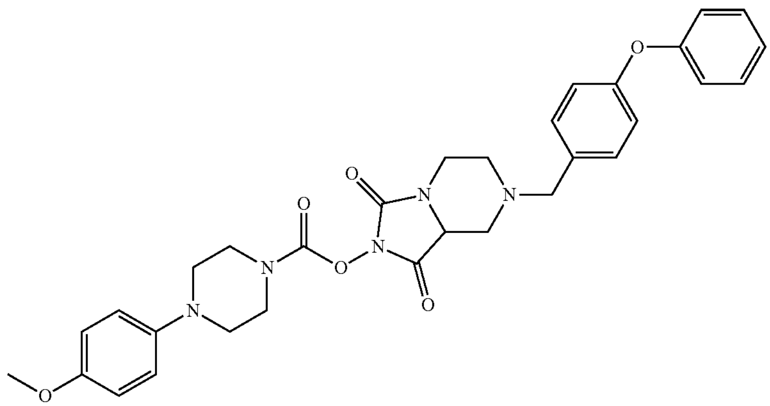 [SMILES: COc1ccc(N2CCN(C(=O)ON3C(=O)C4CN(Cc5ccc(Oc6ccccc6)cc5)CCN4C3=O)CC2)cc1] | 1,3-dioxo-7-(4-phenoxybenzyl)hexahydroimidazo[1,5-a]pyrazin-2(3H)-yl 4-(4-methoxyphenyl)piperazine-1-carboxylate |
| 38 | 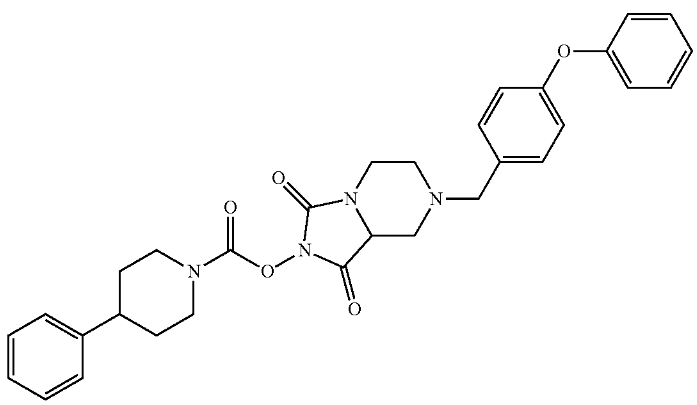 [SMILES: O=C(ON1C(=O)C2CN(Cc3ccc(Oc4ccccc4)cc3)CCN2C1=O)N1CCC(c2ccccc2)CC1] | 1,3-dioxo-7-(4-phenoxybenzyl)hexahydroimidazo[1,5-a]pyrazin-2(3H)-yl 4-phenylpiperidine-1-carboxylate |
| 39 | 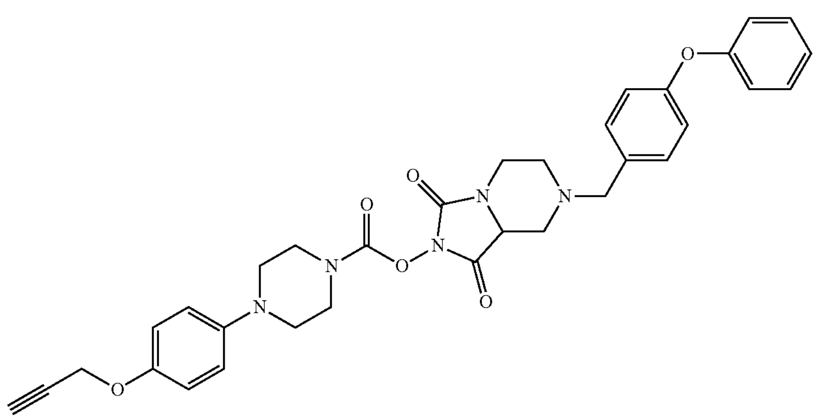 [SMILES: C#CCOc1ccc(N2CCN(C(=O)ON3C(=O)C4CN(Cc5ccc(Oc6ccccc6)cc5)CCN4C3=O)CC2)cc1] | 1,3-dioxo-7-(4-phenoxybenzyl)hexahydroimidazo[1,5-a]pyrazin-2(3H)-yl 4-(4-(prop-2-yn-1-yloxy)phenyl)piperazine-1-carboxylate |
| 40 | 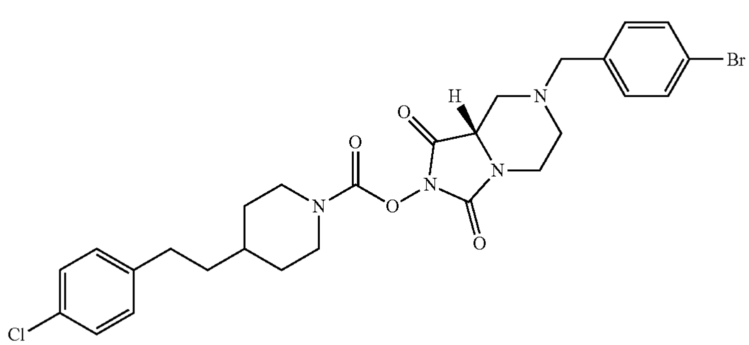 [SMILES: O=C(ON1C(=O)[C@@H]2CN(Cc3ccc(Br)cc3)CCN2C1=O)N1CCC(CCc2ccc(Cl)cc2)CC1] | (S)-7-(4-bromobenzyl)-1,3-dioxohexahydroimidazo[1,5-a]pyrazin-2(3H)-yl 4-(4-chlorophenethyl)piperidine-1-carboxylate |

TABLE 1-continued

| Cpd. | Structure | Name |
|---|---|---|
| 41 | 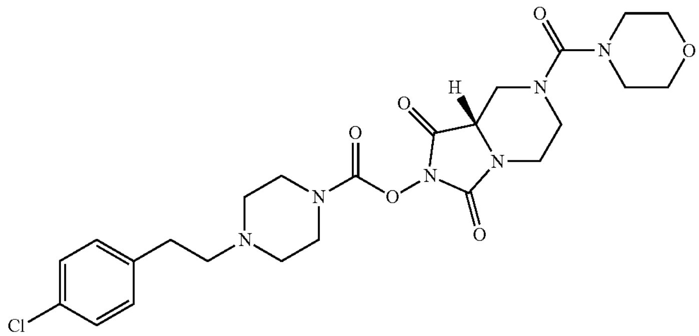 [SMILES: O=C(ON1C(=O)[C@@H]2CN(C(=O)N3CCOCC3)CCN2C1=O)N1CCN(CCc2ccc(Cl)cc2)CC1] | (S)-7-(morpholine-4-carbonyl)-1,3-dioxo-hexahydroimidazo[1,5-a]pyrazin-2(3H)-yl 4-(4-chlorophenethyl)piperazine-1-carboxylate |
| 42 | 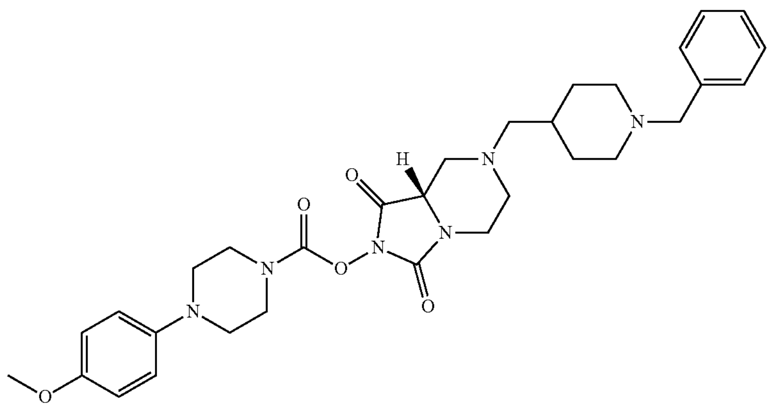 [SMILES: COc1ccc(N2CCN(C(=O)ON3C(=O)[C@@H]4CN(CC5CCN(Cc6ccccc6)CC5)CCN4C3=O)CC2)cc1] | (S)-7-((1-benzylpiperidin-4-yl)methyl)-1,3-dioxo-hexahydroimidazo[1,5-a]pyrazin-2(3H)-yl 4-(4-methoxyphenyl)piperazine-1-carboxylate |
| 43 | 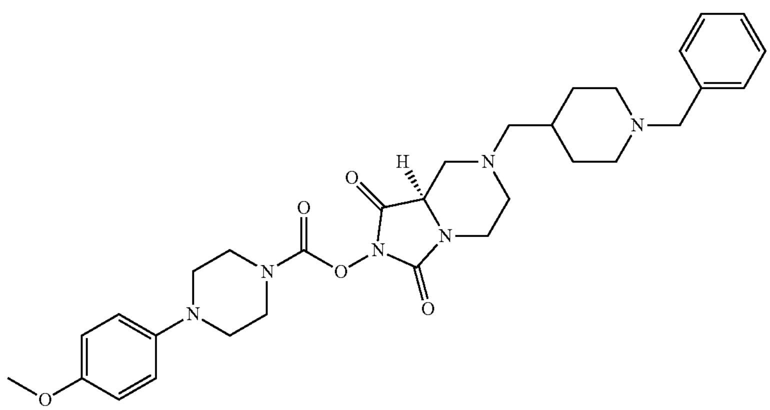 | (R)-7-((1-benzylpiperidin-4-yl)methyl)-1,3-dioxo-hexahydroimidazo[1,5-a]pyrazin-2(3H)-yl 4-(4-methoxyphenyl)piperazine-1-carboxylate |
| 44 | 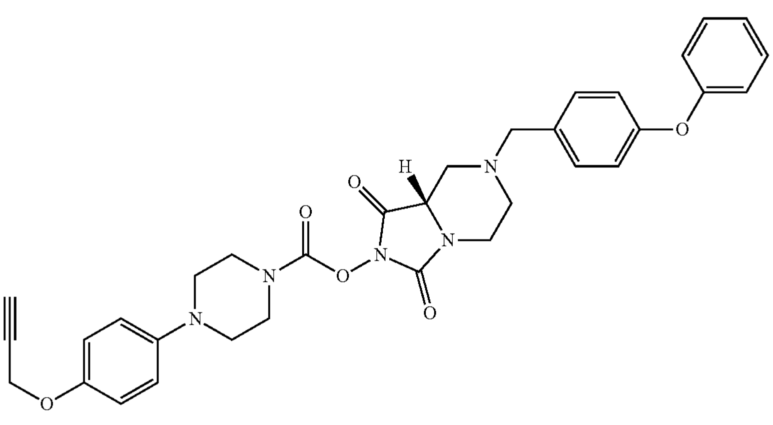 [SMILES: C#CCOc1ccc(N2CCN(C(=O)ON3C(=O)[C@@H]4CN(Cc5ccc(Oc6ccccc6)cc5)CCN4C3=O)CC2)cc1] | (S)-1,3-dioxo-7-(4-phenoxybenzyl)-hexahydroimidazo[1,5-a]pyrazin-2(3H)-yl 4-(4-(prop-2-ynyloxy)phenyl)piperazine-1-carboxylate |

TABLE 1-continued

| Cpd. | Structure | Name |
|---|---|---|
| 45 | 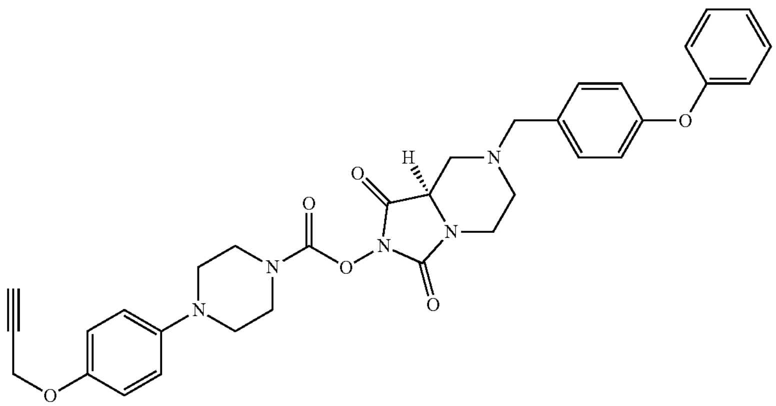 [SMILES: C#CCOc1ccc(N2CCN(C(=O)ON3C(=O)[C@H]4CN(Cc5ccc(Oc6ccccc6)cc5)CCN4C3=O)CC2)cc1] | (R)-1,3-dioxo-7-(4-phenoxybenzyl)-hexahydroimidazo[1,5-a]pyrazin-2(3H)-yl 4-(4-(prop-2-ynyloxy)phenyl)piperazine-1-carboxylate |
| 46 | 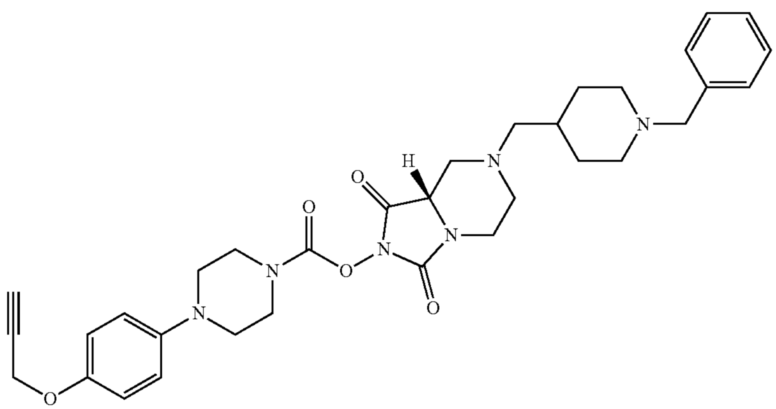 [SMILES: C#CCOc1ccc(N2CCN(C(=O)ON3C(=O)[C@@H]4CN(CC5CCN(Cc6ccccc6)CC5)CCN4C3=O)CC2)cc1] | (S)-7-((1-benzylpiperidin-4-yl)methyl)-1,3-dioxo-hexahydroimidazo[1,5-a]pyrazin-2(3H)-yl 4-(4-(prop-2-ynyloxy)phenyl)piperazine-1-carboxylate |
| 47 | 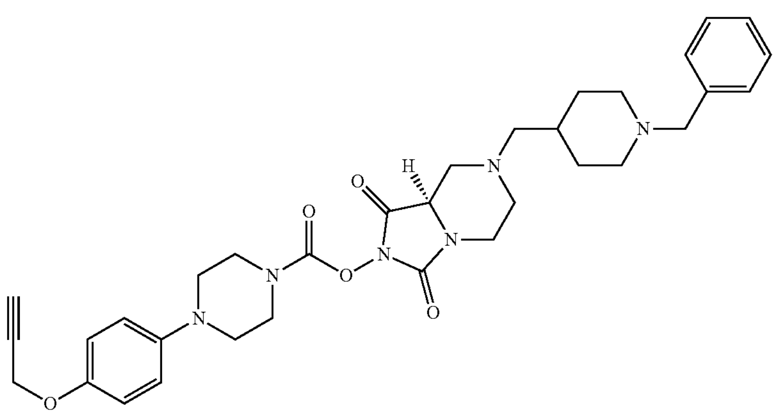 [SMILES: C#CCOc1ccc(N2CCN(C(=O)ON3C(=O)[C@H]4CN(CC5CCN(Cc6ccccc6)CC5)CCN4C3=O)CC2)cc1] | (R)-7-((1-benzylpiperidin-4-yl)methyl)-1,3-dioxo-hexahydroimidazo[1,5-a]pyrazin-2(3H)-yl 4-(4-(prop-2-ynyloxy)phenyl)piperazine-1-carboxylate |
| 48 | 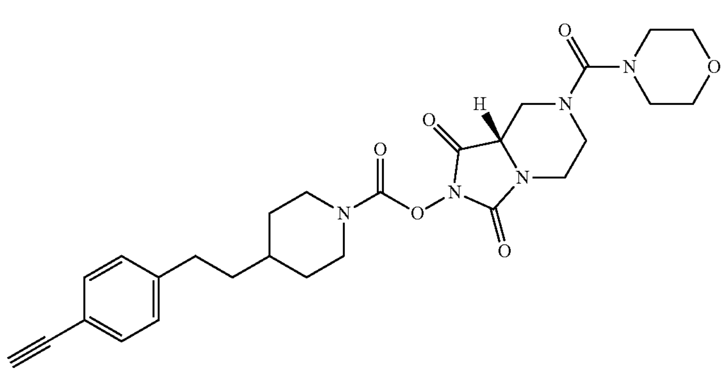 [SMILES: C#Cc1ccc(CCC2CCN(C(=O)ON3C(=O)[C@@H]4CN(C(=O)N5CCOCC5)CCN4C3=O)CC2)cc1] | (S)-7-(morpholine-4-carbonyl)-1,3-dioxo-hexahydroimidazo[1,5-a]pyrazin-2(3H)-yl 4-(4-ethynylphenethyl)piperidine-1-carboxylate |

TABLE 1-continued

| Cpd. | Structure | Name |
|---|---|---|
| 49 | 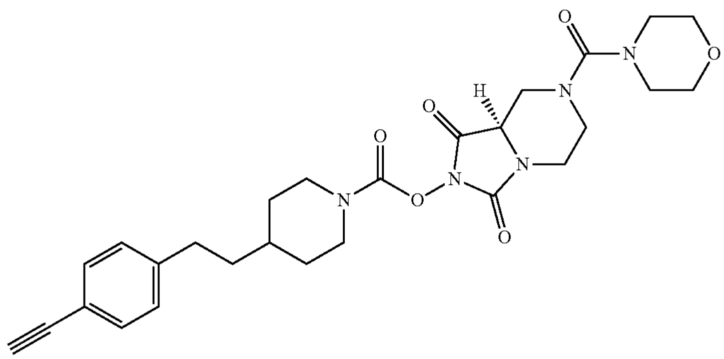 [SMILES: C#Cc1ccc(CCC2CCN(C(=O)ON3C(=O)[C@H]4CN(C(=O)N5CCOCC5)CCN4C3=O)CC2)cc1] | (R)-7-(morpholine-4-carbonyl)-1,3-dioxo-hexahydroimidazo[1,5-a]pyrazin-2(3H)-yl 4-(4-ethynylphenethyl)piperidine-1-carboxylate |
| 50 | 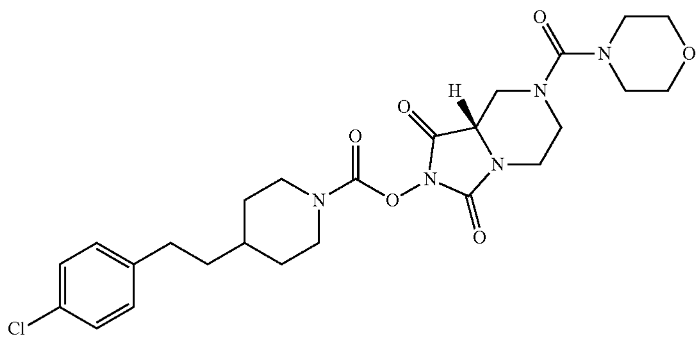 [SMILES: O=C(ON1C(=O)[C@@H]2CN(C(=O)N3CCOCC3)CCN2C1=O)N1CCC(CCc2ccc(Cl)cc2)CC1] | (S)-7-(morpholine-4-carbonyl)-1,3-dioxohexahydroimidazo[1,5-a]pyrazin-2(3H)-yl 4-(4-chlorophenethyl)piperidine-1-carboxylate |
| 51 | 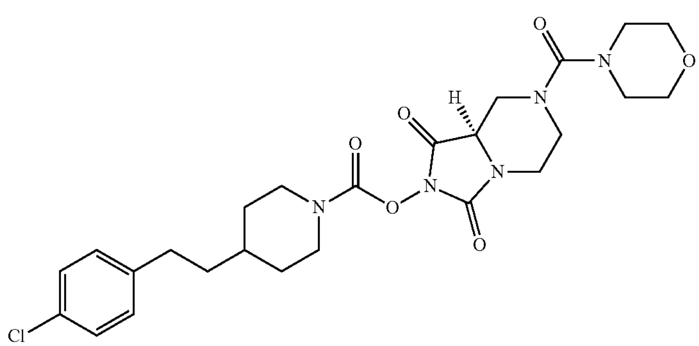 [SMILES: O=C(ON1C(=O)[C@H]2CN(C(=O)N3CCOCC3)CCN2C1=O)N1CCC(CCc2ccc(Cl)cc2)CC1] | (R)-7-(morpholine-4-carbonyl)-1,3-dioxohexahydroimidazo[1,5-a]pyrazin-2(3H)-yl 4-(4-chlorophenethyl)piperidine-1-carboxylate |
| 52 | 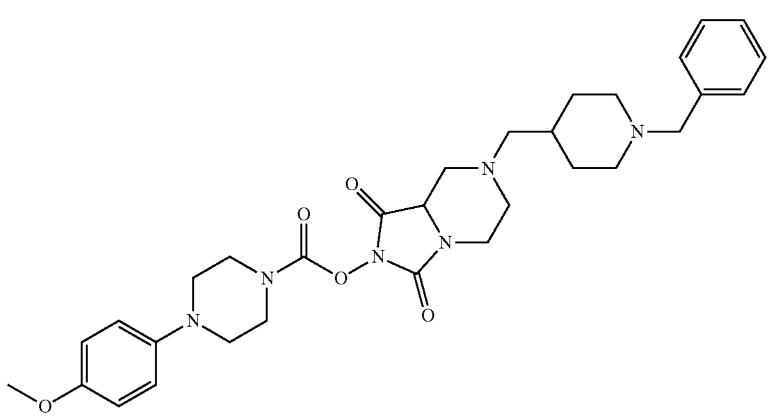 [SMILES: COc1ccc(N2CCN(C(=O)ON3C(=O)C4CN(CC5CCN(Cc6ccccc6)CC5)CCN4C3=O)CC2)cc1] | 7-((1-benzylpiperidin-4-yl)methyl)-1,3-dioxo-hexahydroimidazo[1,5-a]pyrazin-2(3H)-yl 4-(4-methoxyphenyl)piperazine-1-carboxylate |

TABLE 1-continued

| Cpd. | Structure | Name |
|---|---|---|
| 53 | 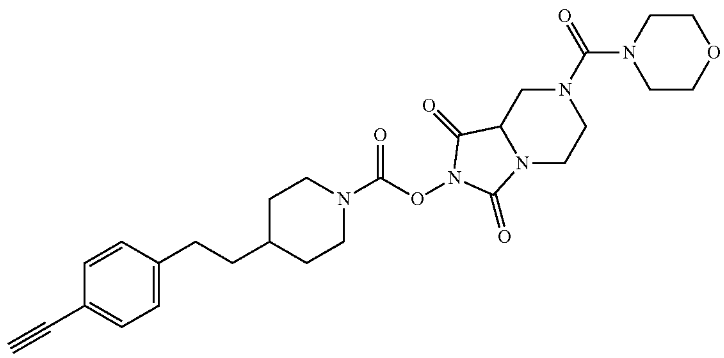 [SMILES: C#Cc1ccc(CCC2CCN(C(=O)ON3C(=O)C4CN(C(=O)N5CCOCC5)CCN4C3=O)CC2)cc1] | 7-(morpholine-4-carbonyl)-1,3-dioxo-hexahydroimidazo[1,5-a]pyrazin-2(3H)-yl 4-(4-ethynylphenethyl)piperidine-1-carboxylate |

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.,). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the N-hydroxy bicyclic hydantoin carbamates described herein is P. H. Stahl & C. G. Wermuth "Handbook of Pharmaceutical Salts", Verlag Helvetica Chimica Acta, Zurich, 2002.

The N-hydroxy bicyclic hydantoin carbamates were prepared by the general synthetic routes described below in Schemes 1-2.

Scheme 1

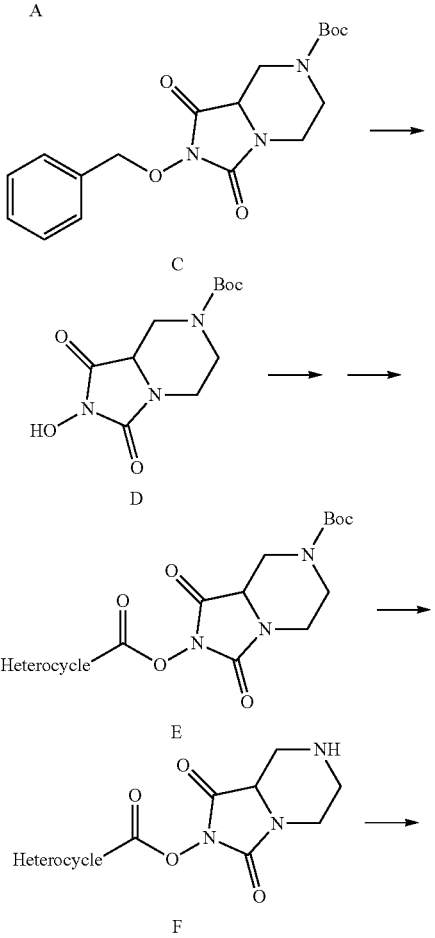

Scheme 2

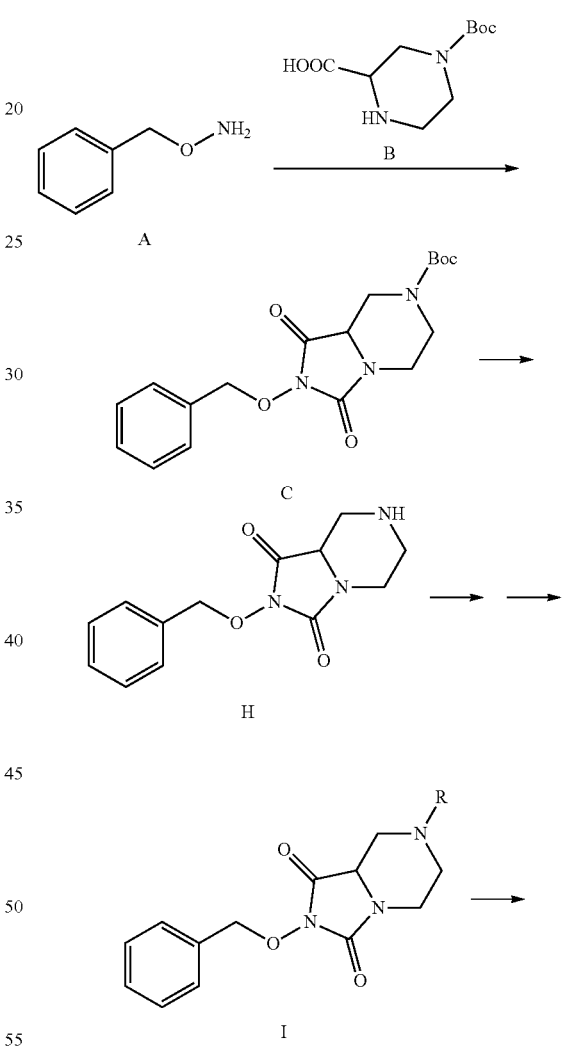

chloride is a morpholine carbonyl chloride. Intermediate E was then deprotected in the presence of an acid to afford Intermedate F which was then further functionalized to produce a compound of formula G. In some embodiments, intermediate F was reacted with a $R^{100}COCl$. In some embodiments, $R^{100}$ is heterocyclyl selected from morpholine, piperidine, or pyrrolidine. In some embodiments, $R^{100}$ is alkyl. In some embodiments, $R^{100}$ is aryl. In some embodiments, $R^{100}$ is aralkyl. In some embodiments, intermediate F was reacted with $R^{101}CHO$ under reductive amination conditions. In some embodiments, $R^{101}$ is aryl. In some embodiments, $R^{101}$ is heterocyclyl.

A method for preparing compounds of formula G is provided in Scheme 1. Coupling of O-benzylhydroxylamine (A) with 4-Boc-piperazine-2-carboxylic acid (B) followed by cyclization afforded intermediate C. Following benzyl deprotection with hydrogen in the presence of a catalytic amount of Pd/C, intermediate D was coupled with a heterocyclyl carbonyl chloride to afford Intermediate E. In some embodiments, the heterocyclyl carbonyl chloride is a piperidine carbonyl chloride. In some embodiments, the heterocyclyl carbonyl chloride is a piperazine carbonyl chloride. In some embodiments, the heterocyclyl carbonyl

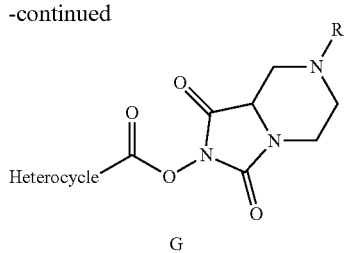

G

An alternate method for preparing compounds of formula G is provided in Scheme 2. The Boc protecting group of Intermediate C was removed in the presence of an acid, followed by reaction with $R^{100}COCl$ or $R^{101}CHO$ as described above to afford Intermediate I. Intermediate I was then deprotected to afford intermediate J. Intermediate J was then coupled with a heterocyclyl carbonyl chloride to afford compound s of formula G as described in Scheme 1.

Further Forms of N-Hydroxy Bicyclic Hydantoin Carbamates Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. In some embodiments, the methods disclosed herein include methods of inhibiting a serine hydrolase by exposing the serine hydrolase to such isotopically-labeled compounds. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions. The invention also provides for methods of inhibiting a serine hydrolase by exposing the serine hydrolase to such pharmaceutically acceptable salts.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions. The invention also provides for methods of inhibiting a serine hydrolase by exposing the serine hydrolase to such solvates.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the N-hydroxy bicyclic hydantoin carbamate as described herein is administered as a pure chemical. In other embodiments, the N-hydroxy bicyclic hydantoin carbamate described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one N-hydroxy bicyclic hydantoin carbamate described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof.

In certain embodiments, the N-hydroxy bicyclic hydantoin carbamate as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous) rectal, vaginal, or aerosol administration.

Methods

Disclosed herein are methods of modulating the activity of a serine hydrolase in mammalian cells. Contemplated methods, for example, comprise exposing said enzyme to a compound described herein. In some embodiments, the method comprises contacting the mammalian cells with a compound described herein. In some embodiments, the compound utilized by one or more of the foregoing methods is one of the generic, subgeneric, or specific compounds described herein, such as a compound of Formula (I). In some embodiments, the method is an in vitro method. In some methods, the method is an in vivo method. The ability of compounds described herein to modulate or inhibit a serine hydrolase is evaluated by procedures known in the art and/or described herein.

Another aspect of this disclosure provides methods of treating a disease associated with expression or activity of a serine hydrolase in a patient. Contemplated methods include administering a pharmaceutically effective amount of a compound disclosed herein or a pharmaceutical composition thereof.

In some embodiments of the methods disclosed herein, the serine hydrolase is: a lysophospholipase, such as, but not limited to, LYPLA1 and LYPLA2; a serine protease, including, but not limited to, trypsin, chymotrypsin, and subtilisin; an extracellular lipase, including, but not limited to, pancreatic lipase, hepatic lipase, gastric lipase, endothelial lipase, and lipoprotein lipase; an intracellular lipase, including, but not limited to, hormone sensitive lipase, monoacylglycerol lipase, adipose triglyceride lipase, and diacylglycerol lipase; a cholinesterase, including, but not limited to, acetylcholinesterase and butyrylcholinesterase; a thioesterase, including, but not limited to, fatty acid synthase (such as palmitoyl), acyl-CoA thioesterases; a phospholipase, including, but not limited to, phospholipase A2 and platelet activating factor acetylhydrolase; a protein or glycan hydrolase, including, but not limited to, protein phosphate methylesterase 1, acyloxyacyl hydrolase and sialic acid acetylesterase; an amidase, including, but not limited to, fatty acid amide hydrolase; or a peptidase, including, but not limited to, dipeptidyl peptidase 4, fibroblast activation protein, and prolylendopeptidase.

In some embodiments of the methods disclosed herein, the serine hydrolase is DDHD2, FAM108B1, FAM108A1, RBBP9, NCEH1, LYPLAL1, CES2, CES3, PAFAH2, PAFAH1B2, PAFAH1B3, SCPEP1, ACHE, DPP8, PRCP, PLAT, PNPLA4, PNPLA6, PNPLA8, PARL, OVCA2, DAGLB, PREP, PREPL, ESD, PPME1, CPVL, CTSA, PPT1, PPT2, PLA2G15, ABHD3, ABHD4, ABHD6, ABHD10, ABHD11, ABHD12, ABHD16A, APEH, SIAE, ACOT2, ACOT7, DPP4, DPP7, DPP9, PLA2G7, LONP1, FASN, TPP2, MGLL, LYPLA1, LYPLA2, LIPE, LIPA, or FAAH. In some embodiments, the serine hydrolase is DDHD2. In some embodiments, the serine hydrolase is FAM108B1. In some embodiments, the serine hydrolase is FAM108A1. In some embodiments, the serine hydrolase is RBBP9. In some embodiments, the serine hydrolase is NCEH1. In some embodiments, the serine hydrolase is LYPLAL1. In some embodiments, the serine hydrolase is CES2. In some embodiments, the serine hydrolase is CES3. In some embodiments, the serine hydrolase is PAFAH2. In some embodiments, the serine hydrolase is PAFAH1B2. In some embodiments, the serine hydrolase is PAFAH1B3. In some embodiments, the serine hydrolase is SCPEP1. In some embodiments, the serine hydrolase is ACHE. In some embodiments, the serine hydrolase is DPP8. In some embodiments, the serine hydrolase is PRCP. In some embodiments, the serine hydrolase is PLAT. In some embodiments, the serine hydrolase is PNPLA4. In some embodiments, the serine hydrolase is PNPLA6. In some embodiments, the serine hydrolase is PNPLA8. In some embodiments, the serine hydrolase is PARL. In some embodiments, the serine hydrolase is OVCA2. In some embodiments, the serine hydrolase is DAGLB. In some embodiments, the serine hydrolase is PREP. In some embodiments, the serine hydrolase is PREPL. In some embodiments, the serine hydrolase is ESD. In some embodiments, the serine hydrolase is PPME1. In some embodiments, the serine hydrolase is CPVL. In some embodiments, the serine hydrolase is CTSA. In some embodiments, the serine hydrolase is PPT1. In some embodiments, the serine hydrolase is PPT2. In some embodiments, the serine hydrolase is PLA2G15. In some embodiments, the serine hydrolase is ABHD3. In some embodiments, the serine hydrolase is ABHD4. In some embodiments, the serine hydrolase is ABHD6. In some embodiments, the serine hydrolase is ABHD10. In some embodiments, the serine hydrolase is ABHD11. In some embodiments, the serine hydrolase is ABHD12. In some embodiments, the serine hydrolase is ABHD16A. In some embodiments, the serine hydrolase is APEH. In some embodiments, the serine hydrolase is SIAE. In some embodiments, the serine hydrolase is ACOT2. In some embodiments, the serine hydrolase is ACOT7. In some embodiments, the serine hydrolase is DPP4. In some embodiments, the serine hydrolase is DPP7. In some embodiments, the serine hydrolase is DPP9. In some embodiments, the serine hydrolase is PLA2G7. In some embodiments, the serine hydrolase is LONP1. In some embodiments, the serine hydrolase is FASN. In some embodiments, the serine hydrolase is TPP2. In some embodiments, the serine hydrolase is MGLL. In some embodiments, the serine hydrolase is LYPLA1. In some embodiments, the serine hydrolase is LYPLA2. In some embodiments, the serine hydrolase is LIPE. In some embodiments, the serine hydrolase is LIPA. In some embodiments, the serine hydrolase is FAAH.

Another embodiment provides a method of modulation of a protein-palmitoyl thioesterase, comprising contacting the protein-palmitoyl thioesterase with an effective amount or concentration of an N-hydroxy bicyclic hydantoin carbamate described herein. In some embodiments, the protein-palmitoyl thioesterase is LYPLA1, LYPLA2, or both. In some embodiments, the protein-palmitoyl thioesterase is PPT1.

Another embodiment provides a method of treatment of a medical condition in a patient, wherein modulation of a protein-palmitoyl thioesterase is medically indicated, comprising administering an effective dose of an N-hydroxy bicyclic hydantoin carbamate described herein or a pharmaceutical composition thereof. In some embodiments, the protein-palmitoyl thioesterase is LYPLA1, LYPLA2, or both. In some embodiments, the protein-palmitoyl thioesterase is PPT1.

Another embodiment provides a method of modulation of a phospholipase, comprising contacting the phospholipase with an effective amount or concentration of an N-hydroxy bicyclic hydantoin carbamate described herein. In some embodiments, the phospholipase is ABHD3, ABHD4, ABHD6, ABHD10, ABHD11, ABHD12, or ABHD16A. In some embodiments the phospholipase is ABHD3, ABHD4, or both.

Another embodiment provides a method of treatment of a medical condition in a patient, wherein modulation of a phospholipase is medically indicated, comprising administering an effective dose of an N-hydroxy bicyclic hydantoin carbamate described herein or a pharmaceutical composition thereof. In some embodiments, the phospholipase is ABHD3, ABHD4, ABHD6, ABHD10, ABHD11, ABHD12, or ABHD16A. In some embodiments the phospholipase is ABHD3, ABHD4, or both.

Also disclosed herein are methods of treating and/or preventing in a patient in need thereof a disorder such as one or more of cancer, pain, diabetes, obesity/metabolic syndrome, epilepsy, traumatic brain injury, and inflammation. In some embodiments, the disorder is cancer.

In some embodiments, the disorder is pain. In some embodiments, the disorder is diabetes. In some embodiments, the disorder is obesity/metabolic syndrome. In some embodiments, the disorder is epilepsy. In some embodiments, the disorder is traumatic brain injury. In some embodiments, the disorder is inflammation. In some embodiments, the disorder is pain and inflammation. In some embodiments, the disorder is pain or inflammation. Disclosed methods include administering a pharmaceutically effective amount of an N-hydroxy bicyclic hydantoin carbamate described herein or a pharmaceutical composition thereof.

In certain embodiments, a disclosed compound utilized by one or more of the foregoing methods is one of the generic, subgeneric, or specific compounds described herein, such as a compound of Formula (I).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

For example, e.g., for contemplated treatment of pain and/or inflammation, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics, e.g., for the treatment of pain that are co-administered include, but are not limited to, morphine, codeine, hydromorphone, hydrocodone, oxymorphone, fentanyl, tramadol, and levorphanol.

Other contemplated therapeutics for co-administration include, but are not limited to, aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

The following examples are provided merely as illustrative of various embodiments and shall not be construed to limit the invention in any way.

EXAMPLES

I. Chemical Synthesis

Unless otherwise noted, all reagents, including dry solvents, were purchased from Sigma-Aldrich, Acros, Fisher, Fluka, Thermo, or CellGro and used without further purification. All chemical synthesis reactions were carried out under a nitrogen atmosphere using oven-dried glassware. Flash chromatography was performed using 230-400 mesh silica gel. NMR spectra were recorded on a Varian Inova-400 spectrometer and were referenced to trimethylsilane (TMS) or the residual solvent peak. Chemical shifts are reported in ppm relative to TMS and J values are reported in Hz. High resolution mass spectrometry (HRMS) experiments were performed on an Agilent mass spectrometer using electrospray ionization-time of flight (ESI-TOF). Mass spectrometry (MS) experiments were performed on an Agilent 1100 series MSD. All other protocols are summarized below.

Compound 1 was erroneously described as being commercially available from Sigma as ALD00010 in U.S. Provisional Application No. 62/001,869 filed on May 22, 2014 from which this international application claims priority. Compound 1 was in fact not commercially available at the time of filing of U.S. Provisional Application No. 62/001,869.

Example 1: Preparation of 7-(morpholine-4-carbonyl)-1,3-dioxohexahydroimidazo[1,5-a]pyrazin-2(3H)-yl 4-(4-chloro-phenethyl)piperidine-1-carboxylate (Compound 1, JJH-254)

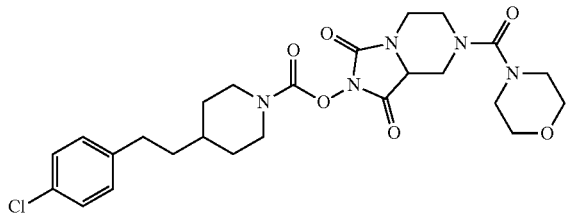 [SMILES: O=C(ON1C(=O)C2CN(C(=O)N3CCOCC3)CCN2C1=O)N1CCC(CCc2ccc(Cl)cc2)CC1]

Step 1: tert-Butyl 2-(benzyloxy)-1,3-dioxohexahydroimidazo[1,5-a]pyrazine-7(1H)-carboxylate

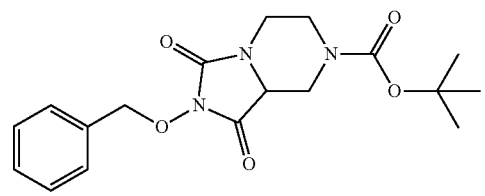 [SMILES: CC(C)(C)OC(=O)N1CCN2C(=O)N(OCc3ccccc3)C(=O)C2C1]

To a stirred solution of O-benzylhydroxylamine (1.73 g, 10.8 mmol, 1 equiv) and N-methylmorpholine (NMM; 1.3 mL, 1.1 equiv) in $CH_2Cl_2$ (55 mL) at 0° C. was added 1,1'-carbonyldiimidazole (CDI; 1.76 g, 1 equiv). The resulting solution was allowed to warm to 25° C. and stirred for 2 h. At this time, 4-Boc-piperazine-2-carboxylic acid (2.0 g, 8.7 mmol, 0.8 equiv) was added in one portion, followed by additional NMM (1.9 mL, 1.6 equiv). The resulting suspension was stirred for 24 h at 2° C., at which time moisture was notably generated in the reaction vessel; $Na_2SO_4$ was added, followed by additional $CH_2Cl_2$ (110 mL), and the mixture was stirred for an additional 24 h. The suspension was then filtered, concentrated by rotary evaporation under reduced pressure, and the resulting residue separated by silica gel flash chromatography (40% EtOAc/hexanes) to yield tert-butyl 2-(benzyloxy)-1,3-dioxohexahydroimidazo[1,5-a]pyrazine-7(1H)-carboxylate (2.1 g, 66%) as a white solid. $^1$H NMR ($CDCl_3$, 400 MHz) δ 7.50 (m, 2H), 7.39 (m, 3H), 5.17 (s, 2H), 4.43 (bs, 1H), 4.14 (bs, 1H), 4.01 (dd, J=13.6 Hz, 3.6 Hz, 1H), 3.86 (m, 1H), 2.96 (m, 1H), 2.64 (m, 1H), 2.47 (m, 1H), 1.46 (s, 9H). MS calculated for $C_{18}H_{23}N_3O_5$ [M+H]$^+$ 362.2, found 362.3.

Step 2: tert-Butyl 2-hydroxy-1,3-dioxohexahydroimidazo[1,5-a]pyrazine-7(1H)-carboxylate

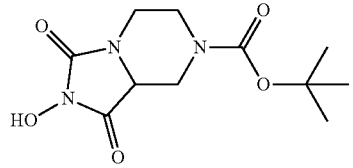 [SMILES: CC(C)(C)OC(=O)N1CCN2C(=O)N(O)C(=O)C2C1]

To tert-butyl 2-(benzyloxy)-1,3-dioxohexahydroimidazo[1,5-a]pyrazine-7(1H)-carboxylate (300 mg, 0.83 mmol, 1 equiv) dissolved in EtOAc (4 mL) was added palladium on carbon (10% w/w; 85 mg, ~10 mol %). The suspension was sparged with hydrogen gas, and then stirred under an atmosphere of hydrogen at ambient pressure overnight at 25° C. At this time, the mixture was filtered over celite and concentrated, quantitatively yielding tert-butyl 2-hydroxy-1,3-dioxohexahydroimidazo[1,5-a]pyrazine-7(1H)-carboxylate as a crystalline white solid that was used without further purification. $^1$H NMR (CDCl$_3$, 400 MHz) δ 4.56 (bs, 1H), 4.13 (m, 2H), 4.04 (m, 2H), 3.06 (m, 1H), 2.78 (m, 2H), 1.46 (s, 9H). MS calculated for C$_{11}$H$_{17}$N$_3$O$_5$ [M+H]$^+$ 272.1, found 272.1.

Step 3: tert-Butyl 2-(4-(4-chlorophenethyl)piperidine-1-carbonyloxy)-1,3-dioxohexahydroimidazo[1,5-a]pyrazine-7(1H)-carboxylate

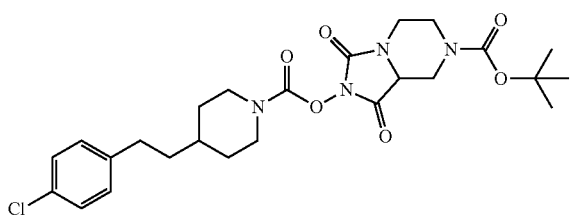 [SMILES: CC(C)(C)OC(=O)N1CCN2C(=O)N(OC(=O)N3CCC(CCc4ccc(Cl)cc4)CC3)C(=O)C2C1]

To a stirred solution of tert-butyl 2-hydroxy-1,3-dioxohexahydroimidazo[1,5-a]pyrazine-7(1H)-carboxylate (225 mg, 0.83 mmol, 1 equiv) in THF (3 mL) at 25° C. was added triethylamine (260 μL, ~3 equiv), and a catalytic amount of 4-dimethylaminopyridine (4-DMAP). After solubilization of the reagents, 4-(4-chlorophenethyl)piperidine-1-carbonyl chloride (350 mg, 1.5 equiv) was added to the reaction, and the solution warmed to 60° C. and stirred for 2 h. The reaction was cooled to 25° C., and the precipitate (triethylammonium hydrochloride) filtered off and washed with additional THF. The combined filtrates were concentrated by rotary evaporation under reduced pressure, and the residue was used in the next step without further purification. An analytical sample was purified by prep-TLC (50% EtOAc/hexanes) to yield tert-butyl 2-(4-(4-chlorophenethyl)piperidine-1-carbonyloxy)-1,3-dioxohexahydroimidazo[1,5-a]pyrazine-7(1H)-carboxylate as a white solid. MS calculated for C$_{25}$H$_{33}$ClN$_4$O$_6$ [M+Na]$^+$ 543.2, found 543.2.

Step 4: 1,3-Dioxohexahydroimidazo[1,5-a]pyrazin-2(3H)-yl 4-(4-chlorophenethyl)piperidine-1-carboxylate hydrochloride tert-Butyl 2-(4-(4-chlorophenethyl)piperidine-1-carbonyloxy)-1,3-dioxohexahydroimidazo[1,5-a]pyrazine-7(1H)-carboxylate was dissolved in 2 N methanolic HCl (10 mL) at 0° C. The stirred solution was allowed to warm to 25° C. over the course of 30 minutes. The solvent was removed, and the resulting 1,3-dioxohexahydroimidazo[1,5-a]pyrazin-2(3H)-yl 4-(4-chlorophenethyl)piperidine-1-carboxylate hydrochloride was used without further purification (325 mg, 86% over 2 steps). An analytical sample was prepared by recrystallization of the salt from MeOH/Et$_2$O, yielding white needles. $^1$H NMR (CDCl$_3$, 400 MHz) δ 7.25 (d, J=8 Hz, 2H), 7.09 (d, J=8 Hz, 2H), 4.85 (d, J=10.8 Hz, 1H), 4.28 (d, J=14.4 Hz, 1H), 4.18 (d, J=13.6 Hz, 1H), 4.05 (m, 2H), 3.68 (m, 2H), 3.02 (m, 3H), 2.63 (m, 1H) 1.45-1.81 (m, 9H), 1.33 (m, 1H). MS calculated for C$_{20}$H$_{25}$ClN$_4$O$_4$ [M+H]$^+$ 421.2, found 421.1.

Step 5: 7-(Morpholine-4-carbonyl)-1,3-dioxohexahydroimidazo[1,5-a]pyrazin-2(3H)-yl 4-(4-chlorophenethyl)piperidine-1-carboxylate 1,3-Dioxohexahydroimidazo[1,5-a]pyrazin-2(3H)-yl 4-(4-chlorophenethyl)piperidine-1-carboxylate hydrochloride (40 mg, 0.09 mmol, 1 equiv) was suspended in THF (500 μL) at 25° C., and triethylamine (30 μL, 3 equiv) was added, followed by a catalytic amount of 4-DMAP, and then 4-morpholinecarbonyl chloride (16 μL, 1.5 equiv). The resulting solution was heated at 60° C. for 2 h. After cooling to 25° C., the triethylammonium hydrochloride was removed by filtration, and the filtrates concentrated by rotary evaporation under reduced pressure. The residue was separated by prep-TLC (100% EtOAc) to yield 7-(morpholine-4-carbonyl)-1,3-dioxohexahydroimidazo[1,5-a]pyrazin-2(3H)-yl4-(4-chloro-phenethyl)piperidine-1-carboxylate as a white solid (39.8 mg, 85%). $^1$H NMR (CDCl$_3$, 400 MHz) δ 7.25 (d, J=8.4 Hz, 2H), 7.09 (d, J=8.4 Hz, 2H), 4.22 (m, 2H), 4.09 (m, 2H) (4.06, s, 1H), 3.70 (m, 4H), 3.68 (s, 1H), 3.32 (m, 4H), 3.12 (m, 1H), 2.95 (m, 2H), 2.87 (m, 1H), 2.61 (m, 2H), 1.79 (d, J=13.2 Hz, 2H), 1.25-1.59 (m, 6H). HRMS calculated for C$_{25}$H$_{32}$ClN$_5$O$_6$ [M+H]$^+$ 534.2114, found 534.2116.

Example 2: Preparation of 1,3-dioxo-7-(piperidine-1-carbonyl)hexahydroimidazo[1,5-a]pyrazin-2(3H)-yl 4-(4-chlorophenethyl)piperidine-1-carboxylate (Compound 2, JJH-250)

The title compound was prepared by the method of Example 1 using 1-piperidinecarbonyl chloride in place of 4-morpholinecarbonyl chloride. MS calculated for $C_{26}H_{34}ClN_5O_5$ [M+H]$^+$ 532. found 532.

Example 3: Preparation of 1,3-dioxo-7-(pyrrolidine-1-carbonyl)hexahydroimidazo[1,5-a]pyrazin-2(3H)-yl 4-(4-chlorophenethyl)piperidine-1-carboxylate (Compound 3, JJH-247)

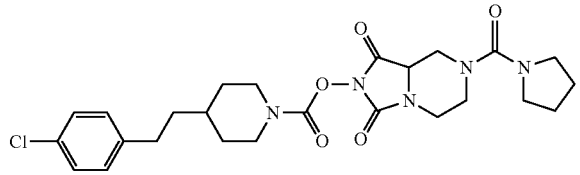 [SMILES: O=C(ON1C(=O)C2CN(C(=O)N3CCCC3)CCN2C1=O)N1CCC(CCc2ccc(Cl)cc2)CC1]

The title compound was prepared by the method of Example 1 using 1-pyrrolidinecarbonyl chloride in place of 4-morpholinecarbonyl chloride. MS calculated for $C_{25}H_{32}ClN_5O_5$ [M+H]$^+$ 518, found 518.

Example 4: Preparation of 7-(3,3-dimethylbutanoyl)-1,3-dioxohexahydroimidazo[1,5-a]pyrazin-2(3H)-yl 4-(4-chlorophenethyl)piperidine-1-carboxylate (Compound 4, JJH-246)

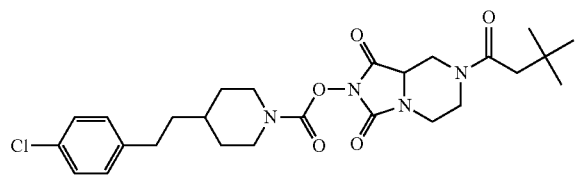 [SMILES: CC(C)(C)CC(=O)N1CCN2C(=O)N(OC(=O)N3CCC(CCc4ccc(Cl)cc4)CC3)C(=O)C2C1]

The title compound was prepared by the method of Example 1 using t-butylacetyl chloride in place of 4-morpholinecarbonyl chloride. MS calculated for $C_{26}H_{35}ClN_4O_5$ [M+H]$^+$ 519, found 519.

Example 5: Preparation of tert-butyl 2-(4-(4-chlorophenethyl)piperidine-1-carbonyloxy)-1,3-dioxohexahydroimidazo[1,5-a]pyrazine-7(1H)-carboxylate (Compound 5, JJH-221)

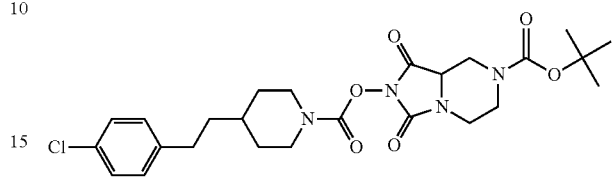

The title compound 5 was prepared as shown in Step 3 of Example 1. MS calculated for $C_{25}H_{33}ClN_4O_6$ [M+H]$^+$ 521, found 521.

Example 6: Preparation of 1,3-dioxo-7-(2-phenylacetyl)hexahydroimidazo[1,5-a]pyrazin-2(3H)-yl 4-(4-chlorophenethyl)piperidine-1-carboxylate (Compound 6, JJH-249)

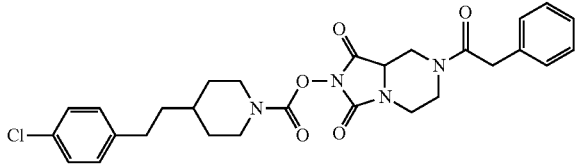 [SMILES: O=C(Cc1ccccc1)N1CCN2C(=O)N(OC(=O)N3CCC(CCc4ccc(Cl)cc4)CC3)C(=O)C2C1]

The title compound was prepared by the method of Example 1 using phenylacetyl chloride in place of 4-morpholinecarbonyl chloride. MS calculated for $C_{28}H_{31}ClN_4O_5$ [M+H]$^+$ 539, found 539.

Example 7: Preparation of 7-(4-bromobenzoyl)-1,3-dioxohexahydroimidazo[1,5-a]pyrazin-2(3H)-yl 4-(4-chlorophenethyl)piperidine-1-carboxylate (Compound 7, JJH-248)

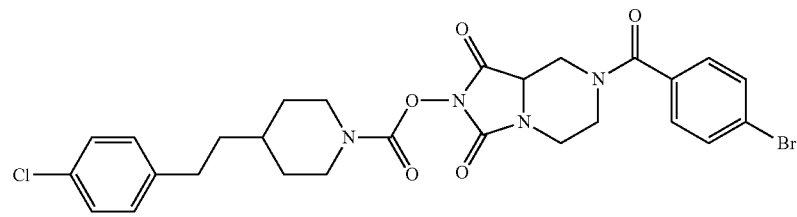

The title compound was prepared by the method of Example 1 using 4-bromobenzoyl chloride in place of 4-morpholinecarbonyl chloride. MS calculated for $C_{27}H_{28}BrClN_4O_5$ [M+H]$^+$ 603, found 603.

Example 8: Preparation of 7-(4-methylbenzoyl)-1,3-dioxohexahydroimidazo[1,5-a]pyrazin-2(3H)-yl 4-(4-chlorophenethyl)piperidine-1-carboxylate (Compound 8, JJH-258)

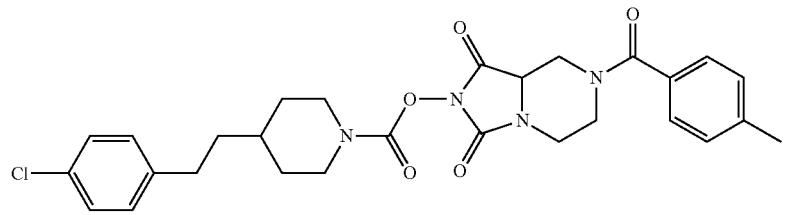 [SMILES: Cc1ccc(C(=O)N2CCN3C(=O)N(OC(=O)N4CCC(CCc5ccc(Cl)cc5)CC4)C(=O)C3C2)cc1]

The title compound was prepared by the method of Example 1 using toluoyl chloride in place of 4-morpholinecarbonyl chloride. MS calculated for $C_{28}H_{31}ClN_4O_5$ [M+H]$^+$ 539, found 539.

Example 9: Preparation of 7-(4-fluoro-3-nitrobenzoyl)-1,3-dioxohexahydroimidazo[1,5-a]pyrazin-2(3H)-yl 4-(4-chlorophenethyl)piperidine-1-carboxylate (Compound 9, JJH-259)

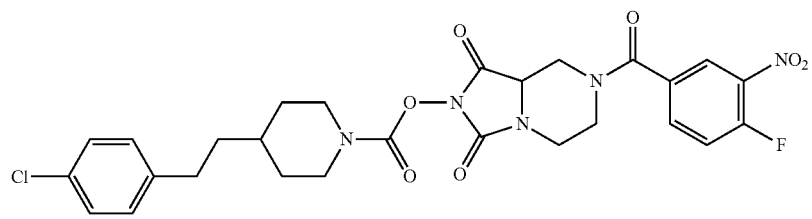 [SMILES: O=C(ON1C(=O)C2CN(C(=O)c3ccc(F)c([N+](=O)[O-])c3)CCN2C1=O)N1CCC(CCc2ccc(Cl)cc2)CC1]

The title compound was prepared by the method of Example 1 using 4-fluoro-3-nitrobenzoyl chloride in place of 4-morpholinecarbonyl chloride. MS calculated for $C_{27}H_{27}ClFN_5O_7$ [M+NH$_4$]$^+$ 605, found 605.

Example 10: Preparation of 7-(4-(dimethylamino)benzoyl)-1,3-dioxohexahydroimidazo[1,5-a]pyrazin-2(3H)-yl4-(4-chlorophenethyl)piperidine-1-carboxylate (Compound 10, JJH-260)

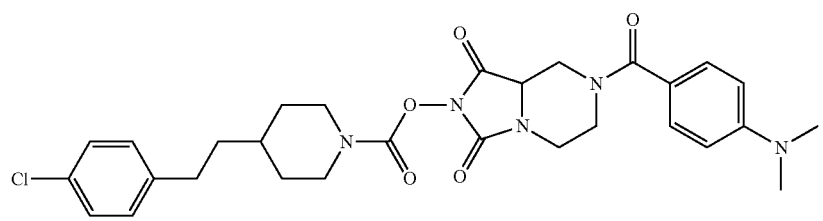 [SMILES: CN(C)c1ccc(C(=O)N2CCN3C(=O)N(OC(=O)N4CCC(CCc5ccc(Cl)cc5)CC4)C(=O)C3C2)cc1]

The title compound was prepared by the method of Example 1 using 4-dimethylaminobenzoyl chloride in place of 4-morpholinecarbonyl chloride. MS calculated for $C_{29}H_{34}ClN_5O_5$ [M+H]$^+$ 568, found 568.

Example 11: Preparation of 7-(4-methoxybenzoyl)-1,3-dioxohexahydroimidazo[1,5-a]pyrazin-2(3H)-yl 4-(4-chlorophenethyl)piperidine-1-carboxylate (Compound 11, JJH-261)

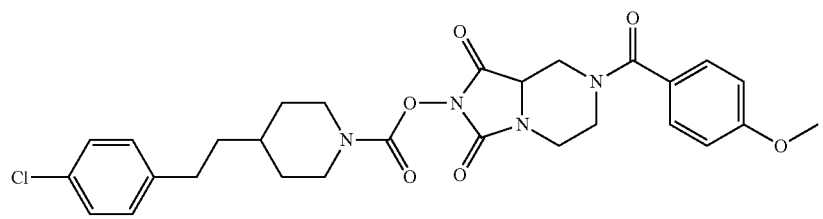 [SMILES: COc1ccc(C(=O)N2CCN3C(=O)N(OC(=O)N4CCC(CCc5ccc(Cl)cc5)CC4)C(=O)C3C2)cc1]

The title compound was prepared by the method of Example 1 using 4-methoxybenzoyl chloride in place of 4-morpholinecarbonyl chloride. MS calculated for $C_{28}H_{31}ClN_4O_6$ [M+H]$^+$ 555, found 555.

Example 12: Preparation of 1,3-dioxo-7-phenethyl-hexahydroimidazo[1,5-a]pyrazin-2(3H)-yl 4-(4-chlorophenethyl)piperidine-1-carboxylate (Compound 12, JJH-252)

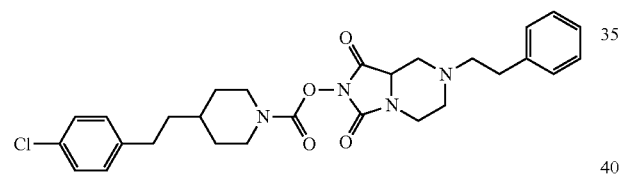

The title compound was prepared by the method of Example 1, but the final acylation step was substituted with a reductive amination (according to the method of Example 13, see below) using 1,3-dioxohexahydroimidazo[1,5-a]pyrazin-2(3H)-yl 4-(4-chlorophenethyl)piperidine-1-carboxylate hydrochloride (1 equiv) (Example 1, step 4), phenylacetaldehyde (2.4 equiv), and NaBH(OAc)$_3$ (1.4 equiv). MS calculated for $C_{28}H_{33}ClN_4O_4$ [M+H]$^+$ 525, found 525.

Example 13: Preparation of 7-(4-bromobenzyl)-1,3-dioxohexahydroimidazo[1,5-a]pyrazin-2(3H)-yl 4-(4-chlorophenethyl)piperidine-1-carboxylate (Compound 13, JJH-251)

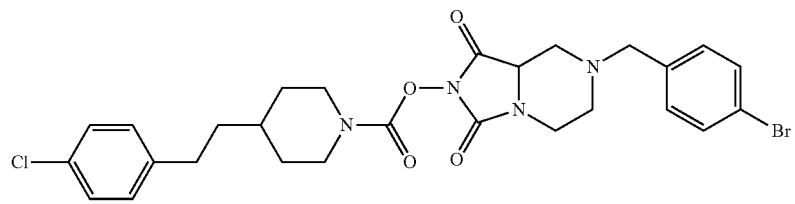 [SMILES: O=C(ON1C(=O)C2CN(Cc3ccc(Br)cc3)CCN2C1=O)N1CCC(CCc2ccc(Cl)cc2)CC1]

The title compound was prepared by the method of Example 1, but the final acylation step was substituted with the following reductive amination: 7.3 mg (0.016 mmol, 1 equiv) of 1,3-dioxohexahydroimidazo[1,5-a]pyrazin-2(3H)-yl 4-(4-chlorophenethyl)piperidine-1-carboxylate hydrochloride (Example 1, step 4) was suspended in 0.2 ml THF, followed by 1 µl HOAc (~1 equiv), 7 mg (2.4 equiv) 4-bromobenzaldehyde and 5.5 mg (1.4 equiv) NaBH(OAc)$_3$. The resultant slurry was stirred at room temperature overnight, diluted with sat. aq. NaHCO$_3$, and extracted twice with CH$_2$Cl$_2$. The combined extracts were combined, dried over Na$_2$SO$_4$, and concentrated in vacuo. The resulting residue was purified by prep-TLC (40% EtOAc/hexanes+1% triethylamine) yielding a white solid (5.4 mg, 57%). MS calculated for $C_{27}H_{30}BrClN_4O_4$ [M+H]$^+$ 589, found 589.

Example 14: Preparation of tert-butyl 1,3-dioxo-2-(piperidine-1-carbonyloxy)hexahydroimidazo[1,5-a]pyrazine-7(1H)-carboxylate (Compound 14, JJH-235)

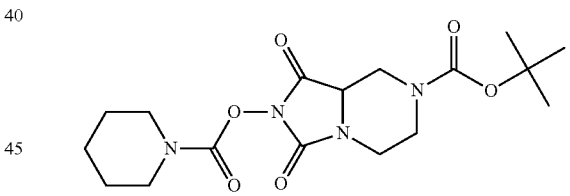

The title compound was prepared by the method of Example 1, Step 3, using 1-piperidinecarbonyl chloride in place of 4-(4-chlorophenethyl)piperidine-1-carbonyl chloride. MS calculated for $C_{17}H_{26}N_4O_6$ [M+NH$_4$]$^+$ 400, found 400.

Example 15: Preparation of 1-(7-(tert-butoxycarbonyl)-1,3-dioxohexahydroimidazo[1,5-a]pyrazin-2(3H)-yl) 4-methyl piperidine-1,4-dicarboxylate (Compound 15, JJH-238)

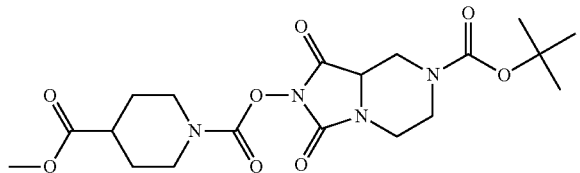 [SMILES: COC(=O)C1CCN(C(=O)ON2C(=O)C3CN(C(=O)OC(C)(C)C)CCN3C2=O)CC1]

The title compound was prepared by the method Example 1, Step 3, using 4-carboxymethylpiperidine carbonyl chloride in place of 4-(4-chlorophenethyl)piperidine-1-carbonyl chloride. MS calculated for $C_{19}H_{28}N_4O_8$ $[M+NH_4]^+$ 458, found 458.

Example 16: Preparation of 7-(tert-butoxycarbonyl)-1,3-dioxohexahydroimidazo[1,5-a]pyrazin-2(3H)-yl 3-benzylmorpholine-4-carboxylate (Compound 16, JJH-240)

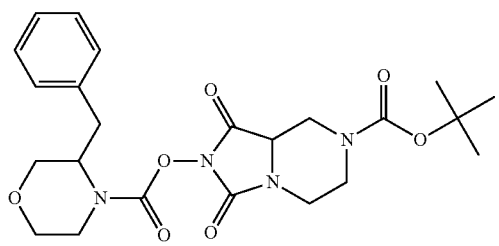 [SMILES: CC(C)(C)OC(=O)N1CCN2C(=O)N(OC(=O)N3CCOCC3Cc3ccccc3)C(=O)C2C1]

The title compound was prepared by the method of Example 1, Step 3, using racemic 3-benzylmorpholinecarbonyl chloride in place of 4-(4-chlorophenethyl)piperidine-1-carbonyl chloride. MS calculated for $C_{23}H_{30}N_4O_7$ $[M+NH_4]^+$ 492, found 492.

Example 17: Preparation of tert-butyl 1,3-dioxo-2-(4-phenethylpiperazine-1-carbonyloxy)hexahydroimidazo[1,5-a]pyrazine-7(1H)-carboxylate (Compound 17, JJH-241)

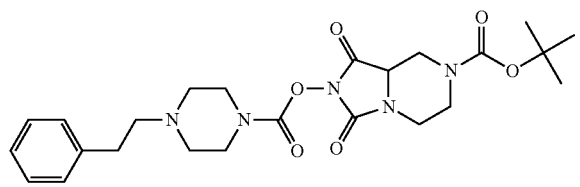 [SMILES: CC(C)(C)OC(=O)N1CCN2C(=O)N(OC(=O)N3CCN(CCc4ccccc4)CC3)C(=O)C2C1]

The title compound was prepared by the method of Example 1, Step 3, using 4-phenethyl-1-piperazinecarbonyl chloride in place of 4-(4-chlorophenethyl)piperidine-1-carbonyl chloride. MS calculated for $C_{24}H_{33}N_5O_6$ $[M+H]^+$ 488, found 488.

Example 18: Preparation of tert-butyl 2-(4-(bis(4-chlorophenyl)methyl)piperazine-1-carbonyloxy)-1,3-dioxohexahydroimidazo[1,5-a]pyrazine-7(1H)-carboxylate (Compound 18, JJH-242)

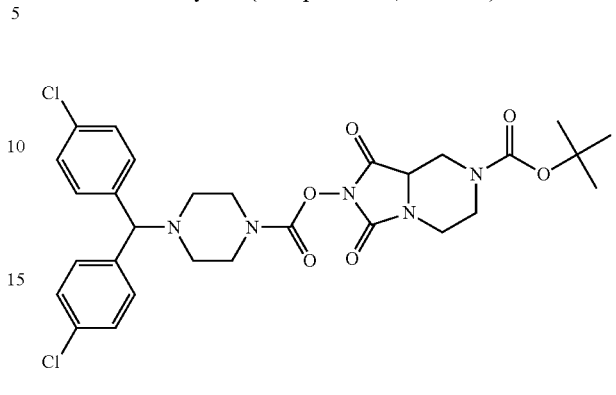

The title compound was prepared by the method of Example 1, Step 3, using 4-(bis(4-chlorophenyl)methyl)piperazine-1-carbonyl chloride in place of 4-(4-chlorophenethyl)piperidine-1-carbonyl chloride. MS calculated for $C_{29}H_{33}Cl_2N_5O_6$ $[M+H]^+$ 618, found 618.

Example 19: Preparation of tert-butyl 1,3-dioxo-2-(4-(phenylcarbamoyl)piperidine-1-carbonyloxy)hexahydroimidazo[1,5-a]pyrazine-7(1H)-carboxylate (Compound 19, JJH-243)

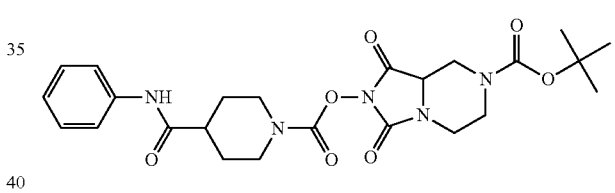

The title compound was prepared by the method of Example 1, Step 3, using 4-(phenylcarbamoyl)piperidine-1-carbonyl chloride in place of 4-(4-chlorophenethyl)piperidine-1-carbonyl chloride. MS calculated for $C_{24}H_{31}N_5O_7$ $[M+NH_4]^+$ 519, found 519.

Example 20: Preparation of tert-butyl 2-(4-(ethyl(phenyl)carbamoyl)piperidine-1-carbonyloxy)-1,3-dioxohexahydroimidazo[1,5-a]pyrazine-7(1H)-carboxylate (Compound 20, JJH-244)

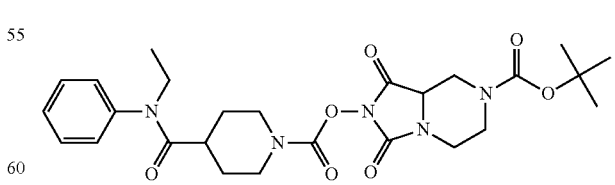

The title compound was prepared by the method of Example 1, Step 3, using 4-(ethyl(phenyl)carbamoyl)piperidine-1-carbonyl chloride in place of 4-(4-chlorophenethyl)piperidine-1-carbonyl chloride. MS calculated for $C_{26}H_{35}N_5O_7$ $[M+NH_4]^+$ 547, found 547.

Example 21: Preparation of tert-butyl 2-((4-(4-methoxyphenyl)piperazine-1-carbonyl)oxy)-1,3-dioxohexahydroimidazo[1,5-a]pyrazine-7(1H)-carboxylate (Compound 21, MJN202)

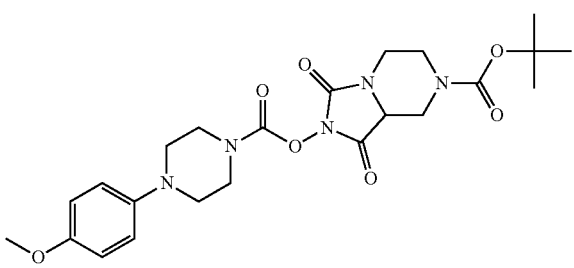 [SMILES: COc1ccc(N2CCN(C(=O)ON3C(=O)C4CN(C(=O)OC(C)(C)C)CCN4C3=O)CC2)cc1]

Step 1: 4-(4-methoxyphenyl)piperazine-1-carbonyl chloride

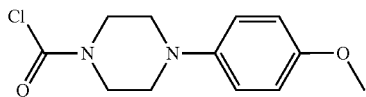

1-(4-Methoxyphenyl)piperazine (14.25 g, 74.1 mmol, 1 equiv) was dissolved in 120 ml dry THF, and pyridine (30 ml, ~5 equiv) was added, and the resulting solution was cooled to 0° C. At this time, triphosgene (11 g, 0.5 equiv) was added in small portions. The resulting mixture was allowed to warm to room temperature and was stirred overnight. The mixture was filtered, concentrated, and the residue was separated by flash chromatography over SiO₂ to yield 4-(4-methoxyphenyl)piperazine-1-carbonyl chloride (1.0 g, 5%) as a pale yellow solid. ¹H NMR (CDCl₃, 400 MHz) δ 6.88 (m, 4H), 3.90 (m, 2H), 3.81 (m, 2H), 3.78 (s, 3H), 3.11 (m, 4H). HRMS calculated for $C_{12}H_{16}ClN_2O_2$ [M+H]⁺ 255.0895, found 255.0895.

Step 2: tert-butyl 2-((4-(4-methoxyphenyl)piperazine-1-carbonyl)oxy)-1,3-dioxohexahydroimidazo[1,5-a]pyrazine-7(1H)-carboxylate

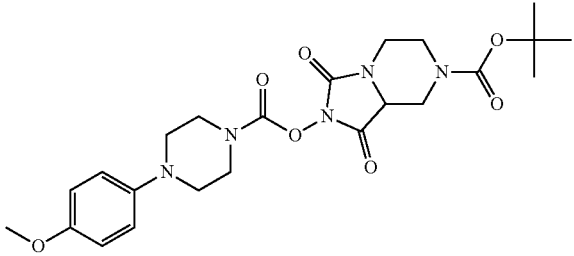 [SMILES: COc1ccc(N2CCN(C(=O)ON3C(=O)C4CN(C(=O)OC(C)(C)C)CCN4C3=O)CC2)cc1]

tert-Butyl 2-hydroxy-1,3-dioxohexahydroimidazo[1,5-a]pyrazine-7(1H)-carboxylate (Example 1, Step 2, 200 mg, 0.737 mmol, 1 equiv) was dissolved in 3.5 ml dry THF, and triethylamine (225 µl, 3 equiv) and a catalytic amount of 4-DMAP, followed by 4-(4-methoxyphenyl)piperazine-1-carbonyl chloride (188 mg, 1 equiv) at room temperature. The solution was heated at 60° C. for 2 h, filtered, and concentrated to a residue without further purification (267 mg, 93% over two steps). A sample was separated by prep-TLC (60% EtOAc/hexanes) for analysis to yield an off-white solid. ¹H NMR (CDCl3, 500 MHz) δ 6.90 (m, 2H), 6.84 (m, 2H), 4.55 (m, 1H), 4.18 (m, 1H), 4.08 (m, 2H), 3.80 (m, 2H), 3.77 (s, 3H), 3.67 (m, 2H), 3.07 (m, 4H), 3.02 (m, 1H), 2.84 (m, 2H), 1.46 (s, 9H). HRMS calculated for $C_{23}H_{32}N_5O_7$ [M+H]⁺ 490.2296, found 490.2296.

Example 22: Preparation of 1,3-dioxohexahydroimidazo[1,5-a]pyrazin-2(3H)-yl 4-(4-methoxyphenyl)piperazine-1-carboxylate (Compound 22, JJH331)

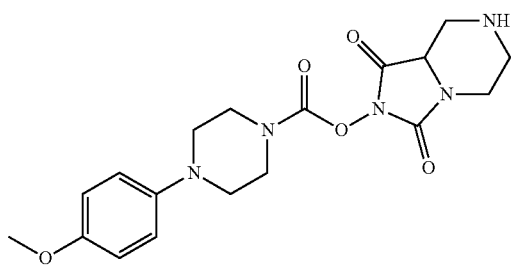 [SMILES: COc1ccc(N2CCN(C(=O)ON3C(=O)C4CNCCN4C3=O)CC2)cc1]

tert-Butyl 2-((4-(4-methoxyphenyl)piperazine-1-carbonyl)oxy)-1,3-dioxohexahydroimidazo[1,5-a]pyrazine-7(1H)-carboxylate was Boc deprotected using methanolic HCl as described for Example 1, Step 4, yielding a white solid, after recrystallization from MeOH/ether (266.6 mg, 93%). ¹H NMR (D₂O, 400 MHz) δ 7.47 (d, J=6.8 Hz, 2H), 7.14 (d, J=6.8 Hz, 2H), 4.85 (m, 1H), 4.37 (m, 1H), 4.09 (m, 2H), 3.98 (m, 1H), 3.94 (m, 2H), 3.88 (s, 3H), 3.68 (m, 1H), 3.66 (m, 4H), 3.56 (m, 1H), 3.41 (m, 1H), 3.29 (m, 1H). HRMS calculated for $C_{18}H_{24}N_5O_5$ [M+H]⁺ 390.1772, found 390.1772.

Example 23: Preparation of 7-methyl-1,3-dioxohexahydroimidazo[1,5-a]pyrazin-2(3H)-yl 4-(4-methoxyphenyl)piperazine-1-carboxylate (Compound 23, MJN200)

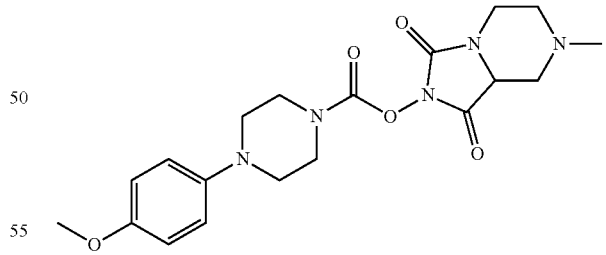

1,3-Dioxohexahydroimidazo[1,5-a]pyrazin-2(3H)-yl 4-(4-methoxyphenyl)piperazine-1-carboxylate (hydrochloride; 20 mg, 0.047 mmol, 1 equiv) was suspended in 0.2 ml dry THF, and formaldehyde (6 µl, 37% wt. in water, 1.5 equiv), acetic acid (2.8 µl, 1 equiv) and NaBH(OAc)₃ (11 mg, 1.1 equiv) were added at room temperature. The resulting suspension was stirred at room temperature overnight, concentrated to a residue, and separated by prep-TLC (EtOAc+1% triethylamine) to yield 7-methyl-1,3-dioxohexahydroimidazo[1,5-a]pyrazin-2(3H)-yl 4-(4-methoxyphenyl)piperazine-1-carboxylate as an off-white solid (12 mg, 63%). ¹H NMR (CDCl₃, 400 MHz) δ 6.90 (m, 2H), 6.85 (m, 2H), 4.18 (m, 1H), 4.06 (m, 1H), 3.80 (m, 2H), 3.77 (s, 3H), 3.67 (m, 2H), 3.23 (m, 1H), 3.17 (m, 1H), 3.14 (m, 4H), 3.06 (m, 1H), 2.80 (m, 1H), 2.37 (s, 3H), 2.08 (m, 2H). HRMS calculated for $C_{19}H_{26}N_5O_5$ [M+H]⁺ 404.1928, found 404.1930.

Example 24: Preparation of 7-((1-(tert-butoxycarbonyl)piperidin-4-yl)methyl)-1,3-dioxohexahydroimidazo[1,5-a]pyrazin-2(3H)-yl 4-(4-methoxyphenyl)piperazine-1-carboxylate (Compound 24, ABC37)

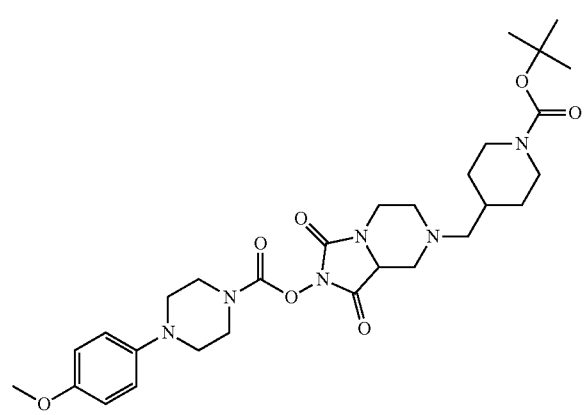 [SMILES: COc1ccc(N2CCN(C(=O)ON3C(=O)C4CN(CC5CCN(C(=O)OC(C)(C)C)CC5)CCN4C3=O)CC2)cc1]

The title compound was prepared as described in Example 23, using N-Boc-4-piperidine carboxaldehyde in place of formaldehyde. (36.4 mg, 66%). ¹H NMR (CDCl₃, 500 MHz) δ 6.90 (d, J=10 Hz, 2H), 6.85 (d, J=10 Hz, 2H), 4.15 (m, 2H), 4.04 (m, 2H), 3.77 (s, 3H), 3.67 (m, 2H), 3.26 (m, 1H), 3.14 (m, 1H), 3.11 (m, 4H), 2.80 (m, 1H), 2.69 (m, 2H), 2.27 (m, 2H), 2.12 (m, 2H), 1.68 (m, 5H), 1.46 (s, 9H), 1.10 (m, 2H). HRMS calculated for $C_{29}H_{43}N_6O_7$ [M+H]⁺ 587.3188, found 587.3188.

Example 25: Preparation of 1,3-dioxo-7-(piperidin-4-ylmethyl)hexahydroimidazo[1,5-a]pyrazin-2(3H)-yl 4-(4-methoxyphenyl)piperidine-1-carboxylate (Compound 25, ABC38)

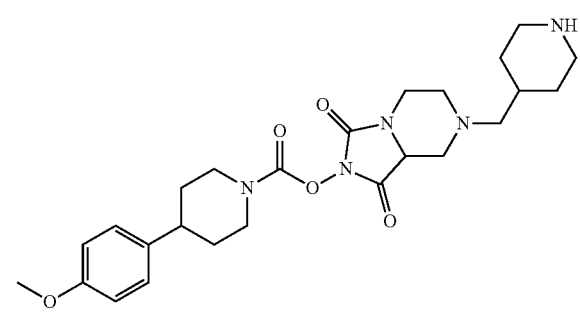 [SMILES: COc1ccc(C2CCN(C(=O)ON3C(=O)C4CN(CC5CCNCC5)CCN4C3=O)CC2)cc1]

7-((1-(tert-Butoxycarbonyl)piperidin-4-yl)methyl)-1,3-dioxohexahydroimidazo[1,5-a]pyrazin-2(3H)-yl4-(4-methoxyphenyl)piperazine-1-carboxylate was Boc-deprotected using methanolic HCl as described for Example 1, Step 4, yielding a yellow solid (100%). ¹H NMR (CD₃OD, 500 MHz) δ 7.80 (m, 2H), 7.22 (m, 2H), 5.15 (m, 1H), 4.41 (m, 1H), 4.28 (m, 2H), 4.19 (m, 3H), 3.94 (s, 3H), 3.90 (m, 4H), 3.86 (m, 2H), 3.54 (m, 2H), 3.38 (m, 3H), 3.14 (m, 2H), 2.48 (m, 1H), 2.33 (m, 2H), 1.66 (m, 2H). HRMS calculated for $C_{24}H_{35}N_6O_5$ [M+H]⁺ 487.2663, found 487.2664.

Example 26: Preparation of 7-((1-benzylpiperidin-4-yl)methyl)-1,3-dioxohexahydroimidazo[1,5-a]pyrazin-2(3H)-yl 4-(4-methoxyphenyl)piperazine-1-carboxylate (Compound 26, ABC44)

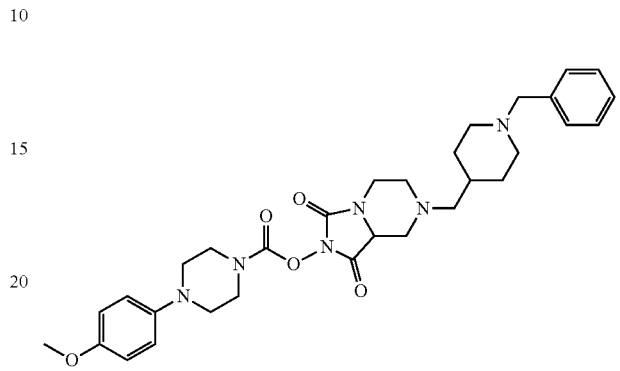

The title compound was prepared as described in Example 23, using N-benzyl-4-piperidine carboxaldehyde in place of formaldehyde. (97 mg, 34%). ¹H NMR (CDCl₃, 400 MHz) δ 7.40 (m, 5H), 6.98 (m, 2H), 6.92 (m, 2H), 4.22 (m, 1H), 4.10 (m, 1H), 3.88 (m, 2H), 3.85 (s, 3H), 3.75 (m, 2H), 3.62 (s, 2H), 3.33 (m, 1H), 3.19 (m, 1H), 3.18 (m, 4H), 2.99 (m, 2H), 2.88 (m, 1H), 2.34 (m, 2H), 2.19 (m, 2H), 2.07 (m, 2H), 1.80 (m, 2H), 1.58 (m, 1H), 1.37 (m, 2H)□ HRMS calculated for $C_{31}H_{41}N_6O_5$ [M+H]⁺ 577.3133, found 577.3133.

Example 27: Preparation of tert-butyl 1,3-dioxo-2-((4-phenylpiperidine-1-carbonyl)oxy)hexahydroimidazo[1,5-a]pyrazine-7(1H)-carboxylate (Compound 27, JJH321)

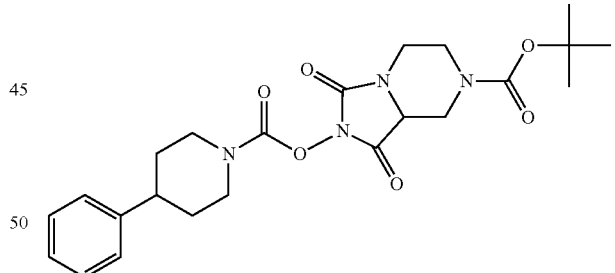

Step 1: (1H-imidazol-1-yl)(4-phenylpiperidin-1-yl)methanone

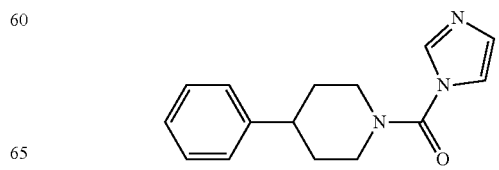

4-Phenylpiperidine (50 mg, 0.31 mmol, 1 equiv) was dissolved in 1.56 ml THF, and triethylamine (63 ml, 2 equiv) and CDI (60 mg, 1.2 equiv) added in order at room temperature. The resulting solution was stirred at room temperature overnight, and concentrated to a residue that was separated by prep-TLC (60% acetone/hexanes) to yield (1H-imidazol-1-yl)(4-phenylpiperidin-1-yl)methanone as a crystalline white solid (19 mg, 24%). $^1$H NMR (CDCl$_3$, 500 MHz) δ 7.93 (s, 1H), 7.36 (m, 2H), 7.29 (s, 1H), 7.26 (m, 3H), 7.13 (s, 1H), 4.30 (m, 2H), 3.18 (m, 2H), 2.84 (m, 2H), 2.00 (m, 2H), 1.82 (m, 2H). HRMS calculated for C$_{15}$H$_{18}$N$_3$O [M+H]$^+$ 256.1444, found 256.1445.

Step 2: tert-butyl 1,3-dioxo-2-((4-phenylpiperidine-1-carbonyl)oxy)hexahydroimidazo[1,5-a]pyrazine-7(1H)-carboxylate

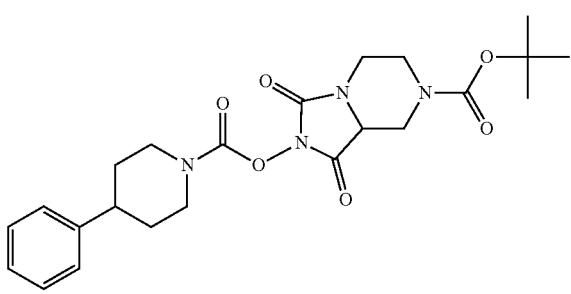 [SMILES: CC(C)(C)OC(=O)N1CCN2C(=O)N(OC(=O)N3CCC(c4ccccc4)CC3)C(=O)C2C1]

tert-Butyl 2-hydroxy-1,3-dioxohexahydroimidazo[1,5-a]pyrazine-7(1H)-carboxylate (Example 1, Step 2, 20 mg, 0.0737 mmol, 1 equiv) was dissolved in 0.4 ml dry THF, and triethylamine (38 μl, 5 equiv) and a catalytic amount of 4-DMAP were added, followed by (1H-imidazol-1-yl)(4-phenylpiperidin-1-yl)methanone (19 mg, 1 equiv) at room temperature. The solution was heated at 70° C. for 5 h, and concentrated to a residue that was separated by prep-TLC (50% EtOAc/hexanes) to yield tert-butyl 1,3-dioxo-2-((4-phenylpiperidine-1-carbonyl)oxy)hexahydroimidazo[1,5-a]pyrazine-7(1H)-carboxylate as a white solid (27 mg, 81%). $^1$H NMR (CDCl$_3$, 400 MHz) δ 7.34 (m, 2H), 7.25 (m, 1H), 7.22 (m, 2H), 4.57 (m, 1H), 4.34 (m, 2H), 4.22 (m, 1H), 4.11 (m, 2H), 3.14 (m, 1H), 3.08 (m, 1H), 3.02 (m, 1H), 2.86 (m, 2H), 2.72 (m, 1H), 1.94 (m, 2H), 1.82 (m, 2H), 1.49 (s, 9H). HRMS calculated for C$_{23}$H$_{30}$N$_4$O$_6$Na [M+Na]$^+$ 481.2057, found 481.2056.

Example 28: Preparation of 1,3-dioxohexahydroimidazo[1,5-a]pyrazin-2(3H)-yl 4-phenylpiperidine-1-carboxylate (Compound 28, JJH322)

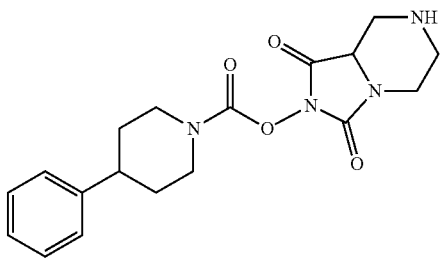 [SMILES: O=C(ON1C(=O)C2CNCCN2C1=O)N1CCC(c2ccccc2)CC1]

tert-Butyl 1,3-dioxo-2-((4-phenylpiperidine-1-carbonyl)oxy)hexahydroimidazo[1,5-a]pyrazine-7(1H)-carboxylate was Boc-deprotected using methanolic HCl as described for Example 1, Step 4, yielding a white solid (100%). $^1$H NMR (CDCl$_3$, 400 MHz) δ 7.32 (m, 2H), 7.25 (m, 1H), 7.22 (m, 2H), 4.89 (m, 1H), 4.33 (m, 2H), 4.21 (m, 1H), 3.67 (m, 1H), 3.13 (m, 2H), 3.01 (m, 2H), 2.72 (m, 1H), 1.94 (m, 2H), 1.79 (m, 2H), 1.64 (m, 2H). HRMS calculated for C$_{18}$H$_{23}$N$_4$O$_4$ [M+H]$^+$ 359.1714, found 359.1715.

Example 29: Preparation of 1-(7-(tert-Butoxycarbonyl)-1,3-dioxohexahydroimidazo[1,5-a]pyrazin-2(3H)-yl) 4-methyl piperidine-1,4-dicarboxylate (Compound 29, JJH238)

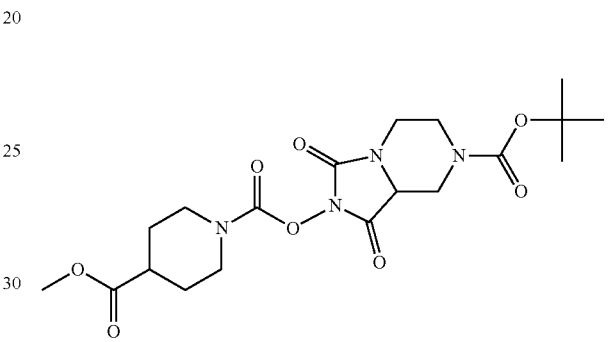

Step 1: Methyl 1-(1H-imidazole-1-carbonyl)piperidine-4-carboxylate

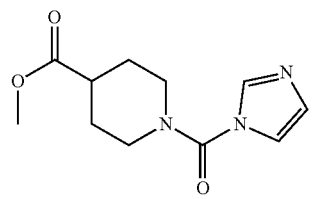 [SMILES: COC(=O)C1CCN(C(=O)n2ccnc2)CC1]

Methyl piperidine-4-carboxylate hydrochloride (358 mg, 2 mmol, 1 equiv) was suspended in CH$_2$Cl$_2$ (8 ml), triethylamine was added, and the solution was cooled to 0° C. CDI (405 mg, 1.25 equiv) was added all at once, and the solution was stirred to room temperature overnight. The resulting mixture was concentrated under reduced pressure, and separated by flash chromatography over SiO$_2$ in 50% acetone/hexanes to yield methyl 1-(1H-imidazole-1-carbonyl)piperidine-4-carboxylate as an off-white solid (255 mg, 54%). $^1$H NMR (CDCl$_3$, 400 MHz) δ 7.89 (s, 1H), 7.20 (s, 1H), 7.11 (s, 1H), 4.04 (m, 2H), 3.99 (s, 3H), 3.24 (m, 2H), 2.66 (m, 1H), 2.04 (m, 2H), 1.84 (m, 2H). HRMS calculated for C$_{11}$H$_{16}$N$_3$O$_3$ [M+H]$^+$ 238.1186, found 238.1185.

Step 2: 1-(7-(tert-Butoxycarbonyl)-1,3-dioxohexahydroimidazo[1,5-a]pyrazin-2(3H)-yl) 4-methyl piperidine-1,4-dicarboxylate

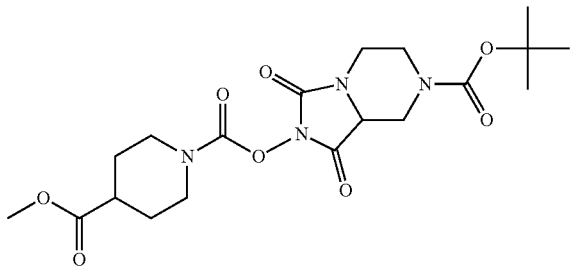 [SMILES: COC(=O)C1CCN(C(=O)ON2C(=O)C3CN(C(=O)OC(C)(C)C)CCN3C2=O)CC1]

tert-Butyl 2-hydroxy-1,3-dioxohexahydroimidazo[1,5-a]pyrazine-7(1H)-carboxylate (Example 1, Step 2, 7 mg, 0.026 mmol, 1.1 equiv) was dissolved in 0.24 ml dry THF, and triethylamine (12 µl, 5 equiv) and a catalytic amount of 4-DMAP were added, followed by methyl 1-(1H-imidazole-1-carbonyl)piperidine-4-carboxylate (5.4 mg, 1 equiv) at room temperature. The solution was heated at 70° C. overnight, and concentrated to a residue that was separated by prep-TLC (75% EtOAc/hexanes) to yield 1-(7-(tert-butoxycarbonyl)-1,3-dioxohexahydroimidazo[1,5-a]pyrazin-2(3H)-yl) 4-methyl piperidine-1,4-dicarboxylate as a white solid (8.3 mg, 73%). $^1$H NMR (CDCl$_3$, 400 MHz) δ 4.56 (m, 1H), 4.17 (m, 1H), 4.07 (m, 3H), 3.98 (m, 1H), 3.71 (s, 3H), 3.25 (m, 1H), 3.08 (m, 2H), 2.84 (m, 2H), 2.54 (m, 1H), 2.01 (m, 2H), 1.82 (m, 2H), 1.49 (s, 9H). HRMS calculated for C$_{19}$H$_{28}$N$_4$O$_8$Na [M+Na]$^+$ 463.1799, found 463.1799.

Example 30: Preparation of 1-(1,3-Dioxohexahydroimidazo[1,5-a]pyrazin-2(3H)-yl) 4-methyl piperidine-1,4-dicarboxylate (Compound 30, JJH257)

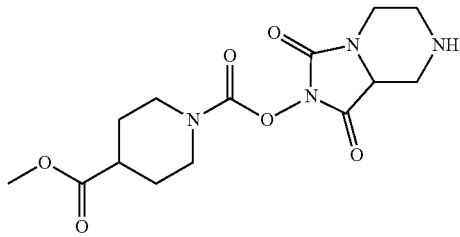 [SMILES: COC(=O)C1CCN(C(=O)ON2C(=O)C3CNCCN3C2=O)CC1]

1-(7-(tert-Butoxycarbonyl)-1,3-dioxohexahydroimidazo[1,5-a]pyrazin-2(3H)-yl) 4-methyl piperidine-1,4-dicarboxylate was Boc deprotected using methanolic HCl as described for Example 1, Step 4, yielding a white solid (100%). $^1$H NMR (CDCl$_3$, 400 MHz) δ 4.94 (m, 1H), 4.28 (m, 1H), 4.06 (m, 2H), 3.93 (m, 2H), 3.71 (s, 3H), 3.22 (m, 2H), 3.10 (m, 2H), 2.56 (m, 2H), 1.99 (m, 2H), 1.81 (m, 2H). HRMS calculated for C$_{14}$H$_{21}$N$_4$O$_6$ [M+H]$^+$ 341.1456, found 341.1455.

Example 31: Preparation of 1-(1,3-dioxo-7-(4-phenoxybenzyl)hexahydroimidazo[1,5-a]pyrazin-2(3H)-yl) 4-methyl piperidine-1,4-dicarboxylate (Compound 31, ABCS)

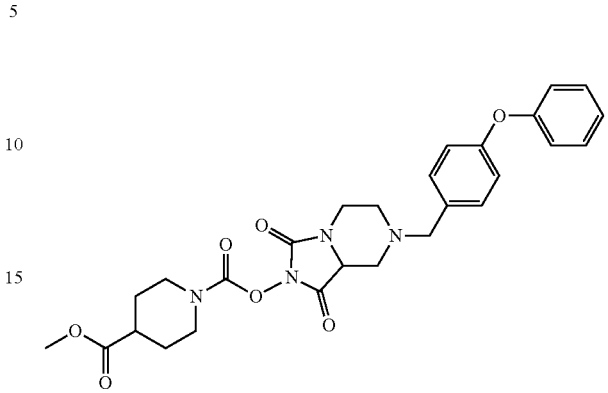

The title compound was prepared as described in Example 23, using 1-(1,3-dioxohexahydroimidazo[1,5-a]pyrazin-2(3H)-yl) 4-methyl piperidine-1,4-dicarboxylate and 3-phenoxybenzaldehyde. (6.8 mg, 87%) $^1$H NMR (CDCl$_3$, 500 MHz) δ 7.36 (m, 2H), 7.28 (m, 1H), 7.11 (m, 1H), 7.01 (m, 4H), 6.92 (m, 1H), 4.12 (m, 2H), 4.02 (m, 1H), 3.96 (m, 1H), 3.70 (s, 3H), 3.61 (d, J=15 Hz, 1H), 3.53 (d, J=15 Hz, 1H), 3.25 (m, 2H), 3.12 (m, 2H), 2.84 (m, 1H), 2.52 (m, 1H), 2.15 (m, 2H), 1.99 (m, 2H), 1.81 (m, 2H). HRMS calculated for C$_{27}$H$_{31}$N$_4$O$_7$ [M+H]$^+$ 523.2187, found 523.2187.

Example 32: Preparation of 7-(tert-butoxycarbonyl)-1,3-dioxohexahydroimidazo[1,5-a]pyrazin-2(3H)-yl morpholine-4-carboxylate (Compound 32, JJH253)

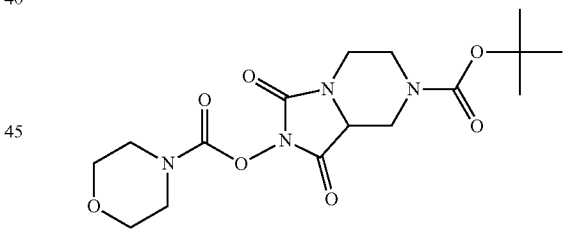

tert-Butyl 2-hydroxy-1,3-dioxohexahydroimidazo[1,5-a]pyrazine-7(1H)-carboxylate (Example 1, Step 2, 29.4 mg, 0.108 mmol, 1 equiv) was dissolved in dry CH$_2$Cl$_2$ (0.5 mL), and diisopropylethylamine (45 µl, 3 equiv) and a catalytic amount of 4-DMAP were added, followed by morpholine-4-carbonyl chloride (30 µl, ~2 equiv). The resulting solution was sealed and heated at 50° C. for 1 h, concentrated to a residue, and separated by prep-TLC (80% EtOAc/hexanes) to yield 7-(tert-butoxycarbonyl)-1,3-dioxohexahydroimidazo[1,5-a]pyrazin-2(3H)-ylmorpholine-4-carboxylate as a white solid (33 mg, 79%). $^1$H NMR (CDCl3, 500 MHz) δ 4.54 (m, 1H), 4.17 (m, 1H), 4.07 (m, 2H), 3.74 (m, 4H), 3.65 (m, 2H), 3.51 (m, 2H), 3.04 (m, 1H), 2.83 (m, 2H), 1.48 (s, 9H). HRMS calculated for C$_{16}$H$_{25}$N$_4$O$_7$ [M+H]$^+$ 385.1718, found 385.1710.

Example 33: Preparation of 1,3-dioxohexahydroimidazo[1,5-a]pyrazin-2(3H)-yl morpholine-4-carboxylate (Compound 33, JJH256)

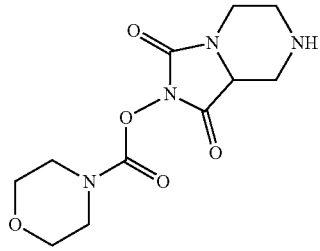 [SMILES: O=C(ON1C(=O)C2CNCCN2C1=O)N1CCOCC1]

7-(tert-Butoxycarbonyl)-1,3-dioxohexahydroimidazo[1,5-a]pyrazin-2(3H)-yl morpholine-4-carboxylate was Boc deprotected using methanolic HCl as described in Example 1, Step 4, yielding a white solid (100%). $^1$H NMR (D$_2$O, 500 MHz) δ 4.85 (m, 1H), 4.36 (m, 1H), 3.98 (m, 1H), 3.85 (m, 4H), 3.73 (m, 2H), 3.65 (m, 1H), 3.58 (m, 2H), 3.52 (m, 1H), 3.36 (m, 1H), 3.25 (m, 1H). HRMS calculated for C$_{11}$H$_{17}$N$_4$O$_5$ [M+H]$^+$ 285.1193, found 285.1193.

Example 34: Preparation of 1,3-dioxo-7-(4-phenoxybenzyl)hexahydroimidazo[1,5-a]pyrazin-2(3H)-yl morpholine-4-carboxylate (Compound 34, ABC51)

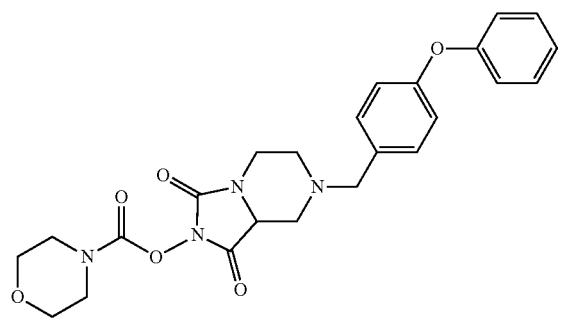 [SMILES: O=C(ON1C(=O)C2CN(Cc3ccc(Oc4ccccc4)cc3)CCN2C1=O)N1CCOCC1]

The title compound was prepared as described in Example 23, using 1,3-dioxohexahydroimidazo[1,5-a]pyrazin-2(3H)-yl morpholine-4-carboxylate and 4-phenoxybenzaldehyde. (18 mg, 64%). $^1$H NMR (CDCl$_3$, 400 MHz) δ 7.37 (m, 2H), 7.27 (m, 2H), 7.13 (m, 1H), 6.98 (m, 2H), 6.96 (m, 2H), 4.16 (m, 1H), 4.06 (m, 1H), 3.75 (m, 4H), 3.66 (m, 2H), 3.59 (m, 1H), 3.51 (m, 2H), 3.50 (m, 1H), 3.30 (m, 1H), 3.15 (m, 2H), 2.89 (m, 2H), 2.10 (m, 1H). HRMS calculated for C$_{24}$H$_{27}$N$_4$O$_6$ [M+H]$^+$ 467.1925, found 467.1927.

Example 35: Preparation of 1,3-dioxo-7-(3-phenoxybenzyl)hexahydroimidazo[1,5-a]pyrazin-2(3H)-yl 4-(4-chlorophenethyl)piperidine-1-carboxylate (Compound 35, ABC16)

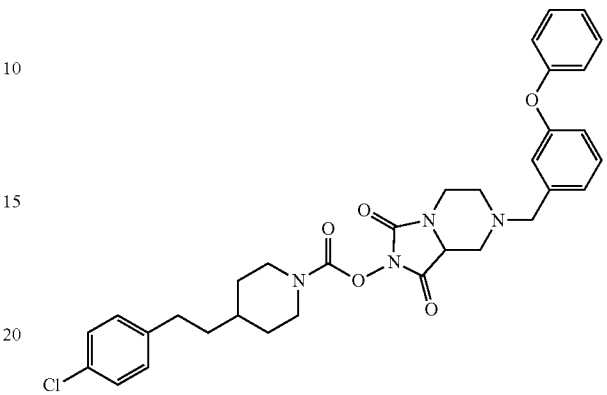

The title compound was prepared as described in Example 23, using 1,3-dioxohexahydroimidazo[1,5-a]pyrazin-2(3H)-yl 4-(4-chlorophenethyl)piperidine-1-carboxylate and 3-phenoxybenzaldehyde. (22 mg, 69%). $^1$H NMR (CDCl$_3$, 500 MHz) δ 7.36 (m, 2H), 7.28 (m, 3H), 7.11 (m, 3H), 7.00 (m, 3H), 6.92 (m, 1H), 4.21 (m, 1H), 4.12 (m, 2H), 4.02 (m, 1H), 3.61 (d, J=15 Hz, 1H), 3.53 (d, J=15 Hz, 1H), 3.26 (m, 1H), 3.11 (m, 1H), 2.99 (m, 2H), 2.86 (m, 2H), 2.60 (t, J=10 Hz, 2H), 2.14 (m, 1H), 1.76 (m, 2H), 1.58 (m, 2H), 1.48 (m, 1H), 1.34 (m, 2H). HRMS calculated for C$_{33}$H$_{36}$ClN$_4$O$_5$ [M+H]$^+$ 603.2369, found 603.2370.

Example 36: Preparation of 1,3-dioxo-7-(3-phenoxybenzyl)hexahydroimidazo[1,5-a]pyrazin-2(3H)-yl 4-(4-methoxyphenyl)piperazine-1-carboxylate (Compound 36, ABC23)

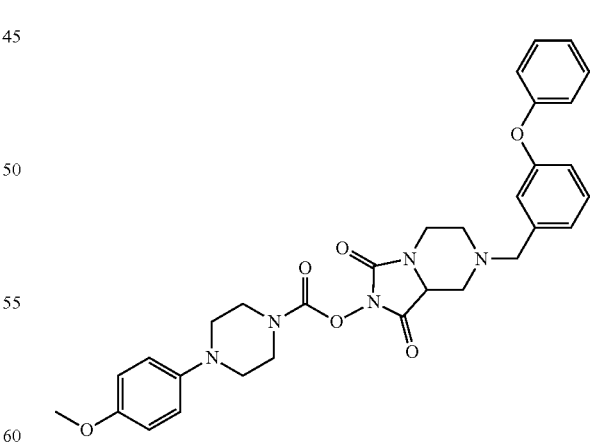

The title compound was prepared as described in Example 23, using 3-phenoxybenzaldehyde in place of formaldehyde. (4.6 mg, 17%). $^1$H NMR (CDCl$_3$, 500 MHz) δ 7.36 (m, 2H), 7.33 (m, 1H), 7.13 (m, 1H), 7.02 (m, 4H), 6.92 (m, 3H), 6.86 (d, J=10 Hz, 2H), 4.14 (m, 1H), 4.05 (m, 1H), 3.79 (m, 2H), 3.77 (s, 3H), 3.68 (m, 2H), 3.62 (d, J=15 Hz, 1H), 3.54 (d, J=15 Hz, 1H), 3.28 (m, 1H), 3.15 (m, 1H), 3.10 (m, 4H), 3.06 (m, 1H), 2.87 (m, 1H). HRMS calculated for $C_{31}H_{34}N_5O_6$ [M+H]$^+$ 572.2503, found 572.2504.

Example 37: Preparation of 1,3-dioxo-7-(4-phenoxybenzyl)hexahydroimidazo[1,5-a]pyrazin-2(3H)-yl 4-(4-methoxyphenyl)piperazine-1-carboxylate (Compound 37, ABC34)

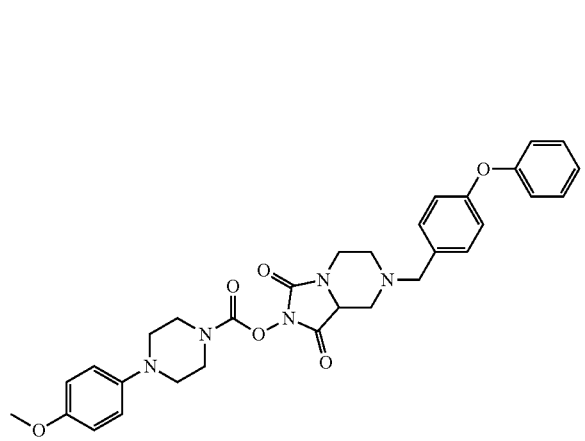 [SMILES: COc1ccc(N2CCN(C(=O)ON3C(=O)C4CN(Cc5ccc(Oc6ccccc6)cc5)CCN4C3=O)CC2)cc1]

The title compound was prepared as described in Example 23, using 4-phenoxybenzaldehyde in place of formaldehyde. (6.1 mg, 45%). $^1$H NMR (CDCl$_3$, 500 MHz) δ 7.36 (m, 2H), 7.24 (d, J=10 Hz, 2H), 7.12 (m, 1H), 7.04 (d, J=10 Hz, 2H), 6.97 (d, J=10 Hz, 2H), 6.90 (d, J=10 Hz, 2H), 6.86 (d, J=8 Hz, 2H), 4.16 (m, 1H), 4.06 (m, 1H), 3.80 (m, 2H), 3.78 (s, 3H), 3.68 (m, 2H), 3.62 (d, J=15 Hz, 1H), 3.53 (d, J=15 Hz, 1H), 3.30 (m, 1H), 3.18 (m, 1H), 3.11 (m, 4H), 3.04 (m, 1H), 2.89 (m, 1H). HRMS calculated for $C_{31}H_{34}N_5O_6$ [M+H]$^+$ 572.2503, found 572.2504.

Example 38: Preparation of 1,3-dioxo-7-(4-phenoxybenzyl)hexahydroimidazo[1,5-a]pyrazin-2(3H)-yl 4-phenylpiperidine-1-carboxylate (Compound 38, ABC47)

The title compound was prepared as described in Example 23, using 1,3-dioxohexahydroimidazo[1,5-a]pyrazin-2(3H)-yl 4-phenylpiperidine-1-carboxylate and 4-phenoxybenzaldehyde. (19 mg, 62%). $^1$H NMR (CDCl$_3$, 500 MHz) δ 7.36 (m, 4H), 7.28 (m, 5H), 7.11 (m, 1H), 7.04 (m, 2H), 6.97 (m, 2H), 4.36 (m, 1H), 4.28 (m, 1H), 4.17 (m, 1H), 4.08 (m, 1H), 3.63 (d, J=15 Hz, 1H), 3.54 (d, J=15 Hz, 1H), 3.31 (m, 1H), 3.16 (m, 2H), 3.01 (m, 1H), 2.90 (m, 1H), 2.74 (m, 1H), 2.18 (m, 2H), 1.91 (m, 2H), 1.80 (m, 2H). HRMS calculated for $C_{31}H_{33}N_4O_5$ [M+H]$^+$ 541.2445, found 541.2448.

Example 39: Preparation of 1,3-dioxo-7-(4-phenoxybenzyl)hexahydroimidazo[1,5-a]pyrazin-2(3H)-yl 4-(4-(prop-2-yn-1-yloxy)phenyl)piperazine-1-carboxylate (Compound 39, ABC45)

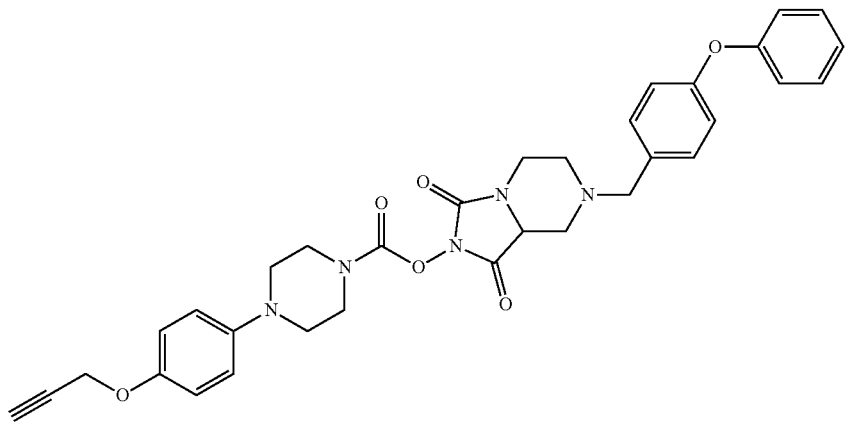 [SMILES: C#CCOc1ccc(N2CCN(C(=O)ON3C(=O)C4CN(Cc5ccc(Oc6ccccc6)cc5)CCN4C3=O)CC2)cc1]

Step 1: tert-Butyl 4-(4-(prop-2-yn-1-yloxy)phenyl) piperazine-1-carboxylate

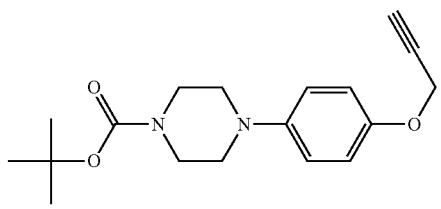 [SMILES: C#CCOc1ccc(N2CCN(C(=O)OC(C)(C)C)CC2)cc1]

tert-Butyl 4-(4-hydroxyphenyl)piperazine-1-carboxylate (100 mg, 360 µmol, 1 equiv) was suspended in 0.75 mL DMF, and propargyl bromide (80% by weight in toluene, 67 µL, 440 µmol, 1.25 equiv) and potassium carbonate (75 mg, 540 µmol, 1.5 equiv) were added. The resulting mixture was stirred at 60° C. for 18 h, cooled to room temperature, concentrated under a stream of nitrogen, and separated by prep-TLC (25% EtOAc/hexanes) to yield an off-white solid (62 mg, 54%). $^1$H NMR (CDCl3, 500 MHz) δ 6.91 (m, 4H), 4.64 (d, J=2.4 Hz, 2H), 3.57 (t, J=5.0 Hz, 4H), 3.02 (t, J=5.0 Hz, 4H), 2.50 (t, J=2.4 Hz, 1H), 1.48 (s, 9H). HRMS calculated for $C_{18}H_{25}N_2O_3$ [M+H]$^+$ 317.186, found 317.1858.

Step 2: 1-(4-(Prop-2-yn-1-yloxy)phenyl)piperazine hydrochloride

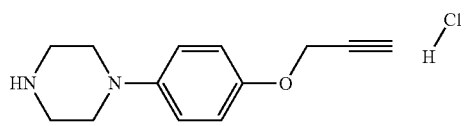

tert-Butyl 4-(4-(prop-2-yn-1-yloxy)phenyl)piperazine-1-carboxylate was Boc deprotected using methanolic HCl as described for Example 1, Step 4, yielding an off-white solid (100%). $^1$H NMR (D$_2$O, 500 MHz) δ 7.43 (m, 2H), 7.18 (m, 2H), 4.83 (d, J=2.3 Hz, 2H), 3.76 (m, 4H), 3.67 (m, 4H), 2.98 (t, J=2.4 Hz, 1H). HRMS calculated for $C_{13}H_{17}N_2O$ [M+H]$^+$ 217.1335, found 217.1335.

Step 3: (1H-Imidazol-1-yl)(4-(4-(prop-2-yn-1-yloxy)phenyl)piperazin-1-yl)methanone

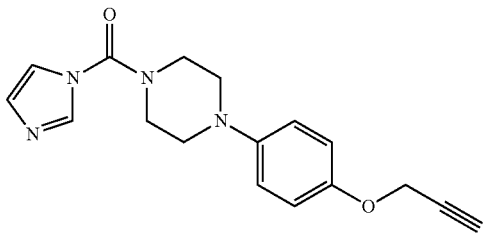 [SMILES: C#CCOc1ccc(N2CCN(C(=O)n3ccnc3)CC2)cc1]

1-(4-(Prop-2-yn-1-yloxy)phenyl)piperazine hydrochloride (49 mg, 196 µmol, 1 equiv) was taken up in CH$_2$Cl$_2$ (2 mL), and triethylamine (27 µL, 196 µmol, 1 equiv) and CDI (48 mg, 294 µmol, 1.5 equiv) were added. The resulting mixture was stirred at room temperature overnight, concentrated and separated by flash chromatography over SiO$_2$ in 60% EtOAc/hexanes to yield the corresponding imidazole urea (47 mg, 77%). $^1$H NMR (CDCl$_3$, 500 MHz) δ 7.92 (s, 1H), 7.23 (t, J=1.4 Hz, 1H), 7.13 (br m, 1H), 6.93 (m, 4H), 4.65 (d, J=2.4 Hz, 2H), 3.77 (m, 4H), 3.15 (m, 4H), 2.51 (t, J=2.3 Hz, 1H). HRMS calculated for $C_{17}H_{19}N_4O_2$ [M+H]$^+$ 311.1502, found 311.1504.

Step 4: tert-Butyl 1,3-dioxo-2-((4-(4-(prop-2-yn-1-yloxy)phenyl)piperazine-1-carbonyl)oxy)hexahydroimidazo[1,5-a]pyrazine-7(1H)-carboxylate

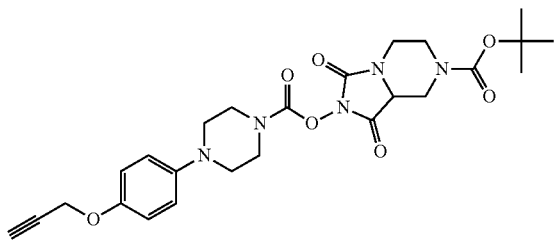 [SMILES: C#CCOc1ccc(N2CCN(C(=O)ON3C(=O)C4CN(C(=O)OC(C)(C)C)CCN4C3=O)CC2)cc1]

tert-Butyl 2-hydroxy-1,3-dioxohexahydroimidazo[1,5-a]pyrazine-7(1H)-carboxylate (Example 1, Step 2, 9.5 mg, 35.2 µmol, 1.1 equiv) was dissolved in 0.35 mL THF, and triethylamine (13 µl, 96 µmol, 3 equiv) was added, followed by (1H-imidazol-1-yl)(4-(4-(prop-2-yn-1-yloxy)phenyl)piperazin-1-yl)methanone (10 mg, 32 µmol, 1 equiv) at room temperature. The solution was stirred and heated at 70° C. for 2 h, concentrated to a residue, and separated by prep-TLC (25% EtOAc/hexanes) to yield an off-white solid (14 mg, 85%). $^1$H NMR (CDCl$_3$, 500 MHz) δ 6.92 (m, 4H), 4.65 (d, J=2.3 Hz, 2H), 4.56 (s, 1H), 4.19 (s, 1H), 4.08 (m, 2H), 3.80 (s, 2H), 3.67 (s, 2H), 3.13 (s, 4H), 3.05 (t, J=12.0 Hz, 1H), 2.85 (s, 2H), 2.51 (t, J=2.4 Hz, 1H), 1.49 (s, 9H). HRMS calculated for $C_{25}H_{32}N_5O_7$ [M+H]$^+$ 514.2296, found 514.2296.

Step 5: 1,3-Dioxohexahydroimidazo[1,5-a]pyrazin-2 (3H)-yl4-(4-(prop-2-yn-1-yloxy)phenyl)piperazine-1-carboxylate hydrochloride

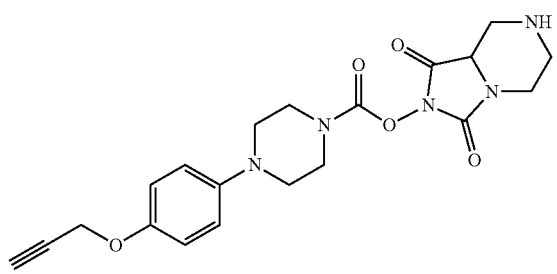 [SMILES: C#CCOc1ccc(N2CCN(C(=O)ON3C(=O)C4CNCCN4C3=O)CC2)cc1]

tert-Butyl 1,3-dioxo-2-((4-(4-(prop-2-yn-1-yloxy)phenyl) piperazine-1-carbonyl)oxy)hexahydroimidazo[1,5-a]pyrazine-7(1H)-carboxylate was Boc deprotected using methanolic HCl as described for Example 1, Step 4, yielding an off-white solid (100%). $^1$H NMR (D$_2$O, 500 MHz) δ 7.58 (m, 2H), 7.25 (m, 2H), 4.87 (m, 3H), 4.36 (m, 1H), 4.16 (s, 2H), 3.99 (m, 3H), 3.80 (br s, 4H), 3.64 (dd, J=13.3, 3.5 Hz, 1H), 3.54 (ddd, J=15.0, 12.8, 3.7 Hz, 1H), 3.39 (t, J=12.5 Hz, 1H), 3.28 (td, J=12.9, 4.5 Hz, 1H), 3.00 (t, J=2.4 Hz, 1H). HRMS calculated for $C_{20}H_{24}N_5O_5$ [M+H]$^+$ 414.1772, found 414.1771.

Step 6: 1,3-Dioxo-7-(4-phenoxybenzyl)hexahydroimidazo[1,5-a]pyrazin-2(3H)-yl 4-(4-(prop-2-yn-1-yloxy)phenyl)piperazine-1-carboxylate

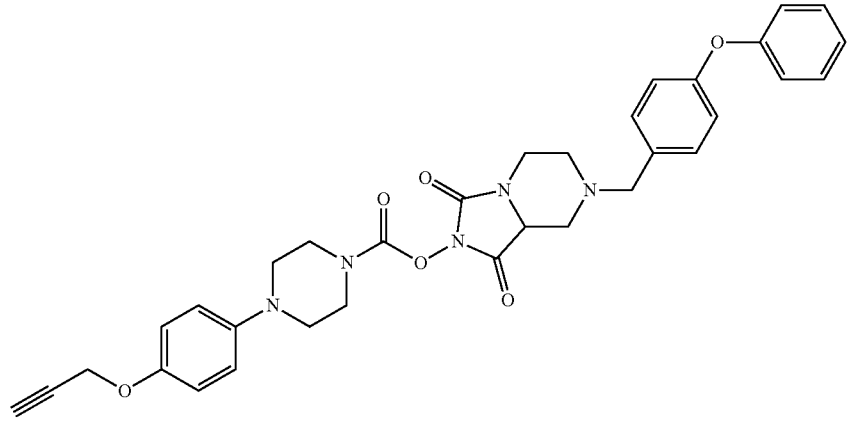 [SMILES: C#CCOc1ccc(N2CCN(C(=O)ON3C(=O)C4CN(Cc5ccc(Oc6ccccc6)cc5)CCN4C3=O)CC2)cc1]

1,3-Dioxohexahydroimidazo[1,5-a]pyrazin-2(3H)-yl 4-(4-(prop-2-yn-1-yloxy)phenyl)piperazine-1-carboxylate hydrochloride (12 mg, 27 μmol, 1 equiv) was suspended in $CH_2Cl_2$ (270 μL), and 4-phenoxy benzaldehyde (22 mg, 109 μmol, 4 equiv) was added followed by NaBH(OAc)$_3$ (12.2 mg, 54 μmol, 2 equiv). The resulting mixture was stirred at room temperature overnight, concentrated and separated by prep-TLC (50% EtOAc/hexanes) to yield 1,3-dioxo-7-(4-phenoxybenzyl)hexahydroimidazo[1,5-a]pyrazin-2(3H)-yl 4-(4-(prop-2-yn-1-yloxy)phenyl)piperazine-1-carboxylate as a clear oil (11.6 mg, 72%). $^1$H NMR (CDCl$_3$, 500 MHz) δ 7.35 (m, 2H), 7.24 (m, 3H), 7.12 (t, J=7.3 Hz, 1H), 7.03 (m, 2H), 6.96 (m, 2H), 6.92 (m, 3H), 4.65 (br s, J=2.7, 1.5 Hz, 2H), 4.15 (d, J=10.5 Hz, 1H), 4.05 (d, J=13.3 Hz, 1H), 3.79 (s, 2H), 3.67 (s, 2H), 3.60 (d, J=13.0 Hz, 1H), 3.51 (d, J=12.7 Hz, 1H), 3.29 (d, J=9.5 Hz, 1H), 3.13 (s, 5H), 2.88 (d, J=11.1 Hz, 1H), 2.51 (s, 1H), 2.14 (br s, 2H). HRMS calculated for $C_{33}H_{34}N_5O_6$ [M+H]$^+$ 596.2503, found 596.2507.

Example 40: Preparation of (S)-7-(4-bromobenzyl)-1,3-dioxohexahydroimidazo[1,5-a]pyrazin-2(3H)-yl4-(4-chlorophenethyl)piperidine-1-carboxylate (Compound 40)

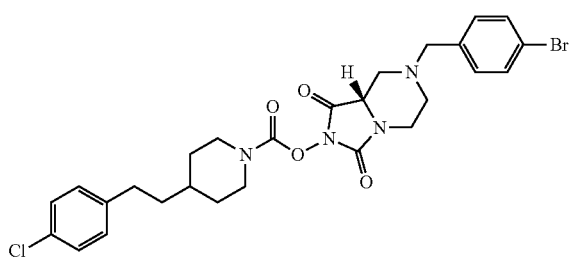 [SMILES: O=C(ON1C(=O)[C@@H]2CN(Cc3ccc(Br)cc3)CCN2C1=O)N1CCC(CCc2ccc(Cl)cc2)CC1]

7-(4-Bromobenzyl)-1,3-dioxo-hexahydroimidazo[1,5-a]pyrazin-2(3H)-yl4-(4-chlorophenethyl)piperidine-1-carboxylate (Example 13, 95.7 mg, 0.162 mmol, 1.00 equiv) was separated by SFC using the following gradient conditions: Column: Phenomenex Lux 5u Cellulose-3 5*25 cm, 5 um; Mobile Phase A: $CO_2$ (60%), Mobile Phase B: acetonitrile (40%); Flow rate: 140 mL/min; Detector, UV 220 nm; RT1: 5.2 min; RT2: 6.55 min. SFC separation resulted in 75.3 mg (79% yield) of (S)-7-(4-bromobenzyl)-1,3-dioxo-hexahydroimidazo[1,5-a]pyrazin-2(3H)-yl4-(4-chlorophenethyl)piperidine-1-carboxylate as an off-white semi-solid. $^1$H NMR (CDCl$_3$, 300 MHz) δ 7.46 (d, J=8.4 Hz, 2H), 7.19-7.24 (m, 4H), 7.09 (d, J=8.4 Hz, 2H), 4.02-4.22 (m, 4H), 3.56 (br, 2H), 3.16-3.34 (m, 2H), 2.85-3.01 (m, 3H), 2.60 (t, J=7.8 Hz, 2H), 2.17 (br, 2H), 1.75-1.79 (m, 2H), 1.54-1.61 (m, 2H), 1.25-1.33 (m, 3H). LCMS (ESI, m/z): 591 [M+H]$^+$.

Or alternatively:

Step 1: (S)-tert-Butyl 2-(benzyloxy)-1,3-dioxohexahydroimidazo[1,5-a]pyrazine-7(1H)-carboxylate

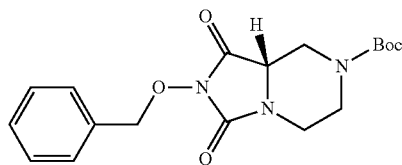 [SMILES: CC(C)(C)OC(=O)N1CCN2C(=O)N(OCc3ccccc3)C(=O)[C@@H]2C1]

A 250-mL round-bottom flask was charged with CDI (16.2 g, 99.9 mmol, 1.00 equiv), $CH_2Cl_2$ (120 mL), O-benzylhydroxylamine (12.3 g, 99.9 mmol, 1.00 equiv). NMM (40.4 g, 399 mmol, 4.00 equiv) was added. The mixture was stirred at room temperature for 2 h. (S)-4-(tert-Butoxycarbonyl)piperazine-2-carboxylic acid (23.0 g, 99.9 mmol, 1.00 equiv) was added. The resulting solution was stirred overnight at room temperature and quenched with water (100 mL). The resulting solution was extracted with $CH_2Cl_2$ (3×200 mL) and the organic layers were combined, washed with water (3×50 mL), dried over anhydrous $Na_2SO_4$, filtered and concentrated under reduced pressure. The residue was chromatographed on a silica gel column with EtOAc/petroleum ether (1/3) to provide 13.7 g (38% yield) of (S)-tert-butyl 2-(benzyloxy)-1,3-dioxo-hexahydroimidazo[1,5-a]pyrazine-7(1H)-carboxylate as a white solid. LCMS (ESI, m/z): 362 [M+H]$^+$.

Step 2: (S)-tert-Butyl 2-hydroxy-1,3-dioxo-hexahydroimidazo[1,5-a]pyrazine-7(1H)-carboxylate

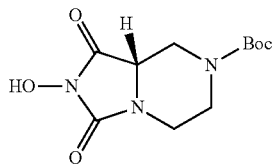

A 25-mL round-bottom flask was charged with (S)-tert-butyl 2-(benzyloxy)-1,3-dioxo-hexahydroimidazo[1,5-a]pyrazine-7(1H)-carboxylate (1.00 g, 2.77 mmol, 1.00 equiv), palladium carbon (200 mg), ethanol (8 mL), EtOAc (2 mL). H$_2$ (g) was introduced in. The resulting solution was stirred overnight at room temperature. The solids were filtered out. The resulting mixture was concentrated to provide 700 mg (93% yield) of (S)-tert-butyl 2-hydroxy-1,3-dioxo-hexahydroimidazo[1,5-a]pyrazine-7(1H)-carboxylate as a white solid. LCMS (ESI, m/z): 272 [M+H]$^+$.

Step 3: 4-[2-(4-Chlorophenyl)ethyl]piperidine-1-carbonyl chloride

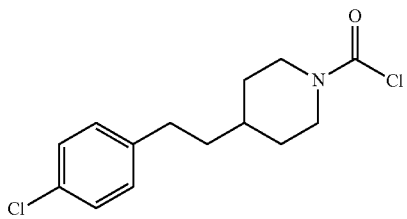 [SMILES: O=C(Cl)N1CCC(CCc2ccc(Cl)cc2)CC1]

A 25-mL round-bottom flask was charged with triphosgene (110 mg, 0.370 mmol, 0.50 equiv), CH$_2$Cl$_2$ (5 mL). The mixture was cooled to 0° C. 4-[2-(4-Chlorophenyl)ethyl]piperidine (165 mg, 0.737 mmol, 1.00 equiv) was added. N,N-Diisopropylethylamine (381 mg, 2.95 mmol, 4.00 equiv) was added dropwise. The resulting solution was stirred for 2 h at room temperature and quenched with water (10 mL). The resulting solution was extracted with CH$_2$Cl$_2$ (3×30 mL) and the organic layers were combined, washed with water (3×10 mL), dried over anhydrous Na$_2$SO$_4$, filtered and concentrated to provide 210 mg (99% yield) of 4-[2-(4-chlorophenyl)ethyl]piperidine-1-carbonyl chloride as yellow oil. LCMS (ESI, m/z): 286 [M+H]$^+$.

Step 4: (S)-tert-Butyl 2-(4-(4-chlorophenethyl)piperidine-1-carbonyloxy)-1,3-dioxo-hexahydroimidazo[1,5-a]pyrazine-7(1H)-carboxylate

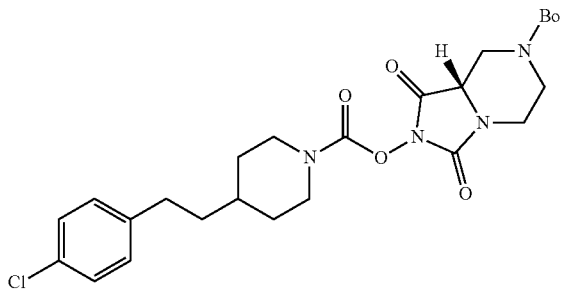

A 25-mL round-bottom flask was charged with 4-[2-(4-chlorophenyl)ethyl]piperidine-1-carbonyl chloride (210 mg, 0.734 mmol, 1.00 equiv), (S)-tert-butyl 2-hydroxy-1,3-dioxo-hexahydroimidazo[1,5-a]pyrazine-7(1H)-carboxylate (240 mg, 0.886 mmol, 1.20 equiv), 4-DMAP (18.0 mg, 0.148 mmol, 0.20 equiv), NMM (224 mg, 2.22 mmol, 3.00 equiv), CH$_2$Cl$_2$ (5 mL). The resulting solution was stirred overnight at room temperature and quenched with water (10 mL). The resulting solution was extracted with CH$_2$Cl$_2$ (3×30 mL) and the organic layers were combined, washed with water (3×10 mL), dried over anhydrous Na$_2$SO$_4$, filtered and concentrated under reduced pressure. The residue was chromatographed on a silica gel column with EtOAc/petroleum ether (1/1) to provide 250 mg (65% yield) of (S)-tert-butyl 2-(4-(4-chlorophenethyl)piperidine-1-carbonyloxy)-1,3-dioxo-hexahydroimidazo[1,5-a]pyrazine-7(1H)-carboxylate as a colorless solid. LCMS (ESI, m/z): 521 [M+H]$^+$.

Step 5: (S)-1,3-Dioxo-hexahydroimidazo[1,5-a]pyrazin-2(3H)-yl 4-(4-chlorophenethyl)piperidine-1-carboxylate

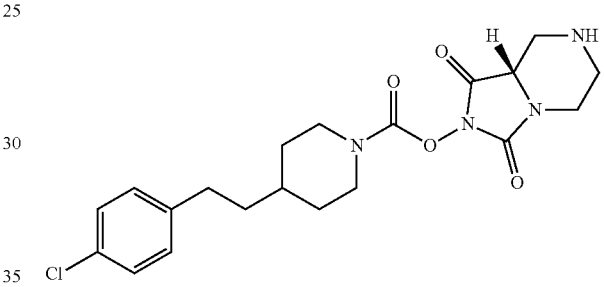

A 25-mL round-bottom flask was charged with (S)-tert-butyl 2-(4-(4-chlorophenethyl)piperidine-1-carbonyloxy)-1,3-dioxo-hexahydroimidazo[1,5-a]pyrazine-7(1H)-carboxylate (250 mg, 0.480 mmol, 1.00 equiv), CH$_2$Cl$_2$ (5 mL). The mixture was cooled to 0° C. Trifluoroacetic acid (1 mL) was added. The resulting solution was stirred for 3 h at room temperature and concentrated to provide 200 mg (99% yield) of (S)-1,3-dioxo-hexahydroimidazo[1,5-a]pyrazin-2(3H)-yl4-(4-chlorophenethyl)piperidine-1-carboxylate as a yellow solid. LCMS (ESI, m/z): 421 [M+H]$^+$.

Step 6: (S)-7-(4-Bromobenzyl)-1,3-dioxo-hexahydroimidazo[1,5-a]pyrazin-2(3H)-yl4-(4-chlorophenethyl)piperidine-1-carboxylate

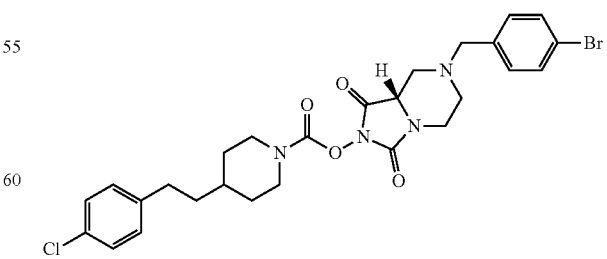

A 25-mL round-bottom flask was charged with (S)-1,3-dioxo-hexahydroimidazo[1,5-a]pyrazin-2(3H)-yl4-(4-chlorophenethyl)piperidine-1-carboxylate (200 mg, 0.475 mmol, 1.00 equiv), 4-bromobenzaldehyde (105 mg, 0.568 mmol, 1.20 equiv), 1,2-dichloroethane (5 mL), triethylamine (144 mg, 1.42 mmol, 3.00 equiv). The mixture was stirred at room temperature for 30 min. NaBH(OAc)₃ (302 mg, 1.42 mmol, 3.00 equiv) was added. The resulting solution was stirred for 3 h at room temperature and quenched with water (10 mL). The resulting solution was extracted with CH₂Cl₂ (3×30 mL) and the organic layers were combined, washed with water (3×10 mL), dried over anhydrous Na₂SO₄, filtered and concentrated. The residue was chromatographed on a silica gel column with MeOH/CH₂Cl₂ (2/98). The crude product (250 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm 5 um; Mobile phase: Phase A: water; Phase B: CH₃CN; Detector, UV220 & 254 nm. Purification resulted in 121.5 mg (43% yield) of (S)-7-(4-bromobenzyl)-1,3-dioxo-hexahydroimidazo[1,5-a]pyrazin-2(3H)-yl4-(4-chlorophenethyl)piperidine-1-carboxylate as a white solid. ¹H NMR (CDCl₃, 300 MHz) δ 7.46 (d, J=8.4 Hz. 2H), 7.18-7.24 (m, 4H), 7.09 (d, J=8.4 Hz, 2H), 4.02-4.22 (m, 4H), 3.49-3.60 (m, 2H), 3.14-3.25 (m, 2H), 2.82-3.01 (m, 3H), 2.60 (t, J=7.8 Hz, 2H), 2.13-2.16 (m, 2H), 1.75-1.79 (m, 2H), 1.54-1.61 (m, 3H), 1.25-1.38 (m, 2H). LCMS (ESI, m/z): 591 [M+H]⁺.

Example 41: (S)-7-(morpholine-4-carbonyl)-1,3-dioxo-hexahydroimidazo[1,5-a]pyrazin-2(3H)-yl 4-(4-chlorophenethyl)piperazine-1-carboxylate (Compound 41)

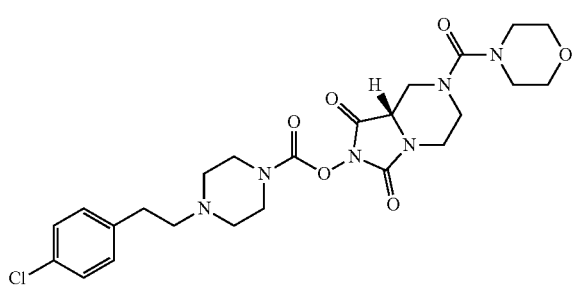

Step 1. (S)-2-(benzyloxy)-hexahydroimidazo[1,5-a]pyrazine-1,3(2H,5H)-dione

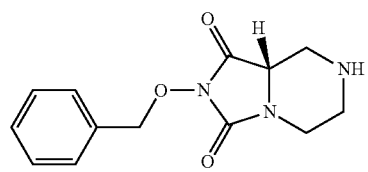 [SMILES: O=C1[C@@H]2CNCCN2C(=O)N1OCc1ccccc1]

A 250-mL round-bottom flask was charged with (S)-tert-butyl 2-(benzyloxy)-1,3-dioxo-hexahydroimidazo[1,5-a]pyrazine-7(1H)-carboxylate (7.22 g, 20.0 mmol, 1.00 equiv), MeOH (70 mL), HCl (14 mL). The resulting solution was stirred overnight at room temperature and concentrated to provide 5.00 g (96% yield) of (S)-2-(benzyloxy)-hexahydroimidazo[1,5-a]pyrazine-1,3(2H,5H)-dione as a white solid. LCMS (ESI, m/z): 262 [M+H]⁺.

Step 2. (S)-2-(benzyloxy)-7-(morpholine-4-carbonyl)-hexahydroimidazo[1,5-a]pyrazine-1,3(2H,5H)-dione

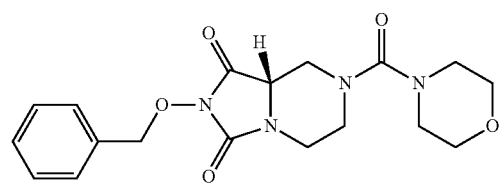 [SMILES: O=C(N1CCOCC1)N1CCN2C(=O)N(OCc3ccccc3)C(=O)[C@@H]2C1]

A 250-mL round-bottom flask was charged with (S)-2-(benzyloxy)-hexahydroimidazo[1,5-a]pyrazine-1,3(2H, 5H)-dione (5.00 g, 19.1 mmol, 1.00 equiv), morpholine-4-carbonyl chloride (3.45 g, 23.1 mmol, 1.20 equiv), 4-DMAP (467 mg, 3.82 mmol, 0.20 equiv), triethylamine (5.80 g, 57.3 mmol, 3.00 equiv), and THF (50 mL). The resulting solution was stirred for 2 h at room temperature and diluted with water (50 mL). The resulting solution was extracted with CH₂Cl₂ (3×100 mL) and the organic layers were combined, washed with water (3×50 mL), dried over anhydrous Na₂SO₄, filtered and concentrated. The residue was chromatographed on a silica gel column with EtOAc/petroleum ether (99/1) to provide 6.80 g (95% yield) of (S)-2-(benzyloxy)-7-(morpholine-4-carbonyl)-hexahydroimidazo[1,5-a]pyrazine-1,3(2H,5H)-dione as a white solid. LCMS (ESI, m/z): 375 [M+H]⁺.

Step 3: (S)-2-hydroxy-7-(morpholine-4-carbonyl)-hexahydroimidazo[1,5-a]pyrazine-1,3(2H,5H)-dione

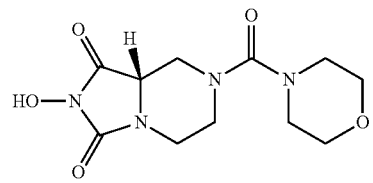 [SMILES: O=C(N1CCOCC1)N1CCN2C(=O)N(O)C(=O)[C@@H]2C1]

A 250-mL round-bottom flask was charged with (S)-2-(benzyloxy)-7-(morpholine-4-carbonyl)-hexahydroimidazo[1,5-a]pyrazine-1,3(2H,5H)-dione (7.20 g, 19.2 mmol, 1.00 equiv), palladium carbon (1.50 g), ethanol (56 mL), EtOAc (14 mL). H₂ (g) was introduced into the reaction mixture. The resulting solution was stirred overnight at room temperature. The solids were filtered out. The resulting mixture was concentrated to provide 5.30 g (97% yield) of (S)-2-hydroxy-7-(morpholine-4-carbonyl)-hexahydroimidazo[1, 5-a]pyrazine-1,3(2H,5H)-dione as a white semi-solid. LCMS (ESI, m/z): 285 [M+H]⁺.

Step 5. (S)-7-(morpholine-4-carbonyl)-1,3-dioxo-hexahydroimidazo[1,5-a]pyrazin-2(3H)-yl 4-(4-chlorophenethyl)piperazine-1-carboxylate

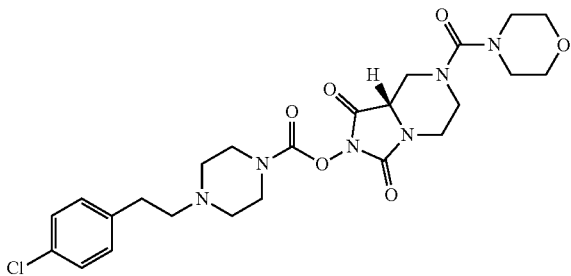

A 25-mL round-bottom flask was charged with 4-[2-(4-chlorophenyl)ethyl]piperazine-1-carbonyl chloride (117 mg, 0.408 mmol, 1.00 equiv), (S)-2-hydroxy-7-(morpholine-4-carbonyl)-hexahydroimidazo[1,5-a]pyrazine-1,3 (2H,5H)-dione (116 mg, 0.407 mmol, 1.00 equiv), 4-DMAP (9.95 mg, 0.0816 mmol, 0.20 equiv), N,N-diisopropylethylamine (158 mg, 1.22 mmol, 3.00 equiv), CH$_2$Cl$_2$ (5 mL). The resulting solution was stirred overnight at room temperature and concentrated. The crude product (200 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm 5 um; Mobile phase: Phase A: water; Phase B: CH$_3$CN; Detector, UV220 & 254 nm. The residue was chromatographed on a silica gel column with MeOH/CH$_2$Cl$_2$ (4/96) to provide 31.6 mg (14% yield) of (S)-7-(morpholine-4-carbonyl)-1,3-dioxo-hexahydroimidazo[1,5-a]pyrazin-2(3H)-yl 4-(4-chlorophenethyl)piperazine-1-carboxylate as a white solid. $^1$H NMR (CDCl$_3$, 300 MHz) δ 7.25-7.27 (m, 2H), 7.12-7.15 (m, 2H), 4.22-4.27 (m, 1H), 4.01-4.10 (m, 2H), 3.65-3.70 (m, 7H), 3.59 (br, 2H), 3.32-3.34 (m, 4H), 3.10-3.20 (m, 1H), 2.96-3.05 (m, 2H), 2.80 (br, 2H), 2.63 (br, 6H). LCMS (ESI, m/z): 535 [M+H]$^+$.

Example 42: Preparation of (S)-7-((1-benzylpiperidin-4-yl)methyl)-1,3-dioxo-hexahydroimidazo[1,5-a]pyrazin-2(3H)-yl 4-(4-methoxyphenyl)piperazine-1-carboxylate (Compound 42)

piperazine-1-carboxylate (Example 26, 320 mg, 0.554 mmol, 1.00 equiv) was separated by SFC using the following gradient conditions: Column: CHIRALPAK AD-H SFC 5*25 cm, 5 μm; Mobile Phase A: CO$_2$: (50%), Mobile Phase B: isopropanol (0.1% diethylamine) (50%); Flow rate: 190 mL/min; Detector, UV 220 nm; RT1: 6.41 min; RT2: 8.50 min. SFC separation resulted in 136.5 mg (42% yield) of (S)-7-((1-benzylpiperidin-4-yl)methyl)-1,3-dioxo-hexahydroimidazo[1,5-a]pyrazin-2(3H)-yl4-(4-methoxyphenyl) piperazine-1-carboxylate as a brown semi-solid. $^1$H NMR (CDCl$_3$, 300 MHz) δ 7.28-7.34 (m, 5H), 6.83-6.92 (m, 4H), 4.10-4.15 (m, 1H), 3.99-4.04 (m, 1H), 3.78 (m, 5H), 3.68 (m, 2H), 3.55 (br, 2H), 3.22-3.27 (m, 1H), 3.06-3.16 (m, 5H), 2.92 (br, 2H), 2.77-2.81 (m, 1H), 2.27 (d, J=6.9 Hz, 2H), 2.00-2.14 (m, 4H), 1.67-1.76 (m, 2H), 1.51 (br, 1H), 1.26-1.29 (m, 2H). LCMS (ESI, m/z): 577 [M+H]$^+$.

Or alternatively:

Step 1: 4-(4-Methoxyphenyl)piperazine-1-carbonyl chloride

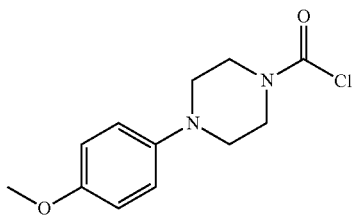 [SMILES: COc1ccc(N2CCN(C(=O)Cl)CC2)cc1]

A 25-mL round-bottom flask was charged with triphosgene (387 mg, 1.30 mmol, 0.50 equiv), CH$_2$Cl$_2$ (5 mL). The mixture was cooled to 0° C. 1-(4-Methoxyphenyl)piperazine (500 mg, 2.60 mmol, 1.00 equiv) was added. N,N-Diisopropylethylamine (1.34 g, 10.4 mmol, 4.00 equiv) was added. The resulting solution was stirred for 2 h at room temperature and quenched with water (10 mL). The resulting solution was extracted with CH$_2$Cl$_2$ (3×30 mL) and the organic layers were combined, washed with water (3×10 mL), dried over anhydrous Na$_2$SO$_4$, filtered and concentrated to provide 600 mg (91% yield) of 4-(4-methoxyphenyl)piperazine-1-carbonyl chloride as yellow oil. LCMS (ESI, m/z): 255 [M+H]$^+$.

Step 2: (S)-tert-Butyl 2-(4-(4-methoxyphenyl)piperazine-1-carbonyloxy)-1,3-dioxo-hexahydroimidazo[1,5-a]pyrazine-7(1H)-carboxylate

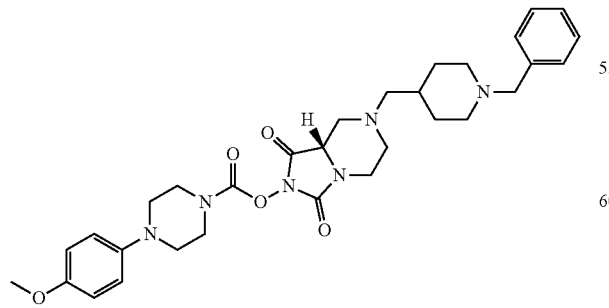

7-((1-Benzylpiperidin-4-yl)methyl)-1,3-dioxo-hexahydroimidazo[1,5-a]pyrazin-2(3H)-yl 4-(4-methoxyphenyl)

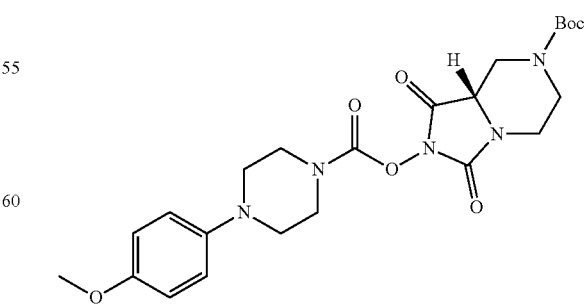

A 25-mL round-bottom flask was charged with (S)-tert-butyl 2-hydroxy-1,3-dioxo-hexahydroimidazo[1,5-a]pyrazine-7(1H)-carboxylate (638 mg, 2.35 mmol, 1.00 equiv), 4-(4-methoxyphenyl)piperazine-1-carbonyl chloride (600 mg, 2.36 mmol, 1.00 equiv), NMM (713 mg, 7.05 mmol, 3.00 equiv), 4-DMAP (57.4 mg, 0.470 mmol, 0.20 equiv), $CH_2Cl_2$ (5 mL). The resulting solution was stirred overnight at room temperature and quenched with water (10 mL). The resulting solution was extracted with $CH_2Cl_2$ (3×30 mL) and the organic layers were combined, washed with water (3×10 mL), dried over anhydrous $Na_2SO_4$, filtered and concentrated. The residue was chromatographed on a silica gel column with EtOAc/petroleum ether (4/6) to provide 590 mg (51% yield) of (S)-tert-butyl 2-(4-(4-methoxyphenyl)piperazine-1-carbonyloxy)-1,3-dioxo-hexahydroimidazo[1,5-a]pyrazine-7(1H)-carboxylate as an off-white solid. LCMS (ESI, m/z): 490 [M+H]$^+$.

Step 3: (S)-1,3-Dioxo-hexahydroimidazo[1,5-a]pyrazin-2(3H)-yl4-(4-methoxyphenyl)piperazine-1-carboxylate

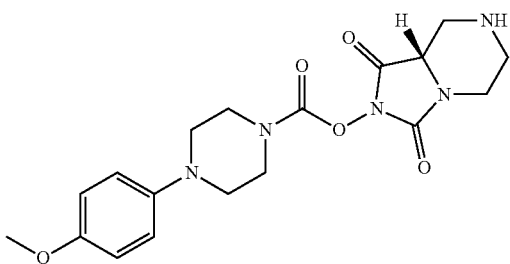 [SMILES: COc1ccc(N2CCN(C(=O)ON3C(=O)[C@@H]4CNCCN4C3=O)CC2)cc1]

A 25-mL round-bottom flask was charged with (S)-tert-butyl 2-(4-(4-methoxyphenyl)piperazine-1-carbonyloxy)-1,3-dioxo-hexahydroimidazo[1,5-a]pyrazine-7(1H)-carboxylate (490 mg, 1.00 mmol, 1.00 equiv), $CH_2Cl_2$ (8 mL), trifluoroacetic acid (2 mL). The resulting solution was stirred overnight at room temperature and concentrated to provide 460 mg (crude) of (S)-1,3-dioxo-hexahydroimidazo[1,5-a]pyrazin-2(3H)-yl 4-(4-methoxyphenyl)piperazine-1-carboxylate as a brown solid. LCMS (ESI, m/z): 390 [M+H]$^+$.

Step 4: (S)-7-((1-Benzylpiperidin-4-yl)methyl)-1,3-dioxo-hexahydroimidazo[1,5-a]pyrazin-2(3H)-yl 4-(4-methoxyphenyl)piperazine-1-carboxylate A 25-mL round-bottom flask was charged with 1-benzylpiperidine-4-carbaldehyde (192 mg, 0.946 mmol, 3.00 equiv), (S)-1,3-dioxo-hexahydroimidazo[1,5-a]pyrazin-2(3H)-yl 4-(4-methoxyphenyl)piperazine-1-carboxylate (123 mg, 0.316 mmol, 1.00 equiv), 1,2-dichloroethane (5 mL). Triethylamine (48.0 mg, 0.480 mmol, 1.50 equiv) was added. The mixture was stirred at room temperature for 30 min. $NaBH(OAc)_3$ (201 mg, 0.948 mmol, 3.00 equiv) was added. The resulting solution was stirred overnight at room temperature and quenched with water (10 mL). The resulting solution was extracted with $CH_2Cl_2$ (3×30 mL) and the organic layers were combined, washed with water (3×10 mL), dried over anhydrous $Na_2SO_4$, filtered and concentrated. The residue was chromatographed on a silica gel column with EtOAc/petroleum ether (95/5). The crude product (300 mg) was purified by preparative HPLC using the following gradient conditions: 20% $CH_3CN$/80% Phase A increasing to 80% $CH_3CN$ over 10 min, then to 100% $CH_3CN$ over 0.1 min, holding at 100% $CH_3CN$ for 1.9 min, then reducing to 20% $CH_3CN$ over 0.1 min, and holding at 20% for 1.9 min, on a Waters 2767-5 Chromatograph. Column: Xbridge Prep C18, 19*150 mm 5 um; Mobile phase: Phase A: water; Phase B: $CH_3CN$; Detector, UV220 & 254 nm. Purification resulted in 128.7 mg (71% yield) of (S)-7-((1-benzylpiperidin-4-yl)methyl)-1,3-dioxo-hexahydroimidazo[1,5-a]pyrazin-2(3H)-yl4-(4-methoxyphenyl)piperazine-1-carboxylate as an off-white semi-solid. $^1$H NMR (CDCl$_3$, 300 MHz) δ 7.27-7.35 (m, 5H), 6.83-6.92 (m, 4H), 4.10-4.15 (m, 1H), 3.99-4.04 (m, 1H), 3.85 (br, 5H), 3.60-3.78 (m, 4H), 3.22-3.27 (m, 1H), 3.06-3.16 (m, 5H), 2.98 (br, 2H), 2.77-2.80 (m, 1H), 2.28 (d, J=6.6 Hz, 2H), 2.07-2.14 (m, 4H), 1.68-1.78 (m, 3H), 1.36 (br, 2H). LCMS (ESI, m/z): 577 [M+H]$^+$.

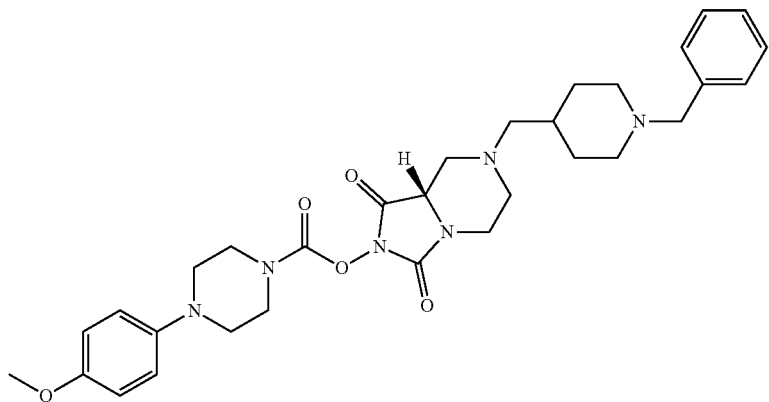 [SMILES: COc1ccc(N2CCN(C(=O)ON3C(=O)[C@@H]4CN(CC5CCN(Cc6ccccc6)CC5)CCN4C3=O)CC2)cc1]

Example 43: Preparation of (R)-7-((1-benzylpiperidin-4-yl)methyl)-1,3-dioxo-hexahydroimidazo[1,5-a]pyrazin-2(3H)-yl 4-(4-methoxyphenyl)piperazine-1-carboxylate (Compound 43)

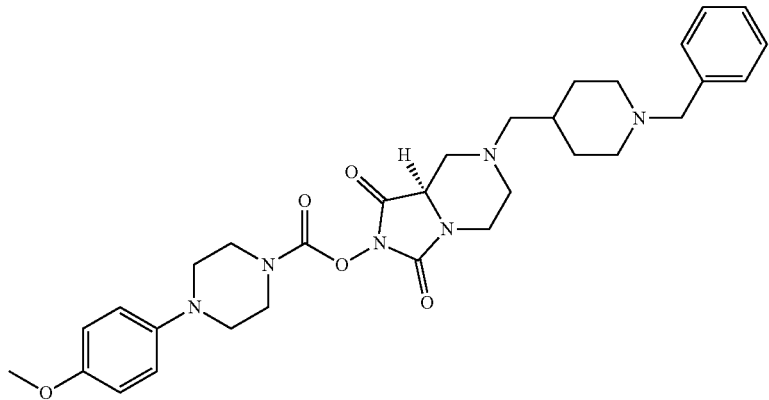 [SMILES: COc1ccc(N2CCN(C(=O)ON3C(=O)[C@H]4CN(CC5CCN(Cc6ccccc6)CC5)CCN4C3=O)CC2)cc1]

7-((1-Benzylpiperidin-4-yl)methyl)-1,3-dioxo-hexahydroimidazo[1,5-a]pyrazin-2(3H)-yl 4-(4-methoxyphenyl)piperazine-1-carboxylate (Example 26, 320 mg, 0.554 mmol, 1.00 equiv) was separated by SFC using the following gradient conditions: Column: CHIRALPAK AD-H SFC 5*25 cm, 5 μm; Mobile Phase A: $CO_2$: (50%), Mobile Phase B: isopropanol (0.1% diethylamine) (50%); Flow rate: 190 mL/min; Detector, UV 220 nm; RT1: 6.41 min; RT2: 8.50 min. SFC separation resulted in 86.1 mg (26% yield) of (R)-7-((1-benzylpiperidin-4-yl)methyl)-1,3-dioxo-hexahydroimidazo[1,5-a]pyrazin-2(3H)-yl 4-(4-methoxyphenyl)piperazine-1-carboxylate as a brown semi-solid. $^1$H NMR (CDCl$_3$, 300 MHz) δ 7.29-7.32 (m, 5H), 6.83-6.92 (m, 4H), 4.10-4.15 (m, 1H), 3.99-4.04 (m, 1H), 3.78 (br, 5H), 3.68 (br, 2H), 3.54 (br, 2H), 3.22-3.27 (m, 1H), 3.06-3.16 (m, 5H), 2.92 (d, J=9.0 Hz, 2H), 2.77-2.81 (m, 1H), 2.27 (d, J=6.9 Hz, 2H), 1.99-2.14 (m, 4H), 1.67-1.76 (m, 2H), 1.46-1.51 (m, 1H), 1.26-1.29 (m, 2H). LCMS (ESI, m/z): 577 [M+H]$^+$.

Alternatively, the title compound was synthesized as described in Example 42 (Step 1-4) using (R)-tert-butyl 2-hydroxy-1,3-dioxo-hexahydroimidazo[1,5-a]pyrazine-7(1H)-carboxylate as the starting material. $^1$H NMR (CDCl$_3$, 300 MHz) δ 7.34-7.36 (m, 5H), 6.83-6.92 (m, 4H), 3.99- 4.15 (m, 2H), 3.49-3.85 (m, 9H), 2.77-3.27 (m, 9H), 2.28 (d, J=6.3 Hz, 2H), 2.05-2.15 (m, 4H), 1.68-1.79 (m, 3H), 1.23-1.33 (m, 2H). LCMS (ESI, m/z): 577 [M+H]$^+$.

Example 44: Preparation of (S)-1,3-dioxo-7-(4-phenoxybenzyl)-hexahydroimidazo[1,5-a]pyrazin-2(3H)-yl 4-(4-(prop-2-ynyloxy)phenyl)piperazine-1-carboxylate (Compound 44)

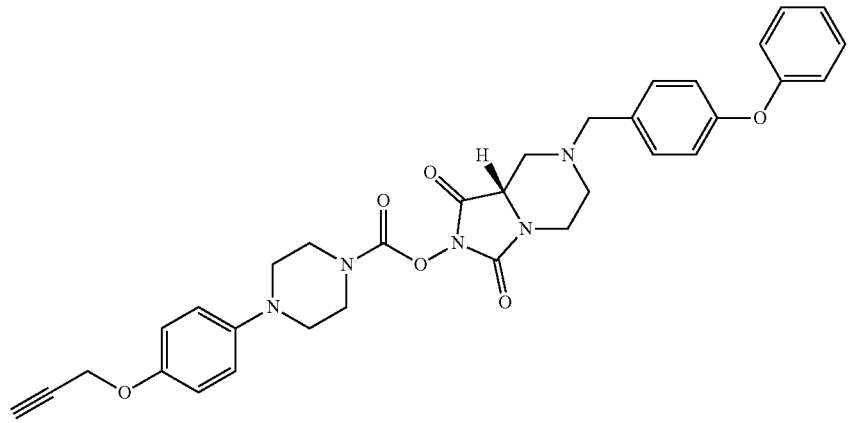 [SMILES: C#CCOc1ccc(N2CCN(C(=O)ON3C(=O)[C@@H]4CN(Cc5ccc(Oc6ccccc6)cc5)CCN4C3=O)CC2)cc1]

1,3-Dioxo-7-(4-phenoxybenzyl)-hexahydroimidazo[1,5-a]pyrazin-2(3H)-yl4-(4-(prop-2-ynyloxy)phenyl)piperazine-1-carboxylate (Example 39, 435 mg, 0.730 mmol, 1.00 equiv) was separated by SFC using the following gradient conditions: Column: Chiralpak IC 2*25 cm, 5 um; Mobile Phase A: $CO_2$ (50%), Mobile Phase B: acetonitrile (50%); Flow rate: 40 mL/min; Detector, UV 220 nm; RT1: 8.95 min; RT2: 10.84 min. SFC separation resulted in 274.4 mg (63% yield) of (S)-1,3-dioxo-7-(4-phenoxybenzyl)-hexahydroimidazo[1,5-a]pyrazin-2(3H)-yl 4-(4-(prop-2-ynyloxy)phenyl)piperazine-1-carboxylate as a white solid. $^1$H NMR (CDCl$_3$, 300 MHz) δ 7.25-7.38 (m, 3H), 6.89-7.14 (m, 10H), 4.65 (d, J=2.4 Hz, 2H), 4.04-4.17 (m, 2H), 3.49-3.80 (m, 6H), 3.13-3.31 (m, 6H), 2.87-2.91 (m, 1H), 2.51 (t, J=2.4 Hz, 1H), 2.13-2.16 (m, 2H). LCMS (ESI, m/z): 596 [M+H]$^+$.

Alternatively, the title compound was prepared as follows.

Step 1: tert-Butyl 4-[4-(prop-2-yn-1-yloxy)phenyl]piperazine-1-carboxylate

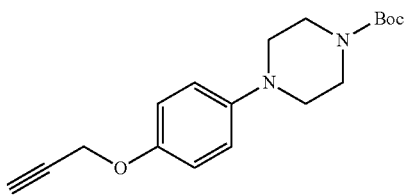 [SMILES: C#CCOc1ccc(N2CCN(C(=O)OC(C)(C)C)CC2)cc1]

A 25-mL round-bottom flask was charged with 3-bromoprop-1-yne (428 mg, 3.60 mmol, 1.00 equiv), tert-butyl 4-(4-hydroxyphenyl)piperazine-1-carboxylate (1.00 g, 3.59 mmol, 1.00 equiv), cesium carbonate (3.52 g, 10.8 mmol, 3.00 equiv), N,N-dimethylformamide (10 mL). The resulting solution was stirred overnight at 50° C. and diluted with water (10 mL). The resulting solution was extracted with $CH_2Cl_2$ (3×30 mL) and the organic layers were combined, washed with water (3×10 mL), dried over anhydrous $Na_2SO_4$, filtered and concentrated. The residue was chromatographed on a silica gel column with EtOAc/petroleum ether (15/85) to provide 1.04 g (91% yield) of tert-butyl 4-[4-(prop-2-yn-1-yloxy)phenyl]piperazine-1-carboxylate as yellow oil. LCMS (ESI, m/z): 317 [M+H]$^+$.

Step 2: 1-[4-(Prop-2-yn-1-yloxy)phenyl]piperazine

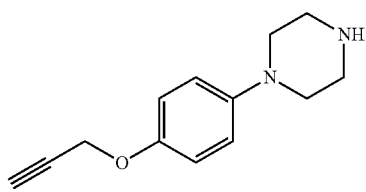 [SMILES: C#CCOc1ccc(N2CCNCC2)cc1]

A 100-mL round-bottom flask was charged with tert-butyl 4-[4-(prop-2-yn-1-yloxy)phenyl]piperazine-1-carboxylate (930 mg, 2.94 mmol, 1.00 equiv), $CH_2Cl_2$ (10 mL). The mixture was cooled to 0° C. Trifluoroacetic acid (2 mL) was added dropwise. The resulting solution was stirred for 3 h at room temperature and concentrated to provide 690 mg (crude) of 1-[4-(prop-2-yn-1-yloxy)phenyl]piperazine as a brown solid. LCMS (ESI, m/z): 217 [M+H]$^+$.

Step 3: 4-[(Prop-2-yn-1-yloxy)phenyl]piperazine-1-carbonyl chloride

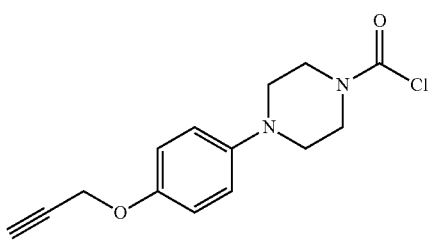 [SMILES: C#CCOc1ccc(N2CCN(C(=O)Cl)CC2)cc1]

A 25-mL round-bottom flask was charged with triphosgene (474 mg, 1.60 mmol, 0.50 equiv), $CH_2Cl_2$ (5 mL). The mixture was cooled to 0° C. 1-[4-(Prop-2-yn-1-yloxy)phenyl]piperazine (690 mg, 3.19 mmol, 1.00 equiv) was added. N,N-Diisopropylethylamine (1.65 g, 12.8 mmol, 4.00 equiv) was added dropwise. The resulting solution was stirred for 2 h at room temperature and quenched with water (10 mL). The resulting solution was extracted with $CH_2Cl_2$ (3×30 mL) and the organic layers were combined, washed with water (3×10 mL), dried over anhydrous $Na_2SO_4$, filtered and concentrated to provide 880 mg (99% yield) of 4-[4-(prop-2-yn-1-yloxy)phenyl]piperazine-1-carbonyl chloride as yellow oil. LCMS (ESI, m/z): 279 [M+H]$^+$.

Step 4: (S)-tert-Butyl 1,3-dioxo-2-(4-(4-(prop-2-ynyloxy)phenyl)piperazine-1-carbonyloxy)-hexahydroimidazo[1,5-a]pyrazine-7(1H)-carboxylate

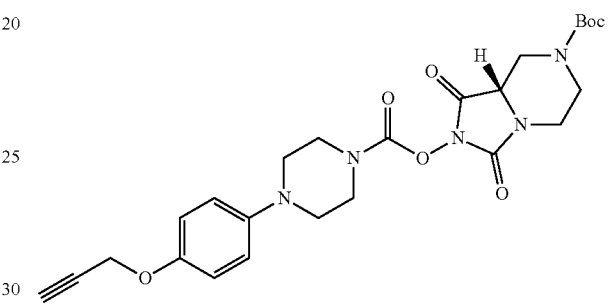

A 25-mL round-bottom flask was charged with (S)-tert-butyl 2-hydroxy-1,3-dioxo-hexahydroimidazo[1,5-a]pyrazine-7(1H)-carboxylate (855 mg, 3.15 mmol, 1.00 equiv), 4-[4-(prop-2-yn-1-yloxy)phenyl]piperazine-1-carbonyl chloride (880 mg, 3.16 mmol, 1.00 equiv), NMM (956 mg, 9.45 mmol, 3.00 equiv), 4-DMAP (77.0 mg, 0.631 mmol, 0.20 equiv), $CH_2Cl_2$ (10 mL). The resulting solution was stirred overnight at room temperature and quenched with water (10 mL). The resulting solution was extracted with $CH_2Cl_2$ (3×30 mL) and the organic layers were combined, washed with water (3×10 mL), dried over anhydrous $Na_2SO_4$, filtered and concentrated. The residue was chromatographed on a silica gel column with EtOAc/petroleum ether (3/1) to provide 1.00 g (62% yield) of (S)-tert-butyl 1,3-dioxo-2-(4-(4-(prop-2-ynyloxy)phenyl)piperazine-1-carbonyloxy)-hexahydroimidazo[1,5-a]pyrazine-7(1H)-carboxylate as an off-white solid. LCMS (ESI, m/z): 514 [M+H]$^+$.

Step 5: (S)-1,3-Dioxo-hexahydroimidazo[1,5-a]pyrazin-2(3H)-yl4-(4-(prop-2-ynyloxy)phenyl)piperazine-1-carboxylate

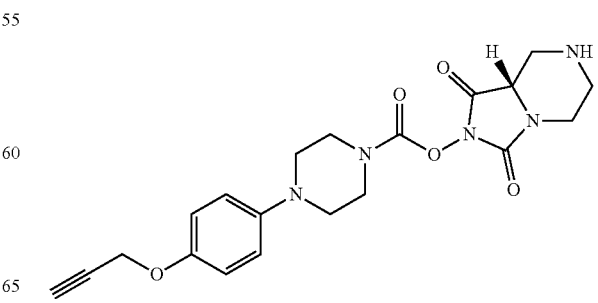

A 25-mL round-bottom flask was charged with (S)-tert-butyl 1,3-dioxo-2-(4-(4-(prop-2-ynyloxy)phenyl)piperazine-1-carbonyloxy)-hexahydroimidazo[1,5-a]pyrazine-7(1H)-carboxylate (900 mg, 1.75 mmol, 1.00 equiv), CH$_2$Cl$_2$ (10 mL). The mixture was cooled to 0° C. Trifluoroacetic acid (2 mL) was added dropwise. The resulting solution was stirred for 3 h at room temperature and concentrated to provide 720 mg (99% yield) of (S)-1,3-dioxo-hexahydroimidazo[1,5-a]pyrazin-2(3H)-yl4-(4-(prop-2-ynyloxy)phenyl)piperazine-1-carboxylate as a brown solid. LCMS (ESI, m/z): 414 [M+H]$^+$.

Step 6: (S)-1,3-Dioxo-7-(4-phenoxybenzyl)-hexahydroimidazo[1,5-a]pyrazin-2(3H)-yl4-(4-(prop-2-ynyloxy)phenyl)piperazine-1-carboxylate

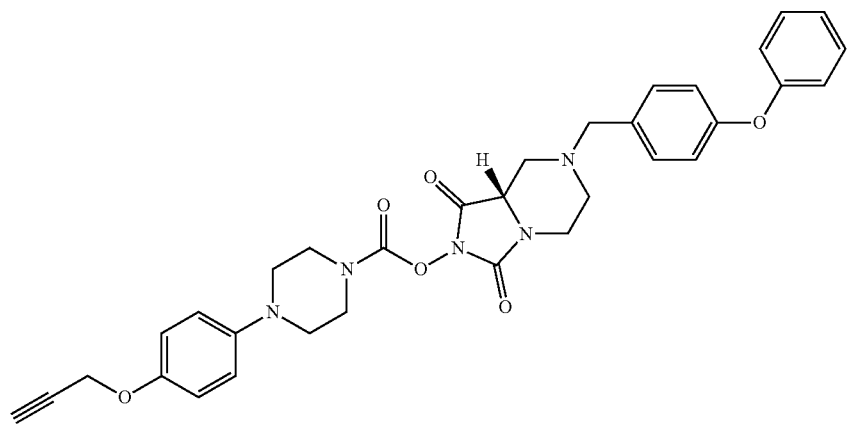 [SMILES: C#CCOc1ccc(N2CCN(C(=O)ON3C(=O)[C@@H]4CN(Cc5ccc(Oc6ccccc6)cc5)CCN4C3=O)CC2)cc1]

A 50-mL round-bottom flask was charged with 4-phenoxybenzaldehyde (414 mg, 2.09 mmol, 1.20 equiv), (S)-1,3-dioxo-hexahydroimidazo[1,5-a]pyrazin-2(3H)-yl4-(4-(prop-2-ynyloxy)phenyl)piperazine-1-carboxylate (720 mg, 1.74 mmol, 1.00 equiv), 1,2-dichloroethane (10 mL), triethylamine (528 mg, 5.22 mmol, 3.00 equiv). The mixture was stirred at room temperature for 30 min. NaBH(OAc)$_3$ (1.11 g, 5.24 mmol, 3.00 equiv) was added. The resulting solution was stirred overnight at room temperature and quenched with water (10 mL). The resulting solution was extracted with CH$_2$Cl$_2$ (3×30 mL) and the organic layers were combined, washed with water (3×10 mL), dried over anhydrous Na$_2$SO$_4$, filtered and concentrated. The residue was chromatographed on a silica gel column with EtOAc/petroleum ether (9/1). The crude product was triturated in EtOAc/hexane (9/1) to provide 399.8 mg (39% yield) of (S)-1,3-dioxo-7-(4-phenoxybenzyl)-hexahydroimidazo[1,5-a]pyrazin-2(3H)-yl4-(4-(prop-2-ynyloxy)phenyl)piperazine-1-carboxylate as a white solid. $^1$H NMR (CDCl$_3$, 300 MHz) δ 7.36 (t, J=7.8 Hz, 2H), 7.26 (br, 2H), 7.12 (t, J=7.4 Hz, 1H), 6.89-7.05 (m, 8H), 4.65 (d, J=2.4 Hz, 2H), 4.04-4.15 (m, 2H), 3.54-3.89 (m, 6H), 2.89-3.31 (m, 7H), 2.51 (t, J=2.4 Hz, 1H), 2.13-2.16 (m, 2H). LCMS (ESI, m/z): 596 [M+H]$^+$.

Example 45: Preparation of (R)-1,3-dioxo-7-(4-phenoxybenzyl)-hexahydroimidazo[1,5-a]pyrazin-2(3H)-yl 4-(4-(prop-2-ynyloxy)phenyl)piperazine-1-carboxylate (Compound 45)

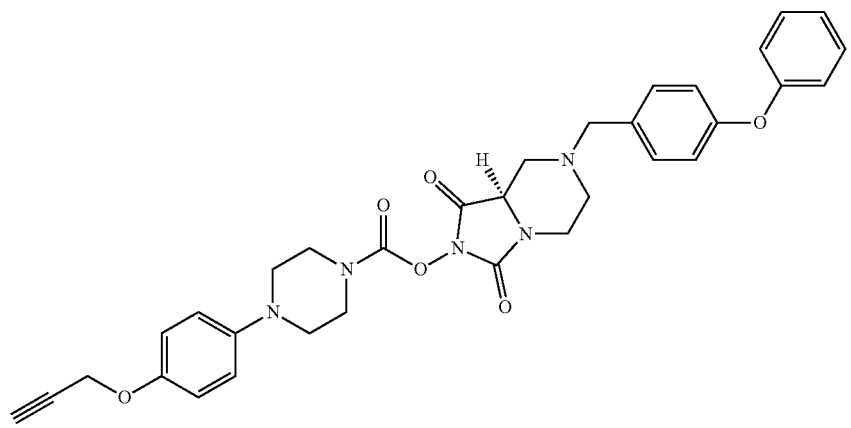 [SMILES: C#CCOc1ccc(N2CCN(C(=O)ON3C(=O)[C@H]4CN(Cc5ccc(Oc6ccccc6)cc5)CCN4C3=O)CC2)cc1]

1,3-Dioxo-7-(4-phenoxybenzyl)-hexahydroimidazo[1,5-a]pyrazin-2(3H)-yl 4-(4-(prop-2-ynyloxy)phenyl)piperazine-1-carboxylate (Example 39, 435 mg, 0.730 mmol, 1.00 equiv) was separated by SFC using the following gradient conditions: Column: Chiralpak IC 2*25 cm, 5 um; Mobile Phase A: $CO_2$ (50%), Mobile Phase B: acetonitrile (50%); Flow rate: 40 mL/min; Detector, UV 220 nm; RT1: 8.95 min; RT2: 10.84 min. SFC separation resulted in 45.2 mg (10% yield) of (R)-1,3-dioxo-7-(4-phenoxybenzyl)-hexahydroimidazo[1,5-a]pyrazin-2(3H)-yl 4-(4-(prop-2-ynyloxy)phenyl)piperazine-1-carboxylate as an off-white solid. $^1$H NMR ($CDCl_3$, 300 MHz) δ 7.26-7.38 (m, 4H), 6.93-7.15 (m, 9H), 4.65 (d, J=2.1 Hz, 2H), 4.04-4.16 (m, 2H), 3.54-3.90 (m, 6H), 3.14-3.29 (m, 6H), 2.90-2.92 (m, 1H), 2.51 (t, J=2.4 Hz, 1H), 2.17 (br, 2H). LCMS (ESI, m/z): 596 [M+H]$^+$.

Alternatively, the title compound was synthesized as described in Example 44 (Step 1-6) using (R)-tert-butyl 2-hydroxy-1,3-dioxo-hexahydroimidazo[1,5-a]pyrazine-7(1H)-carboxylate as the starting material. $^1$H NMR ($CDCl_3$, 300 MHz) δ 7.34-7.36 (m, 5H), 6.83-6.92 (m, 4H), 3.99-4.15 (m, 2H), 3.49-3.85 (m, 9H), 2.77-3.27 (m, 9H), 2.28 (d, J=6.3 Hz, 2H), 2.05-2.15 (m, 4H), 1.68-1.79 (m, 3H), 1.23-1.33 (m, 2H). LCMS (ESI, m/z): 577 [M+H]$^+$.

Example 46: Preparation of (S)-7-((1-benzylpiperidin-4-yl)methyl)-1,3-dioxo-hexahydroimidazo[1,5-a]pyrazin-2(3H)-yl 4-(4-(prop-2-ynyloxy)phenyl)piperazine-1-carboxylate (Compound 46)

phenyl)piperazine-1-carboxylate (300 mg, 0.50 mmol, 1.00 equiv) was separated by chiral-HPLC using the following gradient conditions: Column: Chiralpak IA 2*25 cm, 5 um; Mobile Phase A: acetonitrile (95%), Mobile Phase B: $CH_2Cl_2$ (5%); Flow rate: 20 mL/min; Detector, UV 254 nm; RT1: 11.50 min; RT2: 19.0 min. Chiral-HPLC separation resulted in 128.5 mg (43% yield) of (S)-7-((1-benzylpiperidin-4-yl)methyl)-1,3-dioxo-hexahydroimidazo[1,5-a]pyrazin-2(3H)-yl 4-(4-(prop-2-ynyloxy)phenyl)piperazine-1-carboxylate as a white solid. $^1$H NMR ($CDCl_3$, 300 MHz) δ 7.31-7.33 (m, 5H), 6.88-6.95 (m, 4H), 4.65 (d, J=2.4 Hz, 2H), 4.10-4.15 (m, 1H), 3.99-4.04 (m, 1H), 3.80 (br, 2H), 3.58-3.67 (m, 4H), 3.22-3.27 (m, 1H), 2.95-3.14 (m, 7H), 2.77-2.81 (m, 1H), 2.51 (t, J=2.4 Hz, 1H), 2.28 (d, J=6.9 Hz, 2H), 2.03-2.14 (m, 4H), 1.68-1.78 (m, 3H), 1.32-1.34 (m, 2H). LCMS (ESI, m/z): 601 [M+H]$^+$.

Alternatively, the title compound was synthesized as described in Example 44 (Step 1-6) using 1-benzylpiperidine-4-carbaldehyde in step 6. $^1$H NMR ($CDCl_3$, 300 MHz) δ 7.27-7.33 (m, 5H), 6.89-6.96 (m, 4H), 4.66 (d, J=2.4 Hz, 2H), 4.11-4.16 (m, 1H), 4.00-4.05 (m, 1H), 3.80 (br, 2H), 3.69 (br, 2H), 3.55 (br, 2H), 3.23-3.28 (m, 1H), 3.07-3.16 (m, 5H), 2.92 (br, 2H), 2.79-2.82 (m, 1H), 2.52 (t, J=2.4 Hz, 1H), 2.28 (d, J=7.2 Hz, 2H), 1.99-2.15 (m, 4H), 1.68-1.77

7-((1-Benzylpiperidin-4-yl)methyl)-1,3-dioxo-hexahydroimidazo[1,5-a]pyrazin-2(3H)-yl 4-(4-(prop-2-ynyloxy)

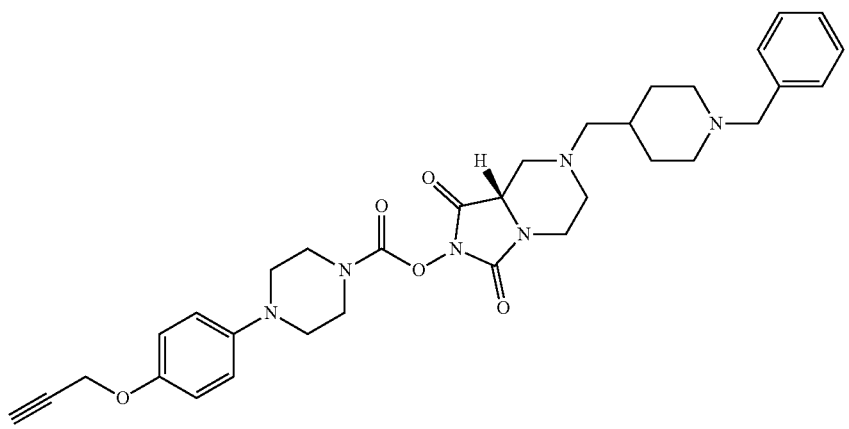 [SMILES: C#CCOc1ccc(N2CCN(C(=O)ON3C(=O)[C@@H]4CN(CC5CCN(Cc6ccccc6)CC5)CCN4C3=O)CC2)cc1]

(m, 2H), 1.48-1.51 (m, 1H), 1.27-1.30 (m, 2H). LCMS (ESI, m/z): 601 [M+H]$^+$.

Example 47: Preparation of (R)-7-((1-benzylpiperi-
din-4-yl)methyl)-1,3-dioxo-hexahydroimidazo[1,5-a]
pyrazin-2(3H)-yl 4-(4-(prop-2-ynyloxy)phenyl)pip-
erazine-1-carboxylate (Compound 47)

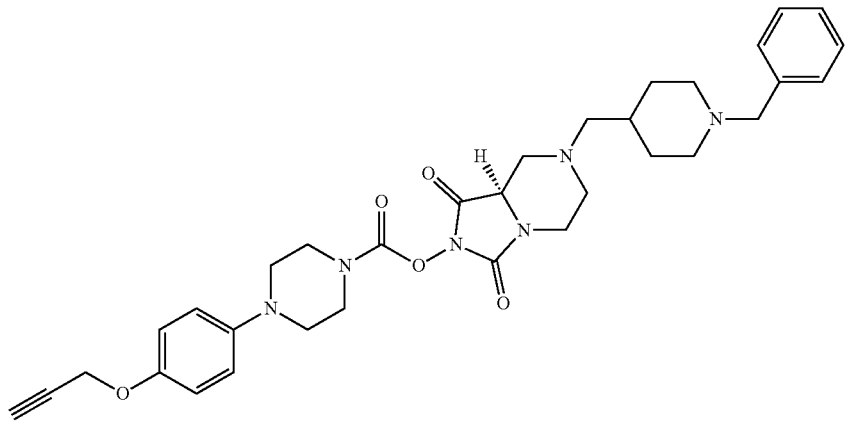 [SMILES: C#CCOc1ccc(N2CCN(C(=O)ON3C(=O)[C@H]4CN(CC5CCN(Cc6ccccc6)CC5)CCN4C3=O)CC2)cc1]

7-((1-Benzylpiperidin-4-yl)methyl)-1,3-dioxo-hexahy-
droimidazo[1,5-a]pyrazin-2(3H)-yl 4-(4-(prop-2-ynyloxy)
phenyl)piperazine-1-carboxylate (300 mg, 0.50 mmol, 1.00
equiv) was separated by chiral-HPLC using the following
gradient conditions: Column: Chiralpak IA 2*25 cm, 5 um;
Mobile Phase A: acetonitrile (95%), Mobile Phase B:
$CH_2Cl_2$ (5%); Flow rate: 20 mL/min; Detector, UV 254 nm;
RT1: 11.50 min; RT2: 19.0 min. Chiral-HPLC separation
resulted in 59.5 mg (20% yield) of (R)-7-((1-benzylpiperi-
din-4-yl)methyl)-1,3-dioxo-hexahydroimidazo[1,5-a]
pyrazin-2(3H)-yl4-(4-(prop-2-ynyloxy)phenyl)piperazine-
1-carboxylate as a white solid. $^1$H NMR (CDCl$_3$, 300 MHz)
δ 7.31-7.33 (m, 5H), 6.88-6.95 (m, 4H), 4.65 (d, J=2.4 Hz,
2H), 4.10-4.15 (m, 1H), 3.99-4.04 (m, 1H), 3.58-3.80 (m,
6H), 3.22-3.27 (m, 1H), 2.97-3.14 (m, 7H), 2.77-2.80 (m,
1H), 2.51 (t, J=2.4 Hz, 1H), 2.28 (d, J=6.6 Hz, 2H),
2.04-2.14 (m, 4H), 1.68-1.79 (m, 2H), 1.32-1.36 (m, 2H).
LCMS (ESI, m/z): 601 [M+H]$^+$.

Alternatively, the title compound was synthesized as
described in Example 46 using (R)-tert-butyl 2-hydroxy-1,
3-dioxo-hexahydroimidazo[1,5-a]pyrazine-7(1H)-carboxy-
late as the starting material. $^1$H NMR (CDCl$_3$, 300 MHz) δ
7.27-7.34 (m, 5H), 6.89-6.96 (m, 4H), 4.66 (d, J=2.4 Hz,
2H), 4.11-4.16 (m, 1H), 4.00-4.05 (m, 1H), 3.80 (br, 2H),
3.68 (br, 2H), 3.56-3.57 (m, 2H), 3.23-3.28 (m, 1H), 3.07-
3.16 (m, 5H), 2.94 (br, 2H), 2.79-2.82 (m, 1H), 2.52 (t, J=2.4
Hz, 1H), 2.28 (d, J=6.6 Hz, 2H), 2.06-2.15 (m, 4H), 1.69-
1.78 (m, 2H), 1.53 (br, 1H), 1.25-1.38 (m, 2H). LCMS (ESI,
m/z): 601 [M+H]$^+$.

Example 48: Preparation of (S)-7-(morpholine-4-
carbonyl)-1,3-dioxo-hexahydroimidazo[1,5-a]
pyrazin-2(3H)-yl 4-(4-ethynylphenethyl)piperidine-
1-carboxylate (Compound 48)

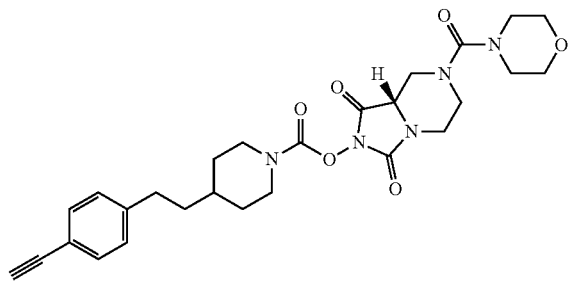 [SMILES: C#Cc1ccc(CCC2CCN(C(=O)ON3C(=O)[C@@H]4CN(C(=O)N5CCOCC5)CCN4C3=O)CC2)cc1]

7-(Morpholine-4-carbonyl)-1,3-dioxo-hexahydroimidazo
[1,5-a]pyrazin-2(3H)-yl4-(4-ethynylphenethyl)piperidine-
1-carboxylate (63.0 mg, 0.220 mmol, 1.00 equiv) was sepa-
rated by Prep-Chiral-HPLC using the following gradient
conditions: Column: Chiralpak IA 2*25 cm, 5 um; Mobile
Phase: MeCN (100%); Flow rate: 20 mL/min; Detector, 254
nm; RT1: 8.5 min; RT2: 14.0 min. Chiral-HPLC separation
resulted in 37.6 mg (59.7% yield) of (S)-7-(morpholine-4-
carbonyl)-1,3-dioxo-hexahydroimidazo[1,5-a]pyrazin-2
(3H)-yl 4-(4-ethynylphenethyl)piperidine-1-carboxylate as
a white solid. $^1$H NMR (CDCl$_3$, 300 MHz) δ 7.45 (d, J=9.0
Hz, 2H), 7.10 (d, J=9.0 Hz, 2H), 4.10-4.28 (m, 2H), 4.02-
4.09 (m, 3H), 3.66-3.71 (m, 5H), 3.30-3.34 (m, 4H), 3.10-
3.19 (m, 1H), 2.82-3.04 (m, 5H), 2.61-2.64 (m, 2H), 1.72-
1.81 (m, 2H), 1.56-1.63 (m, 2H), 1.40-1.52 (m, 1H), 1.30-
1.40 (m, 2H). LCMS (ESI, m/z): 524 [M+H]$^+$.

Alternatively, the title compound was prepared as follows.

Step 1: [(4-Iodophenyl)methyl]triphenylphosphanium bromide

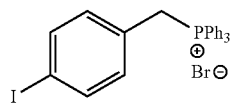

A 250-mL round-bottom flask was charged with 1-(bromomethyl)-4-iodobenzene (10.0 g, 33.7 mmol, 1.00 equiv, toluene (100 mL), triphenylphosphane (12.4 g, 47.3 mmol, 1.40 equiv). The resulting solution was stirred overnight at 100° C. The solid was collected by filtration to provide 20.0 g (crude) of [(4-iodophenyl)methyl]triphenylphosphanium bromide as a yellow solid. LCMS (ESI, m/z): 480 [M−Br]+

Step 2: tert-Butyl 4-[(E)-2-(4-iodophenyl)ethenyl]piperidine-1-carboxylate

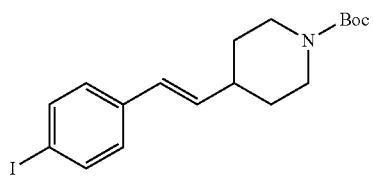 [SMILES: CC(C)(C)OC(=O)N1CCC(/C=C/c2ccc(I)cc2)CC1]

A 500-mL round-bottom flask was charged with [(4-iodophenyl)methyl]triphenylphosphanium bromide (20.0 g, 35.8 mmol, 1.00 equiv), THF (250 mL), tert-butyl 4-formylpiperidine-1-carboxylate (7.62 g, 35.8 mmol, 1.00 equiv), and sodium hydride (60% w/w, 2.15 g, 53.7 mmol, 1.50 equiv). The resulting solution was stirred for 5 h at 0° C. and quenched with water (300 mL). The mixture was extracted with EtOAc (3×100 mL) and the organic layers were combined, washed with brine (2×100 mL), dried over anhydrous Na$_2$SO$_4$, filtered and concentrated. The residue was chromatographed on a silica gel column with EtOAc/petroleum ether (1/8) to provide 11.5 g (67% yield) of tert-butyl 4-[(E)-2-(4-iodophenyl)ethenyl]piperidine-1-carboxylate as yellow oil. LCMS (ESI, m/z): 414 [M+H]+

Step 3: tert-Butyl 4-[2-(4-iodophenyl)ethyl]piperidine-1-carboxylate

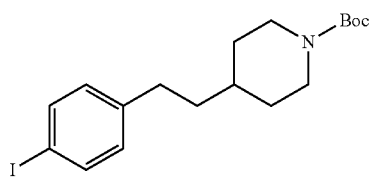 [SMILES: CC(C)(C)OC(=O)N1CCC(CCc2ccc(I)cc2)CC1]

A 50-mL round-bottom flask was charged with tert-butyl 4-[(E)-2-(4-iodophenyl)ethenyl]piperidine-1-carboxylate (2.40 g, 5.81 mmol, 1.00 equiv), ethylene glycol dimethyl ether (30 mL), 4-methylbenzene-1-sulfonohydrazide (2.16 g, 11.6 mmol, 2.00 equiv), sodium acetate (1.43 g, 17.4 mmol, 3.00 equiv), water (8 mL). The resulting solution was stirred overnight at 90° C. and quenched with water (30 mL). The mixture was extracted with EtOAc (3×30 mL) and the organic layers were combined, washed with brine (2×30 mL), dried over anhydrous Na$_2$SO$_4$, filtered and concentrated. The residue was chromatographed on a silica gel column with EtOAc/petroleum ether (1/10) to provide 1.60 g (66% yield) of tert-butyl 4-[2-(4-iodophenyl)ethyl]piperidine-1-carboxylate as yellow oil. LCMS (ESI, m/z): 416 [M+H]+

Step 4: tert-Butyl 4-(2-[4-[2-(trimethylsilyl)ethynyl]phenyl]ethyl)piperidine-1-carboxylate

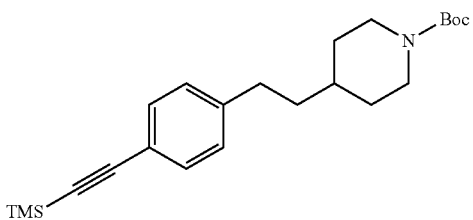 [SMILES: CC(C)(C)OC(=O)N1CCC(CCc2ccc(C#C[Si](C)(C)C)cc2)CC1]

A 50-mL round-bottom flask was charged with tert-butyl 4-[2-(4-iodophenyl)ethyl]piperidine-1-carboxylate (2.40 g, 5.78 mmol, 1.00 equiv), THF (30 mL), ethynyltrimethylsilane (850 mg, 8.65 mmol, 1.50 equiv), copper (I) iodide (220 mg, 1.16 mmol, 0.20 equiv), bis(triphenylphosphine)palladium(II) chloride (406 mg, 0.578 mmol, 0.10 equiv), and triethylamine (1.17 g, 11.6 mmol, 2.00 equiv). The resulting solution was stirred overnight at 30° C. and quenched with water (10 mL). The mixture was extracted with EtOAc (3×10 mL) and the organic layers were combined, washed with brine (2×10 mL), dried over anhydrous Na$_2$SO$_4$, filtered and concentrated. The residue was chromatographed on a silica gel column with EtOAc/petroleum ether (1/10) to provide 2.00 g (90% yield) of tert-butyl 4-[2-(4-[2-(trimethylsilyl)ethynyl]phenyl]ethyl)piperidine-1-carboxylate as a yellow solid. LCMS (ESI, m/z): 386 [M+H]+

Step 5: tert-Butyl 4-[2-(4-ethynylphenyl)ethyl]piperidine-1-carboxylate

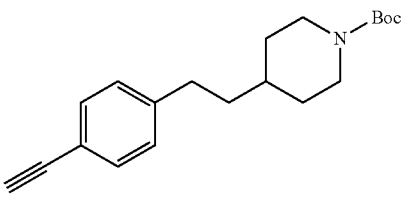 [SMILES: C#Cc1ccc(CCC2CCN(C(=O)OC(C)(C)C)CC2)cc1]

A 50-mL round-bottom flask was charged with a solution of tert-butyl 4-[2-(4-[2-(trimethylsilyl)ethynyl]phenyl]ethyl)piperidine-1-carboxylate (2.40 g, 6.22 mmol, 1.00 equiv) in THF (30 mL), and tetrabutylammonium fluoride (2.44 g, 9.35 mmol, 1.50 equiv). The resulting solution was stirred for 3 h at room temperature and quenched with water (10 mL). The mixture was extracted with CH$_2$Cl$_2$ (3×10 mL) and the organic layers were combined, washed with brine (2×10 mL), dried over anhydrous Na$_2$SO$_4$, filtered and concentrated. The residue was chromatographed on a silica gel column with EtOAc/petroleum ether (1/10) to provide 1.72 g (88% yield) of tert-butyl 4-[2-(4-ethynylphenyl)ethyl]piperidine-1-carboxylate as yellow oil. LCMS (ESI, m/z): 314 [M+H]+

Step 6: 4-[2-(4-Ethynylphenyl)ethyl]piperidine

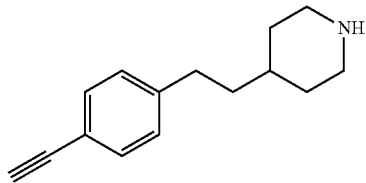 [SMILES: C#Cc1ccc(CCC2CCNCC2)cc1]

A 50-mL round-bottom flask was charged with tert-butyl 4-[2-(4-ethynylphenyl)ethyl]piperidine-1-carboxylate (1.72 g, 5.49 mmol, 1.00 equiv), CH$_2$Cl$_2$ (20 mL), and NMM (1.66 g, 16.5 mmol, 3.00 equiv). Trimethyiodosilane (2.20 g, 11.0 mmol, 2.00 equiv) was added dropwise. The resulting solution was stirred for 3 h at room temperature and quenched with water (10 mL). The mixture was extracted with CH$_2$Cl$_2$ (3×10 mL) and the organic layers were combined, washed with brine (2×10 mL), dried over anhydrous Na$_2$SO$_4$, filtered and concentrated to provide 1.10 g (94% yield) of 4-[2-(4-ethynylphenyl)ethyl]piperidine as a yellow solid. LCMS (ESI, m/z): 214 [M+H]$^+$

Step 7: 4-[2-(4-Ethynylphenyl)ethyl]piperidine-1-carbonyl chloride

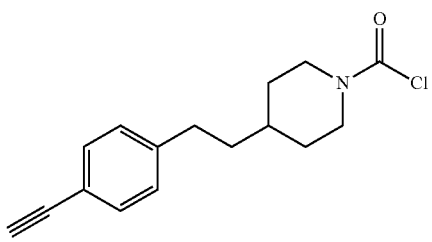 [SMILES: C#Cc1ccc(CCC2CCN(C(=O)Cl)CC2)cc1]

A 50-mL round-bottom flask was charged with triphosgene (615 mg, 2.07 mmol, 0.40 equiv) and CH$_2$Cl$_2$ (20 mL). 4-[2-(4-Ethynylphenyl)ethyl]piperidine (1.10 g, 5.16 mmol, 1.00 equiv) was added. N,N-Diisopropylethylamine (2.00 g, 15.5 mmol, 3.00 equiv) was added dropwise. The resulting solution was stirred overnight at room temperature and quenched with water (10 mL). The mixture was extracted with CH$_2$Cl$_2$ (3×10 mL) and the organic layers were combined, washed with brine (2×10 mL), dried over anhydrous Na$_2$SO$_4$, filtered and concentrated to provide 1.40 g (98% yield) of 4-[2-(4-ethynylphenyl)ethyl]piperidine-1-carbonyl chloride as brown oil. LCMS (ESI, m/z): 276 [M+H]$^+$

Step 8: (S)-7-(Morpholine-4-carbonyl)-1,3-dioxo-hexahydroimidazo[1,5-a]pyrazin-2(3H)-yl 4-(4-ethynylphenethyl)piperidine-1-carboxylate

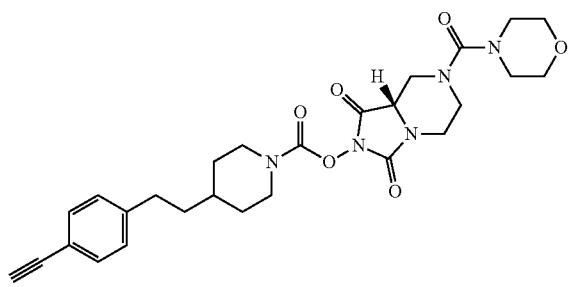 [SMILES: C#Cc1ccc(CCC2CCN(C(=O)ON3C(=O)[C@@H]4CN(C(=O)N5CCOCC5)CCN4C3=O)CC2)cc1]

A 50-mL round-bottom flask was charged with a solution of 4-[2-(4-ethynylphenyl)ethyl]piperidine-1-carbonyl chloride (1.40 g, 5.08 mmol, 1.00 equiv) in CH$_2$Cl$_2$ (20 mL), (S)-2-hydroxy-7-(morpholine-4-carbonyl)-hexahydroimidazo[1,5-a]pyrazine-1,3(2H,5H)-dione (1.74 g, 6.12 mmol, 1.21 equiv), NMM (1.55 g, 15.3 mmol, 3.00 equiv), and 4-DMAP (124 mg, 1.02 mmol, 0.20 equiv). The resulting solution was stirred overnight at room temperature and quenched with water (10 mL). The mixture was extracted with CH$_2$Cl$_2$ (3×10 mL) and the organic layers were combined, washed with brine (2×10 mL), dried over anhydrous Na$_2$SO$_4$, filtered and concentrated. The crude product (400 mg) was purified by preparative HPLC using the following gradient conditions: 30% CH$_3$CN/70% Phase A increasing to 70% CH$_3$CN over 10 min, then to 100% CH$_3$CN over 0.1 min, holding at 100% CH$_3$CN for 1.9 min, then reducing to 30% CH$_3$CN over 0.1 min, and holding at 30% for 1.9 min, on a Waters 2767-5 Chromatograph. Column: Xbridge Prep C18, 19*150 mm 5 um; Mobile phase: Phase A: water; Phase B: CH$_3$CN; Detector, UV220 & 254 nm. Purification resulted in 140 mg (5% yield) of (S)-7-(morpholine-4-carbonyl)-1,3-dioxo-hexahydroimidazo[1,5-a]pyrazin-2(3H)-yl4-(4-ethynylphenethyl)piperidine-1-carboxylate as a white solid. $^1$H NMR (CDCl$_3$, 300 MHz) δ 7.45 (d, J=9.0 Hz, 2H), 7.10 (d, J=9.0 Hz, 2H), 4.10-4.28 (m, 2H), 4.02-4.09 (m, 3H), 3.66-3.71 (m, 5H), 3.30-3.34 (m, 4H), 3.04-3.19 (m, 1H), 2.98 (s, 1H), 2.83-2.96 (m, 4H), 2.61-2.67 (m, 2H), 1.77-1.81 (m, 2H), 1.56-1.63 (m, 2H), 1.40-1.49 (m, 1H), 1.20-1.40 (m, 2H). LCMS (ESI, m/z): 524 [M+H]$^+$.

Example 49: Preparation of (R)-7-(morpholine-4-carbonyl)-1,3-dioxo-hexahydroimidazo[1,5-a]pyrazin-2(3H)-yl 4-(4-ethynylphenethyl)piperidine-1-carboxylate (Compound 49)

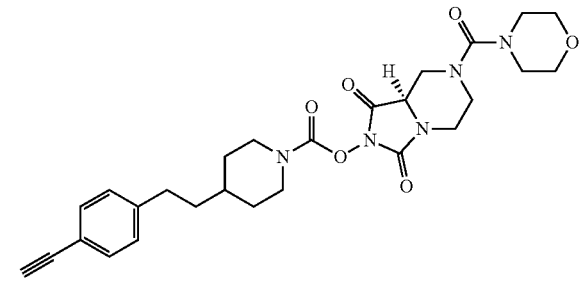 [SMILES: C#Cc1ccc(CCC2CCN(C(=O)ON3C(=O)[C@H]4CN(C(=O)N5CCOCC5)CCN4C3=O)CC2)cc1]

7-(Morpholine-4-carbonyl)-1,3-dioxo-hexahydroimidazo[1,5-a]pyrazin-2(3H)-yl4-(4-ethynylphenethyl)piperidine-1-carboxylate (63.0 mg, 0.220 mmol, 1.00 equiv) was separated by Prep-Chiral-HPLC using the following gradient conditions: Column: Chiralpak IA 2*25 cm, 5 um; Mobile Phase: MeCN (100%); Flow rate: 20 mL/min; Detector, 254 nm; RT1: 8.5 min; RT2: 14.0 min. Chiral-HPLC separation resulted in 9.2 mg (14.6% yield) of (R)-7-(morpholine-4-carbonyl)-1,3-dioxo-hexahydroimidazo[1,5-a]pyrazin-2(3H)-yl 4-(4-ethynylphenethyl)piperidine-1-carboxylate as yellow solid. $^1$H NMR (CDCl$_3$, 300 MHz) δ 7.45 (d, J=9.0 Hz, 2H), 7.10 (d, J=9.0 Hz, 2H), 4.10-4.28 (m, 2H), 4.02-4.09 (m, 3H), 3.66-3.71 (m, 5H), 3.30-3.34 (m, 4H), 3.04-3.19 (m, 1H), 2.98 (s, 1H), 2.83-2.96 (m, 4H), 2.61-2.67 (m, 2H), 1.77-1.81 (m, 2H), 1.56-1.63 (m, 2H), 1.40-1.49 (m, 1H), 1.20-1.40 (m, 2H). LCMS (ESI, m/z): 524 [M+H]$^+$.

Example 50: Preparation of (S)-7-(morpholine-4-carbonyl)-1,3-dioxohexahydroimidazo[1,5-a]pyrazin-2(3H)-yl 4-(4-chloro-phenethyl)piperidine-1-carboxylate (Compound 50)

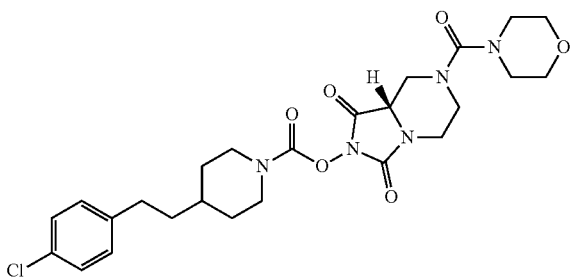

The title compound was separated from 7-(morpholine-4-carbonyl)-1,3-dioxohexahydroimidazo[1,5-a]pyrazin-2(3H)-yl 4-(4-chloro-phenethyl)piperidine-1-carboxylate (Example 1) following the procedure described in Example 40.

Example 51: Preparation of (R)-7-(morpholine-4-carbonyl)-1,3-dioxohexahydroimidazo[1,5-a]pyrazin-2(3H)-yl 4-(4-chloro-phenethyl)piperidine-1-carboxylate (Compound 51)

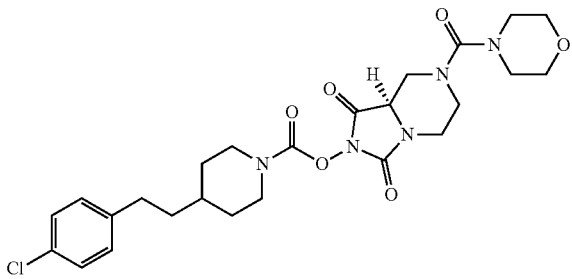 [SMILES: O=C(ON1C(=O)[C@H]2CN(C(=O)N3CCOCC3)CCN2C1=O)N1CCC(CCc2ccc(Cl)cc2)CC1]

The title compound was separated from 7-(morpholine-4-carbonyl)-1,3-dioxohexahydroimidazo[1,5-a]pyrazin-2(3H)-yl 4-(4-chloro-phenethyl)piperidine-1-carboxylate (Example 1) following the procedure described in Example 40.

II. Biological Evaluation

Assays:

Transient Overexpression

HEK293T cells were seeded at 2×105 per well on 6 well plates and grown for 48 h. They were then transfected with mABHD3 (pCMV-Sport6), hABHD4 (pcDNA3.1/myc-his), hPPT1 (pCMV6-XL5), or hPPT1 S115A (pCMV6-XL5), by incubating 0.5 µg of DNA with 3 µL of PEI MAX (1 mg/mL, Polysciences, Inc) in serum-free DMEM for 30 min, then adding them to cells. After 48 h cells were either treated with compound in situ, as described above, or harvested for in vitro studies. The S110A PPT1 mutation was introduced using QuikChange II Site Directed Mutagenesis Kit (Agilent) with the following primers:

```
hPPT1 S→A QC Forward:
aattggcctccctgggcgaatcccatagcattg hPPT1 S→A QC Reverse:
caatgctatgggattcgcccagggaggccaatt
```

Western Blotting

Following SDS-PAGE, PPT1 samples were transferred to nitrocellulose for 2 h at 50 V. Transfers were then washed, blocked with 5% milk, and incubated overnight with Anti-PPT1 (Abcam ab89022, 1:2000 in TBS-T with 5% milk). Transfers were then washed 3× (TBS-T) and incubated with a secondary antibody (Odyssey 926-23310, 1:5000 in TBS-T with 5% milk) for 2 h. Transfers were then washed again (3×, TBS-T) and imaged on a Li-cor Odyssey (Model 9120).

PPT1 Substrate Assay

PPT1 activity was assessed in vitro using a substrate assay adapted from previous studies (van Diggelen et al., Molecular genetics and metabolism 66, 240-244, 1999). Lysates from HEK293T cells transfected with an empty vector, or human PPT1 under a CMV promoter were adjusted to 1 mg/ml in PBS (25 µl), and then combined 1:1 with McIlvain's phosphate/citrate buffer containing 0.375% (v/v) Triton-X 100 and 15 mM DTT (pH 5.0). This sample was pre-treated with inhibitor or DMSO for 30 minutes at 37° C., and 10 µl (5 µg protein) was used in the substrate assay as follows: Samples were diluted in a black 96-well plate (half-area) with 20 µl McIlvain's phosphate/citrate buffer (pH 5.0) containing 0.375% TX-100 and 15 mM DTT, as well as 0.64 mM MU-6S-Palm-PD-Glc and 0.1 U sweet almond glucosidase (Sigma). The reactions were incubated at 37° C. for 1 hour, quenched with 120 µl sodium bicarbonate buffer (pH 10.0), and hydrolysis by 4-MU fluorescence measured by excitement at 380 nM and emission intensity at 460 nM. 16 µg protein was used for analysis of native PC3 cells.

IsoTOP Site-of-Labeling of PPT1

Whole cell lysates (500 µL, 1.5 mg/mL) of hPPT1 transfected HEK239Ts were processed for MS analysis using the previously described isoTOP-ABPP protocol (Weerapana et al., Nature 468, 790-795, 2010). In brief, for analysis of Compound 39-modified peptides, proteomes were split into two fractions, to which Compound 39 (5 µM, 60 min) or DMSO were added. The lysates were then subjected to Click Chemistry-ABPP conditions with either light (Compound 39 treated samples) or heavy (DMSO treated samples) isotopically labeled TEV-tags. Light and heavy-tagged proteomes were then combined, and, following enrichment of probe-labeled targets using streptavidin beads, proteins were digested on-bead with trypsin and remaining immobilized peptides released with a subsequent TEV protease digestion. The resulting probe-modified peptides were pressure loaded onto a 100 µm (inner diameter) fused silica capillary column with a 5 µm tip containing 10 cm C18 resin (5 µm, Phenomenex), eluted with a 180 min gradient from 0% to 100% Buffer B (Buffer A: 5% acetonitrile, 95% water, 0.1% formic acid; Buffer B: 80% acetonitrile, 20% water, 0.1% formic acid), and collected for MS analysis on an LTQ-Orbitrap. Samples were then searched as described above. The mass of the modification used to search for probe-modified peptides was +626.3289 m/z for the probe adduct plus the light TEV-tag and +632.3427 m/z for the heavy counterpart. MS1 peaks for probe-labeled quantified peptides were extracted with Xcalibur Qual Browser 2.2 (Thermo Scientific).

Example A1: Solubility and Stability Assays

Solubility in PBS:

The solubility of compounds were tested in triplicate in phosphate buffered saline (PBS), pH 7.4. Per well, 198 µL PBS is added to a Millipore Solvinert Hydrophilic PTFE 96 well filter plate: pore size: 0.45 µm (MSRLN0450). Test compounds were introduced from 10 mM DMSO stock solutions (2 µL). The final concentration of DMSO was 1 percent. Samples were allowed to incubate at 22° C. for 18 hours. In the morning the plate was centrifuged where the soluble portion passes through the filter and was collected in a capture plate. Clotrimazole was included as a control to assure the assay was working properly. The samples were analyzed by HPLC. Peak area was compared to a standard of known concentration. In cases when the concentration was too low for UV analysis or when the compound did not possess a good chromophore, LC-MS-MS analysis was used.

The solubility of Compound 1 was determined to be 18 µM in PBS.

Solubility in Media: The solubility of compounds were tested in triplicate in complete media (DMEM+10% FBS). Per well, 198 µL PBS is added to a Millipore Solvinert Hydrophilic PTFE 96 well filter plate: pore size: 0.45 µm (MSRLN0450). Test compounds were introduced from 10 mM DMSO stock solutions (2 µL). The final concentration of DMSO was 1 percent. Samples were allowed to incubate at 22° C. for 18 hours. In the morning the plate was centrifuged where the soluble portion passed through the filter and was collected in a capture plate. The samples were analyzed by HPLC (Agilent 1100 with diode-array detector). Peak area was compared to a standard of known concentration. In cases when the concentration was too low for UV analysis or when the compound did not possess a good chromophore, LC-MS-MS analysis was used.

The solubility of compound 1 was determined to be 46 µM in DMEM containing 10% fecal calf serum.

Stability in PBS:

Demonstration of stability in PBS was conducted by addition of 10 µM compound from a DMSO stock to PBS in HPLC autosampler vials. Samples were held in the HPLC autosampler at ambient temperature. At approximately 0, 1, 2, 4, 8, 24, and 48 hours the samples were injected on the HPLC. Peak area and retention time were compared between injections. Data was log transformed and represented as half-life. DMSO was added as a co-solvent as needed for solubility.

The stability of compound 1 was determined to be 19 h in PBS, likely due to hydrolytic opening of the NHS group.

Example A2: Determination of Glutathione Reactivity

Compound (10 µM) was incubated at 37° C. for 6 hours in the presence of 50 µM freshly prepared reduced glutathione. At 0 and 6 hours the samples were injected into the HPLC instrument. Peak area and retention time were compared between injections. Samples were evaluated for a glutathione dependent decrease in compound concentration. DMSO was added as a co-solvent as needed for solubility.

Compound 1 did not show any reactivity with glutathione (50 µM), indicating that the compound has a tempered electrophilicity and specific structural elements that direct reactivity towards a highly selective enzyme subset (LYPLAs and ABHD6). Gel-based and LC-MS/MS (MudPIT)-based ABPP selectivity profiling also confirmed high target specificity for over 20 SHs.

Example A3: Gel-Based ABPP Analysis of Potency and Selectivity In Vitro

Assay Overview: The purpose of this assay was to determine whether test compounds can inhibit LYPLA1 and LYPLA2 in a complex proteomic lysate and to assess anti-target inhibition using a competitive activity-based proteomic profiling (ABPP) assay. In this assay, a complex proteome endogenously expressing LYPLA1/2 was incubated with test compound followed by reaction with a rhodamine-conjugated fluorophosphonate (FP-Rh) serine-hydrolase specific activity-based probe. The reaction products were separated by SDS-PAGE and visualized in-gel using a flatbed fluorescence scanner. The percentage activity remaining was determined by measuring the integrated optical density of the bands. As designed, test compounds that act as LYPLA1 and/or LYPLA2 inhibitors prevented enzyme-probe interactions, thereby decreasing the proportion of bound fluorescent probe, giving lower fluorescence intensity in the band in the gel. Percent inhibition was calculated relative to a DMSO (no compound) control.

Protocol Summary: Mouse brain membrane proteome (50 µL reaction volume, 1 mg/mL in DPBS) was treated with 0.1-100 µM test compound (1 µL of a 50× stock in DMSO) for 30 minutes at 37° C. FP-Rh (1 µL of 50× stock in DMSO, Thermo #88318) was added to a final concentration of 2 µM. The reactions were incubated for 30 minutes at 25° C., quenched with 16 µL 4×SDS-PAGE loading buffer (reducing), separated by SDS-PAGE and visualized by in-gel fluorescent scanning. The percentage activity remaining was determined by measuring the integrated optical density of the bands relative to a DMSO-only (no compound) control. Assay Cutoff: Compounds with ≥50% inhibition of targets at 1 µM test compound concentration were considered active.

N-Hydroxy bicyclic hydantoin carbamates (Compounds 1-20) listed in Table 1 were subjected to gel-based competitive ABPP screening to assess SH reactivity against more than 20 FP-sensitive SHs visible by 1D SDS-PAGE separation and fluorescent detection in the mouse brain proteome (see FIG. 1). Mouse brain was selected due to its abundance of SH enzymes and high homology between human and mouse SHs (e.g., comparable potency for mouse and human isoforms of LYPLAs observed for Compound 1). Compound treatment (0.1-1000 nM, 30 minutes) was followed by labeling with SH-specific ABPP probe FP-Rh (2 µM, 30 minutes), 1D-SDS-PAGE, and in-gel fluorescent visualization of FP-labeled proteins. Assignment of LYPLA1/2 bands was based on correlation of molecular weights, expression and inhibition profiles with LC-MS/MS data and recombinant enzyme expression. Proteins were listed as anti-targets if at least 50% inhibition was observed as quantified relative to the DMSO control. Compound 1 exhibited the best combination of potent target inhibition and high selectivity; other than ABHD6, out of the 20+ SHs visible by gel, the only anti-target with appreciable inhibition at a dose below 10 µM was FAAH ($IC_{50}$=3150 nM, selectivity of ~13-fold).

Compounds 1-20 were subjected to gel-based competitive ABPP profiling to assess potency and selectivity against several dozen FP-sensitive SHs in the mouse brain membrane proteome, which endogenously expresses LYPLA1 and LYPLA2, as well a diversity of potential SH anti-targets. Compounds were tested at 100 µM, 10 µM, 1 µM, and/or 0.1 µM compound concentration.

Tables 2 and 3 summarize $IC_{50}$ and % inhibition as well as anti-target activity for Compounds 1-20.

TABLE 2

| | | LYPLA1 | | | | | LYPLA2 | | | | | Anti-target(s)¶ | | |
|---|---|---|---|---|---|---|---|---|---|---|---|---|---|---|
| | | % INH‡ | | | | | % INH‡ | | | | | | | |
| Cpd. | $IC_{50}$§ | 100 μM | 10 μM | 1 μM | 0.1 μM | $IC_{50}$§ | 100 μM | 10 μM | 1 μM | 0.1 μM | 100 μM | 10 μM | 1 μM | 0.1 μM |
| 1 | 122 | 100 | 100 | 100 | NT* | 245 | 100 | 100 | 100 | NT | FAAH, ABHD12, MAGL, ABHD6 | FAAH, ABHD6 | ABHD6 | NT |
| 2 | 154 | 100 | 100 | 100 | 50 | 258 | 100 | 100 | 100 | 50 | FAAH, ABHD12, ABHD4, MAGL, ABHD6 | FAAH, ABHD12, ABHD4, MAGL, ABHD6 | FAAH, ABHD6 | ABHD6 |
| | 225 | 100 | 100 | 100 | 50 | 384 | 100 | 100 | 100 | 50 | FAAH, ABHD12, ABHD4, MAGL, ABHD6 | FAAH, ABHD6 | FAAH, ABHD6 | ABHD6 |
| 4 | 92 | 100 | 100 | 100 | 80 | 217 | 100 | 100 | 100 | 80 | FAAH, ABHD12, ABHD4, MAGL, ABHD6 | FAAH, ABHD12, MAGL, ABHD6 | FAAH, ABHD6 | ABHD6 |
| 5 | NT | 100 | 100 | 80 | 50 | NT | 100 | 100 | 80 | 50 | FAAH, ABHD12, MAGL, ABHD6 | FAAH, ABHD12, ABHD6 | FAAH, ABHD6 | ABHD6 |
| 6 | NT | 100 | 100 | 95 | 25 | NT | 100 | 100 | 95 | 25 | FAAH, MAGL, ABHD6 | FAAH, MAGL, ABHD6 | FAAH, ABHD6 | ABHD6 |
| 7 | 306 | 100 | 95 | 80 | 0 | 726 | 100 | 95 | 80 | 0 | FAAH, ABHD12, ABHD4, MAGL, ABHD6 | FAAH, ABHD12, ABHD6 | ABHD6 | ABHD6 |
| 8 | NT | 100 | 100 | 75 | NT | NT | 100 | 100 | 75 | NT | FAAH, ABHD12, MAGL, ABHD6 | FAAH, ABHD12, ABHD6 | ABHD6 | NT |
| 9 | NT | 100 | 100 | 90 | NT | NT | 100 | 100 | 90 | NT | FAAH, ABHD12, MAGL, ABHD6 | FAAH, ABHD12, ABHD6 | ABHD6 | NT |
| 10 | NT | 100 | 100 | 75 | NT | NT | 100 | 100 | 75 | NT | FAAH, ABHD12, ABHD6 | FAAH, ABHD12, ABHD6 | ABHD6 | NT |
| 11 | NT | 100 | 100 | 90 | NT | NT | 100 | 100 | 90 | NT | FAAH, ABHD12, MAGL, ABHD6 | FAAH, ABHD12, MAGL, ABHD6 | ABHD6 | NT |
| 12 | NT | 100 | 95 | 25 | 0 | NT | 100 | 95 | 25 | 0 | FAAH, ABHD4, MAGL, ABHD6 | FAAH, ABHD4, MAGL, ABHD6 | ABHD6 | ABHD6 |
| 13 | NT | 90 | 75 | 10 | 0 | NT | 90 | 75 | 10 | 0 | FAAH, ABHD4, MAGL, ABHD6 | FAAH, ABHD4, ABHD6 | FAAH, ABHD4, ABHD6 | ABHD6 |

§$IC_{50}$ values were determined from three replicates at each inhibitor concentration against the human LYPLA isoforms (comparable values obtained for mouse isoform)
‡% Inhibition values were determined from one replicate at each inhibitor concentration
*NT = not tested
¶SHs are listed as anti-targets if at least 50% inhibition was observed at a given compound concentration (see Table 7 for enzyme names)

TABLE 3

| | LYPLA1 % INH‡ | | | | LYPLA2 % INH‡ | | | | Anti-target(s)¶ | | | |
|---|---|---|---|---|---|---|---|---|---|---|---|---|
| Cpd. | 100 μM | 10 μM | 1 μM | 0.1 μM | 100 μM | 10 μM | 1 μM | 0.1 μM | 100 μM | 10 μM | 1 μM | 0.1 μM |
| 14 | 25 | 0 | 0 | 0 | 25 | 0 | 0 | 0 | APEH, ABHD6 | ABHD6 | ABHD6 | ABHD6 |

TABLE 3-continued

| Cpd. | LYPLA1 % INH[‡] | | | | LYPLA2 % INH[‡] | | | | Anti-target(s)[¶] | | | |
|---|---|---|---|---|---|---|---|---|---|---|---|---|
| | 100 μM | 10 μM | 1 μM | 0.1 μM | 100 μM | 10 μM | 1 μM | 0.1 μM | 100 μM | 10 μM | 1 μM | 0.1 μM |
| 15 | 25 | 0 | 0 | 0 | 25 | 0 | 0 | 0 | ABHD6 | ABHD6 | ABHD6 | ABHD6 |
| 16 | 0 | 0 | 0 | 0 | 0 | 0 | 0 | 0 | ABHD6 | ABHD6 | none | none |
| 17 | 90 | 75 | 0 | 0 | 75 | 50 | 0 | 0 | FAAH, ABHD12, ABHD6 | ABHD6 | ABHD6 | ABHD6 |
| 18 | 60 | 50 | 10 | 0 | 60 | 50 | 10 | 0 | ABHD6 | ABHD6 | ABHD6 | ABHD6 |
| 19 | 50 | 10 | 0 | 0 | 25 | 0 | 0 | 0 | FAAH, ABHD6 | ABHD6 | ABHD6 | ABHD6 |
| 20 | 100 | 100 | 10 | 0 | 100 | 75 | 10 | 0 | ABHD6 | ABHD6 | ABHD6 | ABHD6 |

[‡] % Inhibition values were determined from one replicate at each inhibitor concentration
[¶] SHs are listed as anti-targets if at least 50% inhibition was observed at a given compound concentration (see table 7 for enzyme names)

In vitro enzyme activities (mouse brain (mem) proteome) for Compounds 21, 23, 31, 38, 40-53 are shown in Table 4.

TABLE 4

| Cpd. | ABHD3 | FAAH | ABHD12 | ABHD6 | PLA2G7 | LYPLA1 | LYPLA2 |
|---|---|---|---|---|---|---|---|
| 21 | | | | 100% @ 20 μM | | 0% @ 20 μM | 0% @ 20 μM |
| 23 | | | | 100% @ 20 μM | | 0% @ 20 μM | 0% @ 20 μM |
| 31 | | | | | | 0% @ 20 μM | 0% @ 20 μM |
| 38 | | | | 100% @ 20 μM | | 0% @ 20 μM | 0% @ 20 μM |
| 40 | 0% @ 10 μM | 50% @ 10 μM | 0% @ 10 μM | 100% @ 1 μM | 100% @ 10 μM * | 50% @ 10 μM | 50% @ 10 μM |
| 41 | 0% @ 10 μM | 100% @ 10 μM | 0% @ 10 μM | 100% @ 1 μM | 0% @ 10 μM | 100% @ 10 μM | 100% @ 10 μM |
| 42 | 0% @ 10 μM | 0% @ 10 μM | 0% @ 10 μM | 100% @ 1 μM | 100% @ 1 μM | 50% @ 10 μM | 100% @ 10 μM |
| 43 | 0% @ 10 μM | 0% @ 10 μM | 0% @ 10 μM | 100% @ 1 μM | 100% @ 1 μM | 0% @ 10 μM | 0% @ 10 μM |
| 44 | 0% @ 10 μM | 0% @ 10 μM | 0% @ 10 μM | 100% @ 1 μM | 100% @ 1 μM | 0% @ 10 μM | 0% @ 10 μM |
| 45 | 75% @ 10 μM | 0% @ 10 μM | 0% @ 10 μM | 100% @ 1 μM | 100% @ 1 μM | 0% @ 10 μM | 0% @ 10 μM |
| 46 | 0% @ 10 μM | 0% @ 10 μM | 0% @ 10 μM | 100% @ 1 μM | 100% @ 1 μM | 50% @ 10 μM | 50% @ 10 μM |
| 47 | 0% @ 10 μM | 0% @ 10 μM | 0% @ 10 μM | 100% @ 1 μM | 100% @ 1 μM | 0% @ 10 μM | 0% @ 10 μM |
| 48 | 0% @ 10 μM | 75% @ 10 μM | 50% @ 10 μM | 100% @ 1 μM | 75% @ 10 μM | 75% @ 1 μM | 75% @ 1 μM |
| 49 | 0% @ 10 μM | 50% @ 10 μM | 0% @ 10 μM | 100% @ 1 μM | 100% @ 10 μM | 75% @ 1 μM | 75% @ 1 μM |
| 50 | 0% @ 10 μM | 0% @ 10 μM | 0% @ 10 μM | 100% @ 1 μM | 100% @ 10 μM | 100% @ 1 μM | 100% @ 1 μM |
| 51 | 0% @ 10 μM | 0% @ 10 μM | 0% @ 10 μM | 100% @ 1 μM | 100% @ 10 μM | 100% @ 1 μM | 100% @ 1 μM |
| 52 | 0% @ 10 μM | 0% @ 10 μM | 0% @ 10 μM | 100% @ 1 μM | 50% @ 1 μM | 0% @ 10 μM | 0% @ 10 μM |
| 53 | 0% @ 10 μM | 50% @ 10 μM | 50% @ 10 μM | 100% @ 1 μM | 0% @ 10 μM | 75% @ 1 μM | 75% @ 1 μM |

In vitro potencies ($IC_{50}$, nM) for Compounds 31, 34-38, 42, 48-51 are shown in Table 5.

TABLE 5

| Cpd. | mLYPLA1/2 | mABHD6 | hPPT1 | mABHD3 | hABHD4 | hLYPLA1/2 |
|---|---|---|---|---|---|---|
| 31 | | | | >10,000 | 8200 | |
| 34 | | | | >10,000 | ~1000 | |
| 35 | | | | >10,000 | 1000 | |
| 36 | | | | >10,000 | 200 | |
| 37 | | | | 7600 | 100 | |
| 38 | | | | 100 | 30 | |
| 42 | 29300 | | 3971 | | | |

TABLE 5-continued

| Cpd. | mLYPLA1/2 | mABHD6 | hPPT1 | mABHD3 | hABHD4 | hLYPLA1/2 |
|---|---|---|---|---|---|---|
| 48 | | | | | | 1750/1829 |
| 49 | | | | | | 842/1434 |
| 50 | 117 | 2.2 | | | | |
| 51 | 97 | 2.5 | | | | |

Table 6 shows in situ and in vivo enzyme activity data for Compounds 24-26, 34, and 37.

TABLE 6

| Cpd. | hPPT1 (in situ) | mPPT1 (in vivo) | hLYPLA1/2 (in situ) | mLYPLA1/2 (in vivo) |
|---|---|---|---|---|
| 1 | 500 nM | 100% @ 10 mg/kg (testis) | 87/143 nM | 100% @ 5 mg/kg (liver and kidney) |
| 24 | 100% @ 2 µM | | | |
| 25 | 100% @ 2 µM | | | |
| 26 | 100 nM | 100% @ 5 mg/kg (testis) | | 0% @ 40 mg/kg (testis) |
| 34 | 3900 nM | | | |
| 37 | 100% @ 2 µM | | | |

Table 7 shows the enzyme names and identifiers.

TABLE 7

| Assay Target | Name | GeneID | Protein GI | Taxonomy |
|---|---|---|---|---|
| ABHD4 | alpha/beta hydrolase domain containing protein 4 | 105501 | 326937491 | Mus musculus |
| ABHD6 | alpha/beta hydrolase domain containing protein 6 | 66082 | 31560264 | Mus musculus |
| | | 57406 | 189027141 | Homo sapiens |
| ABHD10 | alpha/beta hydrolase domain containing protein 10 | 55347 | 8923001 | Homo sapiens |
| ABHD11 | alpha/beta hydrolase domain-containing protein 11 | 83451 | 74751292 | Homo sapiens |
| ABHD12 | alpha/beta hydrolase domain containing protein 12 | 26090 | 109689718 | Homo sapiens |
| | | 76192 | 159110817 | Mus musculus |
| ACOT2 | acyl-coenzyme A thioesterase 2 | 10965 | 269849771 | Homo sapiens |
| APEH | acylpeptide hydrolase | 327 | 23510451 | Homo sapiens |
| | | 235606 | 19343726 | Mus musculus |
| CTSA | lysosomal protective protein | 5476 | 20178316 | Homo sapiens |
| DPP8 | dipeptidyl peptidase 8 | 54878 | 67460301 | Homo sapiens |
| ESD | esterase D/formylglutathione hydrolase | 2098 | 33413400 | Homo sapiens |
| FAAH | fatty acid amide hydrolase | 14073 | 123253900 | Mus musculus |
| FAM108B1 | alpha/beta hydrolase domain-containing protein 17B isoform 1 precursor | 51104 | 71051600 | Homo sapiens |
| FAP | isoform 1 of Seprase | 2191 | 292495099 | Homo sapiens |
| LYPLA1 | lysophospholipase 1 | 10434 | 5453722 | Homo sapiens |
| | | 18777 | 71059731 | Mus musculus |
| LYPLA2 | lysophospholipase 2 | 11313 | 9966764 | Homo sapiens |
| | | 26394 | 123122209 | Mus musculus |
| LYPLAL1 | lysophospholipase-like 1 | 127018 | 20270341 | Homo sapiens |
| MAGL (MGLL) | monoacylglycerol lipase | 11343 | 6005786 | Homo sapiens |
| | | 23945 | 261878511 | Mus musculus |
| NCEH1 | neutral cholesterol ester hydrolase 1 | 57552 | 68051721 | Homo sapiens |
| PAFAH1B2 | platelet-activating factor acetylhydrolase IB subunit beta | 5049 | 55977294 | Homo sapiens |
| PAFAH1B3 | platelet-activating factor acetylhydrolase IB subunit gamma | 5050 | 3024344 | Homo sapiens |
| PAFAH2 | platelet-activating factor acetylhydrolase 2 | 5051 | 6647691 | Homo sapiens |
| PLA2G15 | group XV phospholipase A2 | 23659 | 44888104 | Homo sapiens |
| PNPLA4 | patatin-like phospholipase domain-containing protein 4 | 8228 | 116242718 | Homo sapiens |
| PNPLA6 | patatin-like phospholipase domain containing protein 6 | 10908 | 260656037 | Homo sapiens |
| PRCP | lysosomal Pro-X carboxypeptidase precursor | 5547 | 1172047 | Homo sapiens |
| PREPL | prolyl endopeptidase-like | 9581 | 121944206 | Homo sapiens |
| SCPEP1 | isoform 1 of Retinoid-inducible serine carboxypeptidase precursor | 59342 | 11055992 | Homo sapiens |

Example A4: Determination of $IC_{50}$ by Gel-Based Competitive ABPP In Vitro

Assay Overview: The purpose of this assay was to determine $IC_{50}$ values of powder samples of test compounds for enzyme of interest activity, and anti-targets in a complex proteomic lysate using a gel-based competitive ABPP assay. In this assay, a complex proteome was incubated with test compound followed by reaction with FP-Rh and SDS-PAGE analysis as described above.

Protocol Summary: Soluble HeLa cell proteome (50 µL reaction volume, 1 mg/mL in DPBS) or mouse brain membrane proteome (50 µL reaction volume, 1 mg/mL in DPBS) was treated with varying concentrations of test compound (1

µL of a 50× stock in DMSO) for 30 minutes at 37° C. FP-Rh (1 µL of 50× stock in DMSO) was added to a final concentration of 2 µM. The reaction was incubated for 30 minutes at 25° C., quenched with 16 µL 4×SDS-PAGE loading buffer (reducing), separated by SDS-PAGE and visualized by in-gel fluorescent scanning. The percentage activity remaining was determined by measuring the integrated optical density of the enzymes of interest, and anti-target bands relative to a DMSO-only (no compound) control. $IC_{50}$ values were determined from dose-response curves from three replicates at each inhibitor concentration: 1, 10, 100, 1000, 10000 nM and 0.01, 0.1, 1, 10, 100, 1000, 10000, 50000, and 100000 nM. Assay Cutoff: Compounds with an $IC_{50}$ less than or equal to 1000 nM were considered active.

Example A5: In Situ Inhibitor Treatment of Human Cell Lines

In situ inhibitor treatments of human cell lines were performed as described previously (Hsu et al., J Med Chem 56, 8270-8279, 2012). Briefly, PC3 or transfected HEK293T cells were grown to confluency in serum-containing media (RPMI or DMEM, respectively). The culture media was then removed and replaced with fresh media containing DMSO or inhibitor at the desired concentration and incubated for 4 hours in a tissue culture incubator (37° C., 5% $CO_2$). Cells were then washed with PBS, harvested, washed with PBS once more, and lysed with a probe sonicator.

Example A6: Determination of $IC_{50}$ Values by Gel-Based Competitive ABPP In Situ Assay Overview: The purpose of this assay was to determine $IC_{50}$ values of powder samples of test compounds for enzyme of interest activity in situ using a gel-based competitive ABPP assay. In this assay, cultured cells were treated with test compound, harvested, and lysed. The isolated soluble proteome fraction was reacted with FP-Rh and analyzed by SDS-PAGE as described above.

Protocol Summary: To cultured HeLa cells (90% confluent) was added fresh DMEM (5 mL total volume; supplemented with 10% FCS) pre-mixed with DMSO or test compound. After 2 hours at 37° C., cells were harvested by scraping, washed twice with 10 mL DPBS, and homogenized by sonication in DPBS. The soluble fraction was isolated by centrifugation (100K×g, 45 minutes) and the protein concentration was adjusted to 1 mg/mL with DPBS. FP-Rh (1 µL of 50× stock in DMSO) was added to a final concentration of 2 µM in 50 µL total reaction volume. The reaction was incubated for 30 minutes at 25° C., quenched with 16 µL 4×SDS-PAGE loading buffer (reducing), separated by SDS-PAGE and visualized by in-gel fluorescent scanning. The percentage activity remaining was determined by measuring the integrated optical density of the enzymes of interest, and anti-target bands relative to a DMSO-only (no compound) control. $IC_{50}$ values were determined from dose-response curves from three replicates at each inhibitor concentration: 0.1, 1, 50, 250, 1000, 20000 nM. Assay Cutoff: Compounds with an $IC_{50}$ less than or equal to 1000 nM were considered active.

Figure 2A:
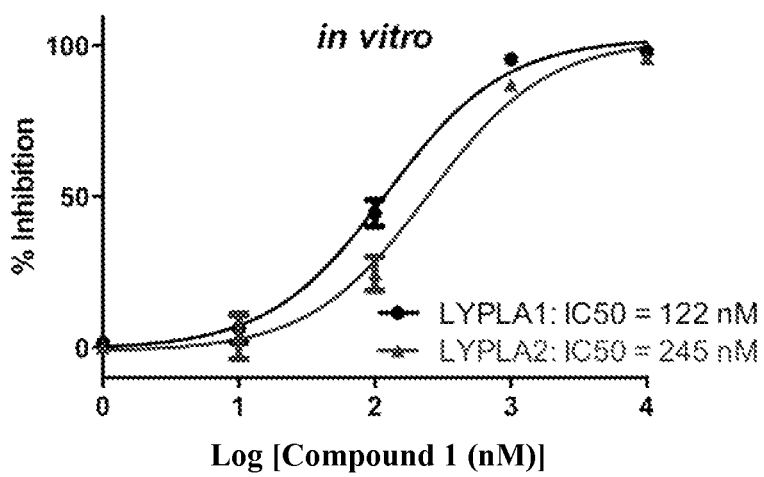
FIG. 2A shows in vitro IC$_{50}$ curves for LYPLA1/2 for Compound 1 in endogenous human LYPLA1/2 in a HeLa soluble proteome.
Figure 2B:
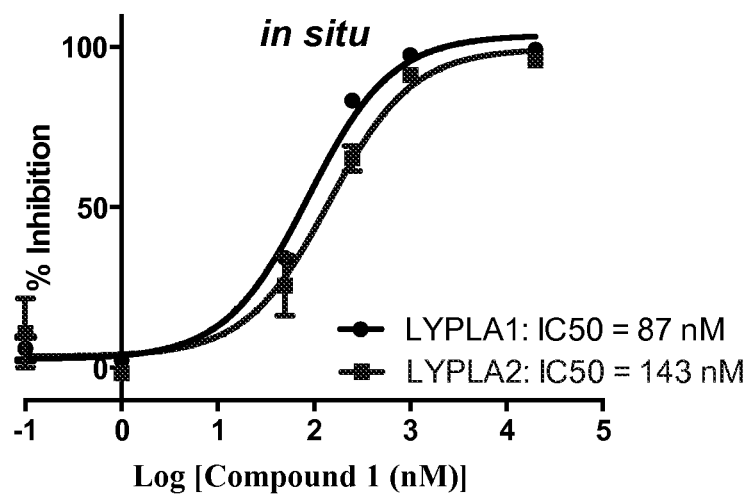
FIG. 2B shows in situ IC$_{50}$ curves for LYPLA1/2 for Compound 1 in endogenous human LYPLA1/2 in a in cultured HeLa cells.
Figure 2C:
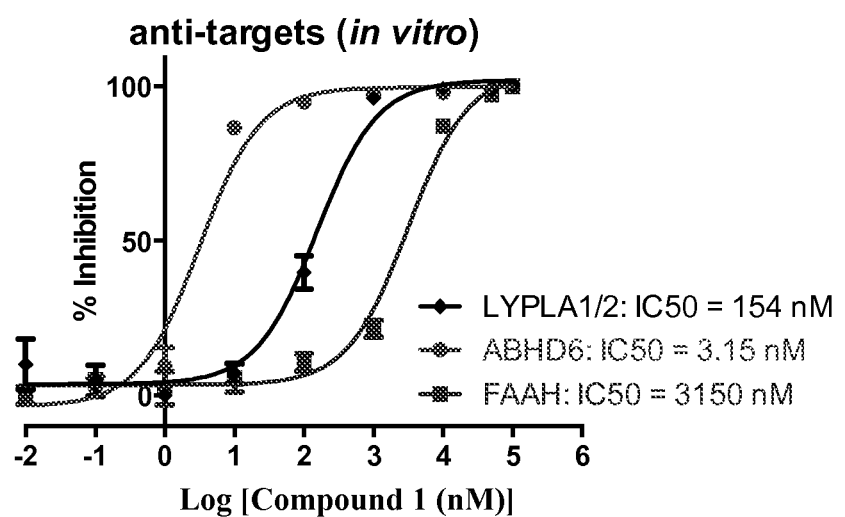
FIG. 2C shows in vitro IC$_{50}$ curves for Compound 1 against endogenous mouse LYPLA1/2 and anti-targets ABHD6 and FAAH in a mouse brain membrane proteome.

$IC_{50}$ values for Compound 1 against the human isoforms of LYPLA1 (122 nM in vitro and 87 nM in situ) and LYPLA2 (245 nM in vitro and 143 nM in situ) were obtained from gel-based competitive-ABPP data using the FP-Rh activity-based probe in both HeLa cell lysates (see FIG. 2A) and cultured HeLa cells (see FIG. 2B). Compound 1 shows comparable in vitro inhibition (collective $IC_{50}$=154 nM) of the mouse isoforms of LYPLA1/2 (see FIG. 2C; note: LYPLA1/2 quantified together due to the overlapping nature of the target bands). $IC_{50}$ values were also determined for anti-targets ABHD6 and FAAH (see FIG. 2C), with Compound 1 showing potent ($IC_{50}$=3.15 nM) inhibition of ABHD6, but good selectivity for FAAH ($IC_{50}$=3150 nM, ~13-fold selectivity).

Figure 3A:
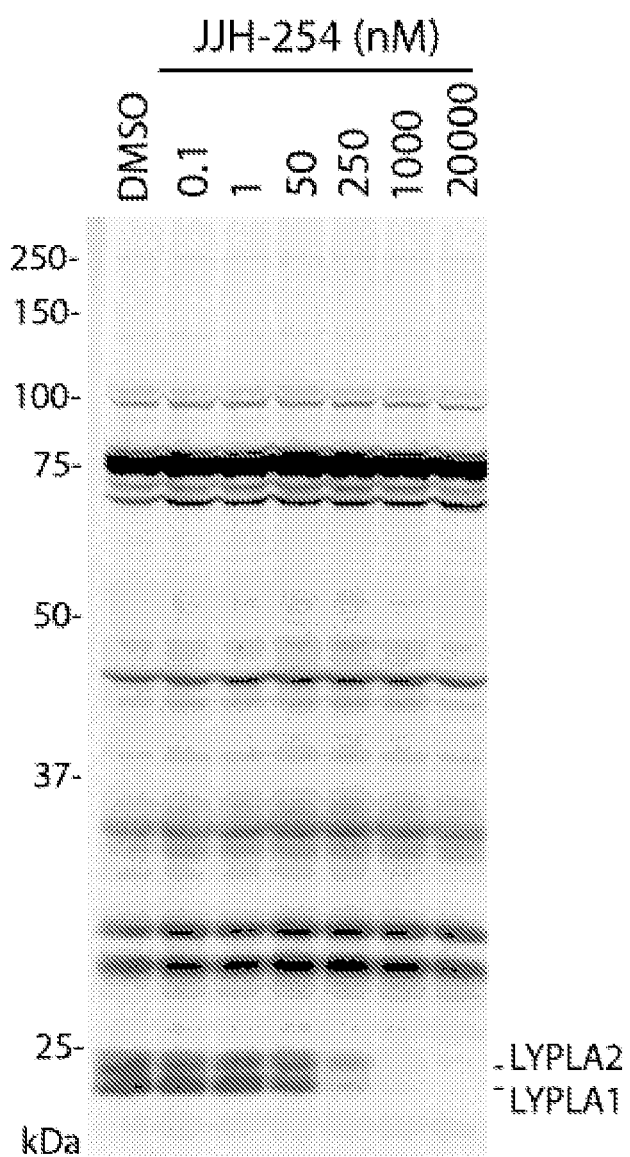
FIG. 3A shows In situ inhibition of LYPLA1 and LYPLA2 by Compound 1.

Compound 1 is active in situ against the LYPLA enzymes (see FIG. 3A) as assessed by gel-based competitive ABPP with FP-Rh following two hours of compound treatment of HeLa cells cultured in serum-supplemented medium. ($IC_{50}$ values of 87 nM and 143 nM were calculated for LYPLA1 and LYPLA2, respectively). No anti-target inhibition is observed at any compound concentration (ABHD6 not visible).

Example A7: Inhibition by Gel-Based Competitive ABPP In Vivo

Assay Overview: The purpose of this assay was to determine whether or not powder samples of test compounds inhibit enzymes of interest in vivo. In this assay, test compounds were administered to mice. Mice were sacrificed, and their tissues harvested, homogenized, and the soluble fractions isolated, reacted with FP-Rh, and separated by SDS-PAGE as described above.

Protocol Summary: Purpose-bred 3-4 month old male C57BL6 laboratory mice were i.p. administered test compound (0.5-50 mg/kg in 18:1:1 saline:PEG-40-castor oil: EtOH vehicle solution, 10 µL/g mouse weight) or vehicle only. After 4 hours, mice were humanely sacrificed (anesthetized with isoflurane followed by cervical dislocation), and tissues (liver, kidney, brain) removed and snap frozen in liquid nitrogen before processing. Tissues were homogenized, and soluble proteome isolated by ultracentrifugation (100 k×g, 45 minutes) and protein concentration adjusted to 1 mg/mL in DPBS. An aliquot (50 µL) was reacted with FP-Rh (2 µM final concentration) for 30 minutes at 25° C. Reactions were quenched with 16 µL 4×SDS-PAGE loading buffer (reducing), separated by SDS-PAGE, and visualized by in-gel fluorescent scanning. The percentage activity remaining was determined by measuring the integrated optical density of test compound bands relative to vehicle bands. Note: Due to the overlapping nature of LYPLA1 and LYPLA2 bands, the proteins were quantified together. Assay Cutoff: Compounds with greater than or equal to 50% inhibition at 5 mg/kg test compound concentration in one or more tissues tested were considered active.

Figure 3B:
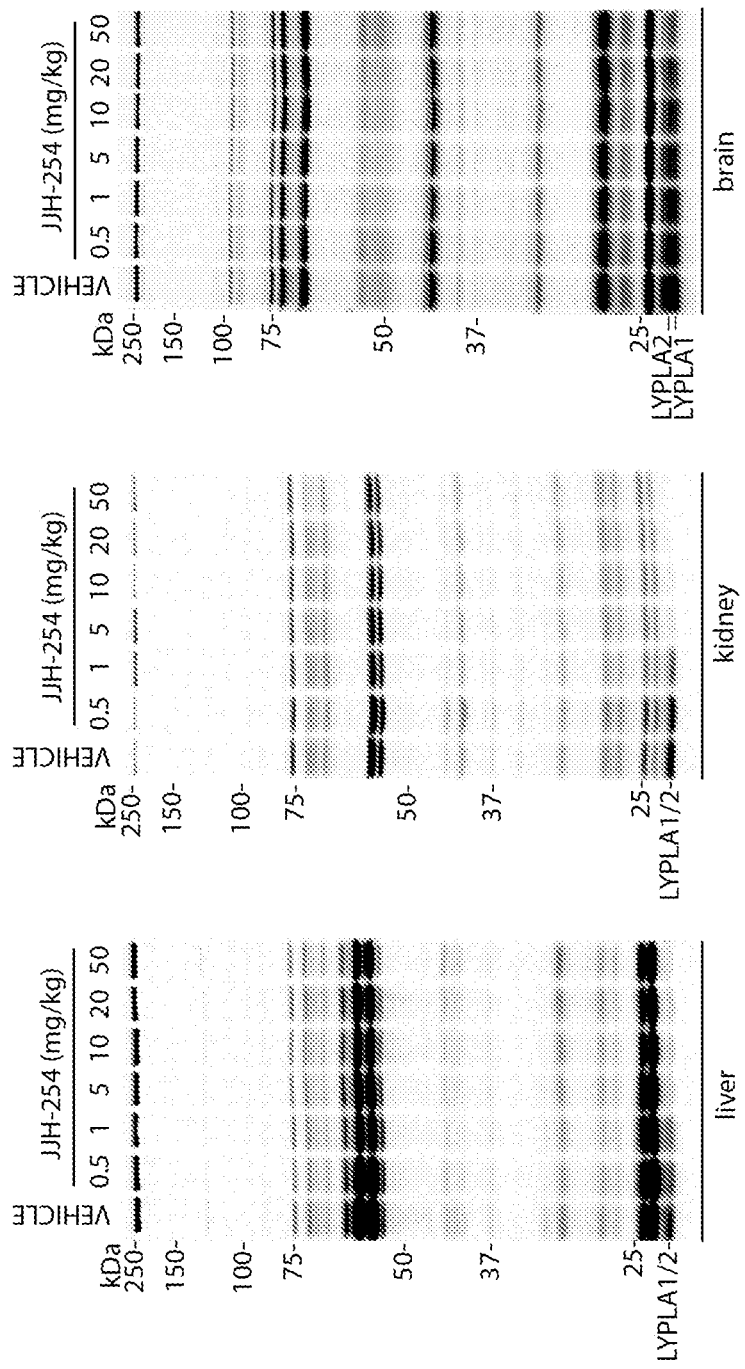
FIG. 3B shows potent and selective in vivo activity for Compound 1.

The in vivo inhibitory activity of Compound 1 was assessed. For this experiment, mice were administered test compound (0.5-50 mg/kg, i.p.) or vehicle only. After four hours mice were sacrificed and their tissues removed, homogenized, and the soluble fractions isolated and labeled with FP-Rh followed by SDS-PAGE and fluorescent detection of FP-labeled SHs (see FIG. 3B).

Near-complete (~90%) inhibition of LYPLA1/2 was observed in liver and kidney. In contrast, only ~75% inhibition was observed in the brain at the highest dose (50 mg/kg). Among the 20+ distinct SH bands, no significant anti-target inhibition was observed in any tissue (ABHD6 not visible); these data indicate that Compound 1 is active and selective in vivo, and that target inhibition appears largely restricted to peripheral tissues.

Example A8: Selectivity Analysis by ABPP-SILAC

Competitive ABPP-SILAC (Adibekian, A., et al. J Am Chem Soc, 2012. 134(25): p. 10345-8) combined competitive ABPP (Leung, D., et al. Nat Biotechnol, 2003. 21(6): p. 687-91) with stable isotope labeling of cells (SILAC) (Ong, S. E., et al. Mol Cell Proteomics, 2002. 1(5): p. 376-86), and allowed for precise quantitation of enzyme inhibition by calculating the isotopic ratios of peptides from inhibitor-treated and control cells.

Assay Overview: The purpose of this assay was to determine the selectivity profile of powder samples of test compounds using stable isotope labeling with amino acids in cell culture (SILAC) ABPP. In this assay, cultured HeLa cells were metabolically labeled with light or heavy amino acids. Light and heavy cells were treated with inhibitor and DMSO, respectively, in situ. Cells were harvested, and proteome fractions were isolated and reacted with the serine-hydrolase-specific activity-based affinity probe fluorophosphonate-biotin (FP-biotin). Light and heavy samples were combined in a 1:1 (w/w) ratio. Biotinylated proteins were enriched, trypsinized, and analyzed by LC/LC-MS/MS (MudPIT) Inhibition of target and anti-target activity was quantified by comparing intensities of light and heavy peptide peaks. As designed, compounds that acted as inhibitors blocked FP-biotin probe labeling, reducing enrichment in the inhibitor-treated (light) sample relative to the DMSO-treated (heavy) sample, giving a smaller light/heavy ratio for each protein. Proteins not targeted by inhibitors were expected to have a ratio close to 1.

Sample Preparation. HeLa cells were initially grown for at least eight passages in either light or heavy SILAC DMEM medium supplemented with 10% dialyzed FCS and 1× PenStrep Glutamine in a humidified incubator (37° C., 5% CO2). Light medium was supplemented with 100 µg/mL L-arginine (Sigma) and 100 µg/mL L-lysine (Sigma). Heavy medium was supplemented with 100 µg/mL [13C615N4]-L-Arginine (Isotek) and 100 µg/mL [13C615N2]-L-Lysine (Isotek). Light cells were treated with test compound (1 µM, from a 1000× stock in DMSO) and heavy cells were treated with DMSO for 2 hours at 37° C. Cells were washed once with cold DPBS, harvested by scraping, and the quadruplicate samples for each condition pooled and lysed in DPBS by sonication. The pooled whole-cell extracts were adjusted to 2 mg/mL [protein], and treated with 10 µM FP-biotin for 1 hour at room temperature in 500 µL DPBS (1 mg protein per condition). Light and heavy samples were then combined 1:1 (w/w protein), and the total protein was precipitated from the samples by addition of 1 mL MeOH and 250 µL CHCl3, followed by vortexing. The protein was pelleted by centrifugation (1400×g, 20 minutes, 4° C.), the supernatant discarded, and the pellet then washed twice more with 1:1 MeOH/CHCl3 (500 µL, then 250 µL, with the protein pellet resuspended by sonication and pelleted by centrifugation, 16 k×g for 10 minutes, following each wash). The washed protein pellets were solubilized first by sonication in 6M urea in aqueous 25 mM ammonium bicarbonate, and then by addition of 140 µL 10% aqueous SDS. Samples were reduced with 10 mM DTT at 65° C. for 15 minutes, and then alkylated with 10 mM iodoacetamide for 30 minutes at room temperature in the dark. Samples were added directly to 6 mL DPBS containing 50 µL avidin-agarose, and biotinylated proteins were then enriched from each sample by incubation over the avidin beads for 1.5 hours with agitation at room temperature. The beads were washed once with 1% SDS, then three times with DPBS, and then transferred to screw-cap tubes in 200 µL 2 M urea/25 mM ammonium bicarbonate. Calcium chloride was added to 2 mM final, and on-bead digestion was performed for 12 hours at 37° C. with sequencing grade modified trypsin (2 µg; Promega). Beads were then filtered from each sample and the resultant peptide samples were acidified with 16 µL formic acid (5% v/v) and stored at −80° C. until analysis.

LC-MS/MS analysis. Samples were analyzed by multidimensional liquid chromatography tandem mass spectrometry (MudPIT) using an Agilent 1200-series quaternary pump and Thermo Scientific LTQ Orbitrap Velos ion trap mass spectrometer. Peptides were eluted in a 5-step MudPIT experiment using 0%, 25%, 50%, 80%, and 100% salt bumps of 500 mM aqueous ammonium acetate and data were collected in data-dependent acquisition mode with dynamic exclusion turned on (20 seconds, repeat count of 1). Specifically, one full MS (MS1) scan (400-1800 m/z) was followed by 30 MS2 scans of the most abundant ions. The MS2 spectra data were extracted from the raw file using RAW Xtractor (version 1.9.9.2; publicly available at http://fields.scripps.edu/researchtools.php). MS2 spectra data were searched using the Sequest algorithm against the latest version of the human UNIPROT database concatenated with the reversed database for assessment of false-discovery rates. Sequest searches allowed for static modification of cysteine residues (+57.02146 due to alkylation), methionine oxidation (+15.9949), mass shifts of labeled amino acids (+10.0083 R, +8.0142 K) and no enzyme specificity. The resulting MS2 spectra matches were assembled into protein identifications and filtered using DTASelect (version 2.0.41; publicly available at http://fields.scripps.edu/researchtools.php) using the —trypstat option (applies different statistical models for the analysis of peptide digestion state), and a maximum false-positive rate set to 1%. Ratios of light/heavy (cpd/DMSO) peaks were calculated using in-house software and normalized at the peptide level to the average ratio of all non-serine hydrolase peptides.

Reported ratios represent the mean of all unique, quantified peptides per protein and do not include peptides that were >3 standard deviations from the median peptide value. Proteins with less than three peptides per protein ID were not included in the analysis. Assay Cutoff A compound was considered active for a particular target/anti-target with a light/heavy ratio of ≤0.5.

Figure 4A:
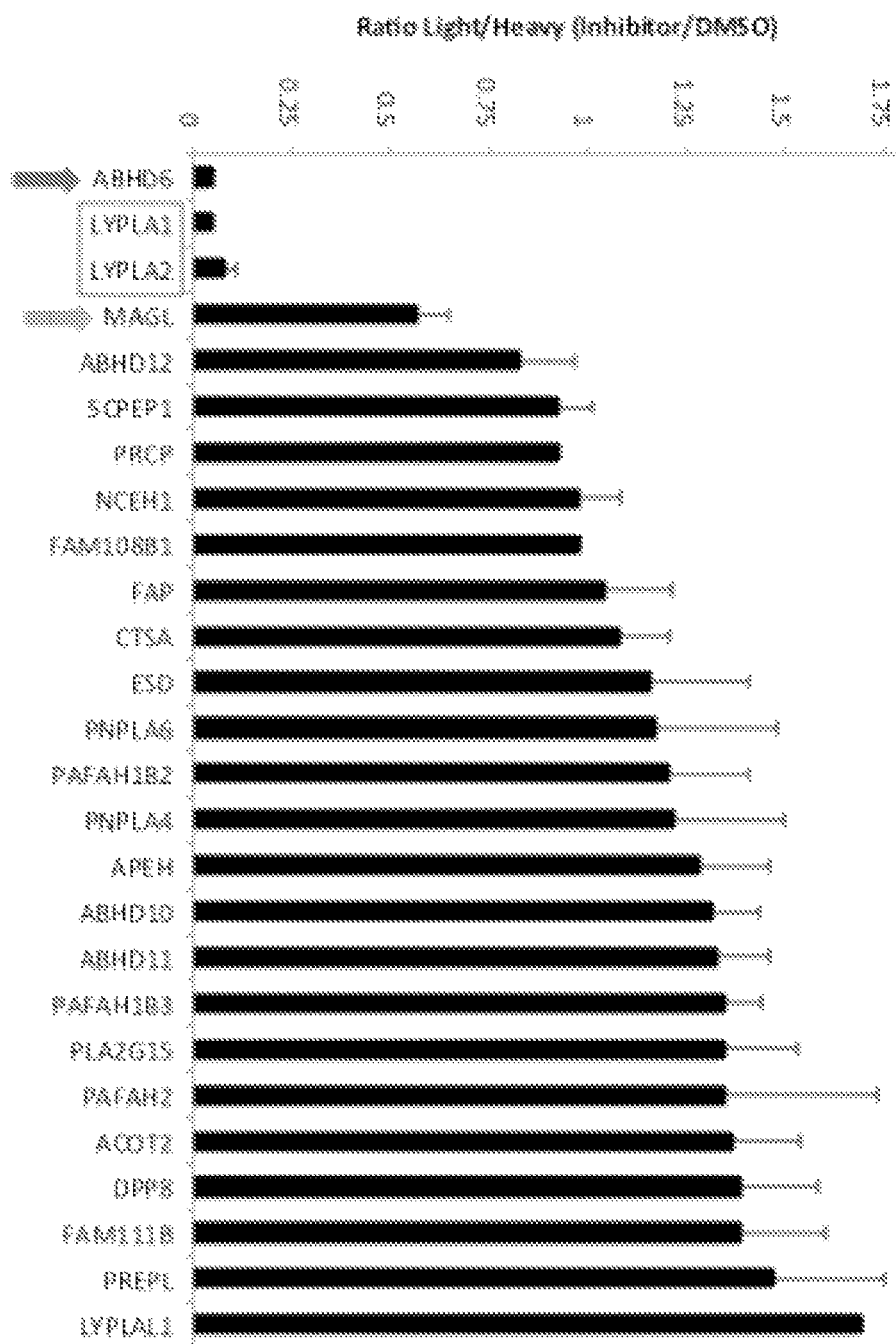
FIG. 4A shows the inhibition profile of Compound 1 (1 µM, 2 hour in situ treatment, serum-supplemented medium)

The results (see FIG. 4A) indicated that Compound 1 achieved near-complete (>90%) inhibition of human LYPLA1/2 (box) and anti-target ABHD6. Of the other 20+ SH anti-targets, only modest (~40%) inhibition of MAGL was observed.

Example A9: Analysis of Cytotoxicity

Assay Overview: The purpose of this assay was to determine cytotoxicity of powder samples of test compounds. In this assay, HeLa cells in either serum-free medium or medium containing fetal calf serum (FCS) were incubated with test compounds, followed by determination of cell viability. The assay utilized the WST-1 substrate, which was converted into colorimetric formazan dye by the metabolic activity of viable cells. The amount of formed formazan directly correlated to the number of metabolically active cells in the culture. As designed, compounds that reduced cell viability resulted in decreased absorbance of the dye.

Protocol Summary: This assay was started by seeding HeLa cells in DMEM medium supplemented with 10% FCS and 1× Pen-Strep-Glutamine in a 96-well plate. Cells were incubated at 37° C. in a humidified incubator until 80% confluent (24 hours). Medium was removed, and 100 µL of fresh medium (serum-free or supplemented with 10% FCS), pre-mixed with DMSO or test compound, was added to each well. Cells were incubated for 48 hours at 37° C. in a humidified incubator and cell viability was determined by the WST-1 assay (Roche) according to manufacturer instructions. $CC_{50}$ values were determined from dose-response curves from three replicates at each inhibitor concentration (10, 100, 1000, 10000, 100000 nM), compared to six replicates of cells treated with DMSO only. Assay Cutoff: Compounds with $CC_{50}$ values less than 10 µM were considered active (cytotoxic).

Figure 5:
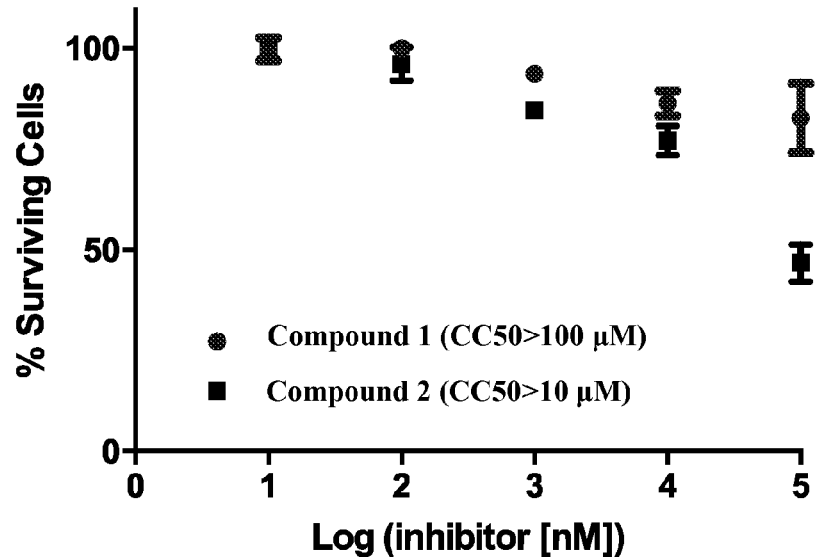
FIG. 5 shows cytotoxicity analysis of Compound 1 and Compound 2 in serum-free and serum-supplemented medium.
Figure 5:
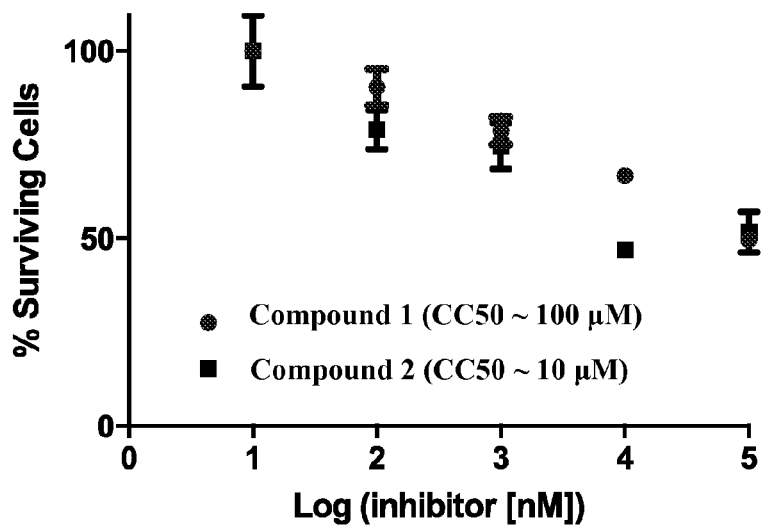

Compound 1 and analog Compound 2 were evaluated for cytotoxicity in HeLa cells cultured in both serum-free and serum-supplemented medium. Compound 1 did not show evidence of cytotoxicity under either condition up to 100 µM test concentration (see FIG. 5). The $CC_{50}$ for the ~equipotent but less selective Compound 2 appeared somewhat lower, with a lower limit of ~10 µM. It should be noted that the solubility of Compound 1 was determined to be 18 µM in medium alone and 46 µM in medium supplemented with 10% serum. As such, the cytotoxicity results should be interpreted with some caution. However, setting a lower $CC_{50}$ limit equal 10 µM (highest test concentration below the determined solubility limit for Compound 1) still afforded a large dosing window (~70-fold, based on in situ $IC_{50}$ values of 87/143 nM for LYPLA1/2) for inhibition of LYPLA1/2 without concern for overt toxicity in biological studies.

Example A10: Gel Filtration to Assess Mode of Action

Assay Overview: The purpose of this assay was to determine whether powder samples of test compounds inhibit LYPLA1 and LYPLA2 in a reversible or irreversible manner. In this assay, a complex proteome was incubated with test compound and a fraction of the assay mixture was passaged over a Sephadex G-25M column before reaction with FP-Rh and SDS-PAGE analysis as described above. As designed, test compounds that acted as irreversible inhibitors prevented enzyme-probe interactions both before and after gel filtration, leading to low fluorescence intensity in the band in the gel. In contrast, compounds that acted as reversible inhibitors showed recovery of probe labeling (and higher fluorescence intensity in the band in the gel) following gel filtration to remove small molecules from the sample.

Protocol Summary: HeLa cell lysate (1 mL of 1 mg/ml in DPBS) was treated with test compound (200 nM or 1000 nM, from 50× stock in DMSO) or DMSO only (no compound control). Test compounds were incubated for 30 minutes at 37° C. An aliquot (50 µL) was removed from each reaction, and the remaining sample was passaged over a Sephadex G-25M desalting column. An aliquot (50 µL, 1 mg/mL protein, eluted in DPBS) was removed, and pre- and post-filtration aliquots were reacted with FP-Rh (50× stock in DMSO; 2 µM final concentration). The reaction was incubated for 30 minutes at 25° C., quenched with 16 µL 4× SDS-PAGE loading buffer (reducing), separated by SDS-PAGE and visualized by in-gel fluorescent scanning. The percentage activity remaining was determined by measuring the integrated optical density of the LYPLA1/2 bands (quantified together) relative to a DMSO-only (no compound) control. The percent recovery was calculated by comparing percent inhibition before and after gel filtration for each test compound concentration.

Figure 6A:
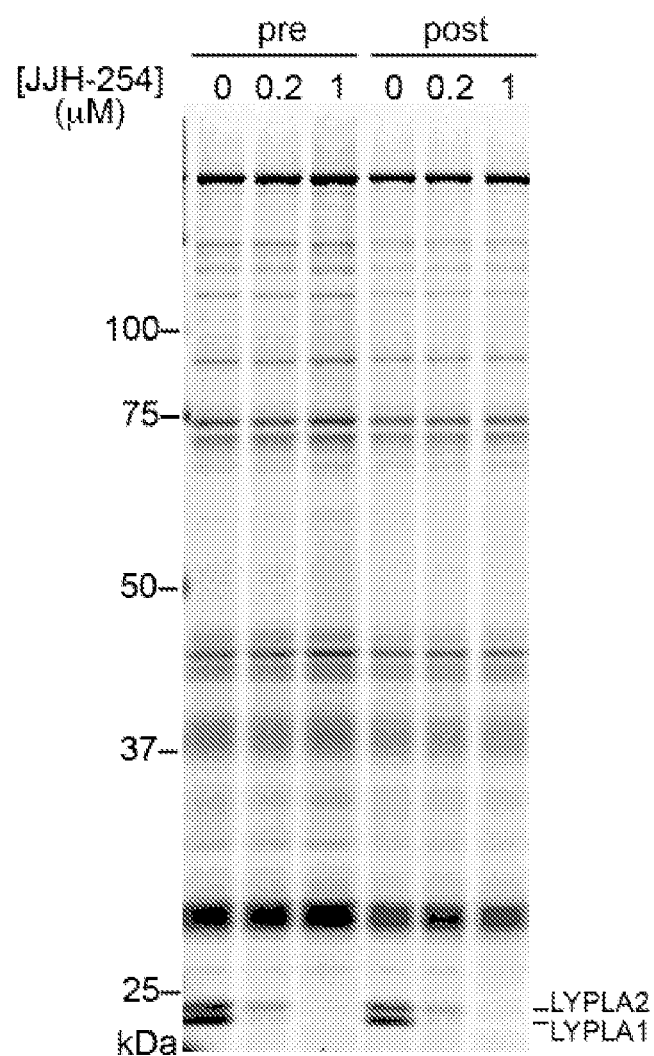
FIG. 6A shows gel filtration studies revealing Compound 1 is an irreversible inhibitor.

An irreversible binding mode for Compound 1 was determined from gel filtration studies, which demonstrated no recovery of ABPP probe FP-Rh labeling for LYPLA1/2 following gel filtration to remove small molecules (e.g., inhibitor compounds), as shown in FIG. 6A.

Example A11: Serine Hydrolase (SH) Inhibition

Figures 1, 7A:
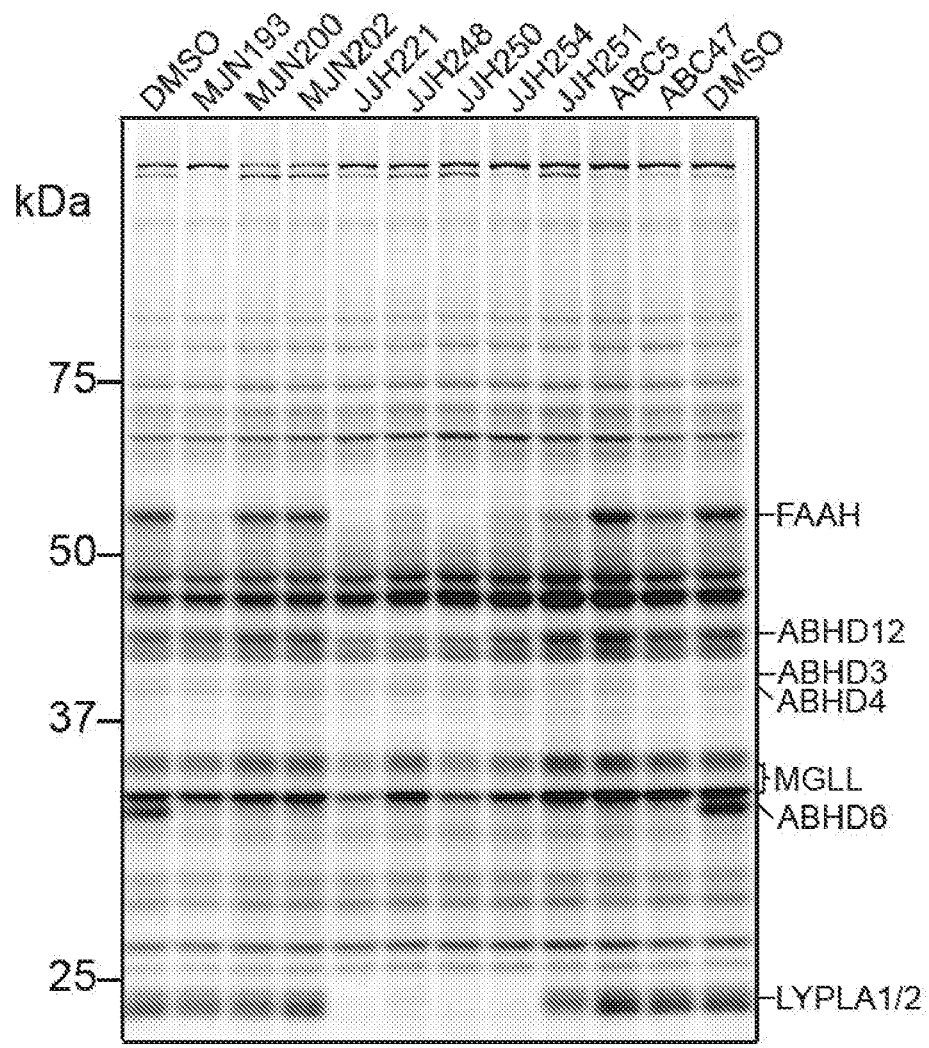

Some N-hydroxy bicyclic hydantoin carbamates showed activity against one or more brain SHs (see FIG. 7A-1).

Figures 2, 7A:
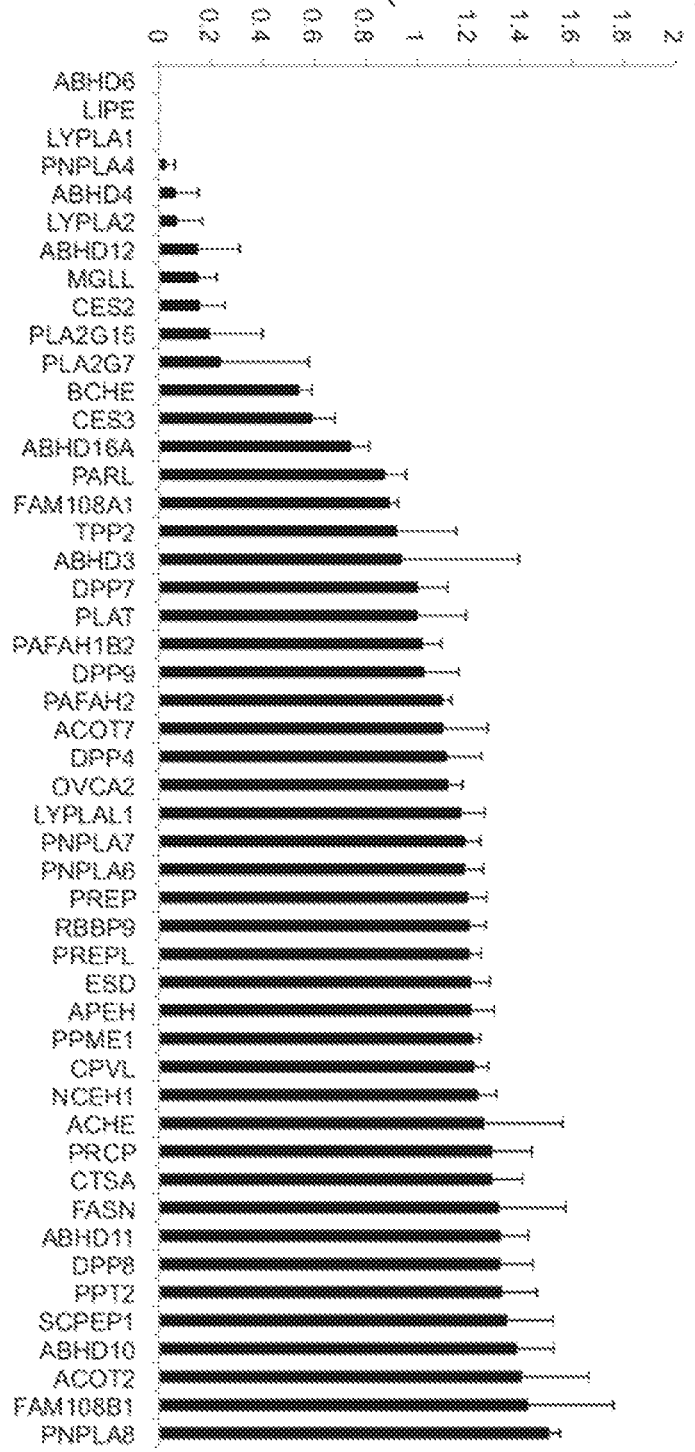

Compound 5 was selected for analysis by mass spectrometry (MS)-based ABPP methods to assess the range of SHs targeted by N-Hydroxy bicyclic hydantoin carbamates. Compound 5-sensitive SHs were identified using the quantitative MS method ABPP-SILAC (Stable isotope labeling by amino acids in cell culture. Compound 5 was found to inhibit several human SHs (defined as proteins showing a three-fold or greater decrease in signal in the Compound 5-treated proteome), including enzymes previously shown to be sensitive to NHS-carbamates (e.g., ABHD6, MGLL) and others for which selective inhibitors are lacking (e.g., ABHD4, ABHD12, PLA2G15, PNPLA4) (see FIG. 7A-2).

Figure 7B:
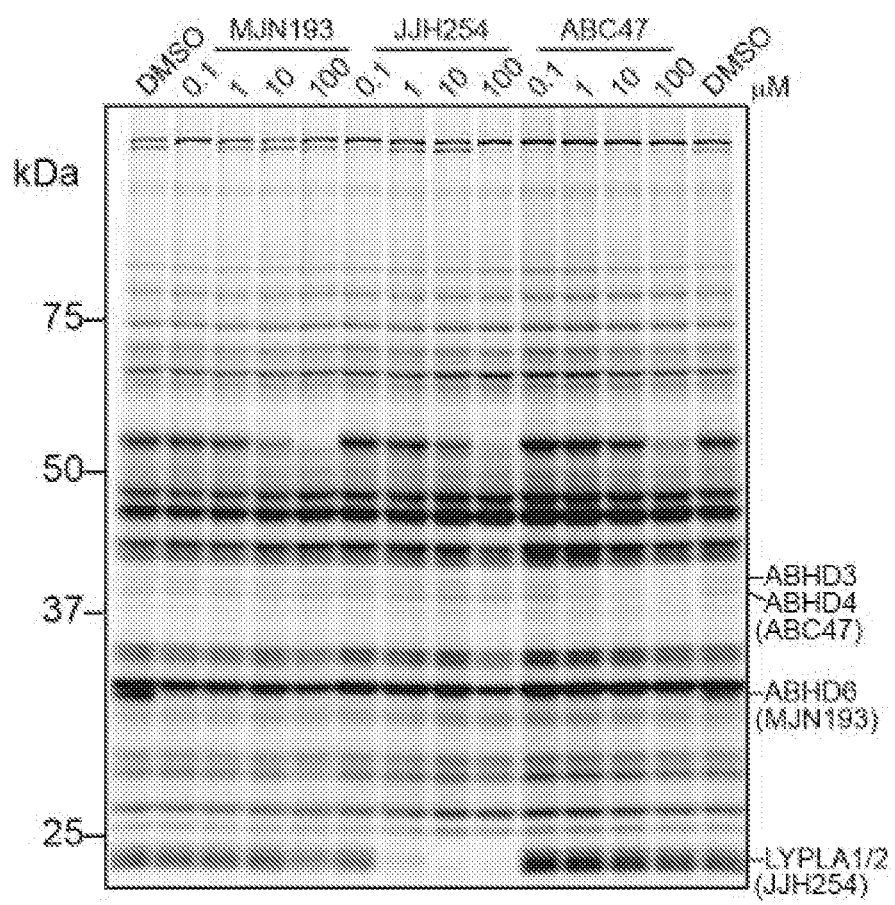
FIG. 7B shows concentration-dependent inhibition of mouse brain membrane SHs by MJN193 (4-isopropyl-2,5-dioxoimidazolidin-1-yl 4-(4-methoxyphenyl)piperazine-1-carboxylate), Compounds 1 and 38, as measured by gel-based competitive ABPP.

A subset of N-hydroxy bicyclic hydantoin carbamates were selected for concentration-dependent profiling, which identified compounds with good potency and selectivity for ABHD6 (4-isopropyl-2,5-dioxoimidazolidin-1-yl 4-(4-methoxyphenyl)piperazine-1-carboxylate, MJN193) and LYPLA1/2 (Compound 1), as well as a promising lead inhibitor for ABHD3 and ABHD4 (Compound 38) (see FIG. 7B).

Example A12: Optimization of N-Hydroxy Bicyclic Hydantoin Carbamate Inhibitors for ABHD3 and ABHD4

Figure 8A:
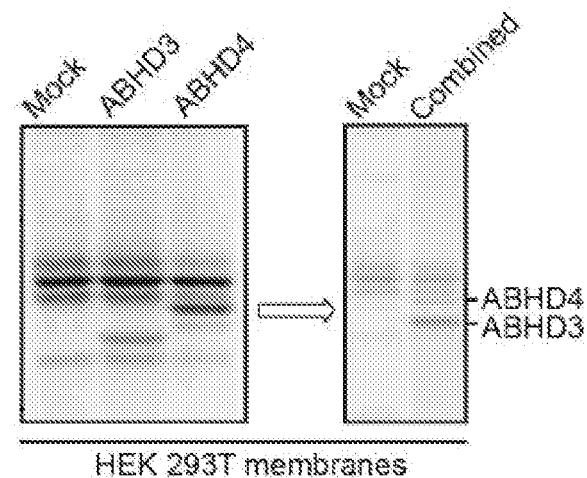
FIG. 8A shows recombinant expression of human ABHD3 and ABHD4 by transient transfection in HEK293T cells and detection of both enzymes in a combined lysate of transfected cells by gel-based ABPP with the FP-Rh probe.
Figure 8B:
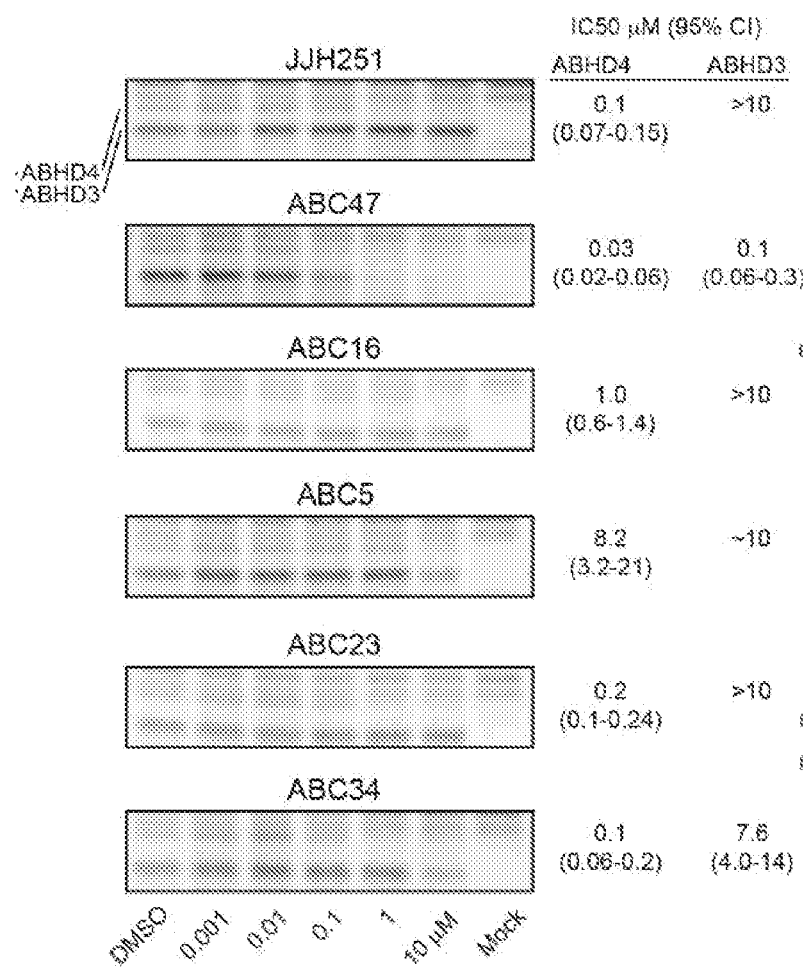
FIG. 8B shows concentration-dependent inhibition of ABHD3 and ABHD4 by Compounds 13, 38, 35, 31, 36, and 37 using gel-based competitive ABPP.
Figure 8C:
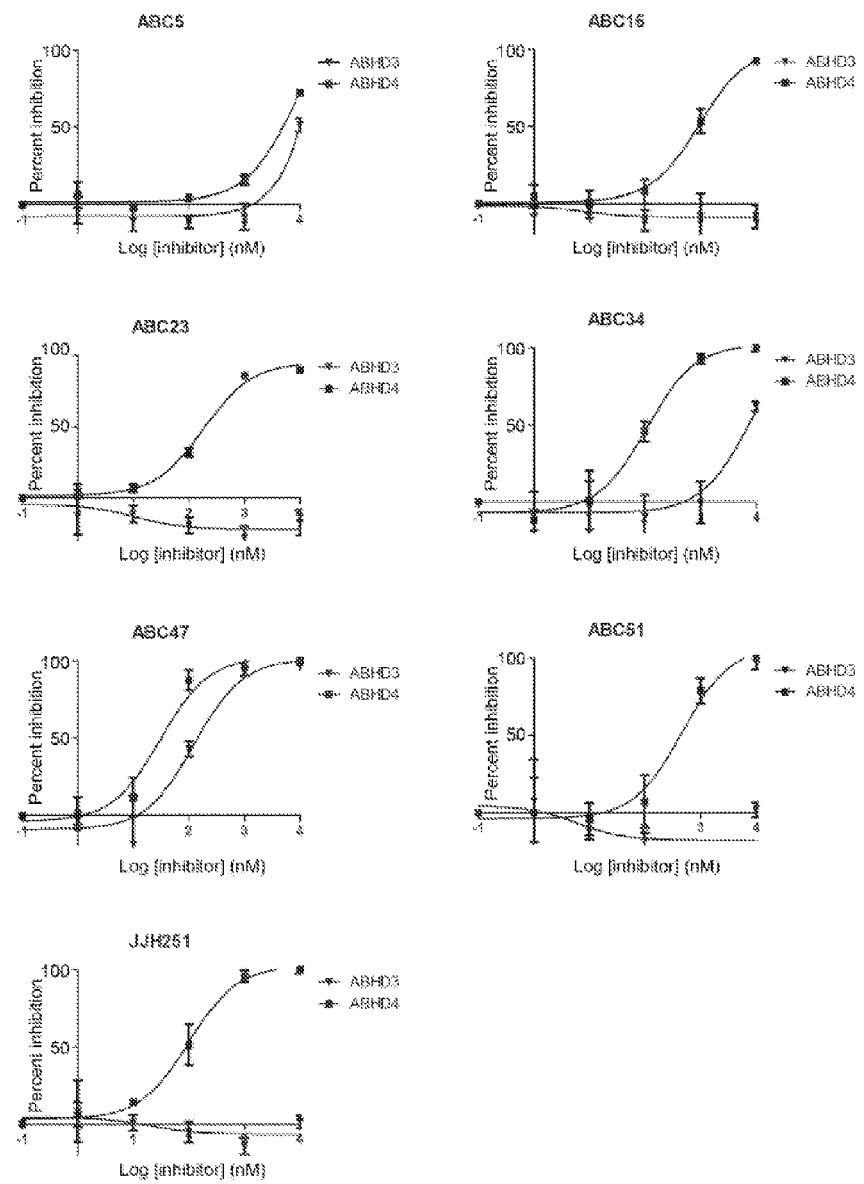
FIG. 8C shows concentration-dependent inhibition of ABHD3 and ABHD4 by Compounds 13, 38, 35, 31, 36, and 37. Data represent competitive gel-based ABPP signals for recombinant ABHD3 and ABHD4 expressed by transient transfection in HEK293T cells.

Human ABHD3 and ABHD4 were recombinantly expressed by transient transfection in HEK293T cells, and the cell lysates were combined to provide a convenient assay for monitor inhibition of both enzymes by gel-based ABPP (see FIG. 8A). Gel-based ABPP confirmed that Compound 38 acted as a potent dual inhibitor of ABHD3 and ABHD4 ($IC_{50}$ values of 0.13 and 0.03 µM, respectively) and identified additional compounds that preferentially inhibited ABHD4 over ABHD3 (e.g., Compound 37, Compound 36, and Compound 13) (see FIGS. 8B and 8C).

Figure 9:
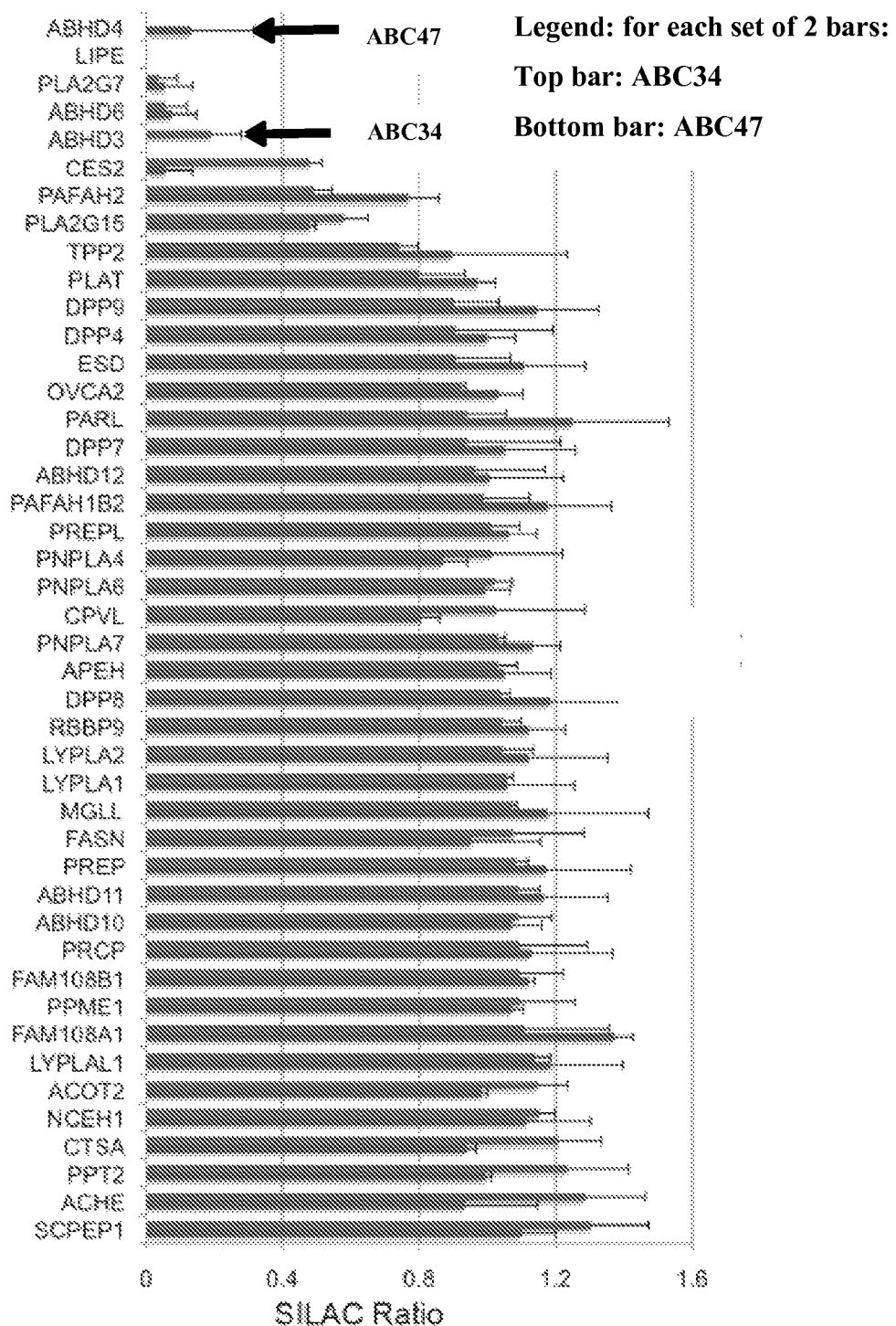
FIG. 9 shows ABPP-SILAC analysis showing overlaid in situ SH inhibition profiles for Compounds 38 (100 nM, 4 h) and 37 (1 µM, 4 h) in PC3 cells. Data represent average values±S.D. for two independent experiments.

The activity and selectivity of dual ABHD3/4 and ABHD4-preferring inhibitors in PC3 cells by ABPP-SILAC was assessed. Isotopically heavy and light PC3 cells were treated in situ with inhibitor (Compound 37 (1 µM) or Compound 38 (0.5 µM)) or DMSO for 4 h and then lysed and processed for ABPP-SILAC analysis. Compound 38 was found to inhibit both ABHD3 and ABHD4 in PC3 cells with good selectivity (see FIG. 9). Among the 44 serine hydrolases detected in this study, only four additional targets were observed for Compound 38—LIPE, PLA2G7, ABHD6, and CES2. Compound 37 completely inhibited ABHD4 and shared a similar off-target profile with Compound 38. Partial inhibition (~80%) of ABHD3 was also observed, which indicates that the selectivity window for ABHD4 over ABHD3 may be compressed in living cells compared to cell lysates.

Figure 10:
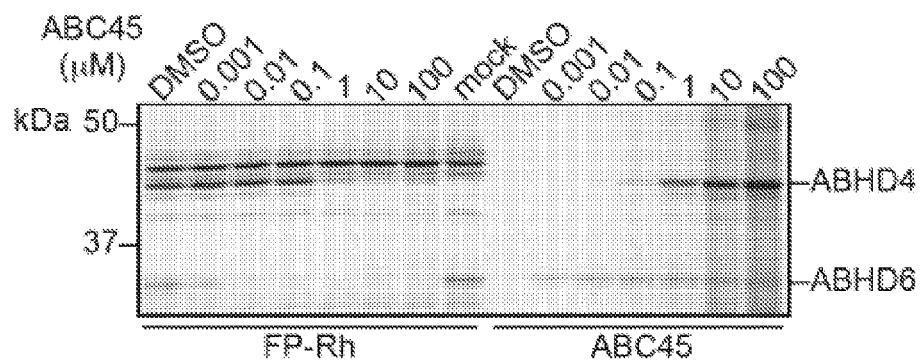
FIG. 10 shows the reactivity with recombinant ABHD4 in transfected cell lysates of Compound 39. Left side of gel shows a competitive ABPP gel of ABHD4-transfected cell lysates treated with the indicated concentrations of Compound 39 (30 min 37° C.) followed by FP-Rh. Right side of gel shows direct labeling of ABHD4 and other SHs by Compound 39 as measured by CuAAC to an Rh-N3 tag.
Figure 11:
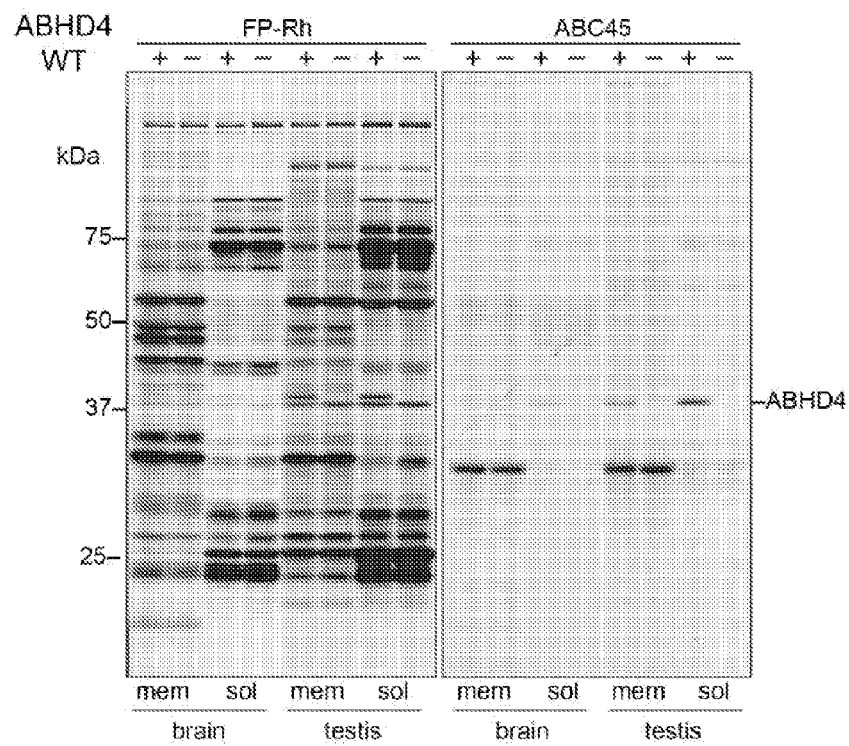
FIG. 11 shows Compound 39 detecting ABHD4 in mouse brain and testis tissues. ABHD4+/+ and −/− tissues were treated with FP-Rh (1 µM, 30 min) or Compound 39 (1 µM, 60 min) and then analyzed by gel-based ABPP. A 37 kDa band matching the predicted molecular mass of ABHD4 was detected by both probes in ABHD4+/+, but not ABHD4−/− tissues.

Example A13: Identification of PPT1 as a Target of N-Hydroxy Bicyclic Hydantoin Carbamates Compound 39 inhibited ABHD4 in transfected HEK293T cell proteome in a concentration-dependent manner as detected by competitive ABPP with FP-Rh, and the Compound 39-ABHD4 adduct was, in a complementary manner, directly visualized by CuAAC conjugation to a rhodamineazide (Rh-N3) tag (see FIG. 10). Compound 39 also identified an Compound 37-sensitive protein in mouse brain that matches the expected molecular mass (~40 kDa) of ABHD4 and was absent in brain tissue from ABHD4−/− mice (see FIG. 11). These data indicate that Compound 39 acts as a tailored activity-based probe for the convenient gel-based detection of ABHD4 in complex biological systems.

Figure 12:
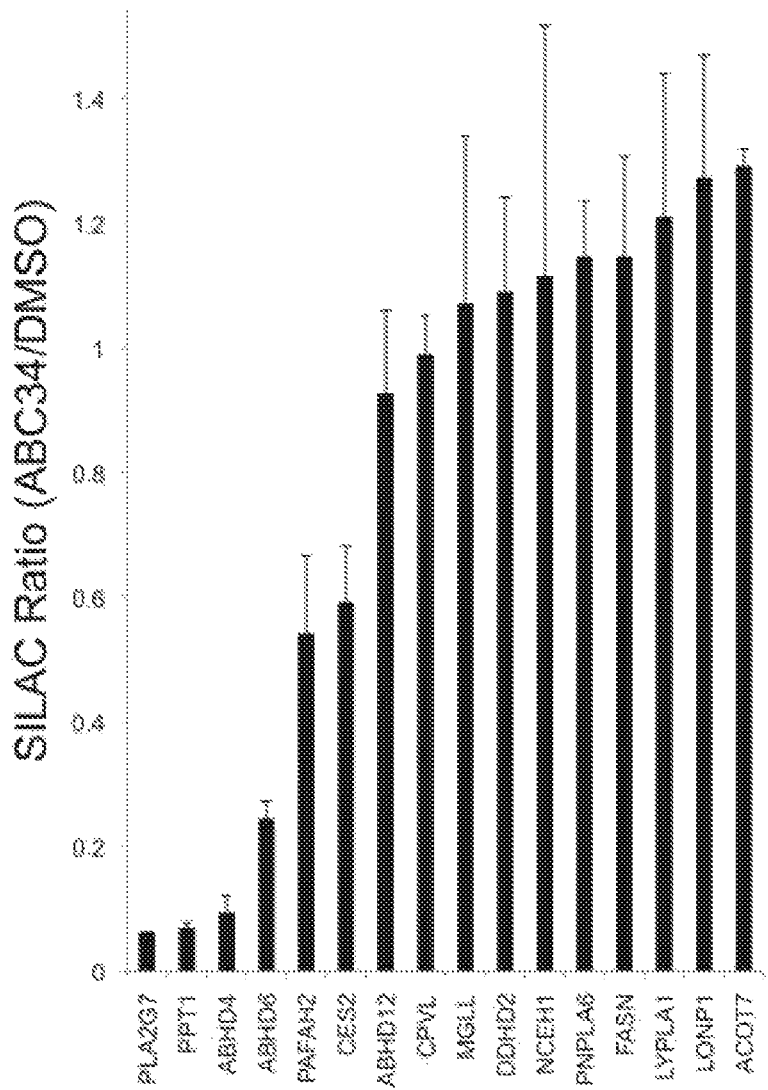
FIG. 12 shows ABPP-SILAC analysis showing the in situ SH inhibition profile for Compound 37 (1 µM, 4 h) in PC3 cells, where SH enrichment and inhibition were measured with the Compound 39 probe. Data represent average values±S.D. for two independent experiments.
Figure 13:
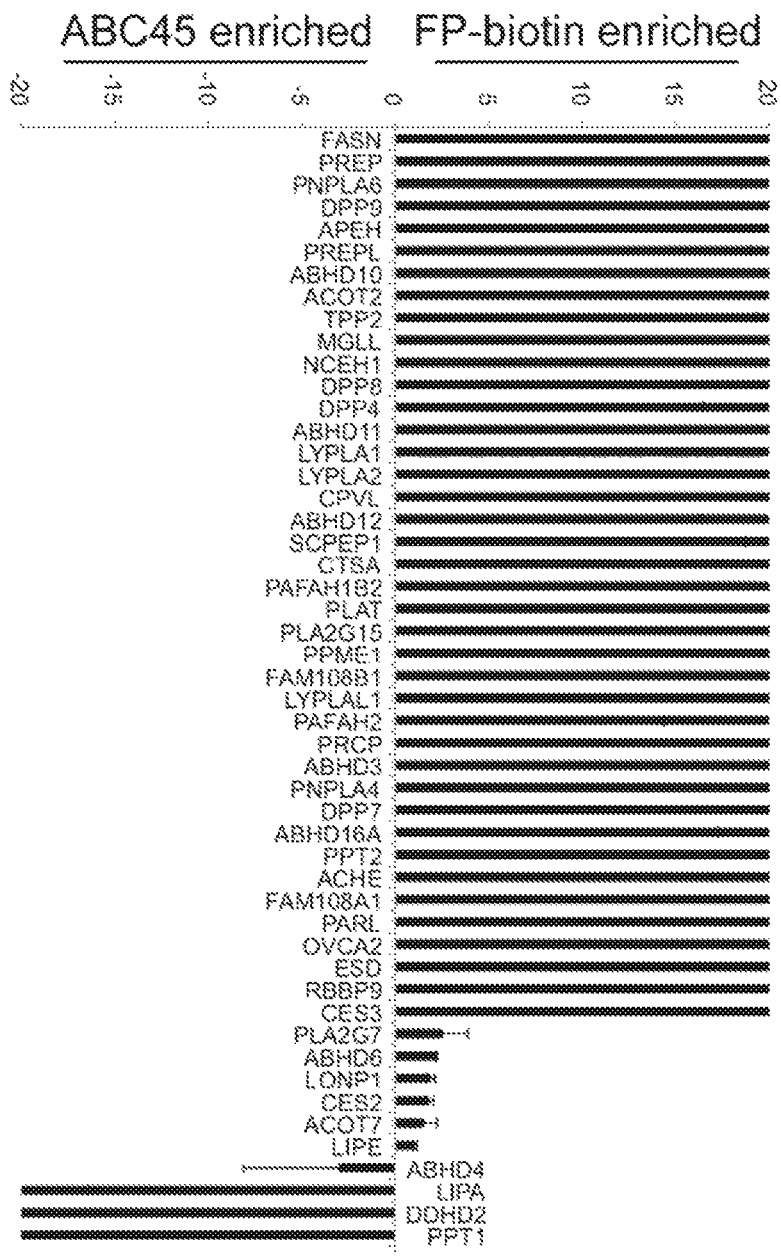
FIG. 13 shows ABPP-SILAC analysis comparing the reactivity and enrichment of SHs with FP-biotin (2.5 µM, 1 h) versus Compound 39 (5 µM, 1 h) in PC3 cell proteomes. Data represent average values±S.D. for two independent experiments.

Example A14: Competitive ABPP-SILAC Experiments to Identify Targets of Compound 37 Using Compound 39 as a Probe Isotopically heavy- and light-labeled PC3 cells were treated with Compound 37 (1 µM) or DMSO for 4 h, respectively, lysed, and then treated Compound 39 (5 µM, 1 h). The heavy and light proteomic samples were then combined and analyzed by LC-MS/MS, which revealed a small subset of SHs, including ABHD4, that were inhibited by Compound 37 (see FIG. 12). Among the handful of additional SH targets of Compound 37 were ABHD6 and PLA2G7, which were expected based on our ABPP-SILAC studies with FP-biotin (see FIG. 9), and protein-palmitoyl thioesterase 1 (PPT1), which was inhibited by more than 90%. PPT1 shows poor reactivity with broad-spectrum FP probes. Accordingly, PPT1 was not detected in our previous ABPP-SILAC studies with FP-biotin (see FIG. 9). The selective enrichment of PPT1 by Compound 39 was confirmed by performing a probe-versus-probe ABPP-SILAC study, where heavy and light PC3 proteomes were treated with FP-biotin (2.5 µM, 1 h) and Compound 39 (5 µM, 1 h), respectively. PPT1, along with two additional SHs LIPA and DDHD2, were preferentially enriched by Compound 39 over FP-biotin, while most of the other SHs were more strongly enriched by FP-biotin (see FIG. 13). A handful of SHs corresponding mostly to enzymes that were identified in our ABPP-SILAC studies as targets of Compound 37 (see FIGS. 9 and 12), were equivalently enriched by Compound 39 and FP-biotin (see FIG. 13).

Figure 14:
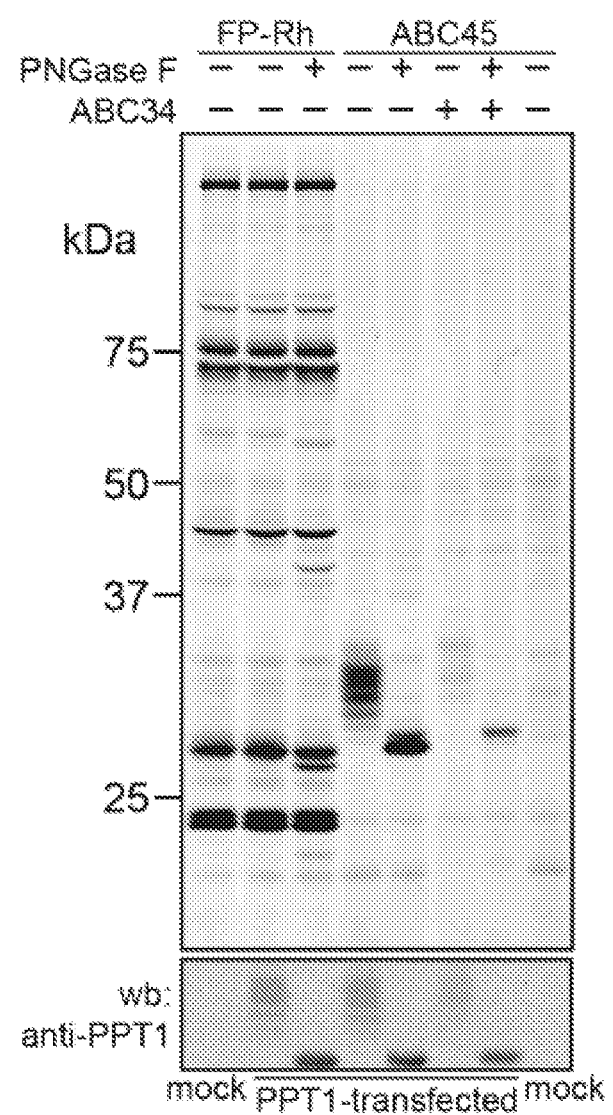
FIG. 14 shows the verification that recombinant human PPT1 expressed by transient transfection in HEK293T cells reacts with Compound 39 (1 µM), but not FP-Rh (1 µM), and the Compound 39 reactivity is blocked by Compound 37 (5 µM, 4 h).

The selective enrichment of PPT1 by Compound 39 and the near-complete blockade of this enrichment by Compound 37 suggested that this enzyme was covalently modified and inhibited by N-hydroxy bicyclic hydantoin carbamates. This possibility was explored by treating HEK293T cells transfected with human PPT1 (hPPT1) with Compound 37 (5 µM, 4 h pre-treatment) or DMSO followed by cell lysis and treatment with Compound 39 (5 µM, 1 h). A strong, but diffuse Compound 37-sensitive, Compound 39-labeled protein band was detected by gel-based ABPP in hPPT1-transfected, but not mock-transfected cell lysates (see FIG. 14), and this diffuse signal was compressed to a tight, faster-migrating band matching the predicted molecular weight of PPT1 following treatment with the glycosidase PNGaseF (see FIG. 14). Western blotting with an anti-PPT1 antibody confirmed a similar migration pattern for hPPT1 protein in transfected cell lysates (see FIG. 14, bottom panel). These data indicated that both Compound 37 and Compound 39 reacted with PPT1 and are consistent with previous studies demonstrating that this enzyme is glycosylated. In contrast, FP-Rh failed to detect hPPT1 in transfected cell lysates (see FIG. 14).

Example A15: Reaction of N-Hydroxy Bicyclic Hydantoin Carbamates with the Catalytic Serine of PPT1-S115

Figure 15:
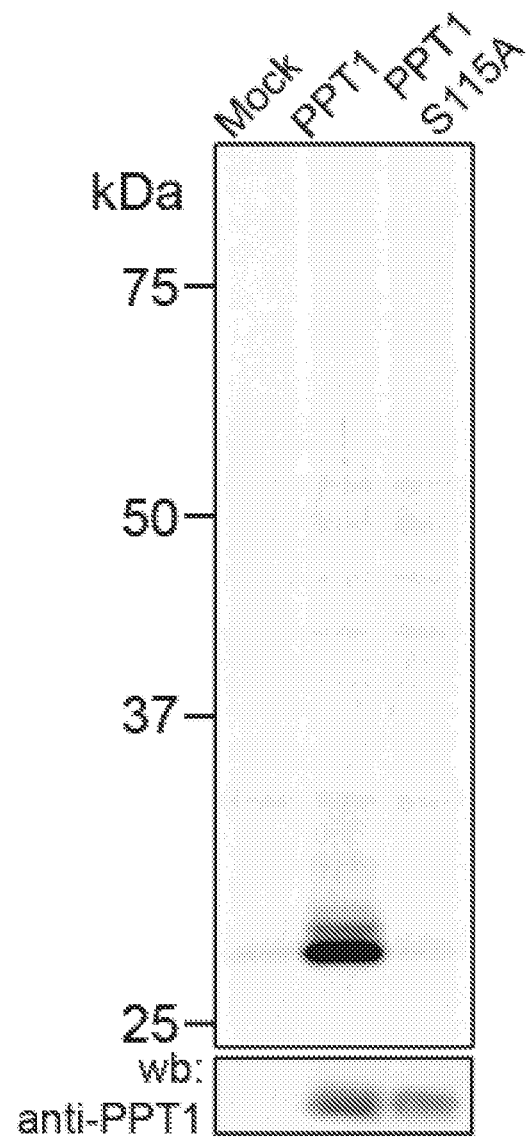
FIG. 15 shows that Compound 39 labels recombinant wild type PPT1, but not the catalytic serine mutant (S115A) of this enzyme.
Figure 16:
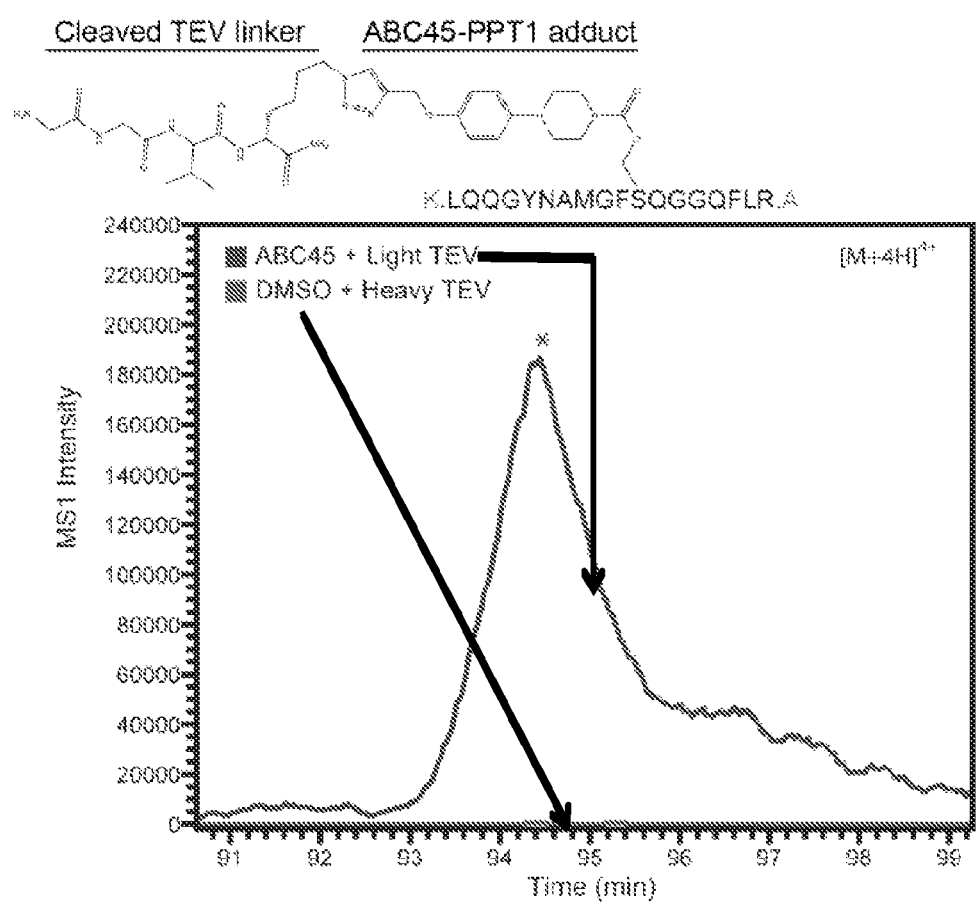
FIG. 16 shows an isoTOP-ABPP experiment identifying the catalytic serine S115 as the site of Compound 39 labeling in PPT1. Shown is the structure of the Compound 39-PPT1 adduct (connected by CuAAC to the azide-tag used to enrich and release Compound 39-reactive peptides in isoTOP-ABPP experiments).

HEK293T cells were transfected with wild type and an S115A mutant of PPT1, lysed, and treated with Compound 39 followed by CuAAC conjugation to an azide-Rh tag, PNGaseF treatment, and analysis by SDS-PAGE. This study revealed strong labeling of wild-type PPT1, but not the S115A mutant (see FIG. 15). S115 was identified as the site of Compound 39 labeling on PPT1 using a quantitative MS method termed isoTOP-ABPP. In brief, PPT1-transfected cell lysates were treated with DMSO or the Compound 39 probe (5 µM) for 1 h and then incubated with isotopically heavy or light azide-biotin tags, respectively, under CuAAC reaction conditions. Each azide biotin tag also contained an intervening TEV protease cleavage site. Heavy and light probe-labeled proteins were then combined, enriched by streptavidin chromatography, digested sequentially on-bead with trypsin (to remove non-probe-modified peptides) and TEV to release Compound 39-modified peptide(s), which were analyzed by LC-MS/MS on an LTQ-Orbitrap instrument. A single Compound 39-modified peptide, corresponding to amino acids 105-122, was detected in the isotopically light, but not heavy samples, and tandem MS analysis assigned the Compound 39 modification site to S115 (see FIG. 16). Taken together, these data indicated that N-hydroxy bicyclic hydantoin carbamates react with PPT1 through carbamylation of the enzyme's conserved serine nucleophile.

Example A16: Selective Inhibitors for ABHD4 and PPT1 Enzymes

A structurally diverse panel of N-hydroxy bicyclic hydantoin carbamates were assayed at 2 or 0.2 µM for in situ inhibition of hPPT1 in transfected HEK293T cells. While many compounds exhibited inhibitory activity toward PPT1 at 2 µM, only Compound 26 showed complete inhibition of hPPT1 at 200 nM. Compound 26 displayed an in situ $IC_{50}$ value for inhibiting recombinant PPT1 of 0.1 µM as measured by gel-based competitive ABPP (Table 7).

Table 7 shows $IC_{50}$ values (µM; with 95% confidence intervals in parentheses) for inhibition of human PPT1 by Compounds 1, measured in PPT1-transfected cells (in situ, competitive ABPP) or cell lysates (in vitro, pH 5.0, MU-6S-Palm-βD-Glc substrate).

| Cpd. | in situ (ABPP) | in vitro (substrate) |
| --- | --- | --- |
| 26 | 0.1 (0.04-0.2) | 6.5 (3.6-12) |
| 34 | 3.9 (2.0-7.4) | >50 |
| 1 | 0.5 (0.3-1.0) | 15 (9.5-25) |

Figure 17A:
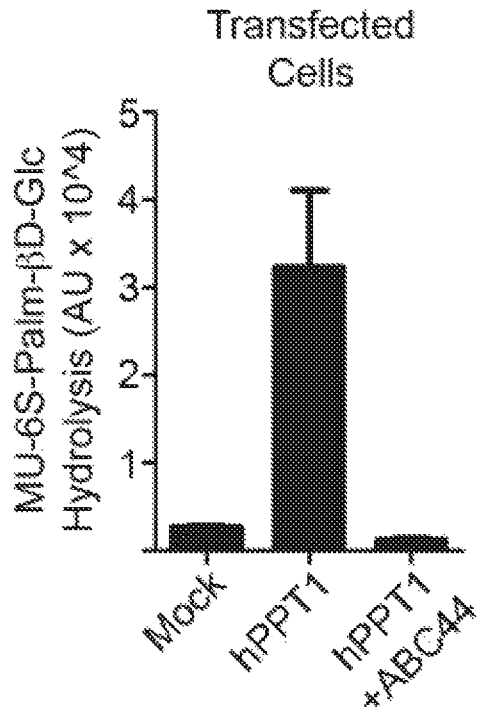
FIG. 17A shows that hPPT1-transfected cell lysates show much greater hydrolytic activity with the 4-methylumbelliferyl oleate (4-MUBO) substrate compared to mock-transfected cell lysates or hPPT1-transfected cell lysates pretreated with Compound 26 (50 µM, 30 min). Data represent average values±S.E. for three independent experiments.
Figure 17B:
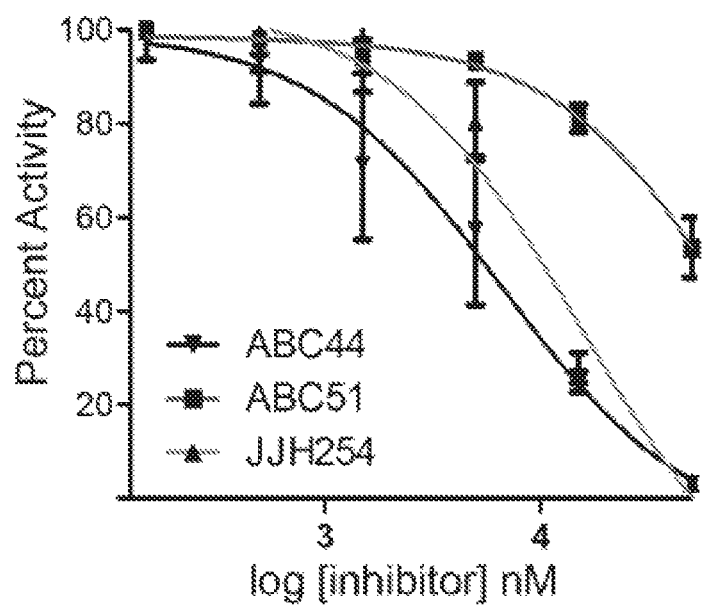
FIG. 17B shows concentration-dependent inhibition of 4-MUBO hydrolytic activity of hPPT1-transfected cell lysates by Compounds 26, 34, and 1. Data represent average values±S.E. for three independent experiments.
Figure 17C:
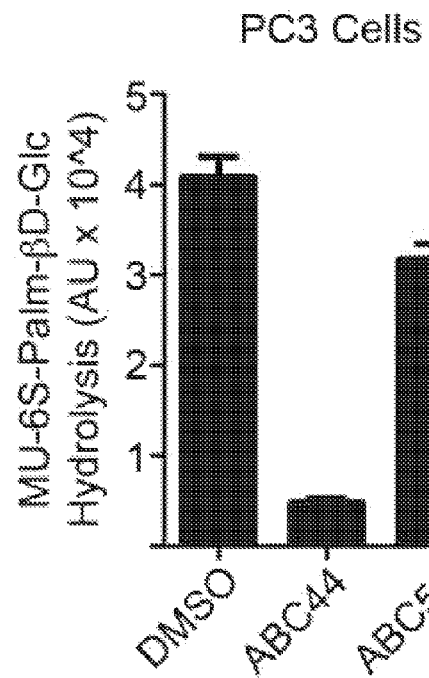
FIG. 17C shows that PC3 cells treated in situ with Compound 26, but not Compound 34 (500 nM inhibitor; 4 h) showed substantial reductions in 4-MUBO hydrolysis activity compared to DMSO-treated control cells. Data represent average values±S.E. for three independent experiments.

Compound 26 was then tested to see if it inhibited PPT1 activity using a substrate assay. Endogenous substrates for PPT1 remain poorly characterized, but this enzyme was assayed with a fluorogenic substrate 4-methylumbelliferyl-6-thio-palmitate-βD-glucopyranoside (MU-6S-Palm-βD-Glc). In this assay, PPT1 hydrolyzes the substrate's palmitoyl thioester bond, and exogenous sweet almond β-glucosidase deglycosylates and frees the fluorophore, 4-methylumbelliferone (4-MU), which is measured to assess PPT1 activity. PPT1-transfected cells displayed a strong increase in MU-6S-Palm-βD-Glc hydrolysis compared to mock-transfected cells (see FIG. 17A), and treatment of these transfected lysates at pH 5.0 with Compound 26 fully blocked PPT1 activity with an $IC_{50}$ value of 6.5 µM (see FIG. 17B and Table 7). Additionally, in situ treatment of PC3 cells with Compound 26 (500 nM, 4 h) showed a 90% reduction in endogenous PPT1 activity based on the MU-6S-Palm-βD-Glc substrate assay (see FIG. 17C).

Figure 17D:
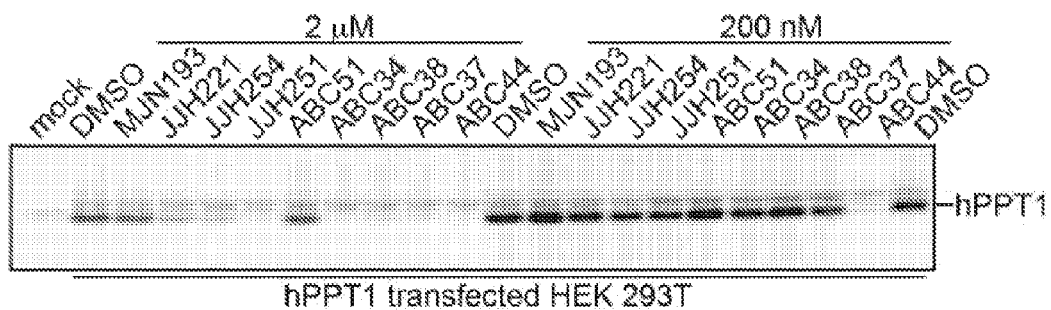
FIG. 17D shows the screening of MJN193 (4-isopropyl-2,5-dioxoimidazolidin-1-yl 4-(4-methoxyphenyl)piperazine-1-carboxylate), Compounds 1, 5, 13, 34, 37, 24, 25, and 26 in hPPT1-transfected HEK293T cells in situ, where PPT1 inhibition was measured by competitive ABPP using the Compound 39 probe.
Figure 18:
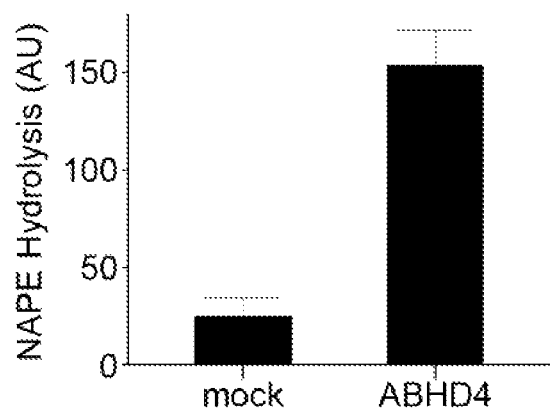
FIG. 18 shows that ABHD4-transfected HEK293T cell lysates show much greater NAPE lipase activity compared to mock-transfected HEK239T cell lysates (top) and this activity is inhibited by N-hydroxy bicyclic hydantoin carbamates (bottom). NAPE hydrolysis was measured by following the release of oleic acid from the NAPE substrate (1,2-dioleoyl-sn-glycero-3-phospho (N-arachidonoyl) ethanolamine).
Figure 18:
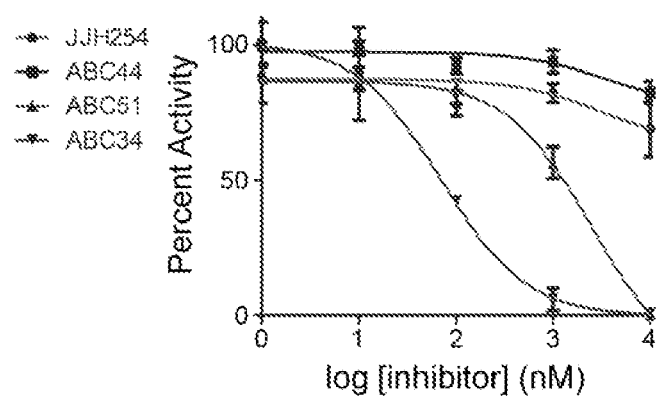

Compound 34, which showed limited activity against PPT1 in situ (see FIG. 17D and Table 7) or in vitro (see FIG. 17A and Table 7), was a good inhibitor of ABHD4 in vitro ($IC_{50}$ value of 0.5 μM) as measured with an N-acyl phosphatidylethanolamine (NAPE) substrate hydrolysis assay performed with lysates from ABHD4-transfected HEK293T cells (see FIG. 18). In contrast, neither Compound 26 nor Compound 1 altered the NAPE hydrolysis activity of ABHD4. Compound 1 did, however, inhibit PPT1 activity both in vitro (see FIG. 17B and Table 7) and in situ (Table 7), albeit with less potency than Compound 26.

Figure 19:
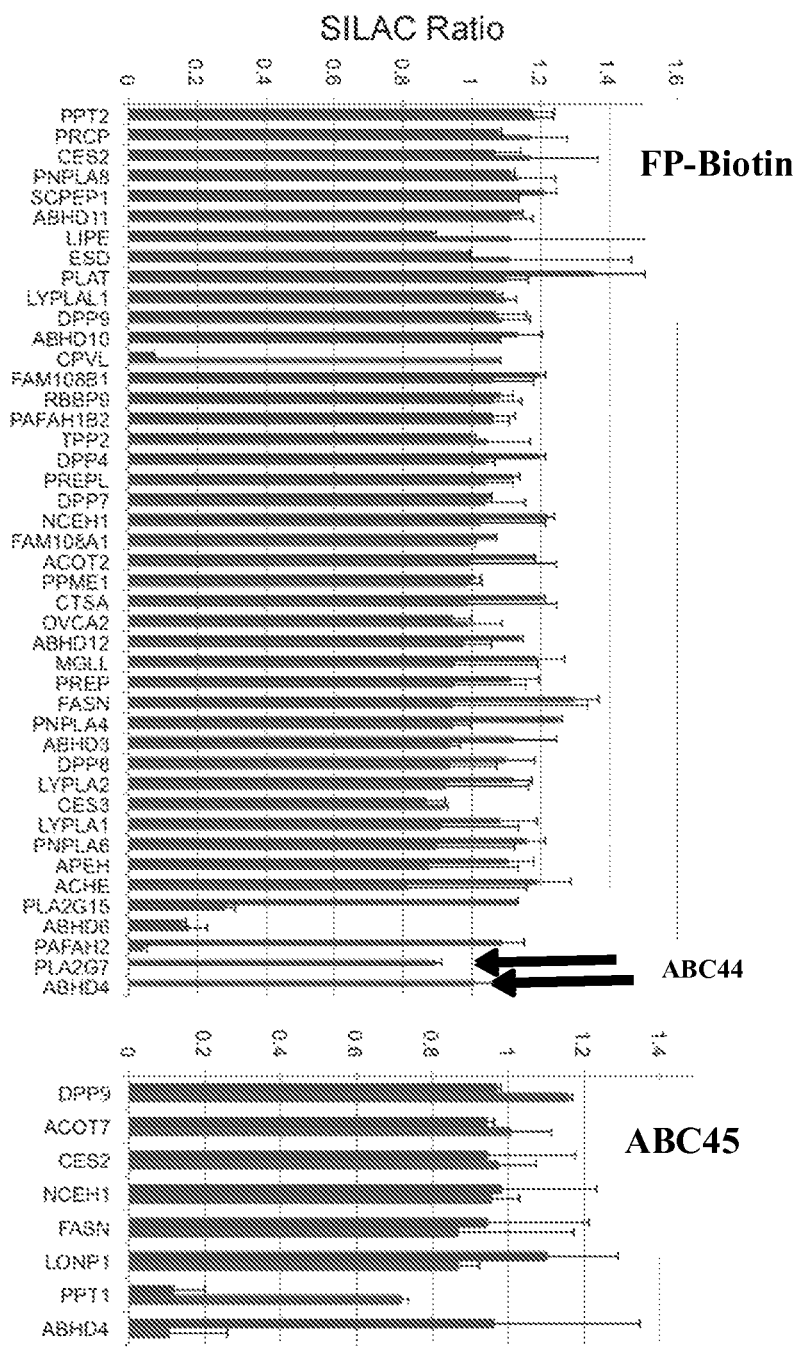
FIG. 19 shows ABPP-SILAC analysis showing overlaid in situ SH inhibition profiles for Compound 26 (0.1 µM, 4 h) and Compound 34 (1 µM, 4 h) in PC3 cells where SH enrichment and inhibition were measured with the FP-biotin (top) or Compound 39 (bottom) probes. Data represent average values±S.D. for two independent experiments.
Figure 20:
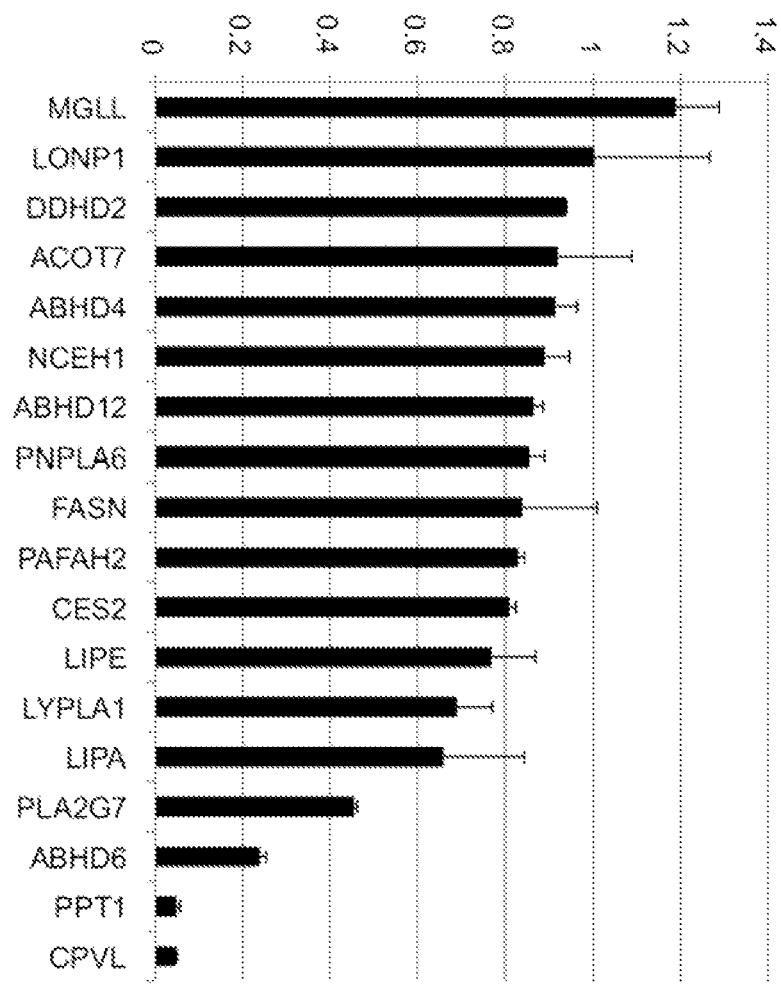
FIG. 20 shows ABPP-SILAC analysis showing in situ SH inhibition profiles for Compound 26 (1 µM, 4 h) in PC3 cells where SH enrichment and inhibition were measured with the Compound 39 probe in Compound 26- versus DMSO-treated cells. Data represent average values±S.D. for two independent experiments.

To evaluate the broader selectivity of Compound 26 and Compound 34 across the SH class, heavy and light isotopically-labeled PC3 cells were treated with inhibitor [Compound 34 (1 μM); or Compound 26 (1 or 0.1 μM); 4 h) and DMSO, respectively, followed by ABPP-SILAC analysis with either the FP-biotin probe or the Compound 39 probe. Compound 26, tested at 1 or 0.1 μM, near-completely inhibited PPT1 (~90%+; as measured with the Compound 39 probe) and showed good selectivity, only cross-reacting with two of the >40 quantified SH activities—ABHD6 and CPVL (see FIGS. 19 and 20). Conversely, Compound 34 inhibited >90% of ABHD4 activity, as measured with either the FP-biotin probe or the Compound 39 probe, and cross-reacted with four additional targets—ABHD6, PAFAH2, PLA2G7, and PLA2G15.

These results, taken together, demonstrate that Compound 26 and Compound 34 were cell-active inhibitors that displayed good potency and selectivity for PPT1 and ABHD4, respectively.

Example A17: In Vivo Activity

Figure 21:
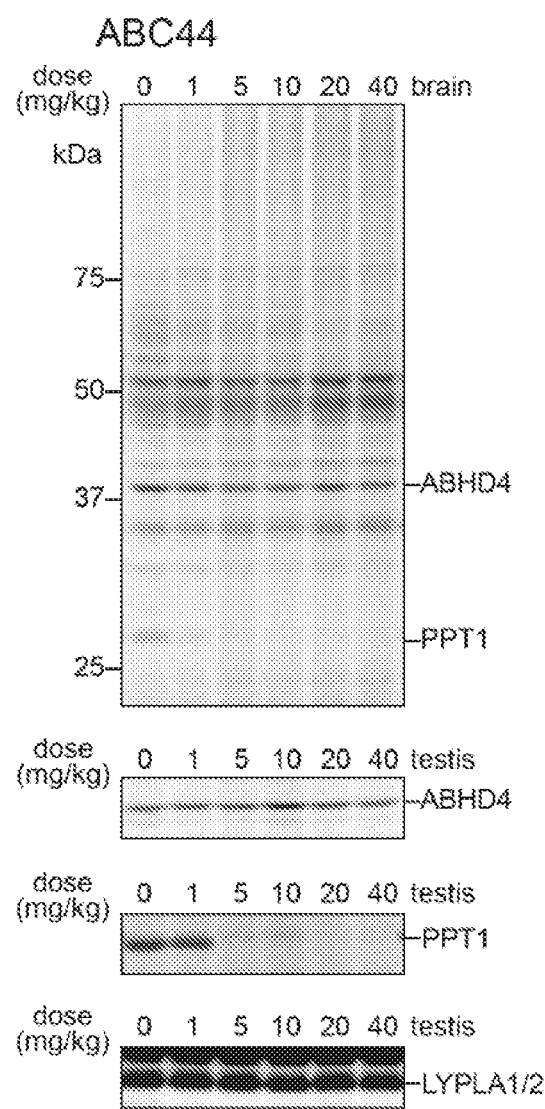
FIG. 21 shows gel-based competitive ABPP analysis of SH activities in tissues from Compound 26 treated mice. The activities of ABHD4 and PPT1 were visualized using the Compound 39 probe in tissue proteomes treated with PNGaseF (post-Compound 39 labeling), while the activities of LYPLA1 and LYPLA2 were visualized using the FP-Rh probe.
Figure 22:
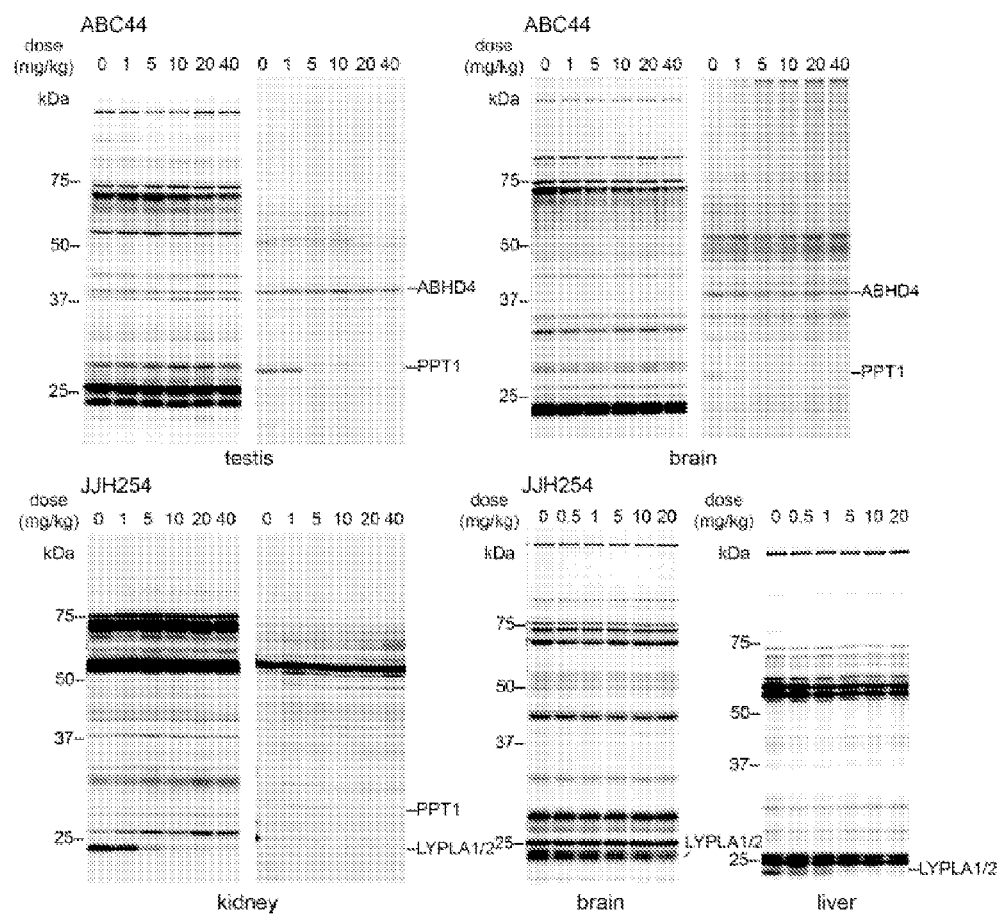
FIG. 22 shows full gels showing competitive ABPP results for tissues from mice treated with Compound 26 or Compound 1. The left and right gels in each pair represent tissues treated with the FP-Rh (1 μM, 30 min) and Compound 39 (2 μM, 60 min), respectively.
Figure 23:
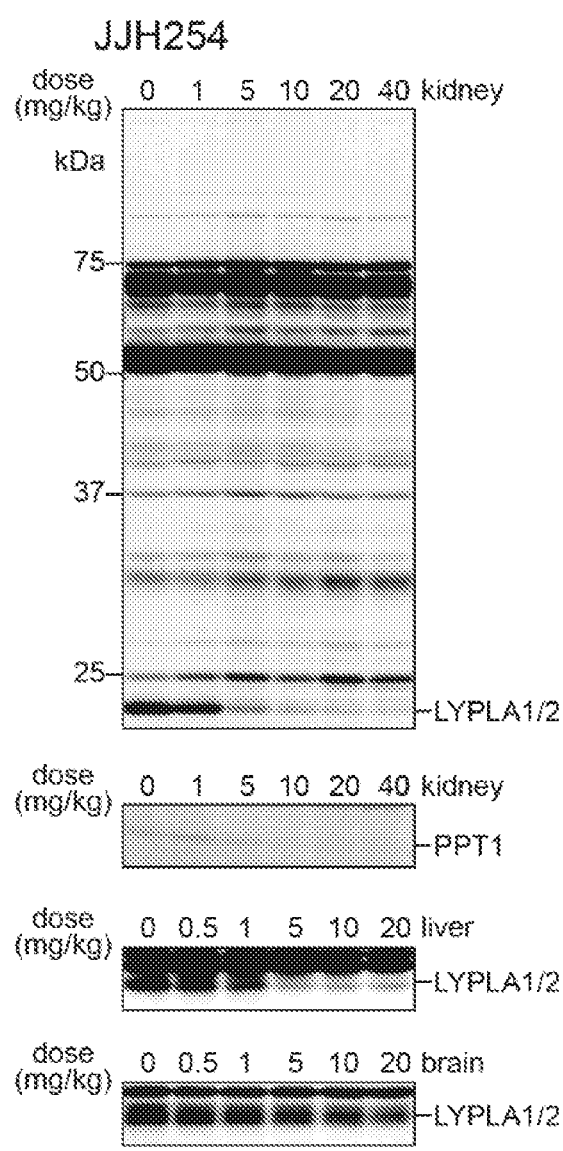
FIG. 23 shows gel-based competitive ABPP analysis of SH activities in tissues from Compound 1 treated mice. The activities of ABHD4 and PPT1 were visualized using the Compound 39 probe in tissue proteomes treated with PNGaseF (post-Compound 39 labeling), while the activities of LYPLA1 and LYPLA2 were visualized using the FP-Rh probe.
Figure 24:
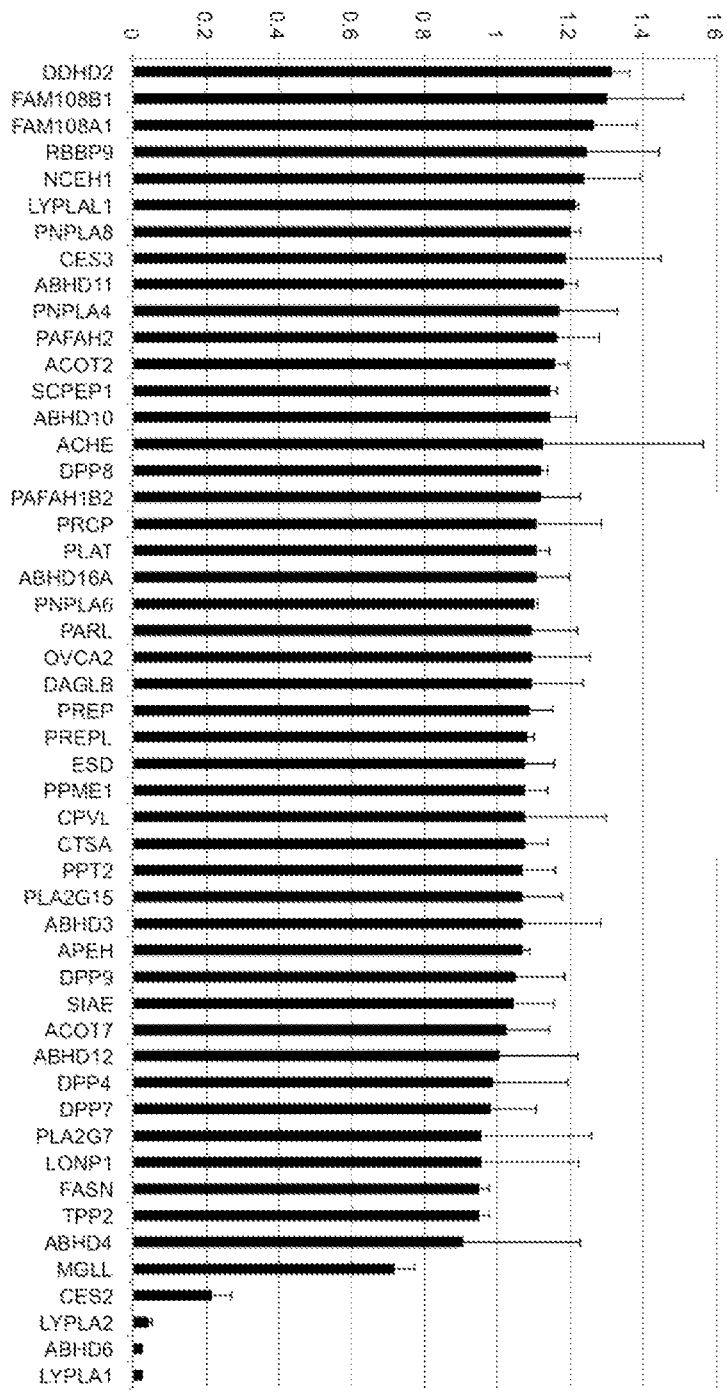
FIG. 24 shows ABPP-SILAC analysis showing in situ SH inhibition profiles for Compound 1 (1 μM, 4 h) in PC3 cells where SH enrichment and inhibition were measured with the FP-biotin probe in Compound 1 versus DMSO-treated cells. Data represent average values±S.D. for two independent experiments.

Compound 26, Compound 34, and Compound 1 were administered across a dose range of 1-40 mg/kg to C57BL6 mice by intraperitoneal injection, and, after 4 hours, animals were sacrificed and tissues harvested for analysis by gel-based ABPP using the FP-Rh probe and the Compound 39 probe. Compound 26 showed potent, dose-dependent inhibition of an Compound 39-reactive protein matching the molecular mass of deglycosylated PPT1 in PNGaseF-treated central and peripheral tissues, producing near-complete blockade of this enzyme activity at 1-5 mg/kg (see FIGS. 21 and 22). Compound 26 showed excellent selectivity for PPT1 and did not inhibit other SHs detected in brain and testis tissues treated with the FP-Rh probe (see FIG. 22) or the Compound 39 probe (see FIGS. 21 and 22). Compound 1 also showed good in vivo activity, producing near-complete blockade of LYPLA1 and LYPLA2 in peripheral (e.g., liver, kidney), but not central (brain) tissues at a dose of 5 mg/kg as measured with the FP-Rh probe (FIG. 23). Compound 1 also showed limited cross-reactivity with other SHs, consistent with competitive ABPP-SILAC studies in human cells (FIG. 24) but did inhibit PPT1 at doses of 10 mg/kg or greater as measured with the Compound 39 probe. Contrasting with these results, Compound 34 did not block the activity of ABHD4 in any tissue examined, possibly indicating that improvements in potency and/or drug-like properties are required to convert this compound into an in vivo-active probe.

We claim:
1. A compound, or a stereoisomer or a pharmaceutically acceptable salt thereof, of formula (I):

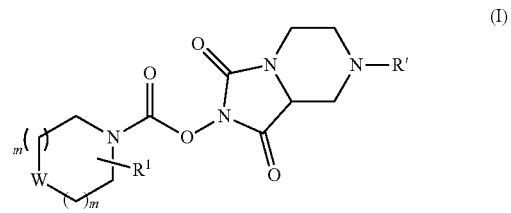

wherein
W is

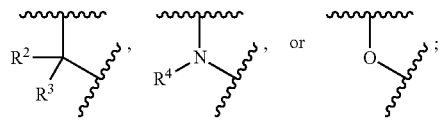

each m is independently 0, 1, or 2;
$R^1$ is H, halo, —OH, cyano, amino, ($C_1$-$C_8$)alkyl, ($C_1$-$C_8$)alkoxy, ($C_6$-$C_{10}$)aryl, or ($C_6$-$C_{10}$)aryl($C_1$-$C_8$)alkyl;
$R^2$ is H, —COOR$^5$, or —CONR$^5$R$^6$;
$R^3$ is H, ($C_6$-$C_{10}$)aryl, 5-9 membered heteroaryl comprising 1 or 2 heteroatoms independently selected from O, N, and S, ($C_6$-$C_{10}$)aryl($C_1$-$C_8$)alkyl, or 5-9-membered heteroaryl($C_1$-$C_8$)alkyl comprising 1 or 2 heteroatoms independently selected from O, N, and S; wherein ($C_6$-$C_{10}$)aryl, 5-9-membered heteroaryl, ($C_6$-$C_{10}$)aryl($C_1$-$C_8$)alkyl, and 5-9-membered heteroaryl($C_1$-$C_8$)alkyl are optionally substituted by one or more substituents independently selected from halo, ($C_1$-$C_8$)alkyl, ($C_1$-$C_8$)alkoxy, ($C_2$-$C_8$)alkenyl, ($C_2$-$C_8$)alkynyl, ($C_2$-$C_8$)alkenyloxy, ($C_2$-$C_8$)alkynyloxy, —C(O)OR$^a$, and —C(O)N(R$^a$)$_2$;
each $R^a$ is independently hydrogen, ($C_1$-$C_8$)alkyl, or ($C_6$-$C_{10}$)aryl;
$R^4$ is ($C_6$-$C_{10}$)aryl, 5-9 membered heteroaryl comprising 1 or 2 heteroatoms independently selected from O, N, and S, ($C_6$-$C_{10}$)aryl($C_1$-$C_8$)alkyl, 5-9-membered heteroaryl($C_1$-$C_8$)alkyl comprising 1 or 2 heteroatoms independently selected from O, N, and S, or di($C_6$-$C_{10}$)aryl($C_1$-$C_8$)alkyl; wherein ($C_6$-$C_{10}$)aryl, 5-9-membered heteroaryl, ($C_6$-$C_{10}$)aryl($C_1$-$C_8$)alkyl, and 5-9-membered heteroaryl($C_1$-$C_8$)alkyl are optionally substituted by one or more substituents independently selected from ($C_1$-$C_8$)alkyl, ($C_2$-$C_8$)alkenyl, ($C_2$-$C_8$)alkynyl, halo, ($C_1$-$C_8$)fluoroalkyl, —OR$^a$, and ($C_6$-$C_{10}$)aryl optionally substituted with one or more halo groups;
$R^5$ is H or ($C_1$-$C_8$)alkyl;
$R^6$ is ($C_6$-$C_{10}$)aryl, 5-9 membered heteroaryl comprising 1 or 2 heteroatoms independently selected from O, N, and S, ($C_6$-$C_{10}$)aryl($C_1$-$C_8$)alkyl, or 5-9-membered heteroaryl($C_1$-$C_8$)alkyl comprising 1 or 2 heteroatoms independently selected from O, N, and S; and
R' is H, ($C_1$-$C_8$)alkyl, ($C_1$-$C_8$)alkoxy, ($C_1$-$C_8$)alkylcarbonyl, ($C_1$-$C_8$)alkoxycarbonyl, ($C_3$-$C_9$)cycloalkyl, ($C_3$-$C_9$)cycloalkyl($C_1$-$C_8$)alkyl, ($C_3$-$C_9$)cycloalkylcarbonyl, ($C_3$-$C_9$)cycloalkoxycarbonyl, ($C_6$-$C_{10}$)aryl, ($C_6$-$C_{10}$)arylcarbonyl, ($C_6$-$C_{10}$)aryloxycarbonyl, ($C_6$-$C_{10}$)aryl($C_1$-$C_8$)alkyl, ($C_6$-$C_{10}$)aryl($C_1$-$C_8$)alkylcarbonyl, ($C_6$-$C_{10}$)aryl($C_1$-$C_8$)alkoxycarbonyl, 5-9 membered heterocyclyl comprising 1 or 2 heteroatoms independently selected from O, N, and S, 5-9 membered heterocyclyl($C_1$-$C_8$)alkyl comprising 1 or 2 heteroatoms independently selected from O, N, and S, 5-9-membered heterocyclylcarbonyl comprising 1 or 2 heteroatoms independently selected from O, N, and S, 5-9 membered heteroaryl comprising 1 or 2 heteroatoms independently selected from O, N, and S, 5-9 membered heteroaryl($C_1$-$C_8$)alkyl comprising 1 or 2 heteroatoms independently selected from O, N, and S, or 5-9-membered heteroarylcarbonyl comprising 1 or 2 heteroatoms independently selected from O, N, and S; wherein ($C_6$-$C_{10}$)arylcarbonyl, ($C_6$-$C_{10}$)aryl($C_1$-$C_8$)alkyl, and 5-9-membered heterocyclyl($C_1$-$C_8$)alkyl are optionally substituted by one or more substituents independently selected from ($C_1$-$C_8$)alkyl, ($C_2$-$C_8$)alkenyl, ($C_2$-$C_8$)alkynyl, halo, ($C_1$-$C_8$)fluoroalkyl, nitro, ($C_6$-$C_{10}$)aryl($C_1$-$C_8$)alkyl, —$OR^a$, —$N(R^a)_2$, —$C(O)OR^a$, and —$C(O)N(R^a)_2$.

2. The compound of claim 1, or a stereoisomer or a pharmaceutically acceptable salt thereof, wherein each m is 1.

3. The compound of claim 2, or a stereoisomer or a pharmaceutically acceptable salt thereof, wherein $R^1$ is H.

4. The compound of claim 3, or a stereoisomer or a pharmaceutically acceptable salt thereof, wherein W is

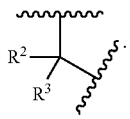

5. The compound of claim 4, or a stereoisomer or a pharmaceutically acceptable salt thereof, wherein:
$R^2$ is H; and
$R^3$ is ($C_6$-$C_{10}$)aryl or ($C_6$-$C_{10}$)aryl($C_1$-$C_8$)alkyl; and $R^3$ is optionally substituted by one or more substituents independently selected from halo, ($C_1$-$C_8$)alkyl, ($C_1$-$C_8$)alkoxy, ($C_2$-$C_6$)alkenyl, ($C_2$-$C_6$)alkynyl, ($C_2$-$C_6$)alkenyloxy, ($C_2$-$C_6$)alkynyloxy, —$C(O)OR^a$, and —$C(O)N(R^a)_2$.

6. The compound of claim 5, or a stereoisomer or a pharmaceutically acceptable salt thereof, wherein $R^3$ is unsubstituted phenyl, unsubstituted benzyl, or unsubstituted phenethyl.

7. The compound of claim 5, or a stereoisomer or a pharmaceutically acceptable salt thereof, wherein $R^3$ is phenyl, benzyl, or phenethyl, and $R^3$ is optionally substituted with one or more substituents independently selected from the group consisting of halo, ($C_1$-$C_8$)alkyl, ($C_1$-$C_8$)alkoxy, ($C_2$-$C_6$)alkenyl, ($C_2$-$C_6$)alkynyl, ($C_2$-$C_6$)alkenyloxy, and ($C_2$-$C_6$)alkynyloxy.

8. The compound of claim 7, or a stereoisomer or a pharmaceutically acceptable salt thereof, wherein $R^3$ is phenyl or phenethyl, and $R^3$ is substituted with one substituent selected from the group consisting of fluoro, chloro, bromo, methoxy, ethynyl, and propargyloxy.

9. The compound of claim 3, or a stereoisomer or a pharmaceutically acceptable salt thereof, wherein W is

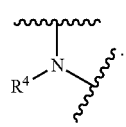

10. The compound of claim 9, or a stereoisomer or a pharmaceutically acceptable salt thereof, wherein $R^4$ is ($C_6$-$C_{10}$)aryl or ($C_6$-$C_{10}$)aryl($C_1$-$C_8$)alkyl; and $R^4$ is optionally substituted by one or more substituents independently selected from halo, ($C_1$-$C_8$)alkyl, ($C_1$-$C_8$)alkoxy, ($C_2$-$C_6$)alkenyl, and ($C_2$-$C_6$)alkynyl.

11. The compound of claim 10, or a stereoisomer or a pharmaceutically acceptable salt thereof, wherein $R^4$ is unsubstituted phenyl, unsubstituted benzyl, or unsubstituted phenethyl.

12. The compound of claim 10, or a stereoisomer or a pharmaceutically acceptable salt thereof, wherein $R^4$ is phenyl, benzyl, or phenethyl, and $R^4$ is optionally substituted with one or more substituents independently selected from the group consisting of halo, ($C_1$-$C_8$)alkyl, ($C_1$-$C_8$)alkoxy, ($C_2$-$C_6$)alkenyl, and ($C_2$-$C_6$)alkynyl.

13. The compound of claim 12, or a stereoisomer or a pharmaceutically acceptable salt thereof, wherein $R^4$ is phenyl or phenethyl, and $R^4$ is substituted with one substituent selected from the group consisting of fluoro, chloro, bromo, methoxy, and ethynyl.

14. The compound of claim 3, or a stereoisomer or a pharmaceutically acceptable salt thereof, wherein R' is H, unsubstituted ($C_1$-$C_8$)alkyl, unsubstituted ($C_1$-$C_8$)alkylcarbonyl, unsubstituted ($C_1$-$C_8$)alkoxycarbonyl, unsubstituted ($C_6$-$C_{10}$)arylcarbonyl, unsubstituted ($C_6$-$C_{10}$)aryl($C_1$-$C_8$)alkyl, unsubstituted 5-9-membered heterocyclyl($C_1$-$C_8$)alkyl comprising 1 or 2 heteroatoms independently selected from O, N, and S, or unsubstituted 5-9-membered heterocyclylcarbonyl comprising 1 or 2 heteroatoms independently selected from O, N, and S.

15. The compound of claim 3, or a stereoisomer or a pharmaceutically acceptable salt thereof, wherein:
R' is ($C_1$-$C_8$)alkylcarbonyl, ($C_6$-$C_{10}$)aryl($C_1$-$C_8$)alkyl, or 5-9 membered heterocyclyl($C_1$-$C_8$)alkyl comprising 1 or 2 heteroatoms independently selected from O, N, and S; wherein ($C_6$-$C_{10}$)arylcarbonyl, ($C_6$-$C_{10}$)aryl($C_1$-$C_8$)alkyl, and 5-9 membered heterocyclyl($C_1$-$C_8$)alkyl are optionally substituted by one or more substituents independently selected from ($C_1$-$C_8$)alkyl halo, nitro, ($C_6$-$C_{10}$)aryl($C_1$-$C_8$)alkyl —$OR^a$ and —$N(R^a)_2$.

16. The compound of claim 14, or a stereoisomer or a pharmaceutically acceptable salt thereof, wherein R' is unsubstituted 5-9-membered heterocyclylcarbonyl comprising 1 or 2 heteroatoms independently selected from O, N, and S.

17. The compound of claim 16, or a stereoisomer or a pharmaceutically acceptable salt thereof, wherein: R' is

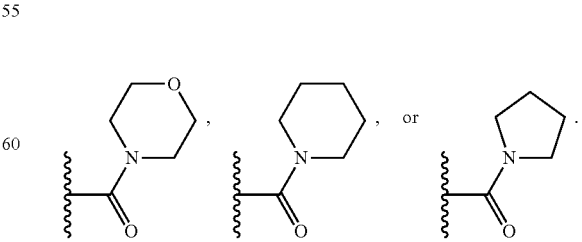

18. A compound, or a stereoisomer or a pharmaceutically acceptable salt thereof, selected from:

181 182
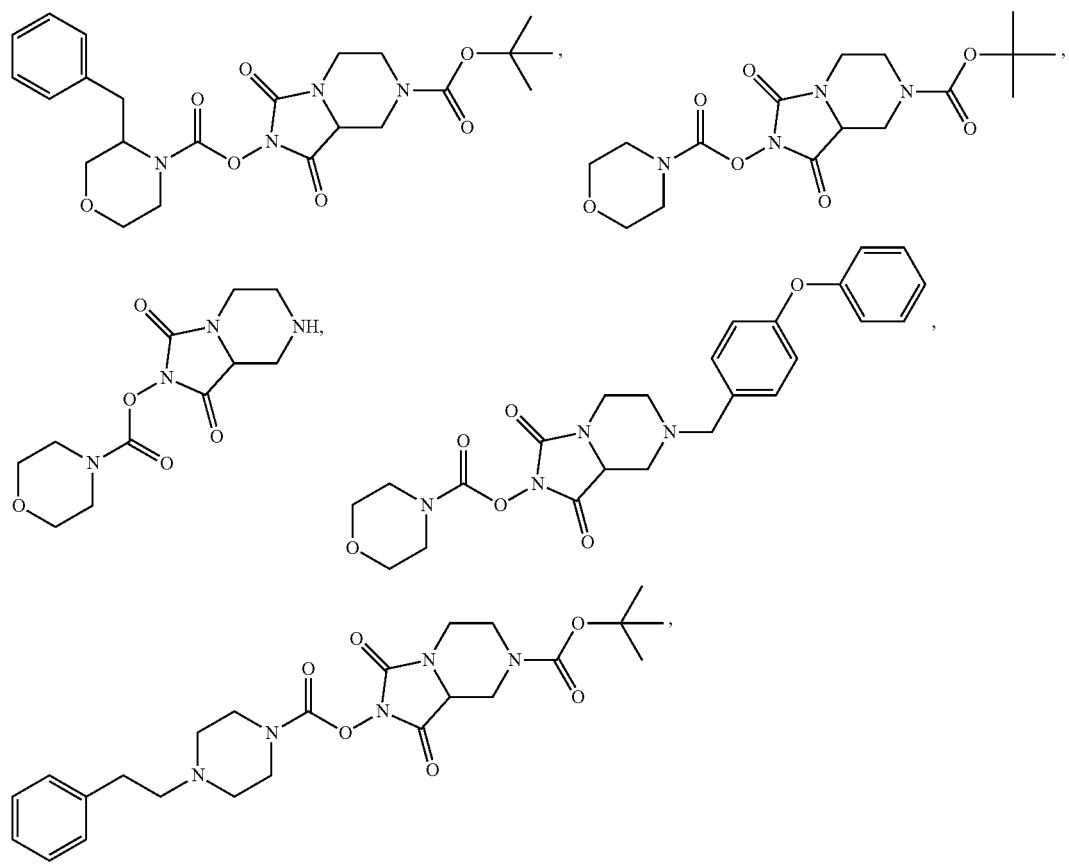
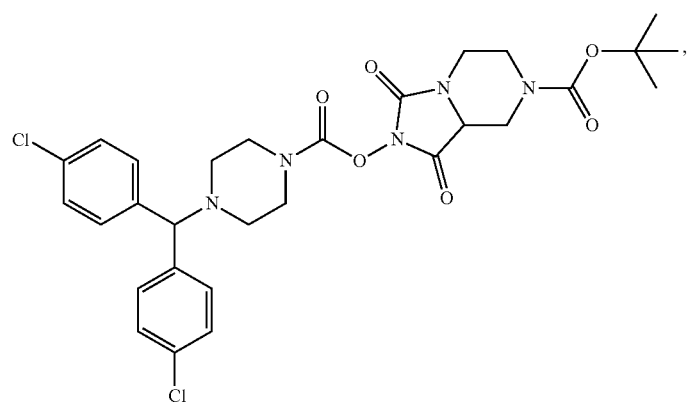
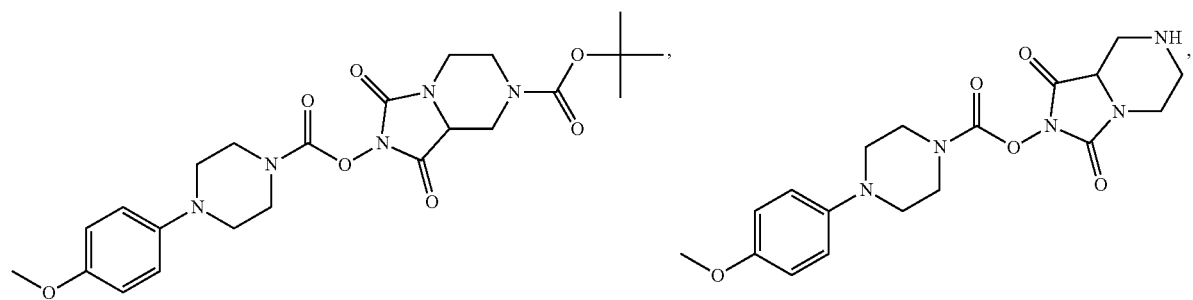

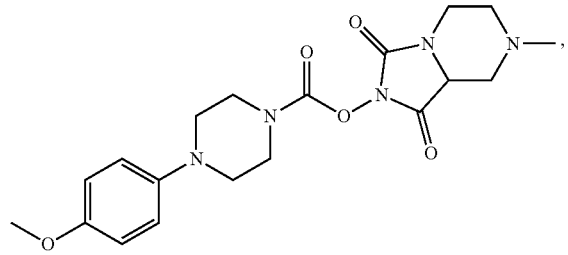
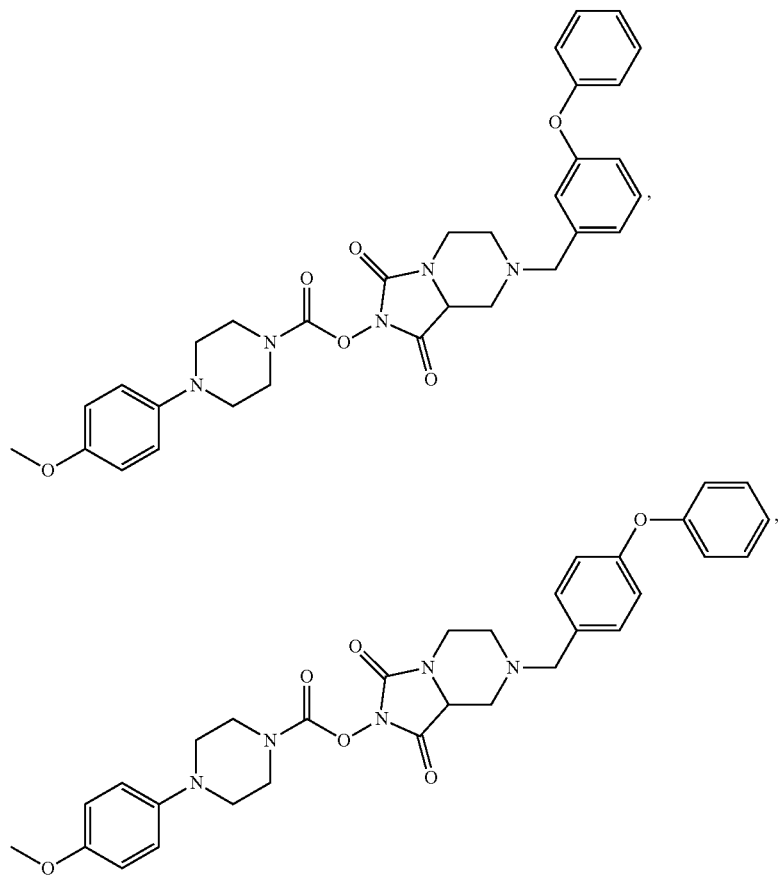
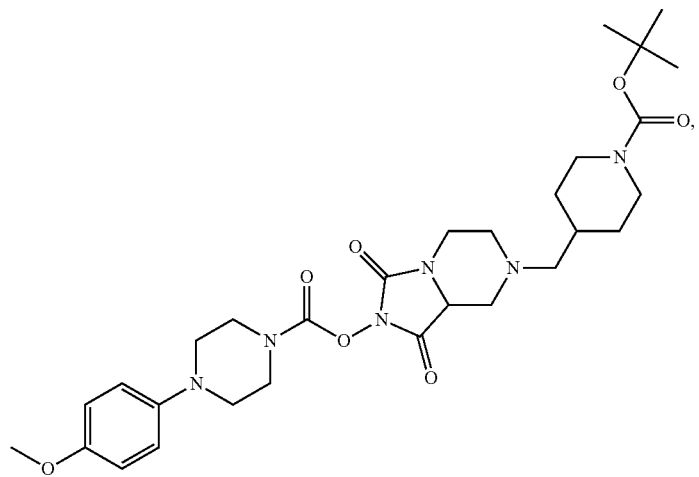

-continued
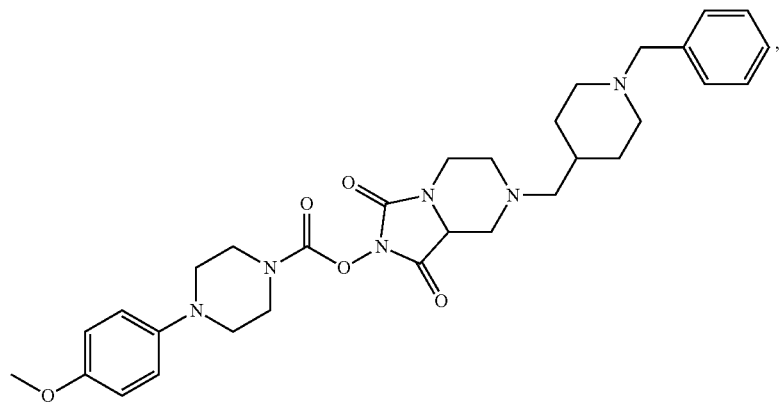
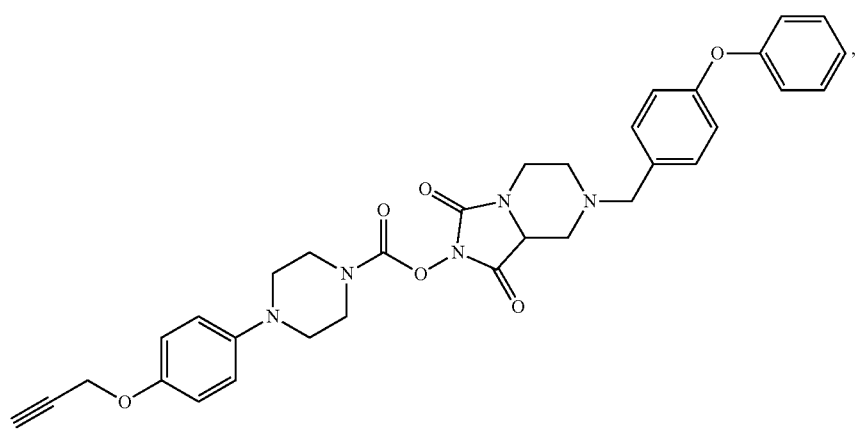
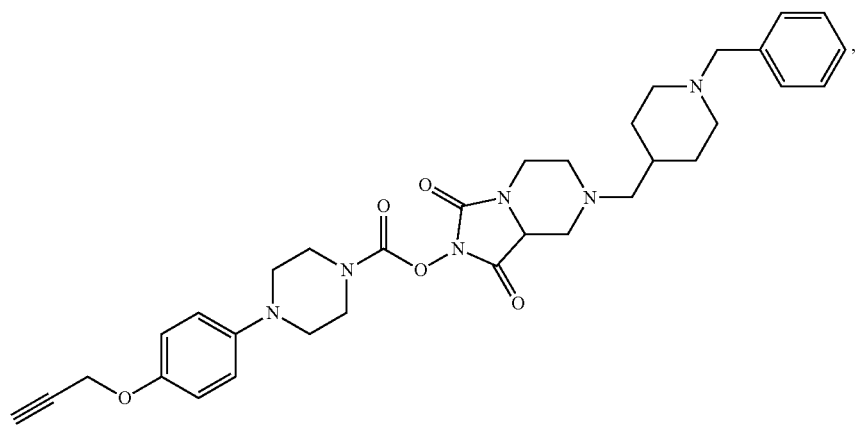
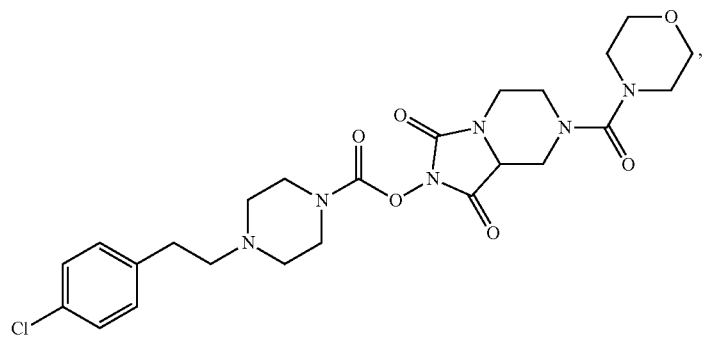

-continued
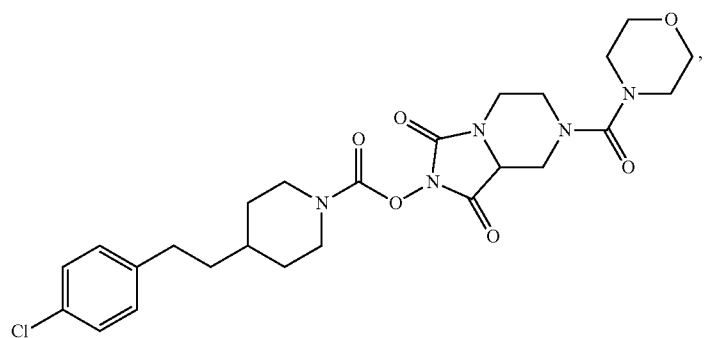
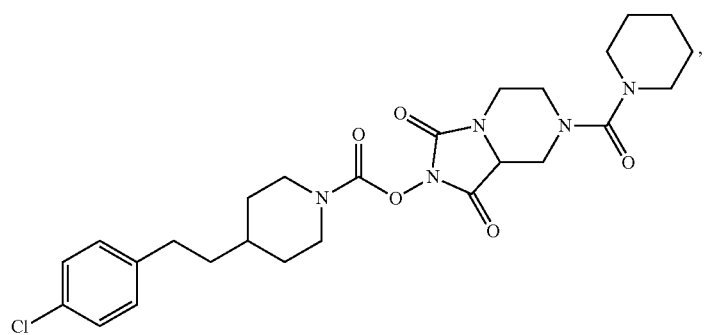
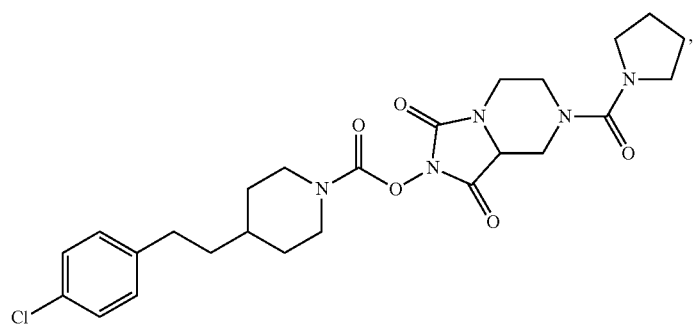
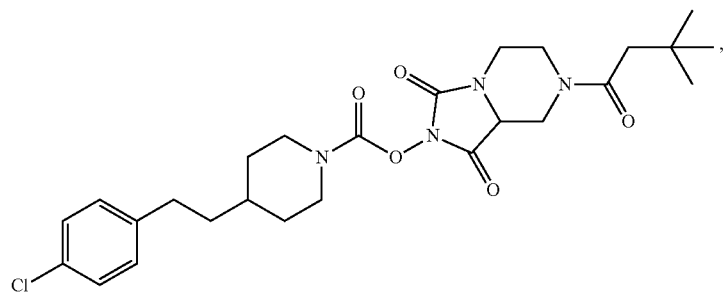
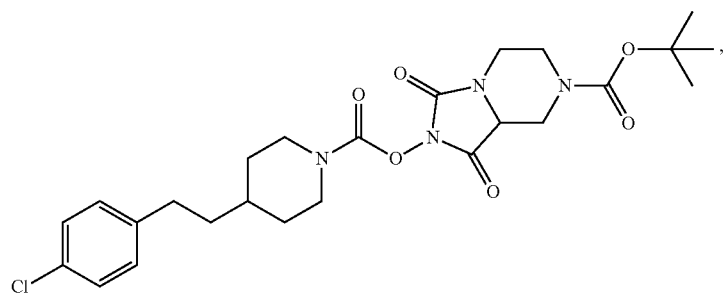

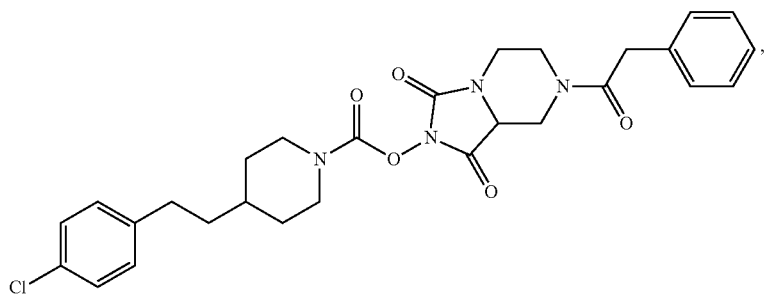
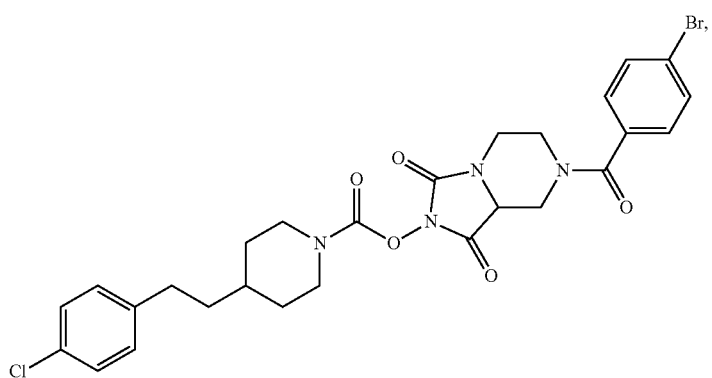
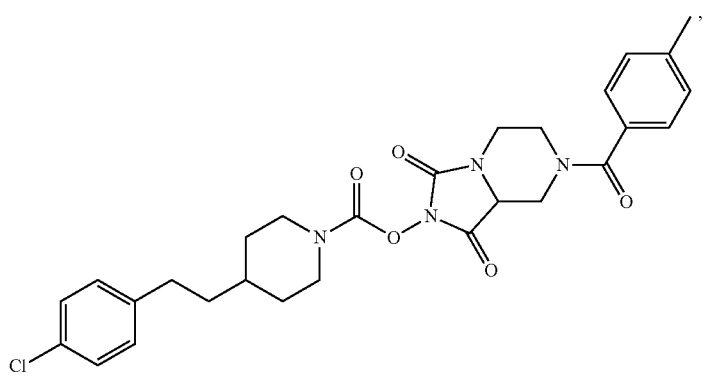
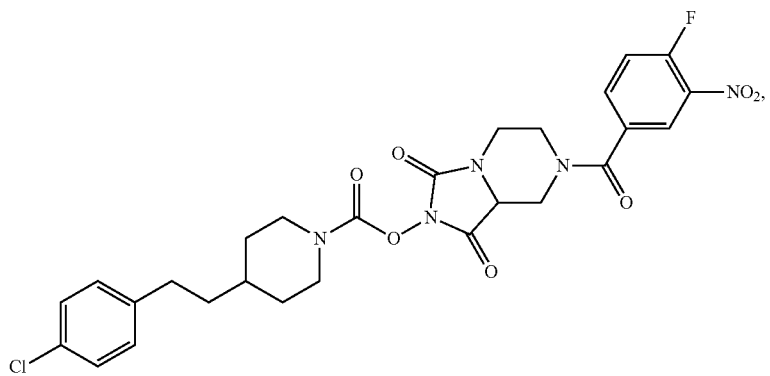

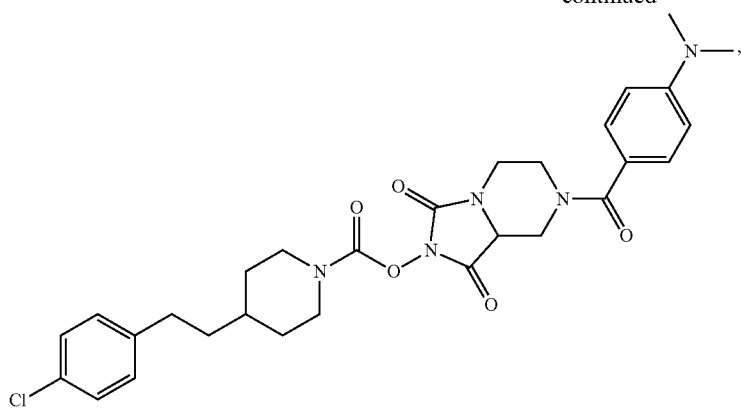
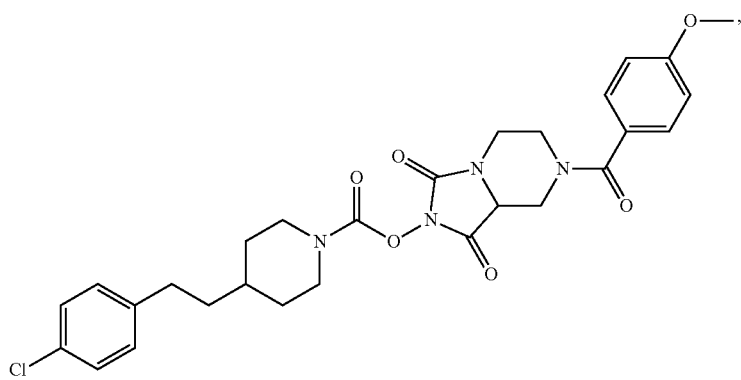
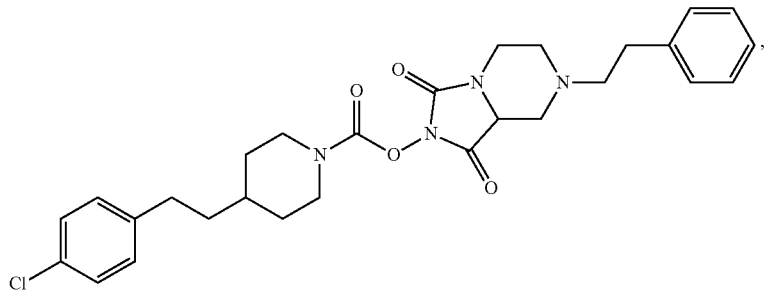
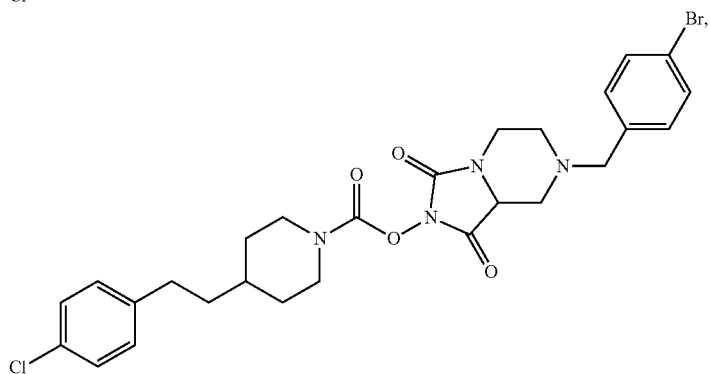
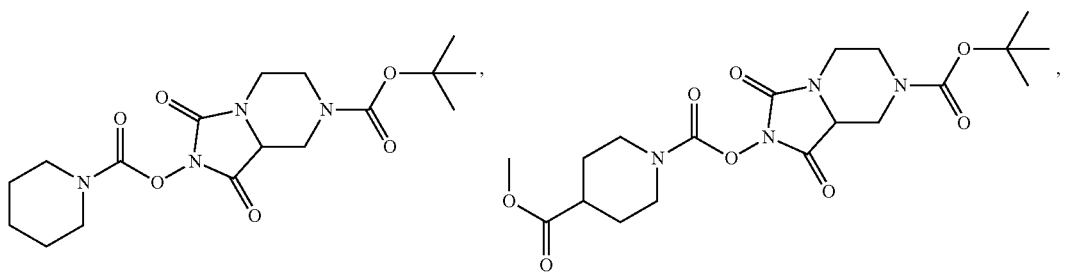

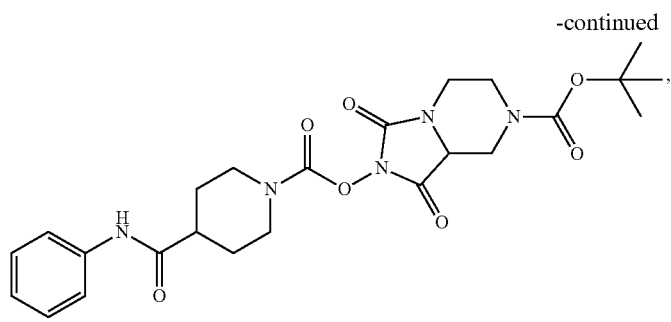
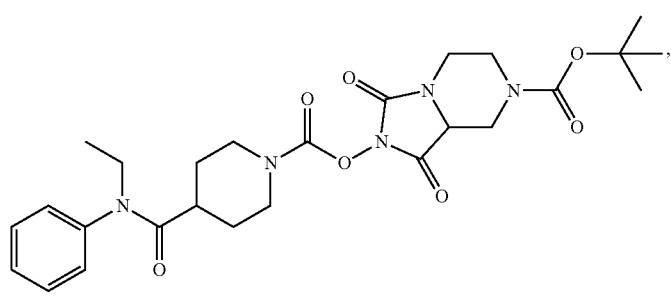
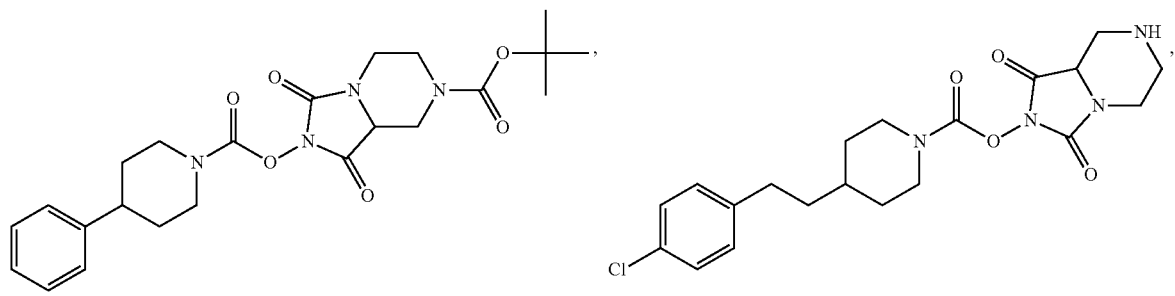
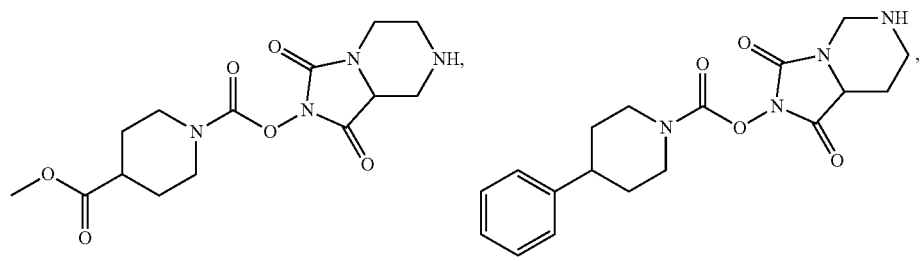
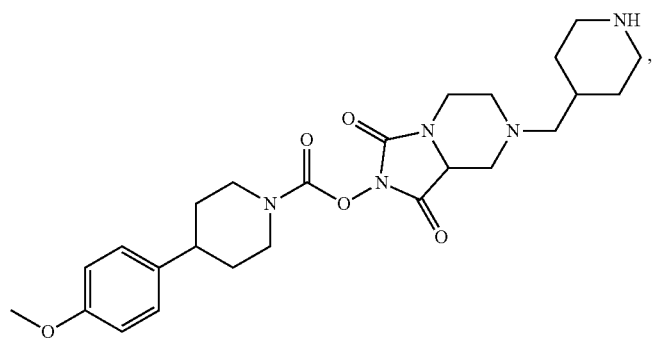

-continued
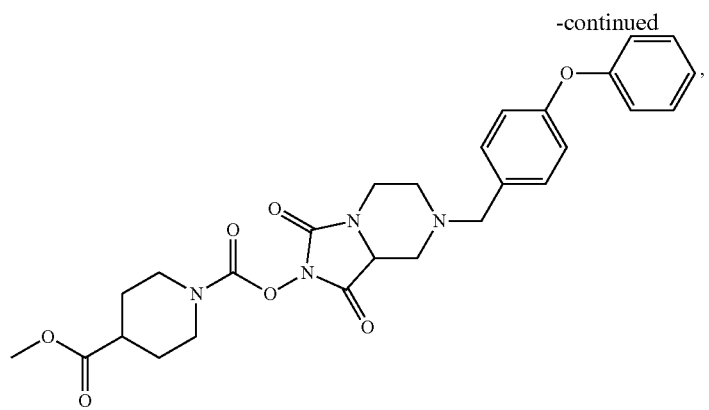
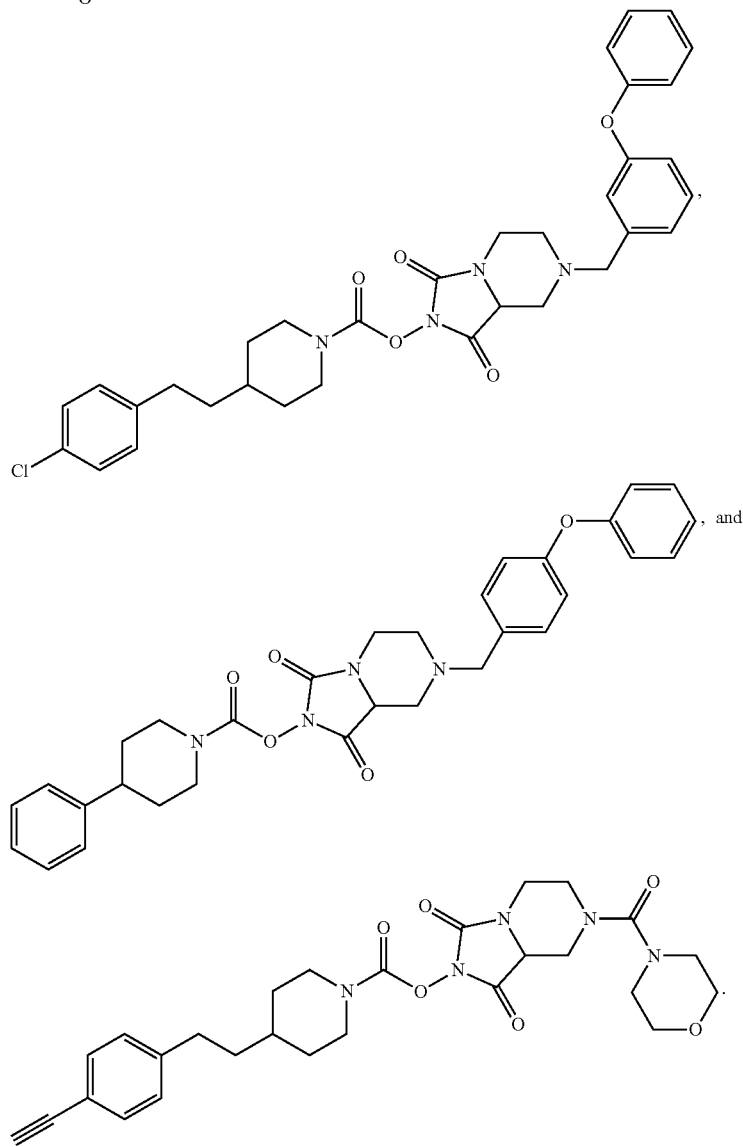
19. A pharmaceutical composition comprising a compound of claim 1 and at least one pharmaceutically acceptable excipient.
20. A method of treatment of a medical condition in a patient comprising administering an effective dose of a compound of claim 1 to the patient, wherein the medical condition is selected from pain, epilepsy, and traumatic brain injury.
* * * * *